United States Patent
Ding

(10) Patent No.: US 10,550,079 B2
(45) Date of Patent: Feb. 4, 2020

(54) ARTIFICIAL SELF-SUFFICIENT CYTOCHROME P450S

(71) Applicant: University of Florida Research Foundation, Incorporated, Gainesville, FL (US)

(72) Inventor: Yousong Ding, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/174,350

(22) Filed: Oct. 30, 2018

(65) Prior Publication Data

US 2019/0119208 A1 Apr. 25, 2019

Related U.S. Application Data

(63) Continuation of application No. 15/552,081, filed as application No. PCT/US2016/018470 on Feb. 18, 2016, now Pat. No. 10,138,205.

(60) Provisional application No. 62/275,018, filed on Jan. 5, 2016, provisional application No. 62/118,445, filed on Feb. 19, 2015.

(51) Int. Cl.
| | |
|---|---|
| *C12N 5/00* | (2006.01) |
| *C07D 209/16* | (2006.01) |
| *C12N 15/00* | (2006.01) |
| *C07D 401/04* | (2006.01) |
| *C12N 9/02* | (2006.01) |
| *A61K 31/4045* | (2006.01) |
| *A61K 31/405* | (2006.01) |

(52) U.S. Cl.
CPC .......... *C07D 209/16* (2013.01); *A61K 31/405* (2013.01); *A61K 31/4045* (2013.01); *C07D 401/04* (2013.01); *C12N 5/00* (2013.01); *C12N 9/0004* (2013.01); *C12N 15/00* (2013.01)

(58) Field of Classification Search
CPC . C12N 5/00; C12N 15/00; C12N 9/02; A61K 31/405; C07D 209/16
See application file for complete search history.

(56) References Cited

PUBLICATIONS

International Search Report and Written Opinion dated Nov. 1, 2016 for Application No. PCT/US2016/018470.
Database Registry [Online]; Chemical Abstracts Service, Columbus, Ohio, CAS Registry File RN 1379872-43-1, STN Entry Date: Jun. 25, 2012.
Barry et al., Cytochrome P450—catalyzed L-tryptophan nitration in thaxtomin phytotoxin biosynthesis. Nat Chem Biol. Oct. 2012;8(10):814-6.
Dodani et al., Structural, functional, and spectroscopic characterization of the substrate scope of the novel nitrating cytochrome P450 TxtE. Chembiochem. Oct. 13, 2014;15(15):2259-67. doi: 10.1002/cbic.201402241. Epub Sep. 2, 2014.
Munro et al., Cytochrome P450—redox partner fusion enzymes. Biochim Biophys Acta. Mar. 2007;1770(3):345-59. Epub Aug. 30, 2006. Review.
Zuo et al., An artificial self-sufficient cytochrome P450 directly nitrates fluorinated tryptophan analogs with a different regioselectivity. Biotechnol J. May 2016;11(5):624-32. doi: 10.1002/biot. 201500416. Epub Feb. 4, 2016.
PCT/US2016/018470, Nov. 1, 2016, International Search Report and Written Opinion.

*Primary Examiner* — Jeffrey H Murray
(74) *Attorney, Agent, or Firm* — Wolf, Greenfield & Sacks, P.C.

(57) ABSTRACT

The disclosure relates to the field of fusion proteins. In some aspects, the invention to artificial fusion proteins comprising cytochrome P450 enzymes linked to reductase enzymes and uses thereof. In some aspects, the disclosures relates to compounds produced by artificial cytochrome P450 enzymes.

9 Claims, 40 Drawing Sheets

Specification includes a Sequence Listing.

FIG. 2A
FIG. 2C
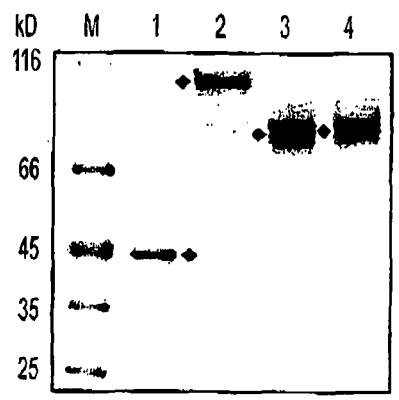
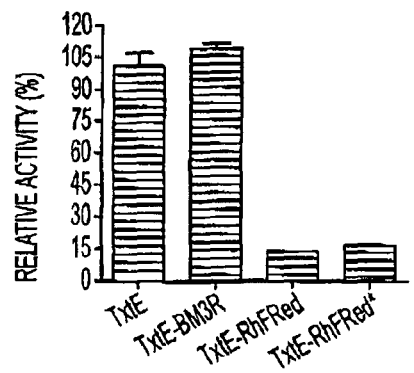
FIG. 2B
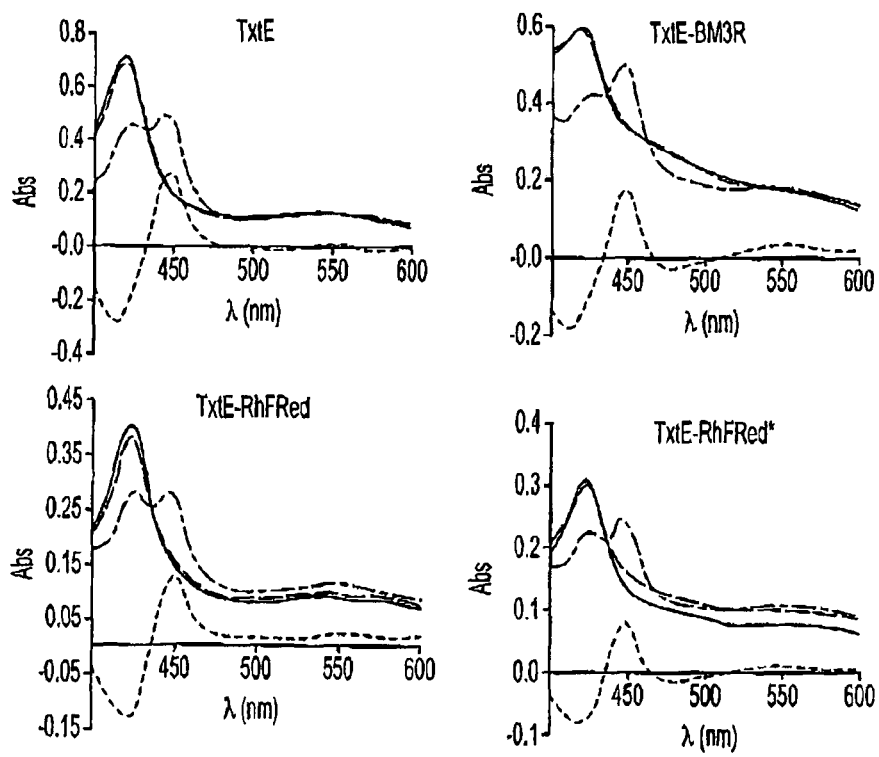

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 1
cacccatggt gaccgtcccc tcgc                                          24

<210> SEQ ID NO 2
<211> LENGTH: 28
<212> TYPE: DNA
<213> ORGANISM: Artificial sequence
<220> FEATURE:
<223> OTHER INFORMATION: Synthetic nucleic acid

<400> SEQUENCE: 2
atataagctt gcggaggctg agcggcag                                      28
```

<210> SEQ ID NO 3
<211> LENGTH: 34
<212> TYPE: DNA
<213> ORGANISM: Artificial sequence
<220> FEATURE:
<223> OTHER INFORMATION: Synthetic nucleic acid

<400> SEQUENCE: 3
gccgctcagc ctccgctctg ctaaaaaagt acgc         34

<210> SEQ ID NO 4
<211> LENGTH: 34
<212> TYPE: DNA
<213> ORGANISM: Artificial sequence
<220> FEATURE:
<223> OTHER INFORMATION: Synthetic nucleic acid

<400> SEQUENCE: 4
gcgtactttt ttagcagagc ggaggctgag cggc         34

<210> SEQ ID NO 5
<211> LENGTH: 32
<212> TYPE: DNA
<213> ORGANISM: Artificial sequence
<220> FEATURE:
<223> OTHER INFORMATION: Synthetic nucleic acid

<400> SEQUENCE: 5
atcgagctcg acccagccca cacgtctttt gc           32

<210> SEQ ID NO 6
<211> LENGTH: 31
<212> TYPE: DNA
<213> ORGANISM: Artificial sequence
<220> FEATURE:
<223> OTHER INFORMATION: Synthetic nucleic acid

<400> SEQUENCE: 6
ccgctcagcc tccgcgtgct gcaccgccat c            31

<210> SEQ ID NO 7
<211> LENGTH: 31
<212> TYPE: DNA
<213> ORGANISM: Artificial sequence
<220> FEATURE:
<223> OTHER INFORMATION: Synthetic nucleic acid

<400> SEQUENCE: 7
gatggcggtg cagcacgcgg aggctgagcg g            31

<210> SEQ ID NO 8
<211> LENGTH: 33
<212> TYPE: DNA
<213> ORGANISM: Artificial sequence
<220> FEATURE:
<223> OTHER INFORMATION: Synthetic nucleic acid

<400> SEQUENCE: 8
gccgctcagc ctccgccatg tgcgattggc gtc          33

<210> SEQ ID NO 9
<211> LENGTH: 33
<212> TYPE: DNA
<213> ORGANISM: Artificial sequence
<220> FEATURE:
<223> OTHER INFORMATION: Synthetic nucleic acid

```
<400> SEQUENCE: 9
gacgccaatc gcacatggcg gaggctgagc ggc                                    33

<210> SEQ ID NO 10
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 10
ctcaagcttg aggcgcaggg ccaggcg                                           27
```

ARTIFICIAL SELF-SUFFICIENT CYTOCHROME P450S

RELATED APPLICATIONS

This application is a continuation under 35 U.S.C. § 120 of U.S. application Ser. No. 15/552,081, filed Aug. 18, 2017, entitled "ARTIFICIAL SELF-SUFFICIENT CYTOCHROME p450s", which is a national stage filing under 35 U.S.C. § 371 of international application PCT/US2016/018470, filed Feb. 18, 2016, which was published under PTC Article 21(2) in English, and claims the benefit under 35 U.S.C. § 119(e) of U.S. Provisional Application No. 62/118,445, filed Feb. 19, 2015, and U.S. Provisional Patent Application No. 62/275,018, filed Jan. 5, 2016, the entire disclosures of each of which are incorporated by reference herein.

BACKGROUND OF INVENTION

Nitro (—$NO_2$) compounds, particularly nitro aromatic and heterocyclic derivatives, are important industrial chemicals, with an estimated annual production of greater than 108 tons (Kulkarni and Chaudhari 2007). Their applications span a broad range such as food additives, pesticides, herbicides, polymers, explosives, and dyes (Ju and Parales 2010). The nitro group is also an important functional unit in pharmaceuticals such as chloramphenicol, nilutamine, tolcapone, metronidazole, and the recently approved anti-tuberculosis drug delamanid (Martino et al. 2003). Its therapeutic relevance is further illustrated by nitro-containing lead drug candidates such as 9-nitro-noscapine for the treatment of multidrug resistant cancers (Aneja et al. 2006) and 5-nitro-2-furancarboxylamides in treating neglected parasitic protozoa infections (Zhou et al. 2013).

Aromatic nitration is a widely used organic reaction (Yan and Yang 2013). Industrial scale reactions usually include a mixture of nitric acid and sulfuric acid or sometimes nitric acid with other acids. In these reactions, the nitronium ion, $NO_2^+$, is believed to be the active species, albeit the potential minor contribution of a radical mechanism (Olah et al. 1978). Currently used methods and materials present several challenges, such as poor selectivity, low yield, generation of multiple isomers and by-products, and low functional group tolerance frequently occur and limit their uses in generating products with specific requirements. In addition, currently used methods are not environmentally sound. Accordingly, there is a need to develop environmentally benign, selective, practical and efficient direct aromatic nitration approaches.

SUMMARY OF INVENTION

Aromatic nitration, addition of a nitro ($NO_2$) group to an aromatic molecule, is an important chemical reaction in a variety of industries. Current industrial methods of aromatic nitration utilize chemical catalysts, for example the mixing of strong acids (e.g. nitric acid and sulfuric acid). However, this approach is inefficient, leading to low yield of desirable products, as well as environmentally unsound.

The instant invention, in some aspects, overcomes these issues by providing a biocatalyst-based approach for aromatic nitration. The disclosure is based, in part, on the inventors' unexpected discovery that a cytochrome P450 enzyme, and in particular artificial self-sufficient cytochrome P450 enzymes, can transfer a nitro group onto L-tryptophan or L-tryptophan-containing moieties (e.g., a compound of Formulae Ia-IXa) having a substituted indole ring efficiently and with high regio-selectivity. It also was discovered unexpectedly that the regio-selectivity can be altered depending on the particular substituted L-tryptophan used as a starting material. Thus, the invention provides novel enzymes, novel methods, novel substituted indoles and novel substituted L-tryptophan-containing compounds (e.g., compounds of Formulae I, Ia, II, IIa, III, IIIa, IV, IVa, V, Va, VI, VIa, VII, VIIa, VIII, VIIIa, IX, or IXa).

Accordingly, in some aspects the disclosure relates to artificial self-sufficient cytochrome P450 enzymes. In some embodiments, artificial self-sufficient cytochrome P450 enzymes are fusion proteins. In some aspects, the disclosure provides a fusion protein comprising (i) a cytochrome P450 enzyme which catalyzes transfer of a nitro functional group to a L-tryptophan having at least one substitution on its indole ring; (ii) an amino acid linker; and, (iii) a catalytic domain of a reductase enzyme; wherein the linker joins the reductase enzyme to a terminus of the cytochrome P450 enzyme.

Accordingly, in some aspects the disclosure relates to artificial self-sufficient cytochrome P450 enzymes. In some embodiments, artificial self-sufficient cytochrome P450 enzymes are fusion proteins. In some aspects, the disclosure provides a fusion protein comprising (i) a cytochrome P450 enzyme which catalyzes transfer of a nitro functional group to a compound of Formulae Ia-IXa; (ii) an amino acid linker; and, (iii) a catalytic domain of a reductase enzyme; wherein the linker joins the reductase enzyme to a terminus of the cytochrome P450 enzyme.

In some embodiments, the terminus of the cytochrome P450 enzyme is a C-terminus. In some embodiments, the P450 enzyme occurs naturally in *Streptomyces*. In some embodiments, the P450 enzyme is a TxtE enzyme, wherein a TxtE enzyme is defined as:
  (i) TxtE;
  (ii) a portion of TxtE which catalyzes transfer of a nitro functional group to a L-tryptophan having at least one substitution on its indole ring; or,
  (iii) an enzyme which catalyzes transfer of a nitro functional group to a L-tryptophan having at least one substitution on its indole ring and is at least 95% homologous to the amino acid sequence of TxtE.

In some embodiments, the terminus of the cytochrome P450 enzyme is a C-terminus. In some embodiments, the P450 enzyme occurs naturally in *Streptomyces*. In some embodiments, the P450 enzyme is a TxtE enzyme, wherein a TxtE enzyme is defined as:
  (i) TxtE;
  (ii) a portion of TxtE which catalyzes transfer of a nitro functional group to a compound of Formulae Ia-IXa; or,
  (iii) an enzyme which catalyzes transfer of a nitro functional group to a compound of Formulae Ia-IXa and is at least 95% homologous to the amino acid sequence of TxtE.

In some embodiments, the cytochrome P450 enzyme shares at least 90% amino acid sequence similarity with TxtE.

In some embodiments, the reductase enzyme is a prokaryotic reductase enzyme. In some embodiments, the prokaryotic reductase enzyme occurs naturally in a self-sufficient cytochrome P450. In some embodiments, the prokaryotic reductase enzyme occurs naturally in a class II or class III cytochrome P450. In some embodiments, the prokaryotic reductase is a CYP102A1 (P450BM3) reductase or a P450RhF reductase.

In some embodiments, the amino acid linker ranges from about 6 amino acids to about 16 amino acids in length. In some embodiments, the amino acid linker is selected from the group consisting of flexible amino acid linker, rigid amino acid linker and cleavable amino acid linker.

In some aspects, the disclosure relates to an expression construct comprising a nucleic acid encoding a fusion protein as described by the disclosure. In some aspects, the disclosure provides an isolated nucleic acid encoding a fusion protein as described by the disclosure. In some aspects, the disclosure provides a host cell comprising an expression construct as described by the disclosure or an isolated nucleic acid as described by the disclosure.

In some aspects, the disclosure relates to a method for producing a nitro-substituted indole, the method comprising contacting an L-tryptophan molecule having at least one substitution on its indole ring, in the presence of NAD(P)H, with (i) at least one reductase enzyme; and, (ii) a cytochrome P450 enzyme that catalyzes transfer of a nitro functional group to the indole of the L-tryptophan having at least one substitution on its indole ring. In aspects the L-tryptophan having at least one substitution on its indole ring is substituted with other than a nitro group. In aspects the L-tryptophan molecule having at least one substitution on its indole ring is singly-substituted on its indole ring and the resulting nitro-substituted L-tryptophan is a di-substituted nitro indole. In aspects the method further comprises isolating the nitrated L-tryptophan. In aspects the method further comprises isolating the di-substituted nitrated indole portion of the L-tryptophan molecule from the L-tryptophan molecule.

In some aspects, the disclosure relates to a method for producing a nitro-substituted indole, the method comprising contacting a compound of Formulae Ia-IXa, in the presence of NAD(P)H, with (i) at least one reductase enzyme; and, (ii) a cytochrome P450 enzyme that catalyzes transfer of a nitro functional group to the compound of Formulae Ia-IXa. In aspects the compound of Formulae Ia-IXa is substituted with a moiety other than a nitro group. In aspects the compound of Formulae Ia-IXa is singly-substituted on its indole ring and the resulting compound of Formulae I-IX is a di-substituted nitro tryptophan. In aspects the method further comprises isolating the compound of Formulae I-IX. In aspects the method further comprises isolating the di-substituted nitrated indole portion of the compound of Formulae I-IX from the compound of Formulae I-IX.

In some embodiments, the cytochrome P450 enzyme and the reductase enzyme are linked by an amino acid linker to form a fusion protein prior to contacting the indole-substituted L-tryptophan molecule. In some embodiments, the amino acid linker links the reductase enzyme to a terminus of the cytochrome P450 enzyme. In some embodiments, the terminus is a C-terminus.

In some embodiments of the method, the P450 enzyme occurs naturally in *Streptomyces*.

In some embodiments, the cytochrome P450 enzyme is a TxtE enzyme, wherein a TxtE enzyme is defined as:
(i) TxtE;
(ii) a portion of TxtE which catalyzes transfer of a nitro functional group to a L-tryptophan having at least one substitution on its indole ring; or,
(iii) an enzyme that catalyzes transfer of a nitro functional group to a L-tryptophan having at least one substitution on its indole ring and is at least 95% homologous to the amino acid sequence of TxtE.

In some embodiments of the method, the P450 enzyme occurs naturally in *Streptomyces*.

In some embodiments, the cytochrome P450 enzyme is a TxtE enzyme, wherein a TxtE enzyme is defined as:
(i) TxtE;
(ii) a portion of TxtE which catalyzes transfer of a nitro functional group to a compound of Formulae Ia-IXa; or,
(iii) an enzyme that catalyzes transfer of a nitro functional group to a compound of Formulae Ia-IXa and is at least 95% homologous to the amino acid sequence of TxtE.

In some embodiments of the method, the at least one reductase enzyme is ferredoxin reductase. In some embodiments of the method, the ferredoxin reductase is spinach ferredoxin reductase.

In some embodiments, the method further comprises contacting the substituted L-tryptophan molecule with a ferredoxin protein in the presence of NAD(P)H. In some embodiments, the ferredoxin protein is spinach ferredoxin protein.

In some embodiments, the method further comprises contacting the compound of Formulae Ia-IXa with a ferredoxin protein in the presence of NAD(P)H. In some embodiments, the ferredoxin protein is spinach ferredoxin protein.

In some embodiments, the reductase is a prokaryotic reductase enzyme. In some embodiments, the prokaryotic reductase enzyme occurs naturally in a self-sufficient cytochrome P450. In some embodiments, the prokaryotic reductase enzyme occurs naturally in a class II or class III cytochrome P450. In some embodiments, the prokaryotic reductase is a CYP102A1 (P450BM3) reductase or a P450RhF reductase.

In some embodiments, the amino acid linker ranges from about 6 amino acids to about 16 amino acids in length. In some embodiments, the amino acid linker is selected from the group consisting of flexible amino acid linker, rigid amino acid linker and cleavable amino acid linker.

In some aspects, the disclosure provides compounds produced by nitration of L-tryptophan. In some embodiments, the L-tryptophan has a substitution on its indole ring. Accordingly, in some aspects the disclosure relates to a compound represented by Formula I or Formula II.

In some aspects, the disclosure provides compounds produced by nitration of L-tryptophan. In some aspects, the disclosure provides compounds produced by nitration of a compound of Formulae Ia-IXa to afford a compound of Formulae I-IX. In some embodiments, at least one of $X^1$, $X^2$, or $X^3$ in Formula Ia, IVa, or Va or at least one of $Y^1$, $Y^2$, or $Y^3$ in Formulae IIa, IIIa, VIa, VIIa, VIIIa, or IXa, is not hydrogen. Accordingly, in some aspects the disclosure relates to a compound represented by Formulae I-IX.

In embodiments, the compounds of the invention include

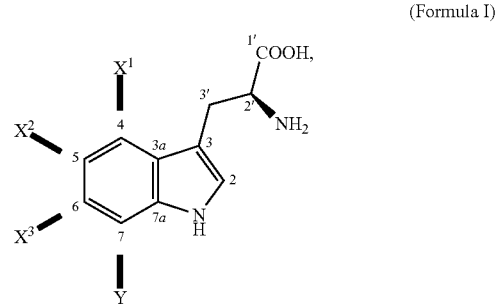

(Formula I)

wherein, in Formula I:
$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring and wherein the Ala of —$OR^{A1a}$ is not H;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring and wherein the Ala of —$OR^{A1a}$ is not H; and Y is $NO_2$.

In embodiments, the disclosure is directed to a compound of Formula I, or a pharmaceutically acceptable salt, prodrug, hydrate, or solvate thereof:

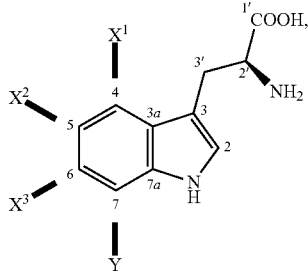

(Formula I)

wherein:

$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring; and Y is $NO_2$.

In embodiments, the disclosure is directed to a compound of Formula IV, or a pharmaceutically acceptable salt, prodrug, hydrate, or solvate thereof:

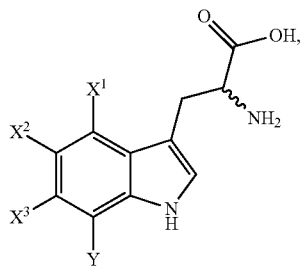

(Formula IV)

wherein:

$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring; and Y is $NO_2$.

In embodiments, the disclosure is directed to a compound of Formula V, or a pharmaceutically acceptable salt, prodrug, hydrate, or solvate thereof:

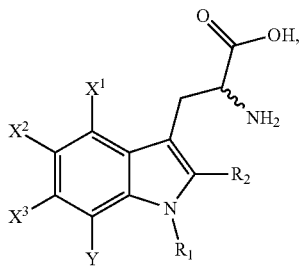

(Formula V)

wherein:

$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and Y is $NO_2$. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In embodiments of Formula I, one of $X^1$, $X^2$, or $X^3$ is halogen. In embodiments the halogen is fluorine. In embodiments of Formula I, $X^1$, $X^2$, or $X^3$ is unsubstituted $C_1$-$C_6$ alkyl. In embodiments the unsubstituted $C_1$-$C_6$ alkyl is methyl (—$CH_3$). In embodiments of Formula I, $X^1$ is halogen. In embodiments the halogen is fluorine. In embodiments of Formula I, $X^1$ is unsubstituted $C_1$-$C_6$ alkyl. In embodiments the unsubstituted $C_1$-$C_6$ alkyl is methyl (—$CH_3$). In embodiments, $X^2$ and $X^3$ are hydrogen.

In some aspects, the compound disclosure relates to a compound of Formulae I, IV, or V, wherein at least one of $X^1$, $X^2$, or $X^3$ is a "weakly deactivating group", a "weakly activating group", a "moderately activating group", or a "strongly activating group", as known in the art and as defined herein. In other aspects, at least one of $X^1$, $X^2$, or $X^3$ is H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$.

In another aspect, $X^1$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and $X^2$ and $X^3$ are each independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$. In another aspect, $X^1$ is halogen or $C_{1-6}$ alkyl (e.g. methyl, $CH_3$). In another aspect, $X^1$ is halogen. In another aspect, $X^1$ is $C_{1-6}$ alkyl (e.g. methyl, $CH_3$). In another aspect, $X^1$ is halogen or $C_{1-6}$ alkyl (e.g. methyl, $CH_3$) and at least one of $X^2$ and $X^3$ is hydrogen. In another aspect, $X^1$ is halogen and each of $X^2$ and $X^3$ is hydrogen. In another aspect, $X^1$ if fluorine and each of $X^2$ and $X^3$ is hydrogen. In another aspect, $X^1$ is $C_{1-6}$ alkyl and each of $X^2$ and $X^3$ is hydrogen. In another aspect, $X^1$ is methyl and each of $X^2$ and $X^3$ is hydrogen.

In embodiments, the compounds of the invention include

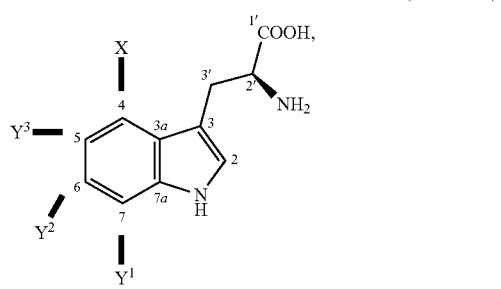

(Formula II)

wherein, in Formula II:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring and wherein the A1a of $-OR^{A1a}$ is not H; and
X is $NO_2$, provided that at least one of $Y^1$, $Y^2$, and $Y^3$ is not hydrogen.

In embodiments, the disclosure is directed to a compound of Formula II, or a pharmaceutically acceptable salt, prodrug, hydrate, or solvate thereof:

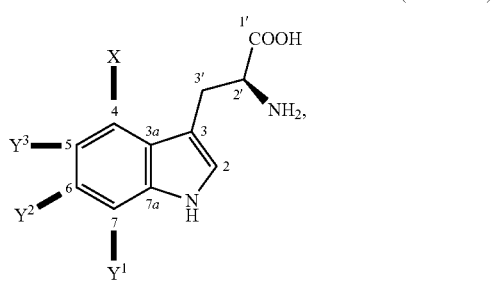

(Formula II)

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring; and
X is $NO_2$, provided that at least one of $Y^1$, $Y^2$, and $Y^3$ is not hydrogen.

In embodiments, the disclosure is directed to a compound of Formula VI, or a pharmaceutically acceptable salt, prodrug, hydrate, or solvate thereof:

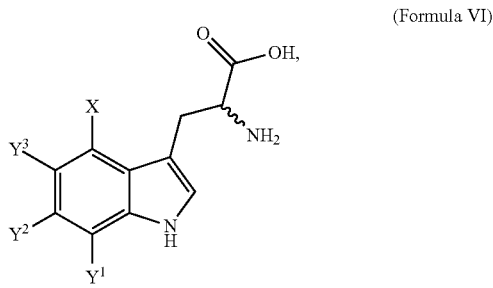

(Formula VI)

wherein:

each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring; and X is $NO_2$, provided that at least one of $Y^1$, $Y^2$, and $Y^3$ is not hydrogen.

In embodiments, the disclosure is directed to a compound of Formula VII, or a pharmaceutically acceptable salt, prodrug, hydrate, or solvate thereof:

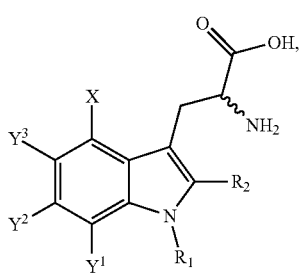

(Formula VII)

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$,
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;
$R_1$ is H or optionally substituted alkyl;
$R_2$ is H, optionally substituted alkyl, optionally substituted alkenyl, optionally substituted alkynyl, optionally substituted aryl, or optionally substituted heteroaryl; and
X is $NO_2$, provided that at least one of $Y^1$, $Y^2$, and $Y^3$ is not hydrogen. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In embodiments, the disclosure is directed to a compound of Formula III, or a pharmaceutically acceptable salt, prodrug, hydrate, or solvate thereof:

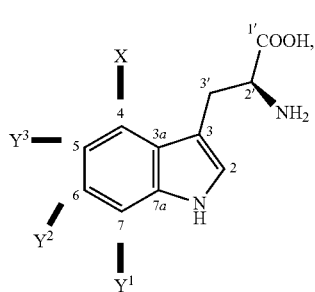

(Formula III)

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$,
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring; and
X is $NO_2$.

In embodiments, the disclosure is directed to a compound of Formula VIII, or a pharmaceutically acceptable salt, prodrug, hydrate, or solvate thereof:

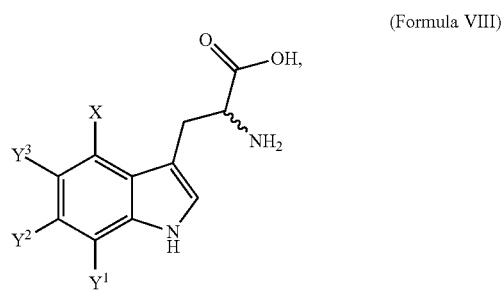

(Formula VIII)

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$,
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring; and
X is $NO_2$.

In embodiments, the disclosure is directed to a compound of Formula IX, or a pharmaceutically acceptable salt, prodrug, hydrate, or solvate thereof:

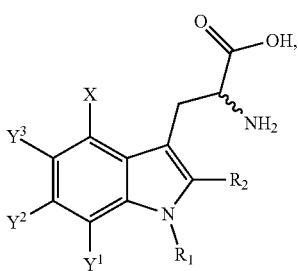

(Formula IX)

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

$R_1$ is H or optionally substituted alkyl;
$R_2$ is H, optionally substituted alkyl, optionally substituted alkenyl, optionally substituted alkynyl, optionally substituted aryl, or optionally substituted heteroaryl; and
X is $NO_2$. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In embodiments, $Y^1$, $Y^2$, or $Y^3$ is halogen and the halogen is fluorine. In embodiments, $Y^1$, $Y^2$, or $Y^3$ is unsubstituted $C_1$-$C_6$ alkyl. In embodiments, the unsubstituted $C_1$-$C_6$ alkyl is methyl ($-CH_3$). In embodiments, two of $Y^1$, $Y^2$ and $Y^3$ are hydrogen. In embodiments, $Y^2$ and $Y^3$ are hydrogen. In embodiments, $Y^1$ and $Y^3$ are hydrogen. In embodiments, $Y^1$ and $Y^2$ are hydrogen.

In some aspects, the disclosure relates to a compound of Formulae II-IX, wherein at least one of $Y^1$, $Y^2$ or $Y^3$ is halogen or $C_{1-6}$ alkyl (e.g. methyl, $CH_3$). In another aspect, $Y^3$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$; and $Y^1$ and $Y^2$ are each independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$. In another aspect, $Y^3$ is is halogen or $C_{1-6}$ alkyl (e.g. methyl, $CH_3$). In another aspect, $Y^3$ is halogen or $C_{1-6}$ alkyl (e.g. methyl, $CH_3$) and at least one of $Y^1$ and $Y^2$ is hydrogen. In another aspect, $Y^3$ is halogen or $C_{1-6}$ alkyl (e.g. methyl, $CH_3$) and $Y^1$ and $Y^2$ are each hydrogen. In another aspect, $Y^3$ is halogen. In another aspect, $Y^3$ is halogen and at least one of $Y^1$ and $Y^2$ is hydrogen. In another aspect, $Y^3$ is halogen and $Y^1$ and $Y^2$ are each hydrogen. In certain embodiments, $Y^3$ is fluorine and at least one of $Y^1$ and $Y^2$ is hydrogen. In another aspect, $Y^3$ is fluorine and $Y^1$ and $Y^2$ are each hydrogen. In another aspect, $Y^3$ is $C_{1-6}$ alkyl. In another aspect, $Y^3$ is $C_{1-6}$ alkyl and at least one of $Y^1$ and $Y^2$ is hydrogen. In another aspect, $Y^3$ is $C_{1-6}$ alkyl and $Y^1$ and $Y^2$ are each hydrogen. In certain embodiments, $Y^3$ is methyl and at least one of $Y^1$ and $Y^2$ is hydrogen. In another aspect, $Y^3$ is methyl and $Y^1$ and $Y^2$ are each hydrogen.

In another aspect, the invention is directed to a compound that is:
(S)-2-amino-3-(5-methyl-4-nitro-1H-indol-3-yl)propanoic acid (8);
(S)-2-amino-3-(6-methyl-4-nitro-1H-indol-3-yl)propanoic acid (9);
(S)-2-amino-3-(7-methyl-4-nitro-1H-indol-3-yl)propanoic acid (10);
(S)-2-amino-3-(4-methyl-7-nitro-1H-indol-3-yl)propanoic acid (11);
(S)-2-amino-3-(5-fluoro-4-nitro-1H-indol-3-yl)propanoic acid;
(S)-2-amino-3-(6-fluoro-4-nitro-1H-indol-3-yl)propanoic acid (12);
(S)-2-amino-3-(7-fluoro-4-nitro-1H-indol-3-yl)propanoic acid (13);
(S)-2-amino-3-(4-fluoro-7-nitro-1H-indol-3-yl)propanoic acid;
(S)-2-amino-3-(5-chloro-4-nitro-1H-indol-3-yl)propanoic acid (14);
(S)-2-amino-3-(6-chloro-4-nitro-1H-indol-3-yl)propanoic acid (15);
(S)-2-amino-3-(7-chloro-4-nitro-1H-indol-3-yl)propanoic acid (16);
(S)-2-amino-3-(4-chloro-7-nitro-1H-indol-3-yl)propanoic acid (17);
(S)-2-amino-3-(5-bromo-4-nitro-1H-indol-3-yl)propanoic acid (18);
(S)-2-amino-3-(6-bromo-4-nitro-1H-indol-3-yl)propanoic acid (19);
(S)-2-amino-3-(7-bromo-4-nitro-1H-indol-3-yl)propanoic acid (20);
(S)-2-amino-3-(4-bromo-7-nitro-1H-indol-3-yl)propanoic acid (21);
(S)-2-amino-3-(5-methoxy-4-nitro-1H-indol-3-yl)propanoic acid (22);
(S)-2-amino-3-(6-methoxy-4-nitro-1H-indol-3-yl)propanoic acid (23);
(S)-2-amino-3-(7-methoxy-4-nitro-1H-indol-3-yl)propanoic acid (24);
(S)-2-amino-3-(4-methoxy-7-nitro-1H-indol-3-yl)propanoic acid (25);
(S)-2-amino-3-(5-amino-4-nitro-1H-indol-3-yl)propanoic acid (26);
(S)-2-amino-3-(6-amino-4-nitro-1H-indol-3-yl)propanoic acid (27);

(S)-2-amino-3-(7-amino-4-nitro-1H-indol-3-yl)propanoic acid (28);
(S)-2-amino-3-(4-amino-7-nitro-1H-indol-3-yl)propanoic acid (29);
(S)-2-amino-3-(5-hydroxy-4-nitro-1H-indol-3-yl)propanoic acid (30);
(S)-2-amino-3-(6-hydroxy-4-nitro-1H-indol-3-yl)propanoic acid (31);
(S)-2-amino-3-(7-hydroxy-4-nitro-1H-indol-3-yl)propanoic acid (32);
(S)-2-amino-3-(4-hydroxy-7-nitro-1H-indol-3-yl)propanoic acid (33);
(S)-2-amino-3-(4-nitro-5-phenyl-1H-indol-3-yl)propanoic acid (34);
(S)-2-amino-3-(4-nitro-6-phenyl-1H-indol-3-yl)propanoic acid (35);
(S)-2-amino-3-(4-nitro-7-phenyl-1H-indol-3-yl)propanoic acid (36);
(S)-2-amino-3-(7-nitro-4-phenyl-1H-indol-3-yl)propanoic acid (37);
(S)-2-amino-3-(5-cyclopropyl-4-nitro-1H-indol-3-yl)propanoic acid (38);
(S)-2-amino-3-(6-cyclopropyl-4-nitro-1H-indol-3-yl)propanoic acid (39);
(S)-2-amino-3-(7-cyclopropyl-4-nitro-1H-indol-3-yl)propanoic acid (40);
(S)-2-amino-3-(4-cyclopropyl-7-nitro-1H-indol-3-yl)propanoic acid (41);
(S)-2-amino-3-(4-nitro-5-vinyl-1H-indol-3-yl)propanoic acid (42);
(S)-2-amino-3-(4-nitro-6-vinyl-1H-indol-3-yl)propanoic acid (43);
(S)-2-amino-3-(4-nitro-7-vinyl-1H-indol-3-yl)propanoic acid (44);
(S)-2-amino-3-(7-nitro-4-vinyl-1H-indol-3-yl)propanoic acid (45);
(S)-2-amino-3-(5-ethynyl-4-nitro-1H-indol-3-yl)propanoic acid (46);
(S)-2-amino-3-(6-ethynyl-4-nitro-1H-indol-3-yl)propanoic acid (47);
(S)-2-amino-3-(7-ethynyl-4-nitro-1H-indol-3-yl)propanoic acid (48);
(S)-2-amino-3-(4-ethynyl-7-nitro-1H-indol-3-yl)propanoic acid (49);
(S)-2-amino-3-(5-morpholino-4-nitro-1H-indol-3-yl)propanoic acid (50);
(S)-2-amino-3-(6-morpholino-4-nitro-1H-indol-3-yl)propanoic acid (51);
(S)-2-amino-3-(7-morpholino-4-nitro-1H-indol-3-yl)propanoic acid (52);
(S)-2-amino-3-(4-morpholino-7-nitro-1H-indol-3-yl)propanoic acid (53);
(S)-2-amino-3-(5-(methylthio)-4-nitro-1H-indol-3-yl)propanoic acid (54);
(S)-2-amino-3-(6-(methylthio)-4-nitro-1H-indol-3-yl)propanoic acid (55);
(S)-2-amino-3-(7-(methylthio)-4-nitro-1H-indol-3-yl)propanoic acid (56);
(S)-2-amino-3-(4-(methylthio)-7-nitro-1H-indol-3-yl)propanoic acid (57);
(S)-2-amino-3-(4-nitro-5-(pyridin-4-yl)-1H-indol-3-yl)propanoic acid (58);
(S)-2-amino-3-(4-nitro-6-(pyridin-4-yl)-1H-indol-3-yl)propanoic acid (59);
(S)-2-amino-3-(4-nitro-7-(pyridin-4-yl)-1H-indol-3-yl)propanoic acid (60);
(S)-2-amino-3-(7-nitro-4-(pyridin-4-yl)-1H-indol-3-yl)propanoic acid (61);
2-amino-3-(5-methyl-4-nitro-1H-indol-3-yl)propanoic acid (62);
2-amino-3-(6-methyl-4-nitro-1H-indol-3-yl)propanoic acid (63);
2-amino-3-(7-methyl-4-nitro-1H-indol-3-yl)propanoic acid (64);
2-amino-3-(4-methyl-7-nitro-1H-indol-3-yl)propanoic acid (65);
2-amino-3-(6-fluoro-4-nitro-1H-indol-3-yl)propanoic acid (66);
2-amino-3-(7-fluoro-4-nitro-1H-indol-3-yl)propanoic acid (67);
2-amino-3-(4-fluoro-7-nitro-1H-indol-3-yl)propanoic acid (68);
2-amino-3-(5-chloro-4-nitro-1H-indol-3-yl)propanoic acid (69);
2-amino-3-(6-chloro-4-nitro-1H-indol-3-yl)propanoic acid (70);
2-amino-3-(7-chloro-4-nitro-1H-indol-3-yl)propanoic acid (71);
2-amino-3-(4-chloro-7-nitro-1H-indol-3-yl)propanoic acid (72);
2-amino-3-(5-bromo-4-nitro-1H-indol-3-yl)propanoic acid (73);
2-amino-3-(6-bromo-4-nitro-1H-indol-3-yl)propanoic acid (74);
2-amino-3-(7-bromo-4-nitro-1H-indol-3-yl)propanoic acid (75);
2-amino-3-(4-bromo-7-nitro-1H-indol-3-yl)propanoic acid (76);
2-amino-3-(5-methoxy-4-nitro-1H-indol-3-yl)propanoic acid (77);
2-amino-3-(6-methoxy-4-nitro-1H-indol-3-yl)propanoic acid (78);
2-amino-3-(7-methoxy-4-nitro-1H-indol-3-yl)propanoic acid (79);
2-amino-3-(4-methoxy-7-nitro-1H-indol-3-yl)propanoic acid (80);
2-amino-3-(5-amino-4-nitro-1H-indol-3-yl)propanoic acid (81);
2-amino-3-(6-amino-4-nitro-1H-indol-3-yl)propanoic acid (82);
2-amino-3-(7-amino-4-nitro-1H-indol-3-yl)propanoic acid (83);
2-amino-3-(4-amino-7-nitro-1H-indol-3-yl)propanoic acid (84);
2-amino-3-(5-hydroxy-4-nitro-1H-indol-3-yl)propanoic acid (85);
2-amino-3-(6-hydroxy-4-nitro-1H-indol-3-yl)propanoic acid (86);
2-amino-3-(7-hydroxy-4-nitro-1H-indol-3-yl)propanoic acid (87);
2-amino-3-(4-hydroxy-7-nitro-1H-indol-3-yl)propanoic acid (88);
2-amino-3-(4-nitro-5-phenyl-1H-indol-3-yl)propanoic acid (89);
2-amino-3-(4-nitro-6-phenyl-1H-indol-3-yl)propanoic acid (90);
2-amino-3-(4-nitro-7-phenyl-1H-indol-3-yl)propanoic acid (91);
2-amino-3-(7-nitro-4-phenyl-1H-indol-3-yl)propanoic acid (92);
2-amino-3-(5-cyclopropyl-4-nitro-1H-indol-3-yl)propanoic acid (93);

2-amino-3-(6-cyclopropyl-4-nitro-1H-indol-3-yl)propanoic acid (94);
2-amino-3-(7-cyclopropyl-4-nitro-1H-indol-3-yl)propanoic acid (95);
2-amino-3-(4-cyclopropyl-7-nitro-1H-indol-3-yl)propanoic acid (96);
2-amino-3-(4-nitro-5-vinyl-1H-indol-3-yl)propanoic acid (97);
2-amino-3-(4-nitro-6-vinyl-1H-indol-3-yl)propanoic acid (98);
2-amino-3-(4-nitro-7-vinyl-1H-indol-3-yl)propanoic acid (99);
2-amino-3-(7-nitro-4-vinyl-1H-indol-3-yl)propanoic acid (100);
2-amino-3-(5-ethynyl-4-nitro-1H-indol-3-yl)propanoic acid (101);
2-amino-3-(6-ethynyl-4-nitro-1H-indol-3-yl)propanoic acid (102);
2-amino-3-(7-ethynyl-4-nitro-1H-indol-3-yl)propanoic acid (103);
2-amino-3-(4-ethynyl-7-nitro-1H-indol-3-yl)propanoic acid (104);
2-amino-3-(5-morpholino-4-nitro-1H-indol-3-yl)propanoic acid (105);
2-amino-3-(6-morpholino-4-nitro-1H-indol-3-yl)propanoic acid (106);
2-amino-3-(7-morpholino-4-nitro-1H-indol-3-yl)propanoic acid (107);
2-amino-3-(4-morpholino-7-nitro-1H-indol-3-yl)propanoic acid (108);
2-amino-3-(5-(methylthio)-4-nitro-1H-indol-3-yl)propanoic acid (109);
2-amino-3-(6-(methylthio)-4-nitro-1H-indol-3-yl)propanoic acid (110);
2-amino-3-(7-(methylthio)-4-nitro-1H-indol-3-yl)propanoic acid (111);
2-amino-3-(4-(methylthio)-7-nitro-1H-indol-3-yl)propanoic acid (112);
2-amino-3-(4-nitro-5-(pyridin-4-yl)-1H-indol-3-yl)propanoic acid (113);
2-amino-3-(4-nitro-6-(pyridin-4-yl)-1H-indol-3-yl)propanoic acid (114);
2-amino-3-(4-nitro-7-(pyridin-4-yl)-1H-indol-3-yl)propanoic acid (115);
2-amino-3-(7-nitro-4-(pyridin-4-yl)-1H-indol-3-yl)propanoic acid (116);
2-amino-3-(1,5-dimethyl-4-nitro-1H-indol-3-yl)propanoic acid (117);
2-amino-3-(1,6-dimethyl-4-nitro-1H-indol-3-yl)propanoic acid (118);
2-amino-3-(1,7-dimethyl-4-nitro-1H-indol-3-yl)propanoic acid (119);
2-amino-3-(1,4-dimethyl-7-nitro-1H-indol-3-yl)propanoic acid (120);
2-amino-3-(6-fluoro-1-methyl-4-nitro-1H-indol-3-yl)propanoic acid (121);
2-amino-3-(7-fluoro-1-methyl-4-nitro-1H-indol-3-yl)propanoic acid (122);
2-amino-3-(4-fluoro-1-methyl-7-nitro-1H-indol-3-yl)propanoic acid (123);
2-amino-3-(5-chloro-1-methyl-4-nitro-1H-indol-3-yl)propanoic acid (124);
2-amino-3-(6-chloro-1-methyl-4-nitro-1H-indol-3-yl)propanoic acid (125);
2-amino-3-(7-chloro-1-methyl-4-nitro-1H-indol-3-yl)propanoic acid (126);
2-amino-3-(4-chloro-1-methyl-7-nitro-1H-indol-3-yl)propanoic acid (127);
2-amino-3-(5-bromo-1-methyl-4-nitro-1H-indol-3-yl)propanoic acid (128);
2-amino-3-(6-bromo-1-methyl-4-nitro-1H-indol-3-yl)propanoic acid (129);
2-amino-3-(7-bromo-1-methyl-4-nitro-1H-indol-3-yl)propanoic acid (130);
2-amino-3-(4-bromo-1-methyl-7-nitro-1H-indol-3-yl)propanoic acid (131);
2-amino-3-(5-methoxy-1-methyl-4-nitro-1H-indol-3-yl)propanoic acid (132);
2-amino-3-(6-methoxy-1-methyl-4-nitro-1H-indol-3-yl)propanoic acid (133);
2-amino-3-(7-methoxy-1-methyl-4-nitro-1H-indol-3-yl)propanoic acid (134);
2-amino-3-(4-methoxy-1-methyl-7-nitro-1H-indol-3-yl)propanoic acid (135);
2-amino-3-(5-amino-1-methyl-4-nitro-1H-indol-3-yl)propanoic acid (136);
2-amino-3-(6-amino-1-methyl-4-nitro-1H-indol-3-yl)propanoic acid (137);
2-amino-3-(7-amino-1-methyl-4-nitro-1H-indol-3-yl)propanoic acid (138);
2-amino-3-(4-amino-1-methyl-7-nitro-1H-indol-3-yl)propanoic acid (139);
2-amino-3-(5-hydroxy-1-methyl-4-nitro-1H-indol-3-yl)propanoic acid (140);
2-amino-3-(6-hydroxy-1-methyl-4-nitro-1H-indol-3-yl)propanoic acid (141);
2-amino-3-(7-hydroxy-1-methyl-4-nitro-1H-indol-3-yl)propanoic acid (142);
2-amino-3-(4-hydroxy-1-methyl-7-nitro-1H-indol-3-yl)propanoic acid (143);
2-amino-3-(1-methyl-4-nitro-5-phenyl-1H-indol-3-yl)propanoic acid (144);
2-amino-3-(1-methyl-4-nitro-6-phenyl-1H-indol-3-yl)propanoic acid (145);
2-amino-3-(1-methyl-4-nitro-7-phenyl-1H-indol-3-yl)propanoic acid (146);
2-amino-3-(1-methyl-7-nitro-4-phenyl-1H-indol-3-yl)propanoic acid (147);
2-amino-3-(5-cyclopropyl-1-methyl-4-nitro-1H-indol-3-yl)propanoic acid (148);
2-amino-3-(6-cyclopropyl-1-methyl-4-nitro-1H-indol-3-yl)propanoic acid (149);
2-amino-3-(7-cyclopropyl-1-methyl-4-nitro-1H-indol-3-yl)propanoic acid (150);
2-amino-3-(4-cyclopropyl-1-methyl-7-nitro-1H-indol-3-yl)propanoic acid (151);
2-amino-3-(1-methyl-4-nitro-5-vinyl-1H-indol-3-yl)propanoic acid (152);
2-amino-3-(1-methyl-4-nitro-6-vinyl-1H-indol-3-yl)propanoic acid (153);
2-amino-3-(1-methyl-4-nitro-7-vinyl-1H-indol-3-yl)propanoic acid (154);
2-amino-3-(1-methyl-7-nitro-4-vinyl-1H-indol-3-yl)propanoic acid (155);
2-amino-3-(5-ethynyl-1-methyl-4-nitro-1H-indol-3-yl)propanoic acid (156);
2-amino-3-(6-ethynyl-1-methyl-4-nitro-1H-indol-3-yl)propanoic acid (157);
2-amino-3-(7-ethynyl-1-methyl-4-nitro-1H-indol-3-yl)propanoic acid (158);
2-amino-3-(4-ethynyl-1-methyl-7-nitro-1H-indol-3-yl)propanoic acid (159);

2-amino-3-(1-methyl-5-morpholino-4-nitro-1H-indol-3-yl)propanoic acid (160);
2-amino-3-(1-methyl-6-morpholino-4-nitro-1H-indol-3-yl)propanoic acid (161);
2-amino-3-(1-methyl-7-morpholino-4-nitro-1H-indol-3-yl)propanoic acid (162);
2-amino-3-(1-methyl-4-morpholino-7-nitro-1H-indol-3-yl)propanoic acid (163);
2-amino-3-(1-methyl-5-(methylthio)-4-nitro-1H-indol-3-yl)propanoic acid (164);
2-amino-3-(1-methyl-6-(methylthio)-4-nitro-1H-indol-3-yl)propanoic acid (165);
2-amino-3-(1-methyl-7-(methylthio)-4-nitro-1H-indol-3-yl)propanoic acid (166);
2-amino-3-(1-methyl-4-(methylthio)-7-nitro-1H-indol-3-yl)propanoic acid (167);
2-amino-3-(1-methyl-4-nitro-5-(pyridin-4-yl)-1H-indol-3-yl)propanoic acid (168);
2-amino-3-(1-methyl-4-nitro-6-(pyridin-4-yl)-1H-indol-3-yl)propanoic acid (169);
2-amino-3-(1-methyl-4-nitro-7-(pyridin-4-yl)-1H-indol-3-yl)propanoic acid (170);
2-amino-3-(1-methyl-7-nitro-4-(pyridin-4-yl)-1H-indol-3-yl)propanoic acid (171);
2-amino-3-(2,5-dimethyl-4-nitro-1H-indol-3-yl)propanoic acid (172);
2-amino-3-(2,6-dimethyl-4-nitro-1H-indol-3-yl)propanoic acid (173);
2-amino-3-(2,7-dimethyl-4-nitro-1H-indol-3-yl)propanoic acid (174);
2-amino-3-(2,4-dimethyl-7-nitro-1H-indol-3-yl)propanoic acid (175);
2-amino-3-(6-fluoro-2-methyl-4-nitro-1H-indol-3-yl)propanoic acid (176);
2-amino-3-(7-fluoro-2-methyl-4-nitro-1H-indol-3-yl)propanoic acid (177);
2-amino-3-(4-fluoro-2-methyl-7-nitro-1H-indol-3-yl)propanoic acid (178);
2-amino-3-(5-chloro-2-methyl-4-nitro-1H-indol-3-yl)propanoic acid (179);
2-amino-3-(6-chloro-2-methyl-4-nitro-1H-indol-3-yl)propanoic acid (180);
2-amino-3-(7-chloro-2-methyl-4-nitro-1H-indol-3-yl)propanoic acid (181);
2-amino-3-(4-chloro-2-methyl-7-nitro-1H-indol-3-yl)propanoic acid (182);
2-amino-3-(5-bromo-2-methyl-4-nitro-1H-indol-3-yl)propanoic acid (183);
2-amino-3-(6-bromo-2-methyl-4-nitro-1H-indol-3-yl)propanoic acid (184);
2-amino-3-(7-bromo-2-methyl-4-nitro-1H-indol-3-yl)propanoic acid (185);
2-amino-3-(4-bromo-2-methyl-7-nitro-1H-indol-3-yl)propanoic acid (186);
2-amino-3-(5-methoxy-2-methyl-4-nitro-1H-indol-3-yl)propanoic acid (187);
2-amino-3-(6-methoxy-2-methyl-4-nitro-1H-indol-3-yl)propanoic acid (188);
2-amino-3-(7-methoxy-2-methyl-4-nitro-1H-indol-3-yl)propanoic acid (189);
2-amino-3-(4-methoxy-2-methyl-7-nitro-1H-indol-3-yl)propanoic acid (190);
2-amino-3-(5-amino-2-methyl-4-nitro-1H-indol-3-yl)propanoic acid (191);
2-amino-3-(6-amino-2-methyl-4-nitro-1H-indol-3-yl)propanoic acid (192);
2-amino-3-(7-amino-2-methyl-4-nitro-1H-indol-3-yl)propanoic acid (193);
2-amino-3-(4-amino-2-methyl-7-nitro-1H-indol-3-yl)propanoic acid (194);
2-amino-3-(5-hydroxy-2-methyl-4-nitro-1H-indol-3-yl)propanoic acid (195);
2-amino-3-(6-hydroxy-2-methyl-4-nitro-1H-indol-3-yl)propanoic acid (196);
2-amino-3-(7-hydroxy-2-methyl-4-nitro-1H-indol-3-yl)propanoic acid (197);
2-amino-3-(4-hydroxy-2-methyl-7-nitro-1H-indol-3-yl)propanoic acid (198);
2-amino-3-(2-methyl-4-nitro-5-phenyl-1H-indol-3-yl)propanoic acid (199);
2-amino-3-(2-methyl-4-nitro-6-phenyl-1H-indol-3-yl)propanoic acid (200);
2-amino-3-(2-methyl-4-nitro-7-phenyl-1H-indol-3-yl)propanoic acid (201);
2-amino-3-(2-methyl-7-nitro-4-phenyl-1H-indol-3-yl)propanoic acid (202);
2-amino-3-(5-cyclopropyl-2-methyl-4-nitro-1H-indol-3-yl)propanoic acid (203);
2-amino-3-(6-cyclopropyl-2-methyl-4-nitro-1H-indol-3-yl)propanoic acid (204);
2-amino-3-(7-cyclopropyl-2-methyl-4-nitro-1H-indol-3-yl)propanoic acid (205);
2-amino-3-(4-cyclopropyl-2-methyl-7-nitro-1H-indol-3-yl)propanoic acid (206);
2-amino-3-(2-methyl-4-nitro-5-vinyl-1H-indol-3-yl)propanoic acid (207);
2-amino-3-(2-methyl-4-nitro-6-vinyl-1H-indol-3-yl)propanoic acid (208);
2-amino-3-(2-methyl-4-nitro-7-vinyl-1H-indol-3-yl)propanoic acid (209);
2-amino-3-(2-methyl-7-nitro-4-vinyl-1H-indol-3-yl)propanoic acid (210);
2-amino-3-(5-ethynyl-2-methyl-4-nitro-1H-indol-3-yl)propanoic acid (211);
2-amino-3-(6-ethynyl-2-methyl-4-nitro-1H-indol-3-yl)propanoic acid (212);
2-amino-3-(7-ethynyl-2-methyl-4-nitro-1H-indol-3-yl)propanoic acid (213);
2-amino-3-(4-ethynyl-2-methyl-7-nitro-1H-indol-3-yl)propanoic acid (214);
2-amino-3-(2-methyl-5-morpholino-4-nitro-1H-indol-3-yl)propanoic acid (215);
2-amino-3-(2-methyl-6-morpholino-4-nitro-1H-indol-3-yl)propanoic acid (216);
2-amino-3-(2-methyl-7-morpholino-4-nitro-1H-indol-3-yl)propanoic acid (217);
2-amino-3-(2-methyl-4-morpholino-7-nitro-1H-indol-3-yl)propanoic acid (218);
2-amino-3-(2-methyl-5-(methylthio)-4-nitro-1H-indol-3-yl)propanoic acid (219);
2-amino-3-(2-methyl-6-(methylthio)-4-nitro-1H-indol-3-yl)propanoic acid (220);
2-amino-3-(2-methyl-7-(methylthio)-4-nitro-1H-indol-3-yl)propanoic acid (221);
2-amino-3-(2-methyl-4-(methylthio)-7-nitro-1H-indol-3-yl)propanoic acid (222);
2-amino-3-(2-methyl-4-nitro-5-(pyridin-4-yl)-1H-indol-3-yl)propanoic acid (223);
2-amino-3-(2-methyl-4-nitro-6-(pyridin-4-yl)-1H-indol-3-yl)propanoic acid (224);
2-amino-3-(2-methyl-4-nitro-7-(pyridin-4-yl)-1H-indol-3-yl)propanoic acid (225);

2-amino-3-(2-methyl-7-nitro-4-(pyridin-4-yl)-1H-indol-3-yl)propanoic acid (226);
2-amino-3-(1,2,5-trimethyl-4-nitro-1H-indol-3-yl)propanoic acid (227);
2-amino-3-(1,2,6-trimethyl-4-nitro-1H-indol-3-yl)propanoic acid (228);
2-amino-3-(1,2,7-trimethyl-4-nitro-1H-indol-3-yl)propanoic acid (229);
2-amino-3-(1,2,4-trimethyl-7-nitro-1H-indol-3-yl)propanoic acid (230);
2-amino-3-(6-fluoro-1,2-dimethyl-4-nitro-1H-indol-3-yl)propanoic acid (231);
2-amino-3-(7-fluoro-1,2-dimethyl-4-nitro-1H-indol-3-yl)propanoic acid (232);
2-amino-3-(4-fluoro-1,2-dimethyl-7-nitro-1H-indol-3-yl)propanoic acid (233);
2-amino-3-(5-chloro-1,2-dimethyl-4-nitro-1H-indol-3-yl)propanoic acid (234);
2-amino-3-(6-chloro-1,2-dimethyl-4-nitro-1H-indol-3-yl)propanoic acid (235);
2-amino-3-(7-chloro-1,2-dimethyl-4-nitro-1H-indol-3-yl)propanoic acid (236);
2-amino-3-(4-chloro-1,2-dimethyl-7-nitro-1H-indol-3-yl)propanoic acid (237);
2-amino-3-(5-bromo-1,2-dimethyl-4-nitro-1H-indol-3-yl)propanoic acid (238);
2-amino-3-(6-bromo-1,2-dimethyl-4-nitro-1H-indol-3-yl)propanoic acid (239);
2-amino-3-(7-bromo-1,2-dimethyl-4-nitro-1H-indol-3-yl)propanoic acid (240);
2-amino-3-(4-bromo-1,2-dimethyl-7-nitro-1H-indol-3-yl)propanoic acid (241);
2-amino-3-(5-methoxy-1,2-dimethyl-4-nitro-1H-indol-3-yl)propanoic acid (242);
2-amino-3-(6-methoxy-1,2-dimethyl-4-nitro-1H-indol-3-yl)propanoic acid (243);
2-amino-3-(7-methoxy-1,2-dimethyl-4-nitro-1H-indol-3-yl)propanoic acid (244);
2-amino-3-(4-methoxy-1,2-dimethyl-7-nitro-1H-indol-3-yl)propanoic acid (245);
2-amino-3-(5-amino-1,2-dimethyl-4-nitro-1H-indol-3-yl)propanoic acid (246);
2-amino-3-(6-amino-1,2-dimethyl-4-nitro-1H-indol-3-yl)propanoic acid (247);
2-amino-3-(7-amino-1,2-dimethyl-4-nitro-1H-indol-3-yl)propanoic acid (248);
2-amino-3-(4-amino-1,2-dimethyl-7-nitro-1H-indol-3-yl)propanoic acid (249);
2-amino-3-(5-hydroxy-1,2-dimethyl-4-nitro-1H-indol-3-yl)propanoic acid (250);
2-amino-3-(6-hydroxy-1,2-dimethyl-4-nitro-1H-indol-3-yl)propanoic acid (251);
2-amino-3-(7-hydroxy-1,2-dimethyl-4-nitro-1H-indol-3-yl)propanoic acid (252);
2-amino-3-(4-hydroxy-1,2-dimethyl-7-nitro-1H-indol-3-yl)propanoic acid (253);
2-amino-3-(1,2-dimethyl-4-nitro-5-phenyl-1H-indol-3-yl)propanoic acid (254);
2-amino-3-(1,2-dimethyl-4-nitro-6-phenyl-1H-indol-3-yl)propanoic acid (255);
2-amino-3-(1,2-dimethyl-4-nitro-7-phenyl-1H-indol-3-yl)propanoic acid (256);
2-amino-3-(1,2-dimethyl-7-nitro-4-phenyl-1H-indol-3-yl)propanoic acid (257);
2-amino-3-(5-cyclopropyl-1,2-dimethyl-4-nitro-1H-indol-3-yl)propanoic acid (258);
2-amino-3-(6-cyclopropyl-1,2-dimethyl-4-nitro-1H-indol-3-yl)propanoic acid (259);
2-amino-3-(7-cyclopropyl-1,2-dimethyl-4-nitro-1H-indol-3-yl)propanoic acid (260);
2-amino-3-(4-cyclopropyl-1,2-dimethyl-7-nitro-1H-indol-3-yl)propanoic acid (261);
2-amino-3-(1,2-dimethyl-4-nitro-5-vinyl-1H-indol-3-yl)propanoic acid (262);
2-amino-3-(1,2-dimethyl-4-nitro-6-vinyl-1H-indol-3-yl)propanoic acid (263);
2-amino-3-(1,2-dimethyl-4-nitro-7-vinyl-1H-indol-3-yl)propanoic acid (264);
2-amino-3-(1,2-dimethyl-7-nitro-4-vinyl-1H-indol-3-yl)propanoic acid (265);
2-amino-3-(5-ethynyl-1,2-dimethyl-4-nitro-1H-indol-3-yl)propanoic acid (266);
2-amino-3-(6-ethynyl-1,2-dimethyl-4-nitro-1H-indol-3-yl)propanoic acid (267);
2-amino-3-(7-ethynyl-1,2-dimethyl-4-nitro-1H-indol-3-yl)propanoic acid (268);
2-amino-3-(4-ethynyl-1,2-dimethyl-7-nitro-1H-indol-3-yl)propanoic acid (269);
2-amino-3-(1,2-dimethyl-5-morpholino-4-nitro-1H-indol-3-yl)propanoic acid (270);
2-amino-3-(1,2-dimethyl-6-morpholino-4-nitro-1H-indol-3-yl)propanoic acid (271);
2-amino-3-(1,2-dimethyl-7-morpholino-4-nitro-1H-indol-3-yl)propanoic acid (272);
2-amino-3-(1,2-dimethyl-4-morpholino-7-nitro-1H-indol-3-yl)propanoic acid (273);
2-amino-3-(1,2-dimethyl-5-(methylthio)-4-nitro-1H-indol-3-yl)propanoic acid (274);
2-amino-3-(1,2-dimethyl-6-(methylthio)-4-nitro-1H-indol-3-yl)propanoic acid (275);
2-amino-3-(1,2-dimethyl-7-(methylthio)-4-nitro-1H-indol-3-yl)propanoic acid (276);
2-amino-3-(1,2-dimethyl-4-(methylthio)-7-nitro-1H-indol-3-yl)propanoic acid (277);
2-amino-3-(1,2-dimethyl-4-nitro-5-(pyridin-4-yl)-1H-indol-3-yl)propanoic acid (278);
2-amino-3-(1,2-dimethyl-4-nitro-6-(pyridin-4-yl)-1H-indol-3-yl)propanoic acid (279);
2-amino-3-(1,2-dimethyl-4-nitro-7-(pyridin-4-yl)-1H-indol-3-yl)propanoic acid (280); or
2-amino-3-(1,2-dimethyl-7-nitro-4-(pyridin-4-yl)-1H-indol-3-yl)propanoic acid (281);
and a pharmaceutically acceptable salt, prodrug, hydrate, or solvate thereof.

In some aspects, the disclosure relates to a composition comprising the compound of Formula I or Formula II. In some embodiments, the composition further comprises a pharmaceutically acceptable carrier. In some aspects, the disclosure provides a polypeptide comprising the compound of Formula I or Formula II. In some aspects, the disclosure relates to a cell comprising a compound of Formula I or Formula II.

In some aspects, the disclosure relates to methods of producing a compound of Formula I or Formula II. In some aspects, the method comprises contacting a L-tryptophan having at least one substitution on its indole ring with (i) at least one reductase enzyme; and, (ii) a cytochrome P450 enzyme which catalyzes transfer of a nitro functional group to a L-tryptophan having at least one substitution on its indole ring, in the presence of NAD(P)H.

In some aspects, the disclosure relates to a composition comprising the compound of Formulae I-IX, or a pharmaceutically acceptable salt, prodrug, hydrate, or solvate thereof. In some embodiments, the composition further comprises a pharmaceutically acceptable carrier. In some aspects, the disclosure provides a polypeptide comprising the compound of Formulae I-IX. In some aspects, the disclosure relates to a cell comprising a compound of Formulae I-IX.

In some aspects, the disclosure relates to methods of producing a compound of Formulae I-IX, or a pharmaceutically acceptable salt, prodrug, hydrate, or solvate thereof. In some aspects, the method comprises contacting a compound of Formulae Ia-IXa with (i) at least one reductase enzyme; and, (ii) a cytochrome P450 enzyme which catalyzes transfer of a nitro functional group to a compound of Formulae Ia-IXa, in the presence of NAD(P)H.

In another aspect, the disclosure related to a method of producing a compound of Formula I, or a pharmaceutically acceptable salt, prodrug, hydrate, or solvate thereof, the method comprising contacting a compound of Formula Ia:

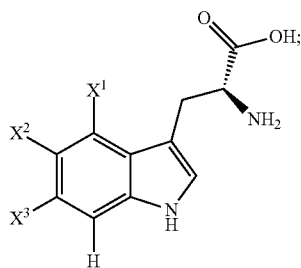

Formula Ia with:
(i) at least one reductase enzyme; and
(ii) a cytochrome P450 enzyme which catalyzes transfer of a nitro functional group to a compound of Formula Ia, in the presence of NAD(P)H;
to produce a compound of Formula I:

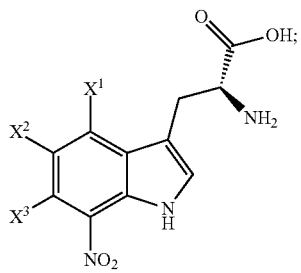

Formula I wherein:
each $X^1$ is independently halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{A1a}$, $—N(R^{A1a})_2$, or $—SR^{A1a}$;
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{A1a}$, $—N(R^{A1a})_2$, or $—SR^{A1a}$;
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring.

In another aspect, the disclosure related to a method of producing a compound of Formula IV, or a pharmaceutically acceptable salt, prodrug, hydrate, or solvate thereof, the method comprising contacting a compound of Formula IVa:

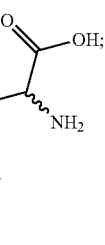

Formula IVa with:
(i) at least one reductase enzyme; and
(ii) a cytochrome P450 enzyme which catalyzes transfer of a nitro functional group to a compound of Formula Ia, in the presence of NAD(P)H;
to produce a compound of Formula IV:

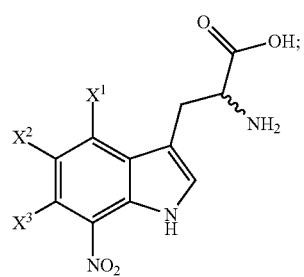

Formula IV wherein:

each $X^1$ is independently halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$;

wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$;

wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring.

In another aspect, the disclosure related to a method of producing a compound of Formula V, or a pharmaceutically acceptable salt, prodrug, hydrate, or solvate thereof, the method comprising contacting a compound of Formula Va:

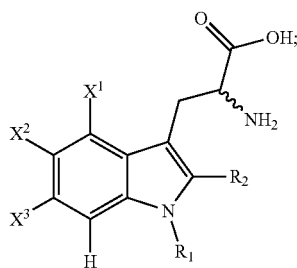

Formula Va with:
(i) at least one reductase enzyme; and
(ii) a cytochrome P450 enzyme which catalyzes transfer of a nitro functional group to a compound of Formula Ia, in the presence of NAD(P)H;

to produce a compound of Formula V:

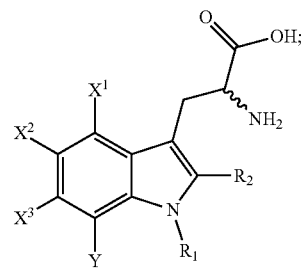

Formula V wherein:

each $X^1$ is independently halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$;

wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$;

wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

Y is $NO_2$;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In another aspect, the disclosure related to a method of producing a compound of Formula II, or a pharmaceutically acceptable salt, prodrug, hydrate, or solvate thereof, the method comprising contacting a compound of Formula IIa:

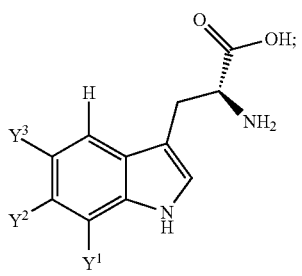

Formula IIa with:
(i) at least one reductase enzyme; and
(ii) a cytochrome P450 enzyme which catalyzes transfer of a nitro functional group to a compound of Formula IIa, in the presence of NAD(P)H;
to produce a compound of Formula II:

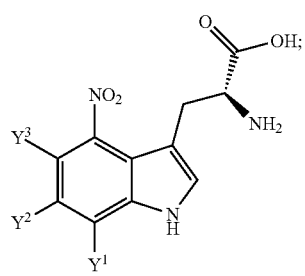

Formula II wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

provided that at least one of $Y^1$, $Y^2$, and $Y^3$ is not hydrogen.

In another aspect, the disclosure related to a method of producing a compound of Formula VI, or a pharmaceutically acceptable salt, prodrug, hydrate, or solvate thereof, the method comprising contacting a compound of Formula VIa:

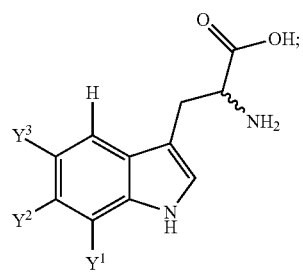

Formula VIa with:
(i) at least one reductase enzyme; and
(ii) a cytochrome P450 enzyme which catalyzes transfer of a nitro functional group to a compound of Formula IIa, in the presence of NAD(P)H;
to produce a compound of Formula VI:

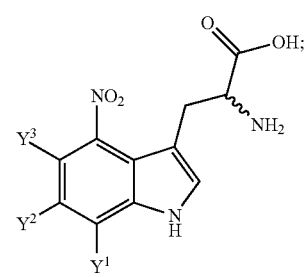

Formula VI wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

provided that at least one of $Y^1$, $Y^2$, and $Y^3$ is not hydrogen.

In another aspect, the disclosure related to a method of producing a compound of Formula VII, or a pharmaceutically acceptable salt, prodrug, hydrate, or solvate thereof, the method comprising contacting a compound of Formula VIIa:

Formula VIIa

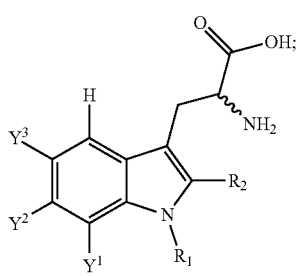

with:
(i) at least one reductase enzyme; and
(ii) a cytochrome P450 enzyme which catalyzes transfer of a nitro functional group to a compound of Formula IIa, in the presence of NAD(P)H;
to produce a compound of Formula VII:

Formula VII

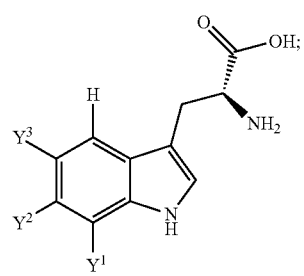

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{A1a}$, $—N(R^{A1a})_2$, or $—SR^{A1a}$; and
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;
$R_1$ is H or optionally substituted alkyl;
$R_2$ is H, optionally substituted alkyl, optionally substituted alkenyl, optionally substituted alkynyl, optionally substituted aryl, or optionally substituted heteroaryl;
provided that at least one of $Y^1$, $Y^2$, and $Y^3$ is not hydrogen. In another aspect, $R_1$ is H or alkyl. In another aspect, $R_1$ is H or alkyl. In another aspect, $R_1$ is H. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In another aspect, the disclosure related to a method of producing a compound of Formula III, or a pharmaceutically acceptable salt, prodrug, hydrate, or solvate thereof. the method comprising contacting a compound of Formula IIIa:

Formula IIIa

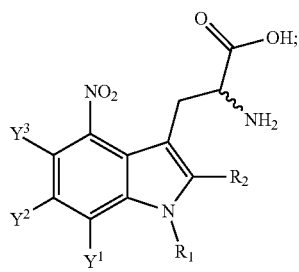

with:
(i) at least one reductase enzyme; and
(ii) a cytochrome P450 enzyme which catalyzes transfer of a nitro functional group to a compound of Formula IIIa, in the presence of NAD(P)H;
to produce a compound of Formula III:

Formula III

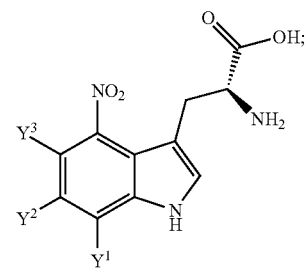

wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{A1a}$, $—N(R^{A1a})_2$, or $—SR^{A1a}$; and
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring.
In another aspect, the disclosure related to a method of producing a compound of Formula VIII, or a pharmaceutically acceptable salt, prodrug, hydrate, or solvate thereof, the method comprising contacting a compound of Formula VIIIa:

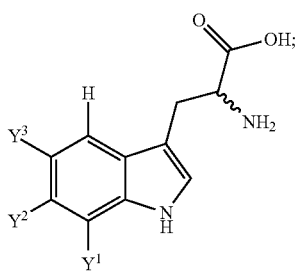

Formula VIIIa with:

(iii) at least one reductase enzyme; and
(iv) a cytochrome P450 enzyme which catalyzes transfer of a nitro functional group to a compound of Formula IIa, in the presence of NAD(P)H;

to produce a compound of Formula VIII:

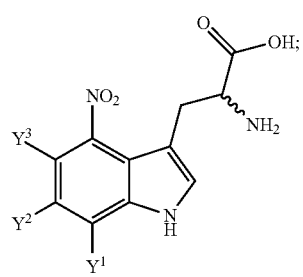

Formula VIII wherein:

each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{A1a}$, —N(R$^{A1a}$)$_2$, or —SR$^{A1a}$; and wherein each R$^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{A1a}$ are joined to form a substituted or unsubstituted, heterocyclic ring, or substituted or unsubstituted, heteroaryl ring.

In another aspect, the disclosure related to a method of producing a compound of Formula IX, or a pharmaceutically acceptable salt, prodrug, hydrate, or solvate thereof, the method comprising contacting a compound of Formula IXa:

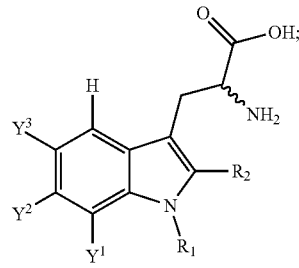

Formula IXa with:

(iii) at least one reductase enzyme; and
(iv) a cytochrome P450 enzyme which catalyzes transfer of a nitro functional group to a compound of Formula IIa, in the presence of NAD(P)H;

to produce a compound of Formula IX:

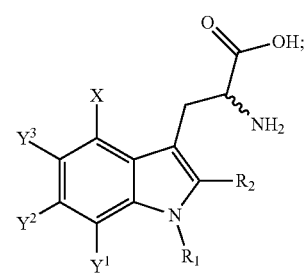

Formula IX wherein:

each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —OR$^{A1a}$, —N(R$^{A1a}$)$_2$, or —SR$^{A1a}$; and wherein each R$^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{A1a}$ are joined to form a substituted or unsubstituted, heterocyclic ring, or substituted or unsubstituted, heteroaryl ring;

X is NO$_2$;

R$_1$ is H or optionally substituted alkyl;

R$_2$ is H, optionally substituted alkyl, optionally substituted alkenyl, optionally substituted alkynyl, optionally substituted aryl, or optionally substituted heteroaryl. In another aspect, R$_1$ is H or alkyl. In another aspect, R$_1$ is H. In another aspect, R$_1$ is alkyl. In another aspect, R$_1$ is H methyl. In another aspect, R$_2$ is H. In another aspect, R$_1$ and R$_2$ are each H. In another aspect, R$_1$ is alkyl and R$_2$ is H. In another aspect, R$_1$ is methyl and R$_2$ is H.

In some embodiments, the reductase enzyme and the cytochrome P450 enzyme are linked by an amino acid linker to form a fusion protein prior to contacting the indole-substituted L-tryptophan molecule. In some embodiments, the amino acid linker links reductase enzyme to a terminus of cytochrome P450. In some embodiments, the terminus is a C-terminus.

In some embodiments, the P450 enzyme occurs naturally in *Streptomyces*. In some embodiments, the cytochrome P450 enzyme is a TxtE enzyme, wherein a TxtE enzyme is defined as:
(i) TxtE;
(ii) a portion of TxtE which catalyzes transfer of a nitro functional group to a L-tryptophan having at least one substitution on its indole ring; or, (iii) an enzyme that catalyzes transfer of a nitro functional group to a L-tryptophan having at least one substitution on its indole ring and is at least 95% homologous to the amino acid sequence of TxtE.

In some embodiments, the at least one reductase enzyme is ferredoxin reductase. In some embodiments, the ferredoxin reductase is spinach ferredoxin reductase. In some embodiments, the method further comprises contacting the substituted L-tryptophan molecule with a ferredoxin protein in the presence of NAD(P)H. In some embodiments, the ferredoxin protein is spinach ferredoxin protein.

In some embodiments, the P450 enzyme occurs naturally in *Streptomyces*. In some embodiments, the cytochrome P450 enzyme is a TxtE enzyme, wherein a TxtE enzyme is defined as:

(i) TxtE;

(ii) a portion of TxtE which catalyzes transfer of a nitro functional group to a compound of Formulae Ia-IXa; or, (iii) an enzyme that catalyzes transfer of a nitro functional group to a compound of Formulae Ia-IXa and is at least 95% homologous to the amino acid sequence of TxtE.

In some embodiments, the at least one reductase enzyme is ferredoxin reductase. In some embodiments, the ferredoxin reductase is spinach ferredoxin reductase. In some embodiments, the method further comprises contacting the compound of Formulae I, Ia, II, IIa, III, IIIa, IV, IVa, V, Va, VI, VIa, VII, VIIa, VIII, VIIIa, IX, or IXa with a ferredoxin protein in the presence of NAD(P)H. In some embodiments, the ferredoxin protein is spinach ferredoxin protein.

In some embodiments, the reductase is a prokaryotic reductase enzyme. In some embodiments, the prokaryotic reductase enzyme occurs naturally in a self-sufficient cytochrome P450. In some embodiments, the prokaryotic reductase enzyme occurs naturally in a class II or class III cytochrome P450. In some embodiments, the prokaryotic reductase is a CYP102A1 (P450BM3) reductase or a P450RhF reductase.

In some embodiments, the amino acid linker ranges from about 6 amino acids to about 16 amino acids in length. In some embodiments, the amino acid linker is a flexible amino acid linker, a rigid amino acid linker, and/or a cleavable amino acid linker.

BRIEF DESCRIPTION OF DRAWINGS

FIG. 1 shows TxtE catalyzes an aromatic nitration reaction on the C4 of L-tryptophan indole ring. $O_2$ and NO act as co-substrates. Nicotinamide adenine dinucleotide phosphate (NADPH) is consumed and recycled with glucose dehydrogenase (GDH) in the reaction. Wild-type TxtE requires spinach ferredoxin (Fer) and ferredoxin reductase (Frd) in this reaction while created artificial TxtE variants (TxtE fusions) are self-sufficient.

FIGS. 2A-2C show characterization of recombinant TxtE variants. FIG. 2A depicts SDS-PAGE analysis of TxtE and its self-sufficient variants. Recombinant proteins were purified with a single Ni-NTA affinity column, and showed expected molecular weights (MW). Lane M: protein marker; lane 1, TxtE [calculated MW (cal. MW): 46.3 kDa]; lane 2, TxtE-BM3R (cal. MW: 112.1 kDa); lane 3: TxtE-RhFRed (cal. MW: 81.8 kDa); lane 4: TxtE-RhFRed* (cal. MW: 82.7 kDa). FIG. 2B shows spectroscopic analysis of TxtE, TxtEBM3R, TxtE-RhFRed, and TxtE-RhFRed*. FIG. 2C shows relative catalytic activities of recombinant TxtE self-sufficient variants in nitrating L-tryptophan. TxtE was used as the control and its activity was set as 100%. TxtE-BM3R activity was slightly higher than the control, while both TxtE-RhFRed and TxtE-RhFRed* only retained less than 15% of TxtE activity.

FIGS. 3A-3B show thermostability and pH dependence of TxtE and TxtE-BM3R. FIG. 3A shows the thermostability of TxtE and TxtE-BM3R. Both enzymes showed the similar $T_{50}$ at around 45° C. FIG. 3B shows pH dependence of TxtE and TxtE-BM3R. Both enzymes exhibited the highest activity at a range of between pH 8.0 and 9.0.

FIGS. 4A-4C depict MS2 spectra. FIG. 4A shows MS2 spectrum of 4-nitro-L-tryptophan. FIG. 4B shows MS2 spectrum of nitrated 5-F-L-tryptophan. FIG. 4C shows MS2 spectrum and nitrated 4-F-DL-tryptophan. The fragmentation pattern in (FIG. 4A) and (FIG. 4B) was the same but it was different between (FIG. 4B) and (FIG. 4C). Compared with those in (FIG. 4A), the C5-F substitution increased the m/z values of most ions in (FIG. 4B) by 18 Da. Putative chemical structures of ions in grey labeled peaks were shown in FIG. 7.

FIG. 5 shows the effect of pH stability on activity of TxtE and TxtE-BM3R. Both enzymes were incubated in the buffers with pH from 4.5 to 9.5 for 15 min and then used in the reactions with 0.5 mM L-tryptophan, 1 mM $NADP^+$, 1 mM glucose, ~10 units/mL self-prepared glucose dehydrogenase crude extract, 1 mM NOC-5 in 100 μL of Tris-HCl buffer (100 mM, pH 8.0). For TxtE reactions, 0.43 μM spinach ferredoxin and 0.33 μM spinach ferredoxin-$NADP^+$ reductase were included. The reactions were incubated at 20° C., 300 rpm on a thermostat (Eppendorf) for 30 minutes. All experiments were performed in duplicate.

FIG. 6 shows substrate binding to TxtE and TxtE-BM3R. Fusion of BM3R to TxtE slightly tightened the binding of 4-F-DL-tryptophan and 5-F-L-tryptophan to the enzyme. All experiments were performed at least in duplicate.

FIG. 7 shows putative fragmentation pathways of 4-nitro-L-tryptophan, 4-nitro-5-F-L-tryptophan, and 7-nitro-4-F-L-tryptophan. Exact masses of all putative ions were shown.

FIGS. 8A-8B show high resolution mass spectrometry (HRMS) spectra of nitrated products in TxtE-BM3R reactions.

FIGS. 9A-9B show $^1H$ nuclear magnetic resonance (NMR) spectra of nitrated F-tryptophan products.

FIGS. 10A-10B show $^{13}C$ NMR spectra of nitrated F-tryptophan products.

FIGS. 11A-11B show Heteronuclear Single Quantum Coherence (HSQC) NMR spectra of nitrated F-tryptophan products.

FIGS. 12A-12B show HMBC NMR spectra of nitrated F-tryptophan products.

FIGS. 13A-13C show TxtE nitrates the indole $C_4$ of l-tryptophan (FIG. 13A) and 5-F-l-tryptophan (FIG. 13B) and the C7 of 4-F-l-tryptophan indole ring (FIG. 13C). $O_2$ and NO act as co-substrates. NADPH is consumed in the reaction and can be recycled with glucose dehydrogenase (GDH). Wild-type TxtE requires spinach Fer and Frd in this reaction while created artificial TxtE variants are self-sufficient.

FIGS. 14A-14C show characterization of recombinant TxtE variants. FIG. 14A shows SDS-PAGE analysis of TxtE and its self-sufficient variants. Recombinant proteins were purified with a single Ni-NTA affinity column. Lane M: protein marker; lane 1, TxtE [calculated molecular weight (cal. MW): 46.3 kD]; lane 2, TxtE-BM3R (cal. MW: 112.1 kD); lane 3: TxtE-RhFRed (cal. MW: 81.8 kD); lane 4: TxtE-RhFRed* (cal. MW: 82.7 kD). FIG. 14B shows spectroscopic analysis of TxtE, TxtEBM3R, TxtE-RhFRed, and TxtE-RhFRed*. Black lines: P450 absorbance spectra; green dashed lines: CO-oxidized spectra; blue dotted-dashed line: CO-reduced spectra; red dotted lines: CO-reduced difference spectra. FIG. 14C shows catalytic activities of recombinant TxtE self-sufficient variants in nitrating l-tryptophan. TxtE was used as the control.

FIG. 15 shows HPLC analysis of enzyme nitration reaction mixtures with l-Trp as the substrate. The reactions were performed for 2 hours. L-Trp was eluted at 1.51 min while the product has a retention time of 1.93 min.

FIGS. 16A-16B show substrate binding assays. FIG. 16A shows the changes of spin state of heme iron in TxtE, TxtE-BM3R, TxtE-RhFRed and TxtE-RhFRed* induced by different concentrations of substrates. Black: spectra in the absence of substrate; red: spectra induced by 100 µM substrates; orange: spectra induced by 200 µM substrate; and blue: spectra induced by 500 µM substrate. All four enzymes responded to the substrate binding in a highly similar manner. l-Tryptophan induced the highest percentage of heme iron's in the high-spin state, while 4-F-dl-tryptophan had the lowest. FIG. 16B shows spectra changes induced by substrate binding to TxtE, TxtE-BM3R, TxtE-RhFRed and TxtE-RhFRed*.

FIGS. 17A-17B show data related to thermostability (FIG. 17A) and pH dependence (FIG. 17B) of TxtE and TxtE-BM3R. To test enzyme thermostability, enzymes were incubated at a series of temperatures (4 to 65° C.) for 15 min. After cooling on ice, enzyme solutions were centrifuged and used in the l-tryptophan nitration reaction at 20° C., 300 rpm for 30 min. To test pH dependence, l-tryptophan nitration reactions were performed in 100 mM Tris-Cl or sodium phosphate buffers with various pH values (4.5 to 9.5) at 20° C., 300 rpm for 30 min. Products were quantitated by HPLC. All experiments were performed at least three times.

FIG. 18 shows the pH stability of TxtE and TxtE-BM3R. Both enzymes were incubated in the buffers with pH from 4.5 to 9.5 for 15 min and then used in the reactions with 0.5 mM l-tryptophan, 1 mM NADP$^+$, 1 mM glucose, ~10 units/mL self-prepared glucose dehydrogenase crude extract, 1 mM NOC-5 in 100 µL of Tris-HCl buffer (100 mM, pH 8.0). For TxtE reactions, 0.43 µM spinach ferredoxin and 0.33 µM spinach ferredoxin-NADP$^+$ reductase were included. The reactions were incubated at 20° C., 300 rpm on a thermostat (Eppendorf) for 30 minutes. All experiments were performed in duplicate.

FIG. 19 shows substrate binding to TxtE and TxtE-BM3R. Fusion of BM3R to TxtE slightly tightened the binding of 4-F-dl-tryptophan and 5-F-l-tryptophan to the enzyme. All experiments were performed at least in duplicate.

FIGS. 20A-20C show LC-MS analysis of Marfey's derivatized l-Trp and 4-nitro-l-Trp (FIG. 20A), 5F-l-Trp and 4-nitro-5-F-l-Trp (FIG. 20B), and 4F-dl-Trp and nitrated product (FIG. 20C). Blue: ion extract spectra of Marfey's derivatized tryptophan analogs; Red: ion extract spectra of Marfey's derivatized nitration product directly from enzyme reaction mixtures; Green: ion extract spectra of Marfey's derivatized, purified nitration products.

FIGS. 21A-21C show the MS2 spectra of 4-nitro-l-tryptophan (FIG. 21A), nitrated 5-F-l-tryptophan (FIG. 21B), and nitrated 4-F-dl-tryptophan (FIG. 21C). The reaction mixtures were quenched with twice volumes of methanol. After centrifugation, 10 µl of each sample was used for the LC/MS/MS analysis. Putative chemical structures of ions in red labeled peaks were shown in FIG. 23.

DETAILED DESCRIPTION OF INVENTION

Figure 1:
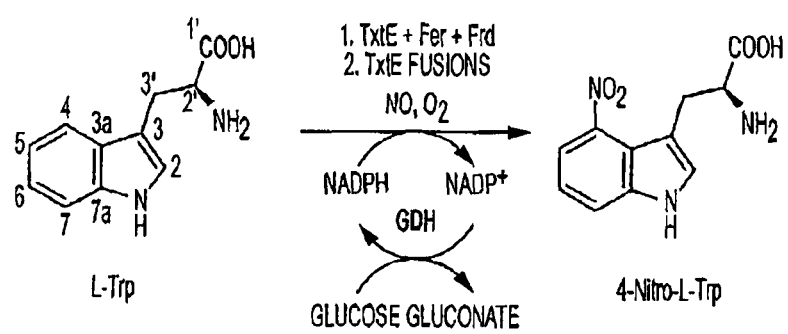

Aromatic nitration is an essential chemical reaction for the production of a variety of important industrial chemicals. For example, nitro compounds are used in the production of food additives, herbicides and pharmaceuticals. However, currently used technologies to perform aromatic nitration on an industrial scale are hampered by challenges ranging from lack of reaction efficiency to the production of environmentally unfriendly by-products. Therefore, new approaches for direct aromatic nitration must be developed.

Without wishing to be bound by any particular theory, aromatic nitration using biocatalysts offers a number of distinct advantages, such as high efficiency, high degree of selectivity, mild reaction conditions, and environmental friendliness, over currently used chemical catalysis. Accordingly, provided herein are methods and compositions for nitration of aromatic compounds. In some aspects, the present invention relates to the use of a biocatalyst for aromatic nitration. In some embodiments, the biocatalyst is a cytochrome P450 enzyme. As discussed above, it is believed that the active nitration species in the nitration processes delineated herein is the nitronium ion, $NO_2^+$. Thus, it is believed that the nitration processes presented herein proceed via an electrophilic aromatic substitution mechanism. Therefore, as is well established in the art for processes involving electrophilic aromatic substitution, substituents on the aromatic system (e.g., $X^1$, $X^2$, $X^3$ in Formulae I, Ia, IV, IVa, V, or Va; and $Y^1$, $Y^2$, $Y^3$ in Formulae II, IIa, III, IIIa, VI, VIa, VII, VIIa, VIII, VIIIa, IX, or IXa) that increase the electron density of the aromatic system are well-known in the art as "activating groups", and increase the rate of electrophilic aromatic substitution (e.g., nitration) relative to the unsubstituted aromatic system, while substituents that decrease the electron density of the aromatic system are well-known in the art as "deactivating groups", and decrease the rate of electrophilic aromatic substitution relative to the unsubstituted aromatic system. The "activating groups" are further classified as "weakly activating groups" (i.e., groups that weakly increase reaction rate), "moderately activating groups" (i.e., groups that moderately increase reaction rate), and "strongly activating groups" (i.e., groups that strongly increase reaction rate), while "deactivating groups" are further classified as "weakly deactivating groups" (i.e., groups that weakly decrease reaction rate), "moderately deactivating groups" (i.e., groups that moderately decrease reaction rate), and "strongly deactivating groups" (i.e., groups that strongly decrease reaction rate).

Non-limiting examples of "weakly activating groups" are alkyl groups (e.g., methyl, ethyl, and the like), aryl groups (e.g., phenyl, naphthyl, and the like), and unsaturated hydrocarbon moieties (e.g., alkenyl, alkynyl, and the like). Non-limiting examples of "moderately activating groups" are N-attached amides (—NHCOR) and O-attached esters (—OCOR). Non-limiting examples of "strongly activating groups" are —$NH_2$, —NHR, —$NR_2$, —OR (e.g., —OMe, —OEt, and the like), and —OH. Non-limiting examples of "weakly deactivating groups" are halogen groups (e.g., —F, —Cl, —Br, and the like). Non-limiting examples of "moderately deactivating groups" are formyl (e.g., —CHO), ketones (—COR), carboxylic acid (—COOH), C-attached carboxylic esters (—COOR), carboxylic acid halides (e.g., —COCl, and the like), and C-attached amides (—$CONH_2$, —CONHR, —$CONHR_2$, and the like). Non-limiting examples of "strongly deactivating groups" are trihaloalkyl moieties (e.g., —$CF_3$, and the like), —CN, S-attached sulfonates (e.g., —$SO_3R$, and the like), quaternary ammonium salts (e.g., —$NH_3^+$, —$NR_3^+$, and the like), and —$NO_2$.

In certain aspects, the invention is based upon the surprising discovery that fusion proteins comprising a cytochrome P450 enzyme and a reductase enzyme can transfer a $NO_2$ functional group to the indole ring of L-tryptophan with high regio-selectivity. Therefore, in some aspects, the disclosure provides a fusion protein comprising (i) a cytochrome P450 enzyme which catalyzes transfer of a nitro functional group to a L-tryptophan having at least one substitution on its indole ring; (ii) an amino acid linker; and, (iii) a catalytic domain of a reductase enzyme. In some aspects, the fusion protein comprises an amino acid linker that joins the reductase enzyme to a terminus of the cytochrome P450 enzyme. In some embodiments, the reductase is joined to the C-terminus of the cytochrome P450 enzyme.

In certain aspects, the invention is based upon the surprising discovery that fusion proteins comprising a cytochrome P450 enzyme and a reductase enzyme can transfer a $NO_2$ functional group to the indole ring of L-tryptophan with high regio-selectivity. Therefore, in some aspects, the disclosure provides a fusion protein comprising (i) a cytochrome P450 enzyme which catalyzes transfer of a nitro functional group to a compound of Formulae Ia-IXa; (ii) an amino acid linker; and, (iii) a catalytic domain of a reductase enzyme. In some aspects, the fusion protein comprises an amino acid linker that joins the reductase enzyme to a terminus of the cytochrome P450 enzyme. In some embodiments, the reductase is joined to the C-terminus of the cytochrome P450 enzyme.

Cytochrome P450 enzymes (CYPs) form a super-family of heme-thiolate containing enzymes. CYP enzymes regio/stereo-selectively catalyze a variety of chemical reactions and generally require the consumption of a reducing agent, for example NADPH. Effectivly transferring electrons from the reducing agent to the heme center requires a proper interaction between the CYP and suitable auxiliary redox proteins. Based on the types of redox proteins required for activity, CYPs typically are organized into three classes (class I, class II and class III). The catalytic activity of class I CYPs depends on both a redoxin protein, such as ferredoxins (Fer), and a reductase enzyme, such as flavin adenine dinucleotide (FAD)-containing reductase (Frd) enzymes. Non-limiting examples of class I CYPs include but are not limited to CYP1A1, CYP2A6, CYP3A5, CYP11A1, CYP101, CYP105 and CYP107A1 and TxtE. TxtE is a cytochrome P450 enzyme naturally found in *Streptomyces scabies* that transfers a nitro group ($NO_2$) to thaxtomin phytotoxins. The natural substrate of TxtE is L-tryptophan. As a class I CYP, catalytic activity of TxtE normally requires the interaction with a small redox 2Fe-2S iron-sulfur ferodoxin and FAD reductase.

Class II and class III CYPs are self-sufficient enzymes, in which the heme domains are fused with reductase domains as single polypeptides (De Mot and Parret 2002). As used herein, the term "self-sufficient enzyme" refers to a cytochrome P450 enzyme linked to a reductase catalytic domain, which does not require the activity of any auxiliary redox protein (e.g. a ferredoxin or reductase enzyme) other than the reductase domain linked to said cytochrome P450 enzyme in order to perform its intended function. Examples of naturally occurring self-sufficient cytochrome P450 enzymes include but are not limited to CYP505A1, CYP102A1 (P450BM3), P450 PFOR, and P450RhF.

The skilled artisan recognizes that additional examples of class I, II and III CYPs may be identified using methods generally known in the art, for example mining a database of CYP sequences, such as disclosed by Nelson, DR (2009) *The Cytochrome P450 Homepage*. Human Genomics 4, 59-65.

In some aspects, the invention relates to artificial, or non-naturally occurring self-sufficient cytochrome P450 enzymes. As used herein, the term "artificial cytochrome P450 enzyme" refers to a non-naturally occurring fusion protein comprising a non-self-sufficient cytochrome P450 enzyme and a catalytic domain of a reductase enzyme. Without wishing to be bound by any particular theory, the fusion of a reductase domain to a naturally non-self-sufficient cytochrome P450 enzyme confers self-sufficient function to the P450 enzyme yet maintains the functional characteristics of the P450 enzyme. For example, a class I cytochrome P450 enzyme fused to a reductase domain does not require the activity of auxiliary redox proteins in order to transfer a nitro group to a substrate. Therefore, in some embodiments, the self-sufficient cytochrome P450 enzyme is a class I cytochrome P450 enzyme.

In some aspects, the disclosure relates to the transfer of a nitro group ($NO_2$) to an aromatic molecule comprising an indole ring. In some embodiments, the aromatic molecule is L-tryptophan. In some embodiments, the aromatic molecule is substituted. In some embodiments, the aromatic molecule is substituted on its indole ring. In some embodiments, the substituted aromatic molecule is substituted L-tryptophan. Various substitutions on the indole ring of L-tryptophan are contemplated herein. For example, the indole ring of L-tryptophan may comprise one or more substitutions at carbon 4, 5, 6, and/or 7. In embodiments, one of carbon 4 and carbon 7 is not substituted when used as a starting material. The substitution may be halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, provided that the substitution does not comprise a "moderately deactivating group", a "strongly deactivating group", or a group that does not sterically hinder interaction between the P450 enzyme and the reductase enzyme catalytic domain. Steric hindrance may occur if the substitution on the indole ring comprises a large molecule that impedes access of the substrate to the active site of P450 enzyme or prevents interaction of reductase with P450 enzyme.

In some aspects, the disclosure relates to the transfer of a nitro group ($NO_2$) to an aromatic molecule comprising an indole ring. In some embodiments, the aromatic molecule is L-tryptophan. In some embodiments, the aromatic molecule is substituted. In some embodiments, the aromatic molecule is substituted on its indole ring. In some embodiments, the aromatic molecule is substituted on the benzoid portion of an indole moiety (i.e., at the 4-, 5-, 6-, or 7-position). In some embodiments, the substituted aromatic molecule is a compound of Formulae Ia-IXa. The substitution may be halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, provided that the substitution does not comprise a "moderately deactivating group", a "strongly deactivating group", or does not sterically hinder interaction between the P450 enzyme and the reductase enzyme catalytic domain. As used herein, the terms "moderately deactivating group" and "strongly deactivating group" refer to a functional moiety that moderately or strongly reduces the rate of electrophilic aromatic substitution (e.g., nitration), respectively, relative to the corresponding unsubstituted aromatic moiety, as is well-known in the art. Non-limiting examples of "moderately deactivating groups" are formyl (e.g., —CHO), ketones, carboxylic acid (—COOH), C-attached carboxylic esters, carboxylic acid halides (e.g., —COCl, and the like), and C-attached amides. Non-limiting examples of "strongly deactivating groups" are trihaloalkyl moieties (e.g., —$CF_3$, and the like), —CN, S-attached sulfonates, quaternary ammonium salts, and —$NO_2$. Steric hindrance may occur if the substitution on the indole ring comprises a large molecule that impedes access of the substrate to the active site of P450 enzyme or prevents interaction of reductase with P450 enzyme.

In certain aspects, each of $X^1$, $X^2$, $X^3$, $Y^1$, $Y^2$, and $Y^3$ is independently —H, a "weakly deactivating group", a "weakly activating group", a "moderately activating group", or a "strongly activating group". Non-limiting examples of "weakly activating groups" are alkyl groups (e.g., methyl, ethyl, and the like), aryl groups (e.g., phenyl, naphthyl, and the like), and unsaturated hydrocarbon moieties (e.g., alkenyl, alkynyl, and the like). Non-limiting examples of "moderately activating groups" are N-attached amides and O-attached esters. Non-limiting examples of "strongly activating groups" are —$NH_2$, secondary amines, tertiary amines, alkoxy (e.g., —OMe, —OEt, and the like), and —OH. Non-limiting examples of "weakly deactivating groups" are halogen groups (e.g., —F, —Cl, —Br, and the like).

Some aspects of the invention relate to the inventors' recognition and appreciation that cytochrome P450 TxtE transfers a nitro group to substituted L-tryptophan. Accordingly, in some embodiments, the cytochrome P450 enzyme of the fusion protein is a TxtE enzyme. As used herein, the term "TxtE enzyme" refers to a (i) polypeptide comprising the entire amino acid sequence of TxtE, (ii) a portion of TxtE which maintains the function of catalyzing transfer of a nitro functional group to a L-tryptophan having at least one substitution on its indole ring, or (iii) an enzyme which catalyzes transfer of a nitro functional group to a L-tryptophan having at least one substitution on its indole ring and is at least 95% homologous to the amino acid sequence of TxtE. The skilled artisan recognizes that for a portion of TxtE to maintain the nitration function, the portion must include active site residues of TxtE, for example Arg59, Asn293, Thr296 and Glu394. However, genetic modification of residues at a location of the TxtE polypetide remote from the active site may maintain the activity of the enzyme. As used herein, the term "genetic modification" refers to amino acid substitution (conservative, missense and/or non-sense), deletion and/or insertion. Thus in some embodiments, a portion of TxtE comprises at least 1, at least 2, at least 3, at least 4, at least 5, at least 10, at least 20, at least 30, at least 40, at least 50, at least 75, or at least 100 genetic modifications relative to wild-type TxtE. In some embodiments a portion of TxtE is truncated relative to wild-type TxtE. Truncations may occur at the N-terminus or C-terminus of the portion of TxtE. For example, a portion of TxtE may be truncated by 1, 2, 3, 4, 5, 10, 20, 30, 40, 50, 75, 100 or 200 amino acids at it N-terminus or C-terminus relative to wild-type TxtE. Methods of genetically modifying TxtE or portions thereof and screening for retention of functional activity are known in the art and available to the skilled artisan. For example, TxtE may be modified by directed evolution or random mutagenesis and biochemcially assayed for the capability to transfer a nitro group to L-tryptophan having at least one substitution on its indole ring. In some embodiments, a TxtE enzyme may be an enzyme which catalyzes transfer of a nitro functional group to a L-tryptophan having at least one substitution on its indole ring and has less than 95% homologous to the amino acid sequence of TxtE. In some embodiments, the enzyme has about 90%, about 80%, about 70%, about 60% or about 50% homology to the amino acid sequence of TxtE.

Some aspects of the invention relate to the inventors' recognition and appreciation that cytochrome P450 TxtE transfers a nitro group to a compound of Formulae Ia-IXa. Accordingly, in some embodiments, the cytochrome P450 enzyme of the fusion protein is a TxtE enzyme. As used herein, the term "TxtE enzyme" refers to a (i) polypeptide comprising the entire amino acid sequence of TxtE, (ii) a portion of TxtE which maintains the function of catalyzing transfer of a nitro functional group to a compound of Formulae Ia-IXa, or (iii) an enzyme which catalyzes transfer of a nitro functional group to compound of Formulae Ia-IXa and is at least 95% homologous to the amino acid sequence of TxtE. The skilled artisan recognizes that for a portion of TxtE to maintain the nitration function, the portion must include active site residues of TxtE, for example Arg59, Asn293, Thr296 and Glu394. However, genetic modification of residues at a location of the TxtE polypetide remote from the active site may maintain the activity of the enzyme. As used herein, the term "genetic modification" refers to amino acid substitution (conservative, missense and/or non-sense), deletion and/or insertion. Thus in some embodiments, a portion of TxtE comprises at least 1, at least 2, at least 3, at least 4, at least 5, at least 10, at least 20, at least 30, at least 40, at least 50, at least 75, or at least 100 genetic modifications relative to wild-type TxtE. In some embodiments a portion of TxtE is truncated relative to wild-type TxtE.

Truncations may occur at the N-terminus or C-terminus of the portion of TxtE. For example, a portion of TxtE may be truncated by 1, 2, 3, 4, 5, 10, 20, 30, 40, 50, 75, 100 or 200 amino acids at it N-terminus or C-terminus relative to wild-type TxtE. Methods of genetically modifying TxtE or portions thereof and screening for retention of functional activity are known in the art and available to the skilled artisan. For example, TxtE may be modified by directed evolution or random mutagenesis and biochemcially assayed for the capability to transfer a nitro group to a compound of Formulae Ia-IXa. In some embodiments, a TxtE enzyme may be an enzyme which catalyzes transfer of a nitro functional group to a compound of Formulae Ia-IXa and has less than 95% homologous to the amino acid sequence of TxtE. In some embodiments, the enzyme has about 90%, about 80%, about 70%, about 60% or about 50% homology to the amino acid sequence of TxtE.

In some aspects, the disclosure provides fusion proteins comprising a catalytic domain of a reductase enzyme. As used herein, the term "reductase enzyme" refers to an enzyme that catalyzes a reduction reaction. Non-limiting examples of reductase enzymes include thioredoxin reductase, cytochrome P450 reductase and flavin adenine dinucleotide (FAD) reductase. In some embodiments, the reductase enzyme is a prokaryotic reductase enzyme. In some embodiments, the reductase enzyme is a bacterial reducatase enzyme. In some embodiments, the bacterial reductase enzyme naturally occurs in a self-sufficient cytochrome P450, for example CYP102A1 (P450BM3) reductase or a P450RhF reductase.

In some embodiments, the fusion protein comprises an amino acid linker. As used herein, the term "linker" refers to an amino acid sequence that joins two larger polypeptide domains to form a single fusion polypeptide. Amino acid linkers are well known to those skilled in the art and include flexible linkers (e.g. glycine rich linkers such as $[GGGS]_n$ where n>2), rigid linkers (e.g. poly-proline rich linkers) and cleavable linkers (e.g. photocleavable and enzyme-sensitive linkers). In some embodiments, the amino acid linker joins a catalytic domain of a reductase enzyme to a terminus of a cytochrome P450 enzyme. As used herein, the term "terminus" refers to the ends of a polypeptide sequence relative to the start codon of said polypeptide. For example, the N-terminus of a polypeptide is the end of the polypeptide containing the start codon (AUG) of the polypeptide, whereas the C-terminus of the polypeptide is the end of the polypeptide opposite of the start codon. In some embodiments, the amino acid linker joins the a catalytic domain of a reductase enzyme to the C-terminus of a cytochrome P450 enzyme. In some embodiments, the amino acid linker joins CYP102A1 (P450BM3) reductase or P450RhF reductase to the C-terminus of a TxtE enzyme.

The length of amino acid linkers is also contemplated by the disclosure. Amino acid linker length is known to affect the folding and orientation of fusion polypeptides. For example, a linker that is too long can prevent the interaction of a reductase domain with the cytochrome P450 enzyme to which it is linked. (It is also known that long linkers can fold and take on specific orientations that can be desirable.) Conversely, a linker that is too short can cause a reductase enzyme to sterically inhibit binding of substrate to the active site of the P450 enzyme to which it is linked. Generally, linkers may range in length from about 5 to about 30 amino acids. In some embodiments, linkers range from 6 to 20 amino acids in length. In some embodiments, linkers range from 6 to 16 amino acids or from 10 to 16 amino acids in length. In some embodiments, linkers range from 6 to 10 amino acids in length. In some embodiments, the length of the linker is 5, 6, 7, 8, 9, 10, 11, 12, 13, 14, 15, 16, 17, 18, 19, 20, 21, 22, 23, 24, 25, 26, 27, 28, 29, or 30 amino acids in length.

In some aspects, the disclosure relates to an expression construct comprising a fusion protein as described by the disclosure. As used herein, the term "expression construct" refers to an artificially constructed molecule comprising a nucleic acid (e.g. DNA) capable of artificially carrying foreign genetic material into another cell (for example, a bacterial cell). In some embodiments, vectors carry common functional elements including an origin of replication, a multicloning site, a selectable marker and optionally a promoter sequence. In some embodiments, the selectable marker is a bacterial resistance gene, for example kanamycin, chloramphenicol or β-lactamase. Non-limiting examples of vectors include plasmids, viral vectors, cosmids, and artificial chromosomes. In some embodiments, the vector is a high-copy plasmid. In some embodiments, the vector is a low-copy plasmid. In some embodiments, the vectors of the disclosure are maintained inside cells. In some embodiments, the vectors of the disclosure are maintained in a non-cellular environment, for example as part of a kit. Methods of introducing vectors into bacteria are well known in the art and described, for example, in *Current Protocols in Molecular Biology*, Ausubel et al. (Eds), John Wiley and Sons, New York, 2007.

In some aspects, the disclosure relates to isolated nucleic acids encoding the fusion proteins described herein. As used herein "nucleic acid" refers to a DNA or RNA molecule. Nucleic acids are polymeric macromolecules comprising a plurality of nucleotides. In some embodiments, the nucleotides are deoxyribonucleotides or ribonucleotides. In some embodiments, the nucleotides comprising the nucleic acid are selected from the group consisting of adenine, guanine, cytosine, thymine, uracil and inosine. In some embodiments, the nucleotides comprising the nucleic acid are modified nucleotides. Non-limiting examples of natural nucleic acids include genomic DNA and plasmid DNA. In some embodiments, the nucleic acids of the instant disclosure are synthetic. As used herein, the term "synthetic nucleic acid" refers to a nucleic acid molecule that is constructed via the joining nucleotides by a synthetic or non-natural method. One non-limiting example of a synthetic method is solid-phase oligonucleotide synthesis. In some embodiments, the nucleic acids of the instant disclosure are isolated.

In some aspects, the disclosure relates to compounds produced by aromatic nitration. Certain aspects of the disclosure relate to unnatural compounds produced by the transfer of a nitro group to L-tryptophan by a cytochrome P450 enzyme. Accordingly, in some aspects the disclosure provides a method for producing a compound of:

(Formula I)

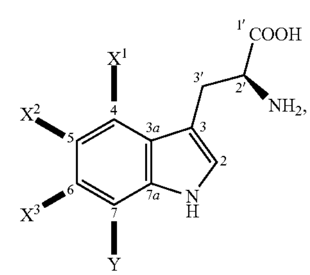

wherein in Formula I, $X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring and wherein the Ala of $-OR^{A1a}$ is not H;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring and wherein the Ala of $-OR^{A1a}$ is not H, and Y is $NO_2$.

In some aspects, the disclosure relates to compounds produced by aromatic nitration. Certain aspects of the disclosure relate to unnatural compounds produced by the transfer of a nitro group to L-tryptophan or an L-tryptophan derivative (e.g., a compound of Formulae Ia-IXa) by a cytochrome P450 enzyme. Accordingly, in some aspects the disclosure provides a method for producing a compound of Formula I, or a pharmaceutically acceptable salt, prodrug, hydrate, or solvate thereof, the method comprising contacting a compound of Formula Ia:

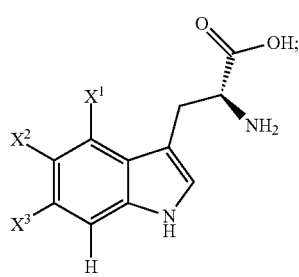

Formula Ia with:
(i) at least one reductase enzyme; and
(ii) a cytochrome P450 enzyme which catalyzes transfer of a nitro functional group to a compound of Formula Ia, in the presence of NAD(P)H;

to produce a compound of Formula I:

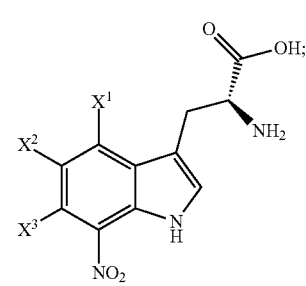

Formula I wherein:
each $X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$;

wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$;

wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring.

In another aspect, the disclosure related to a method of producing a compound of Formula IV, or a pharmaceutically acceptable salt, prodrug, hydrate, or solvate thereof, the method comprising contacting a compound of Formula IVa:

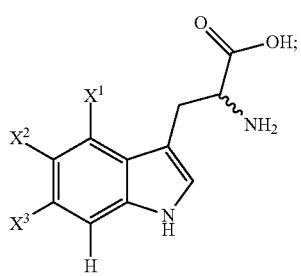

Formula IVa with:
(iii) at least one reductase enzyme; and
(iv) a cytochrome P450 enzyme which catalyzes transfer of a nitro functional group to a compound of Formula Ia, in the presence of NAD(P)H;
to produce a compound of Formula IV:

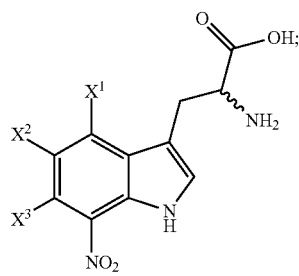

Formula IV wherein:
each $X^1$ is independently halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$;
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;
each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$;
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring.

In another aspect, the disclosure related to a method of producing a compound of Formula V, or a pharmaceutically acceptable salt, prodrug, hydrate, or solvate thereof, the method comprising contacting a compound of Formula Va:

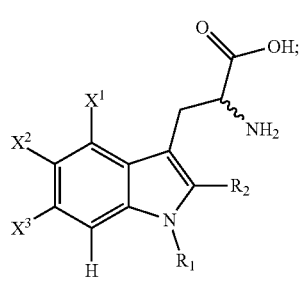

Formula Va with:
(iii) at least one reductase enzyme; and
(iv) a cytochrome P450 enzyme which catalyzes transfer of a nitro functional group to a compound of Formula Ia, in the presence of NAD(P)H;
to produce a compound of Formula V:

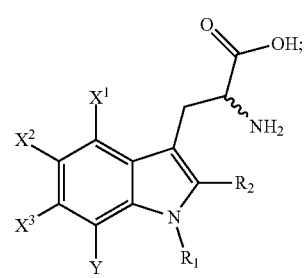

Formula V wherein:
each $X^1$ is independently halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $-OR^{A1a}$, $-N(R^{A1a})_2$, or $-SR^{A1a}$;
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{A1a}$, $—N(R^{A1a})_2$, or $—SR^{A1a}$;

wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

Y is $NO_2$;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In some embodiments, $X^2$ and $X^3$ are hydrogen.

In some aspects the disclosure provides a method for producing a compound of:

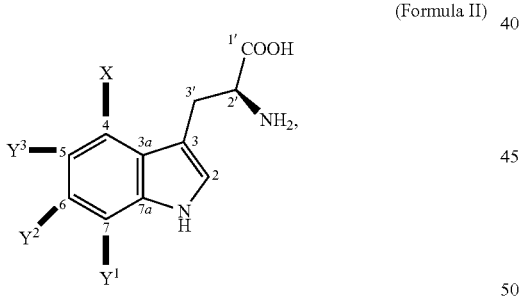

(Formula II)

wherein in Formula II each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{A1a}$, $—N(R^{A1a})_2$, or $—SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring and wherein the Ala of $—OR^{A1a}$ is not H;

and X is $NO_2$, provided that at least one of $Y^1$, $Y^2$, and $Y^3$ is not hydrogen.

In another aspect, the disclosure relates to a method of producing a compound of Formula II, or a pharmaceutically acceptable salt, prodrug, hydrate, or solvate thereof, the method comprising contacting a compound of Formula IIa:

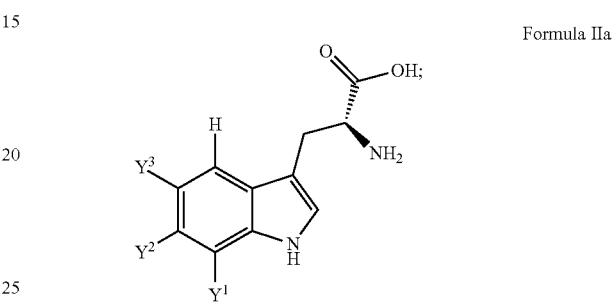

with:

(v) at least one reductase enzyme; and (vi) a cytochrome P450 enzyme which catalyzes transfer of a nitro functional group to a compound of Formula IIa, in the presence of NAD(P)H;

to produce a compound of Formula II:

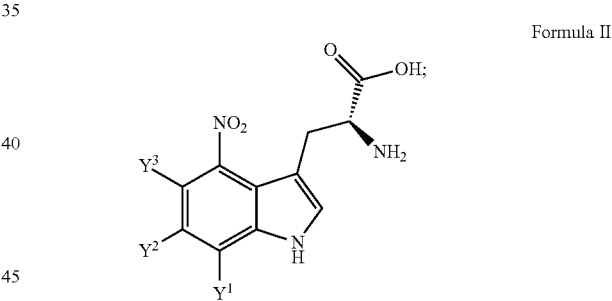

wherein:

each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, $—OR^{A1a}$, $—N(R^{A1a})_2$, or $—SR^{A1a}$; and wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;
provided that at least one of $Y^1$, $Y^2$, and $Y^3$ is not hydrogen.

In another aspect, the disclosure related to a method of producing a compound of Formula VI, or a pharmaceutically acceptable salt, prodrug, hydrate, or solvate thereof, the method comprising contacting a compound of Formula VIa:

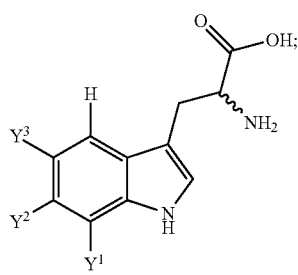

Formula VIa with:
(v) at least one reductase enzyme; and
(vi) a cytochrome P450 enzyme which catalyzes transfer of a nitro functional group to a compound of Formula IIa, in the presence of NAD(P)H;
to produce a compound of Formula VI:

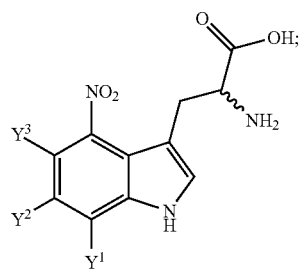

Formula VI wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;
provided that at least one of $Y^1$, $Y^2$, and $Y^3$ is not hydrogen.

In another aspect, the disclosure related to a method of producing a compound of Formula VII, or a pharmaceutically acceptable salt, prodrug, hydrate, or solvate thereof, the method comprising contacting a compound of Formula VIIa:

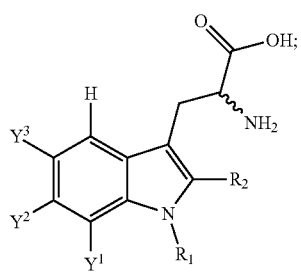

Formula VIIa with:
(vii) at least one reductase enzyme; and
(viii) a cytochrome P450 enzyme which catalyzes transfer of a nitro functional group to a compound of Formula IIa, in the presence of NAD(P)H;
to produce a compound of Formula VII:

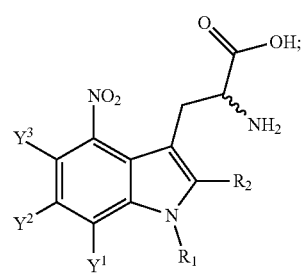

Formula VII wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;
$R_1$ is H or optionally substituted alkyl;
$R_2$ is H, optionally substituted alkyl, optionally substituted alkenyl, optionally substituted alkynyl, optionally substituted aryl, or optionally substituted heteroaryl;

provided that at least one of $Y^1$, $Y^2$, and $Y^3$ is not hydrogen. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In another aspect, the disclosure relates to a method of producing a compound of Formula III, or a pharmaceutically acceptable salt, prodrug, hydrate, or solvate thereof, the method comprising contacting a compound of Formula IIIa:

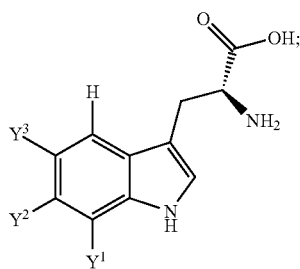

Formula IIIa with:
(iii) at least one reductase enzyme; and
(iv) a cytochrome P450 enzyme which catalyzes transfer of a nitro functional group to a compound of Formula IIIa, in the presence of NAD(P)H;
to produce a compound of Formula III:

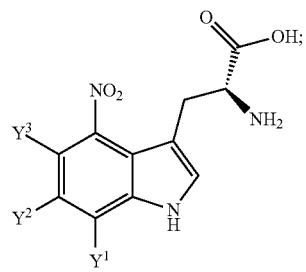

Formula III wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring.

In another aspect, the disclosure related to a method of producing a compound of Formula VIII, or a pharmaceutically acceptable salt, prodrug, hydrate, or solvate thereof, the method comprising contacting a compound of Formula VIIIa:

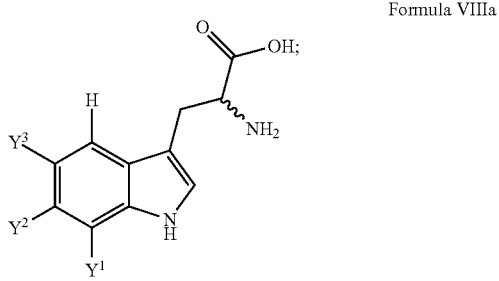

Formula VIIIa with:
(vii) at least one reductase enzyme; and
(viii) a cytochrome P450 enzyme which catalyzes transfer of a nitro functional group to a compound of Formula IIa, in the presence of NAD(P)H;
to produce a compound of Formula VIII:

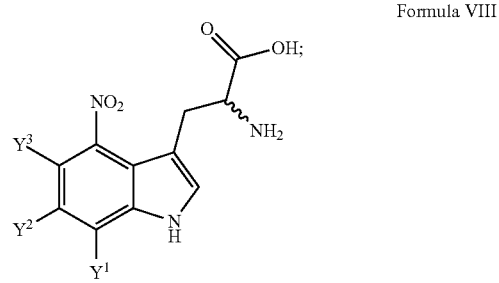

Formula VIII wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring.

In another aspect, the disclosure related to a method of producing a compound of Formula IX, or a pharmaceutically acceptable salt, prodrug, hydrate, or solvate thereof, the method comprising contacting a compound of Formula IXa:

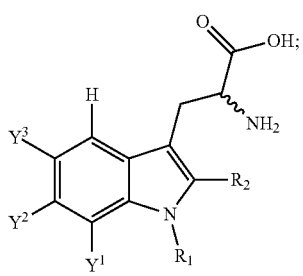

Formula IXa with:
(ix) at least one reductase enzyme; and
(x) a cytochrome P450 enzyme which catalyzes transfer of a nitro functional group to a compound of Formula IIa, in the presence of NAD(P)H;
to produce a compound of Formula IX:

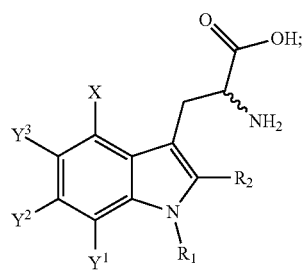

Formula IX wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$; and wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

X is $NO_2$;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms. In general, alkyl, alkenyl, and alkynyl groups contain 1-20 aliphatic carbon atoms. In embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

"Alkyl" in general refers to a radical of a straight-chain or branched saturated hydrocarbon group having from 1 to 20 carbon atoms ("C$_{1-20}$ alkyl"). In embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("C$_{1-4}$ alkyl"). In some embodiments, an alkyl group has 1 to 3 carbon atoms ("C$_{1-3}$ alkyl"). In some embodiments, an alkyl group has 1 to 2 carbon atoms ("C$_{1-2}$ alkyl"). In some embodiments, an alkyl group has 1 carbon atom ("C$_1$ alkyl"). In some embodiments, an alkyl group has 2 to 6 carbon atoms ("C$_{2-6}$ alkyl"). Examples of C$_{1-6}$ alkyl groups include methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), and n-hexyl (C$_6$). Additional examples of alkyl groups include n-heptyl (C$_7$), n-octyl (C$_8$) and the like. Unless otherwise specified, each instance of an alkyl group is independently optionally substituted, i.e., unsubstituted (an "unsubstituted alkyl") or substituted (a "substituted alkyl") with one or more substituents (e.g., halogen, such as F). In certain embodiments, the alkyl group is unsubstituted C$_{1-10}$ alkyl (e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is substituted C$_{1-10}$ alkyl (such as substituted C$_{1-6}$ alkyl, e.g., —CF$_3$, Bn).

"Alkenyl", in general, refers to a radical of a straight-chain or branched hydrocarbon group having from 2 to 20 carbon atoms, one or more carbon-carbon double bonds, and no triple bonds ("C$_{2-20}$ alkenyl"). In embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl", in general, refers to a radical of a straight-chain or branched hydrocarbon group having from 2 to 20 carbon atoms, one or more carbon-carbon triple bonds, and optionally one or more double bonds ("C$_{2-20}$ alkynyl"). In embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic", in general, refers to a radical of a non-aromatic cyclic hydrocarbon group having from 3 to 10 ring carbon atoms ("C$_{3-10}$ carbocyclyl") and zero heteroatoms in the non-aromatic ring system. In embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like.

Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl")

with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

A heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). A heteroaryl group can be a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), $BF_4^-$, $PF_4^-$, $PF_6^-$, $AsF_6^-$, $SbF_6^-$, $B[3,5-(CF_3)_2C_6H_3]_4]^-$, $BPh_4^-$, $Al(OC(CF_3)_3)_4^-$, carborane anions (e.g., $CB_{11}H_{12}^-$ or $(HCB_{11}Me_5Br_6)^-$), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=NR$^{bb}$)$R^{aa}$, —C(=NR$^{bb}$)OR$^{aa}$, —C(=NR$^{bb}$)N($R^{bb}$)$_2$, —C(=O)NR$^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2R^{aa}$, —SO$_2R^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2R^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2R^{aa}$, —SO$_2R^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group described herein is Bn, Boc, Cbz, Fmoc, trifluoroacetyl, triphenylmethyl, acetyl, or Ts.

Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cca}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group described herein is silyl, TBDPS, TBDMS, TIPS, TES, TMS, MOM, THP, t-Bu, Bn, allyl, acetyl, pivaloyl, or benzoyl.

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2$$R^{aa}$, —P(=O)($R^{aa}$)$_2$, —P(=O)($OR^{cc}$)$_2$, —P(=O)$_2$N($R^{bb}$)$_2$, and —P(=O)($NR^{bb}$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. In certain embodiments, a sulfur protecting group described herein is acetamidomethyl, t-Bu, 3-nitro-2-pyridine sulfenyl, 2-pyridine-sulfenyl, or triphenylmethyl.

In some aspects, the compound disclosure relates to a compound of Formula I, wherein $X^1$ is halogen. Examples of halogens include F, Cl, Br, and I. In certain embodiments, the halogen is fluorine. Fluorinated L-tryptophan is a non-specific cytotoxic agent that acts as an antibiotic. In some embodiments, the L-tryptophan is fluorinated at position 4 of the indole ring and nitrated at position 7 of the indole ring. In some aspects, the compound disclosure relates to a compound of Formula II, wherein $Y^1$, $Y^2$ or $Y^3$ is halogen. In certain embodiments, the halogen is fluorine. In some embodiments, the L-tryptophan is fluorinated at position 5, 6 or 7 of the indole ring and nitrated at position 4 of the indole ring.

In some aspects, the compound disclosure relates to a compound of Formula I, IV, or V, wherein at least one of $X^1$, $X^2$, or $X^3$ is a weakly deactivating group, a weakly activating group, a moderately activating group, or a strongly activating group.

In other aspects, at least one of $X^1$, $X^2$, or $X^3$ is H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —N($R^{A1a}$)$_2$, or —$SR^{A1a}$.

In another aspect, $X_1$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —N($R^{A1a}$)$_2$, or —$SR^{A1a}$; and $X^2$ and $X^3$ are each independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —N($R^{A1a}$)$_2$, or —$SR^{A1a}$. In another aspect, $X^1$ is halogen or $C_{1-6}$ alkyl (e.g. methyl, $CH_3$). In another aspect, $X^1$ is halogen. In another aspect, $X^1$ is $C_{1-6}$ alkyl (e.g. methyl, $CH_3$). In another aspect, $X^1$ is halogen or $C_{1-6}$ alkyl (e.g. methyl, $CH_3$) and at least one of $X^2$ and $X^3$ is hydrogen. In another aspect, $X^1$ is halogen and each of $X^2$ and $X^3$ is hydrogen. In another aspect, $X^1$ if fluorine and each of $X^2$ and $X^3$ is hydrogen. In another aspect, $X^1$ is $C_{1-6}$ alkyl and each of $X^2$ and $X^3$ is hydrogen. In another aspect, $X^1$ is methyl and each of $X^2$ and $X^3$ is hydrogen.

In some aspects, the compound disclosure relates to a compound of Formula II, III, VI, VII, VIII, or IX, wherein each of $Y^1$, $Y^2$ or $Y^3$ is independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —N($R^{A1a}$)$_2$, or —$SR^{A1a}$. In another aspect, at least one of $Y^1$, $Y^2$ or $Y^3$ is halogen or $C_{1-6}$ alkyl (e.g. methyl, $CH_3$). In another aspect, $Y^3$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —N($R^{A1a}$)$_2$, or —$SR^{A1a}$; and $Y^1$ and $Y^2$ are each independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —N($R^{A1a}$)$_2$, or —$SR^{A1a}$. In another aspect, $Y^3$ is halogen or $C_{1-6}$ alkyl (e.g. methyl, $CH_3$). In another aspect, $Y^3$ is halogen or $C_{1-6}$ alkyl (e.g. methyl, $CH_3$) and at least one of $Y^1$ and $Y^2$ is hydrogen. In another aspect, $Y^3$ is halogen or $C_{1-6}$ alkyl (e.g. methyl, $CH_3$) and $Y^1$ and $Y^2$ are each hydrogen. In another aspect, $Y^3$ is halogen. In another aspect, $Y^3$ is halogen and at least one of $Y^1$ and $Y^2$ is hydrogen. In another aspect, $Y^3$ is halogen and $Y^1$ and $Y^2$ are each hydrogen. In certain embodiments, $Y^3$ is fluorine and at least one of $Y^1$ and $Y^2$ is hydrogen. In another aspect, $Y^3$ is fluorine and $Y^1$ and $Y^2$ are each hydrogen. In another aspect, $Y^3$ is $C_{1-6}$ alkyl. In another aspect, $Y^3$ is $C_{1-6}$ alkyl and at least one of $Y^1$ and $Y^2$ is hydrogen. In another aspect, $Y^3$ is $C_{1-6}$ alkyl and $Y^1$ and $Y^2$ are each hydrogen. In certain embodiments, $Y^3$ is methyl and at least one of $Y^1$ and $Y^2$ is hydrogen. In another aspect, $Y^3$ is methyl and $Y^1$ and $Y^2$ are each hydrogen. The disclosure also relates to pharmaceutical compositions comprising a compound of Formula I or a compound of Formula II and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

The disclosure also relates to pharmaceutical compositions comprising a compound of Formulae I-IX, or a pharmaceutically acceptable salt, prodrug, hydrate, or solvate thereof, and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

A carrier is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in *Remington's Pharmaceutical Sciences, 4th ed.* (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

In some embodiments, a compound of Formula I or Formula II is incorporated into a polypeptide. For example, nitration of an L-typtophan having a substitution on its indole ring results in formation of a compound of Formula I or Formula II. It is known in the art that L-tryptophan and its derivatives may be incorporated into polypeptides to form artificial or unnatural proteins, for example as disclosed by *Methods in Molecular Biology*, vol. 32: *Protein Engineering Protocols*, Amdt and Müller (Eds.), Humana Press, N J, 2007.

In some embodiments, a compound of Formulae I-IX is incorporated into a polypeptide. For example, nitration of a compound of Formulae Ia-IXa results in formation of a compound of Formulae I-IX. It is known in the art that L-tryptophan and its derivatives (e.g., compounds of Formulae I-IX) may be incorporated into polypeptides to form artificial or unnatural proteins, for example as disclosed by *Methods in Molecular Biology*, vol. 32: Protein Engineering Protocols, Amdt and Muiller (Eds.), Humana Press, N J, 2007.

In some aspects, the disclosure relates to methods for producing a compound of Formula I or Formula II. In some embodiments, the method comprises contacting an L-tryptophan having at least one substitution on its indole ring with at least one reductase enzyme and a cytochrome P450 enzyme which catalyzes transfer of a nitro functional group to an L-tryptophan having at least one substitution on its indole ring in the presence of NADPH. The skilled artisan appreciates that the L-tryptophan may have substitution on any member of the indole ring. For example, the L-tryptophan may have substitution at position 4, 5, 6 or 7 of the indole ring. In some embodiments, the substitution is a halogen substitution. In some embodiments, the halogen substitution is a fluorine substitution. The method may utilize a native cytchrome P450 enzyme and associated redox proteins or a fusion protein. For example, the L-tryptophan may be contacted with wild-type TxtE cytochrome P450 enzyme, ferredoxin and ferredoxin reductase in the presence of NAD(P)H to produce a compound having Formula I or Formula II. In some embodiments, the L-tryptophan is contacted with a fusion protein, for example a TxtE enzyme terminally-linked to a catalytic domain of a reductase enzyme, in the presence of NAD(P)H to produce a a compound having Formula I or Formula II.

In some aspects, the disclosure relates to methods for producing a compound of Formulae I-IX, or a pharmaceutically acceptable salt, prodrug, hydrate, or solvate thereof. In some embodiments, the method comprises contacting a compound of Formulae Ia-IXa with at least one reductase enzyme and a cytochrome P450 enzyme which catalyzes transfer of a nitro functional group to a compound of Formulae Ia-IXa in the presence of NADPH. The skilled artisan appreciates that the compound of Formulae Ia-IXa may have substitution on any member of the indole ring. For example, the compound of Formulae Ia-IXa may have substitution at position 4, 5, 6 or 7 of the indole ring. In some embodiments, the substitution is halogen. In some embodiments, the halogen is fluorine. The method may utilize a native cytochrome P450 enzyme and associated redox proteins or a fusion protein. For example, the compound of Formulae Ia-IXa may be contacted with wild-type TxtE cytochrome P450 enzyme, ferredoxin and ferredoxin reductase in the presence of NAD(P)H to produce a compound having Formulae I-IX. In some embodiments, the compound of Formulae Ia-IXa is contacted with a fusion protein, for example a TxtE enzyme terminally-linked to a catalytic domain of a reductase enzyme, in the presence of NAD(P)H to produce a compound having Formulae I-IX.

The invention also relates, in some aspects, to a method for producing a di-substituted nitrated indole. In some aspects, the method comprises contacting an L-tryptophan molecule having a singly-substituted indole ring, in the presence of NAD(P)H, with at least one reductase enzyme and a cytochrome P450 enzyme that catalyzes transfer of a nitro functional group to an L-tryptophan having at least one substitution on its indole ring. In aspects the L-tryptophan having at least one substitution on its indole ring is substituted with other than a nitrate. In aspects the L-tryptophan molecule having at least one substitution on its indole ring is singly-substituted on its indole ring and the resulting nitro-substituted L-tryptophan is a di-substituted nitrated indole. In aspects the method further comprises isolating the nitrated L-tryptophan. In aspects the method further comprises isolating the di-substituted nitrated indole portion of the L-tryptophan molecule from the L-tryptophan molecule. Methods of removing or isolating indole rings are known in the art. For example, the enzyme tryptophanase may be used to deaminate tryptophan to produce an indole ring.

The invention also relates, in some aspects, to a method for producing a di-substituted nitro-substituted indole. In some aspects, the method comprises contacting a compound of Formulae Ia-IXa wherein $X^2$, and $X^3$ in Formula Ia, IVa, or Va are both hydrogen or one of $Y^1$, $Y^2$, or $Y^3$ in Formulae IIa, IIIa, VIa, VIIa, VIIIa, or IXa is not hydrogen, in the presence of NAD(P)H, with at least one reductase enzyme and a cytochrome P450 enzyme that catalyzes transfer of a nitro functional group to a compound of Formulae Ia-IXa. In aspects the compound of Formulae Ia-IXa is substituted with a substituent other than a nitro group. In aspects $Y^3$ in Formulae IIa, IIIa, VIa, VIIa, VIIIa, or IXa is hydrogen. In aspects the method further comprises isolating the compound of Formulae I-IX. In aspects the method further comprises isolating the indole portion of the compound of Formulae I-IX from the compound of Formulae I-IX. Methods of removing or isolating indole rings are known in the art. For example, the enzyme tryptophanase may be used to deaminate tryptophan to produce an indole ring.

In another aspect, the invention is directed to tryptophan or any tryptophan derivative (e.g., compounds of Formulae I, Ia, II, IIa, III, IIIa, IV, IVa, V, Va, VI, VIa, VII, VIIa, VIII, VIIIa, IX, or IXa) and the use of the aforementioned tryptophan or tryptophan derivatives in any of the processes or methods delineated herein. The tryptophan derivatives, Formulae Ia-IXa, can be prepared according to any synthetic methods known in the art [e.g., Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987]. For example, tryptophan derivatives, Formulae Ia-IXa, can be prepared from the corresponding indole, Formulae Ib-IVb, via reaction with serine and acetic acid/acetic anhydride, as outlined in Blaser, G. et al. (2008) Tetrahedron letters, 49 (17). pp. 2795-2798. Other chemical and enzymatic methods are also known for converting indoles (e.g., compounds of Formulae Ib-IVb) to the corresponding tryptophan derivatives (e.g., compounds of Formulae Ia-IXa) [Eto et al., *Bull. Chem. Soc. Japan* (1989), 62(3), pages 961-963; Li et al., *Tetrahedron* (2014), 70(42), pages 7753-7762; Wartmann et al., *Eur. J. Org. Chem.* (2013), 2013(9), pages 1649-1652; Murai et al., *J. Org. Chem.* (2012), 77(19), pages 8581-8587; Mollica et al., *Tet. Lett.* (2011), 52(20), pages 2583-2585; Heemstra et al., *J. Am. Chem. Soc.*, (2008), 130(43), pages 14024-14025; Yamada et al., *Chem. Pharm. Bull.* (2005), 53(10), pages 1277-1290; Li et al., *Tet. Lett.* (2004), 45(46), pages 8569-8573; Kim et al., *Syn. Comm.* (2004), 34(16), pages 2931-2943; Konda-Yamada et al., *Tetrahedron* (2002), 58(39), pages 7851-7861; WO2001094345; Zhang et al., *Tet. Lett.* (1995), 36(41), pages 7411-7314; Filler et al., *Can. J. Chem.* (1989), 67(11), pages 1837-1841; Ojima et al., *J. Org. Chem.* (1989), 54(19), pages 4511-4522; Schmidt et al., *Liebigs Annalen der Chemie* (1985), 4, pages 785-793; Petrovic et al., *Amino Acids* (2013), 44(5), pages 1329-1336; Frese et al., *ChemCatChem* (2014), 6(5), pages 1270-1276; Smith et al., *Org. Lett.* (2014), 16(10), pages 2622-2625].

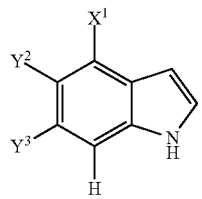

Formula Ib

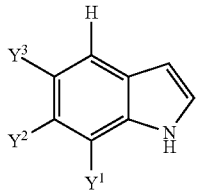

Formula IIb

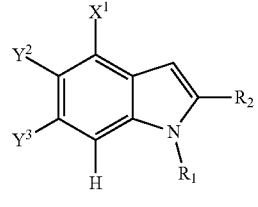

Formula IIIb

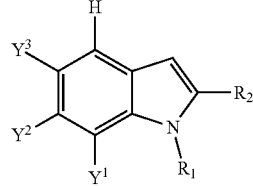

Formula IVb

Indoles of Formulae Ib-IVb can be purchased from commercial sources or can be prepared by any methods known in the art for preparing and/or modifying indoles. Non-limiting examples of such processes are Bartoli indole synthesis, Mannich reaction, Fischer indole synthesis, Nenitzescu indole synthesis, and the like.

The present invention is further illustrated by the following Examples, which in no way should be construed as further limiting.

EXAMPLES

Example 1: Materials and Methods

General Chemicals, DNA Sub-Cloning, and Bacterial Strains

Molecular biology reagents and enzymes were supplied by Fisher Scientific. Primers were ordered from Sigma-Aldrich. 4-F-dl-Tryptophan was purchased from MP Biomedicals (Santa Ana, Calif.), while NOC-5 was purchased from EMD Millipore. Other chemicals and solvents were purchased from Fisher Scientific and Sigma-Aldrich. *Escherichia coli* DH5α (Life Technologies) was used for cloning and plasmid harvesting, while *E. coli* BL21-GOLD (DE3) (Agilent) was used for protein overexpression. *E. coli* strains were grown in Luria-Bertani broth or Terrific broth. Preparation and manipulation of plasmid DNA from *E. coli* was accomplished following manufacture protocols from Thermo Scientific or Zymo Research. DNA sequencing was performed at Eurofins. A Shimadzu Prominence UHPLC system (Kyoto, Japan) fitted with an Agilent Poroshell 120 EC-C18 column (2.7 μm, 3.0×50 mm), coupled with a PDA detector was used for HPLC analysis. A 3200 QTRAP (Applied Biosystems) equipped with a Shimadzu UPLC system was used for LC-MS/MS analysis in the studies. All NMR spectra were recorded in 50 mM DCl on an Agilent 600 MHz spectrometer using a 1.5 mm High Temperature Superconductor Probe in the AMRIS facility at the University of Florida. The instrument was operated at 600.17 MHz for $^1$H and 150.9 MHz for $^{13}$C. Spectroscopy data were collected using VNMRJ Version-4.0. HRMS data were obtained using an Agilent LC-TOF mass spectrometer equipped with electrospray source detector.

Construction of Self-Sufficient TxtE Variants

TxtE gene was amplified from *S. scabies* 87.22 genomic DNA using a pair of TxtEFN and TxtERH primers (Table 1) in PCR reaction. The PCR mixture (50 μL) contained 50 ng template, 2 μM of each primer, 0.1 mM of dNTP, 3% dimethyl sulfoxide, and 0.5 μl Phusion high fidelity DNA polymerase in 1×GC reaction buffer. Reaction conditions consisted of an initial denaturation step at 98° C. for 30 s followed by 30 cycles of 98° C. for 10 s, 70° C. for 20 s, and 72 OC for 30 s, and a final extension of 72° C. for 5 min. The PCR product was analyzed by agarose gel and extracted with a GeneJET Gel Extraction Kit (Thermo) following a manufacture's protocol. To create the TxtE-P450BM3 reductase (BM3R) domain fusion gene, TxtE gene was amplified using a pair of TxtEFN and TxtEBRR primers while TxtEBRF and BRRS primers were used to amplify BM3R gene, which was then followed by an overlapping PCR (Higuchi et al. 1988). Similarly, TxtE-RhFRed and TxtE-RhFRed* fusion genes were generated by fusing TxtE gene with P450RhF reductase domain (RhFRed) gene. Corresponding primers were included in Table 1. Purified PCR products and pET28b were digested with the same sets of restriction enzymes and corresponding linear DNAs were ligated to generate expression constructs. All inserts in the constructs were sequenced to exclude mutations introduced during PCR amplification and gene manipulation.

TABLE 1

Primers for production of fusion protein

| Name | Sequence (5'→3') | Function | SEQ ID NO. |
|---|---|---|---|
| TxtE-FN | CACCCATGGTGACCGTCCCCTCGC | TxtE cloning | 1 |
| TxtE-RH | ATATAAGCTTGCGGAGGCTGAGCG GCAG | TxtE cloning | 2 |
| TxtEBRF | GCCGCTCAGCCTCCGCTCTGCTAA AAAAGTACGC | TxtE-BM3R fusion | 3 |
| TxtEBRR | GCGTACTTTTTTAGCAGAGCGGAG GCTGAGCGGC | TxtE-BM3R fusion | 4 |
| BRRS | ATCGAGCTCGACCCAGCCCACACG TCTTTTGC | TxtE-BM3R fusion | 5 |
| TxtERedF | CCGCTCAGCCTCCGCGTGCTGCAC CGCCATC | TxtE-RhFRed fusion | 6 |
| TxtERedR | GATGGCGGTGCAGCACGCGGAGGC TGAGCGG | TxtE-RhFRed fusion | 7 |

TABLE 1-continued

Primers for production of fusion protein

| Name | Sequence (5'→3') | Function | SEQ ID NO. |
|---|---|---|---|
| TxtE8ARedF | GCCGCTCAGCCTCCGCCATGTGCG ATTGGCGTC | TxtE-RhFRed* fusion | 8 |
| TxtE8ARedR | GACGCCAATCGCACATGGCGGAGG CTGAGCGGC | TxtE-RhFRed* fusion | 9 |
| RedRH | CTCAAGCTTGAGGCGCAGGGCCAG GCG | TxtE-RhFRed fusion | 10 |

Heterologous Expression and Purification of Recombinant Proteins

Insert-validated constructs were transformed into *E. coli* BL21 (DE3)-GOLD competent cells for protein expression. Cells harboring the constructs were cultured in Terrific Broth medium supplemented with kanamycin (50 μg/ml) and 1× trace metal solution (1000× stock solution: 50 mM $FeCl_3$, 20 mM $CaCl_2$, 10 mM $MnSO_4$, 10 mM $ZnSO_4$, 2 mM $CoSO_4$, 2 mM $CuCl_2$, 2 mM $NiCl_2$, 2 mM $Na_2MoO_4$, and 2 mM $H_3BO_3$). Cultures were grown at 37° C., 250 rpm until $OD_{600}$ reached 0.6. Protein expression was then induced by isopropyl-β-D-thiogalactopyranoside (IPTG) with a final concentration of 0.1 mM. The cultures were further grown at 16° C., 250 rpm for 16 hours. After centrifugation (5,000 g, 10 min, and 4° C.), cell pellets were stored in −80° C. or directly used for protein purification. For protein purification, cell pellets were first resuspended in the suitable volumes of lysis buffer (cell biomass:volume=1:4) [25 mM Tris-HCl, pH 8.0, 100 mM NaCl, 20 mM imidazole, 3 mM β-mercaptoethanol (BME) and 10% glycerol]. Soluble proteins were released by sonication. After centrifugation at 35,000×g at 4° C. for 30 min, the clear supernatants were incubated with pre-equilibrated Ni-NTA agarose resin (Thermo) at 4° C. for 2 h. The resins were washed with 10 volumes of lysis buffer with 30 mM imidazole, and recombinant P450s were then eluted in lysis buffer with 50 to 320 mM imidazole. After SDS-PAGE analysis, elution solution fractions containing P450s were combined and concentrated. The proteins were then exchanged into storage buffer (25 mM Tris-HCl, pH8.0, 100 mM NaCl, 3 mM βME, and 10% glycerol) using PD-10 column according to the manufacture's protocol, aliquoted and stored at −80° C. until needed. The concentrations of functional P450s were accurately measured by CO difference spectroscopy (Omura and Sato 1964).

Spectral Analysis of Self-Sufficient TxtE Variants

Purified TxtE and its fusion enzymes were spectrally analyzed following a previous protocol (Ding et al. 2008). Briefly, the absorbance spectra (400-600 nm) of TxtE variants (3 M) in Tris-HCl (25 mM, pH 8) buffer were recorded with a Shimadzu UV2700 dual beam UV-Vis spectrophotometer. The ferric heme of enzymes was then saturated with carbon monoxide (Airgas) through bubbling and the spectra of the saturated enzyme solutions were recorded. Immediately, sodium dithionite solution (30 μL, 0.5 M) was added to reduce ferric ion, and reduced spectra were taken subsequently. CO reduced difference spectra of all enzymes were created by subtracting the CO binding spectra from the reduced spectra. Data were further analyzed by GraphPad Prism 4. Substrate binding affinities to P450s were measured using 1.5 µM of enzyme solutions in 25 mM Tris-HCl, pH 8.0. Not more than 10 µl of substrate stock solutions prepared in the above buffer were added to the sample cuvette with an interval of 0.5 µl, and the spectra were recorded from 300 nm to 500 nm each time. The equal volume of buffer was added to the reference cuvette. The changes in absorbance (ΔA) were determined by subtracting the absorbance at ~420 nm from that at ~390 nm. Data were then fitted to Michaelis-Menten equation using GraphPad Prism 4.

Catalytic Activities of Self-Sufficient TxtE Variants

P450 reactions contained 0.5 mM substrate, 1 mM NADP$^+$, 1 mM glucose, ~10 units/mL self-prepared glucose dehydrogenase crude extract, 1 mM NOC-5 in 100 µL of Tris-HCl buffer (100 mM, pH 8.0). As the positive control, TxtE reaction was also re-constructed in the above mixture further supplemented with 0.43 µM spinach Fer and 0.33 µM Frd. The reactions were initiated by adding 1.5 µM P450s, and incubated at 20° C., 300 rpm on a thermostat (Eppendorf) for 2 hours. Methanol (200 µl) was then added to stop the reactions. After centrifugation, 10 µl solutions were analyzed by HPLC. The HPLC column kept at 40° C. was eluted first with 1% solvent B (acetonitrile with 0.1% formic acid) for 0.5 min and then with a linear gradient of 1-20% solvent B in 2 min, followed by another linear gradient of 20-99% solvent B in 0.5 min. The column was further cleaned with 99% solvent B for 0.5 min and then re-equilibrated with 1% solvent B for 2 min. The flow rate was set as 1.5 ml/min, and the products were detected at 211 nm with a PDA detector. All enzyme reactions were performed at least in duplicate.

Biochemical Characterization of Self-Sufficient TxtE Variants.

The stability of NO donor NOC-5 was first examined. Its solution was incubated at different pH value (4.5 to 9.5) and temperatures (4 to 65° C.) for 30 min. It was then used as NO donor in the P450 nitration reactions. NOC-5 was stable in all tested pH values but was decomposed quickly and significantly at temperatures higher than 25° C. To determine pH effects on the activity of TxtE and TxtEBM3R, enzyme (1.5 µM) reactions were performed in 100 mM Tris-Cl or sodium phosphate with various pH values (4.5 to 9.5) at 20° C., 300 rpm for 30 min. To determine enzyme pH stability, 5 µL of 30 µM enzyme solutions were incubated at buffers with different pH value (4.5 to 9.5). After 15 minutes, other reaction components (95 µL) were mixed to initiate nitration reactions as described above. To test enzyme thermostability, TxtE and TxtEBM3R were incubated in 100 mM Tris-HCl (pH 8.0) at different temperatures (4° C., 15° C., 20° C., 25° C., 30° C., 35° C., 40° C., 45° C., 55° C., and 65° C.) for 15 min. After cooling on ice for 5 min, enzyme solutions were centrifuged and then used to initiate reactions at 20° C., 300 rpm for 30 min. Products were quantitated by HPLC as described above. Conversion rate (%) was calculated by the equation of the area of under the 4-nitro-l-tryptophan peak/the total areas of both substrate and product peaks*100. All experiments were performed at least in duplicate. In this study, the $T_{50}$ is defined as the temperature at which a 15-minute incubation of the enzyme causes the loss of one-half of the enzyme activity, relative to a 100% activity reference enzyme that does not undergo incubation.

Large-Scale Enzymatic Synthesis of Nitrated Fluoro-Tryptophan Analogs

To isolate sufficient amounts of nitrated fluoro-tryptophan analogs for structural determination, 18 µM TxtEBM3R was used in a 10-mL reaction mixture containing 1.5 mM fluorinated substrate, 3 mM NADP$^+$, 3 mM glucose, ~30 units/mL self-prepared glucose dehydrogenase crude extract, 3 mM NOC-5 in 100 mM Tris-HCl buffer (pH 8.0). The reactions in a 200-ml flask were incubated at 20° C., 250 rpm overnight, and then terminated by 20 mL methanol or acidification to pH 1.0 with 6 M HCl. After centrifugation, the supernatants were concentrated in vacuo and then freeze-dried. The powders were redissolved in 3 ml methanol. Semi-preparation was performed by HPLC (Shimazu) with a semi-prep C18 column (Agilent ZORBAX SB-C18, 5 µm, 9.4×250 mm). The column kept at 40° C. was eluted first with 20% solvent B (acetonitrile with 0.1% formic acid) for 3 min and then with a linear gradient of 20-54% solvent B for 3 min, followed by a linear gradient of 54-77% solvent B for 6 min. The column was then cleaned by 99% solvent B for 1 min and re-equilibrated with 20% solvent B for 1 min. The flow rate was set as 3 mL/min, and the products were detected at 211 nm with a PDA detector. All isolates were combined, concentrated, freeze-dried, and then weighed.

LC-MS/MS and NMR Analysis

A SHIMADZU Prominence UPLC system fitted with an Agilent Poroshell 120 EC-C18 column (2.7 µm, 3.0×50 mm) coupled with a Linear Ion Trap Quadrupole LC/MS/MS Mass Spectrometer system was used in the studies. The column was eluted with 1% solvent B (acetonitrile with 0.1% formic acid) for 2 min and then with a linear gradient of 1-20% solvent B in 8 min, followed by another linear gradient of 20-99% solvent B in 2.5 min. The column was then cleaned by 99% solvent B for 0.5 min and re-equilibrated with 1% solvent B for 2.5 min. The flow rate was 0.5 mL/min. For MS detection, the turbo spray conditions were identical for all chemicals (curtain gas: 30 psi; ion spray voltage: 5500 V; temperature: 750° C.; ion source gas 1: 60 psi; ion source gas 2: 70 psi). For MS/MS analysis, the collision energy was 20 eV. In NMR analysis, chemical shifts were reported in parts per million (ppm) downfield from tetramethylsilane. Proton coupling patterns were described as singlet (s), doublet (d), double doublet (dd), triplet (t), and multiplet (m). 5-F-4-nitro-l-tryptophan: $^1$H NMR (600 MHz, 50 mM DCl) δ 7.52 (d, J=8.8 Hz, 1H), 7.35 (s, 1H), 6.95 (dd, J=10.2, 10.2 Hz, 1H), 4.04-3.93 (m, 1H), 3.23 (dd, J=15.3, 5.6 Hz, 2H), 3.05 (dd, J=15.3, 8.4 Hz, 2H); $^{13}$C NMR (151 MHz, 50 mM DCl) δ 171.29, 151.69, 150.03, 134.52, 131.66, 129.49, 129.41, 118.41, 118.34, 117.89, 110.47, 110.30, 105.89, 105.86, 72.01, 62.46, 59.31, 53.65, 27.09. HRMS (ESI$^+$): calc. for $C_{11}H_{11}FN_3O_4$ [M+H]$^+$: 268.0728, found: 268.0728. 4-F-7-nitro-l-tryptophan: $^1$H NMR (600 MHz, 50 mM DCl) δ 7.80 (dd, J=8.1, 8.1 Hz, 1H), 7.29 (s, 1H), 7.22 (d, J=9.1 Hz, 1H), 4.29-4.23 (m, 1H), 3.43 (dd, J=11.7, 6.5 Hz, 2H), 3.32 (dd, J=15.2, 8.2 Hz, 1H); $^{13}$C NMR (151 MHz, 50 mM DCl) δ 171.29, 152.41, 150.65, 142.34, 142.24, 128.59, 128.48, 119.38, 115.29, 115.18, 108.40, 108.35, 72.00, 62.45, 59.30, 53.73, 38.70, 26.72. HRMS (ESI$^-$): calc. for $C_{11}H_{11}FN_3O_4$ [M–H]$^-$ 266.0583, found: 266.0577.

Example 2: Preparation of Self-Sufficient TxtE Variants

TxtE promotes a regio-selective nitration on the C4 of L-tryptophan indole ring using $O_2$ and NO as co-substrates and consuming NADPH (FIG. 1) (Barry et al. 2012). Since the native redox partners of TxtE remain unidentified, spinach Fer and Frd were used to support the reaction. Three artificial self-sufficient TxtE fusion enzymes, TxtE-BM3R, TxtE-RhFRed, and TxtE-RhFRed* were designed by appending NADPH-dependent reductase domains of P450BM3 and of P450RhF to the C-terminus of TxtE. The linker of TxtE-BM3R was predicted from P450BM3 using software Domcut (Suyama and Ohara 2003). Two other fusion enzymes utilizing linkers of different lengths were produced. TxtE-RhFRed contains the native linker length of P450RhF, while TxtE-RhFRed* adds eight additional residues to the native linker. All three fusion enzymes were expressed in *E. coli* and purified to homogeneity with over 85% purity by a single nickel affinity chromatography (FIG. 2A). All recombinant proteins showed calculated molecular weights, 112 kDa for TxtE-BM3R and about 82 kDa for both TxtE-RhFRed and TxtE-RhFRed*, in SDS-PAGE analysis (FIG. 2A). To assess the functional folding of recombinant fusion proteins, UV/Vis spectroscopy was used to record their absorption spectra (FIG. 2B). The CO-bound oxidized form and reduced form of these enzymes resembled similar features to wild type TxtE and other bacterial CYPs. Soret peaks were shifted from around 419 nm in the oxidized forms to around 449 nm in the reduced-CO difference forms, indicating the proper folding of all fusion enzymes. The concentrations of functional heme-enzymes were accurately determined by this spectral approach, following the previously published protocols (Omura and Sato 1964; Ding et al. 2008).

Example 3: Catalytic Activity of TxtE Fusion Enzymes

Next, the catalytic activities of all three fusion enzymes (TxtE-BM3R, TxtE-RhFRed, and TxtE-RhFRed*) were assessed along with NADPH, the NO donor NOC-5 and L-tryptophan. As a control, wild type TxtE was reconstructed with spinach Fer and Fdr. HPLC analysis of reaction mixtures revealed that all fusion enzymes enabled the L-tryptophan nitration reaction to a different extent (FIG. 2C). TxtE-BM3R exhibited a higher conversion (109%) than the control, while both TxtE-RhFRed and TxtE-RhFRed* only reached 13% and 16% of the conversion level of the control, respectively. To examine the extent to which the fusion arrangement influenced the substrate-enzyme interaction, which might induce the observed variation of enzyme activity, the binding affinity of L-tryptophan toward all fusion enzymes was measured. TxtE-RhFRed showed the highest binding affinity with the $K_d$ value of 18.21±1.38 μM, followed by TxtE-BM3R ($K_d$=20.83±0.35 μM) and TxtE-RhFRed* ($K_d$=24.34±1.21 μM). These values remained in the same range as wild type TxtE ($K_d$=24.77±1.07 μM). Therefore, activity differences of fusion enzymes may be originated from electron transfer efficiency between TxtE and reductase domains. Interestingly, no nitrated product was detected by LC-MS analysis when TxtE was incubated with a standalone BM3R (data not shown), indicating the necessity of covalently linking two domains to promote the catalytically active electron transfer.

Example 4: Biochemical Characterization of TxtE and TxtE-BM3R

Figure 3A:
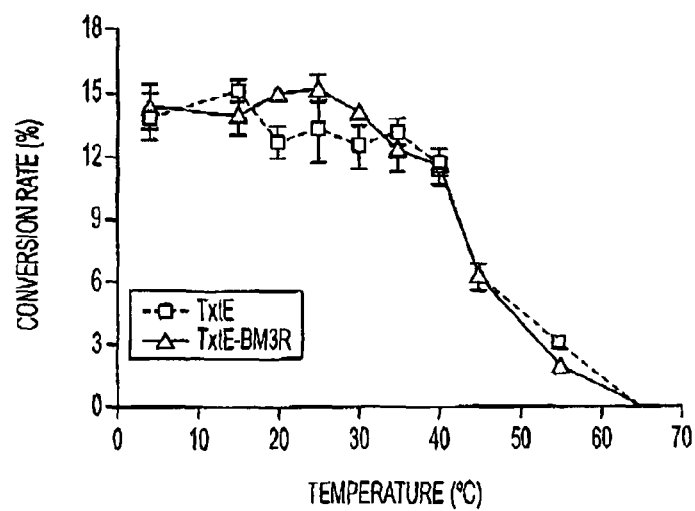
Figure 3B:
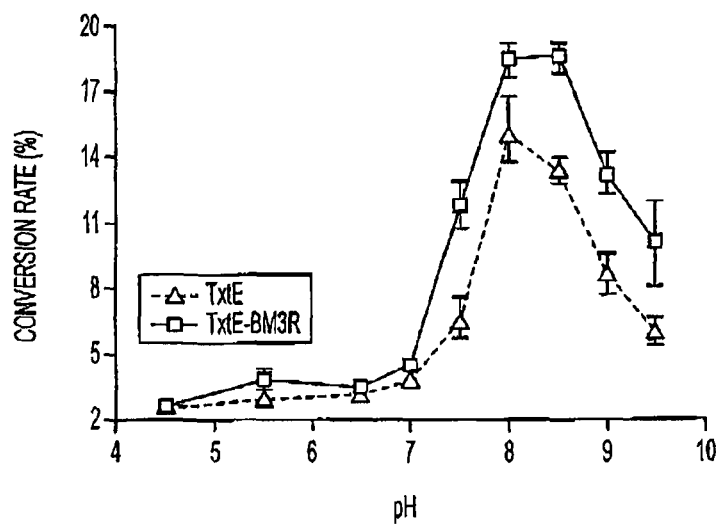
Figure 5:
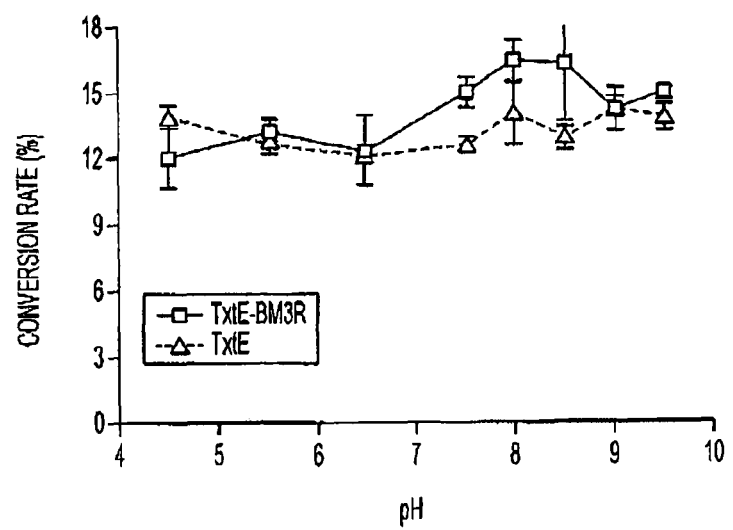

In this example, the thermostability of both TxtE and TxtE-BM3R (FIG. 3A) was examined. These enzymes were incubated under different temperatures (4 to 65° C.) for 15 min and then used in L-tryptophan nitration reaction at 20° C. Both enzymes showed a similar level of thermostability with the $T_{50}$ of around 45° C. (FIG. 3A). After incubation at 65° C. for 15 min, their activity was completely lost, indicating irreversible conformation changes at high temperature. Next, the pH dependence of TxtE and TxtE-BM3R using NOC-5 as the NO donor was examined (FIG. 3B). This reagent is stable over a broad pH range. Both enzymes remained <5% activity at buffers with pH below 7.0. TxtE-BM3R showed over 50% activity from pH 7.5 to pH 9.5 and its optimal pH range was 8.0 to 8.5. TxtE's activity depended on a narrower pH range, and its optimal activity preferred to pH 8.0. The extent to which the stability of both enzymes were affected by buffers with different pH values was further examined. After being incubated in these buffers for 15 min, enzymes were then used to nitrate L-tryptophan at pH 8.0, 20° C. (FIG. 5). HPLC analysis revealed that enzyme activities were only minimally affected by the incubation in different buffers. This result suggested that the pH dependence of enzyme activity (FIG. 3B) was not associated with the enzyme pH stability.

Example 5: Enzymatic Production of Fluorinated Nitro-Tryptophan Analogs

Figure 4A:
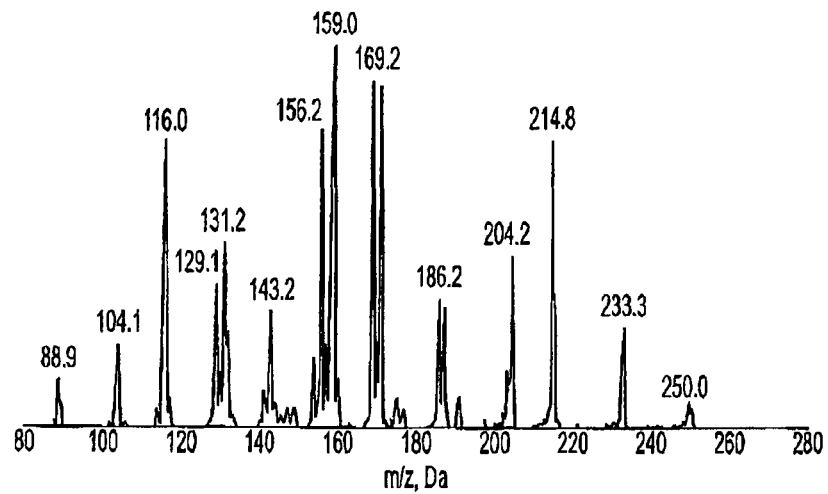
Figure 4B:
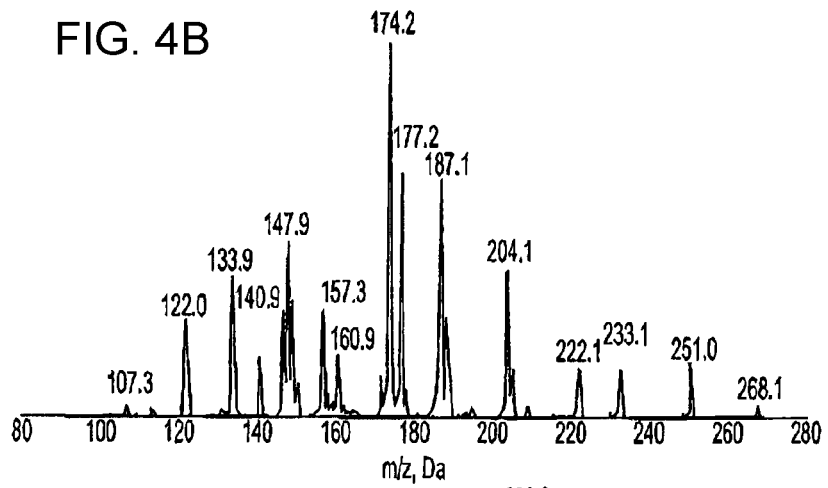
Figure 4C:
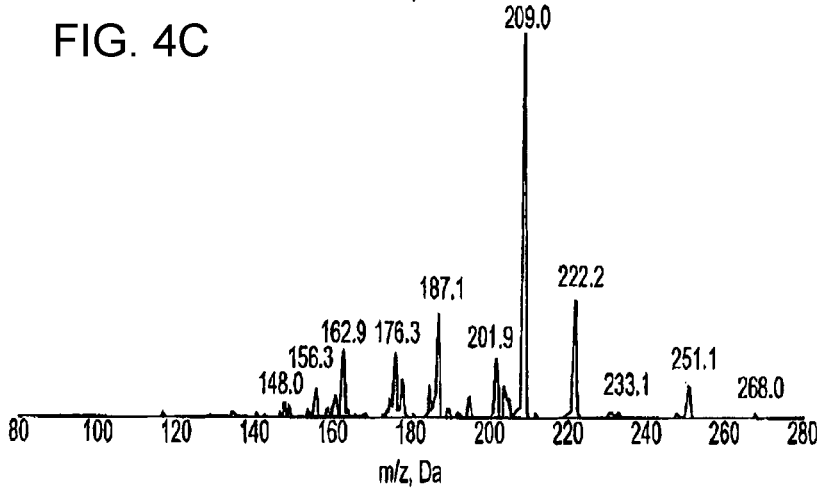
Figure 6:
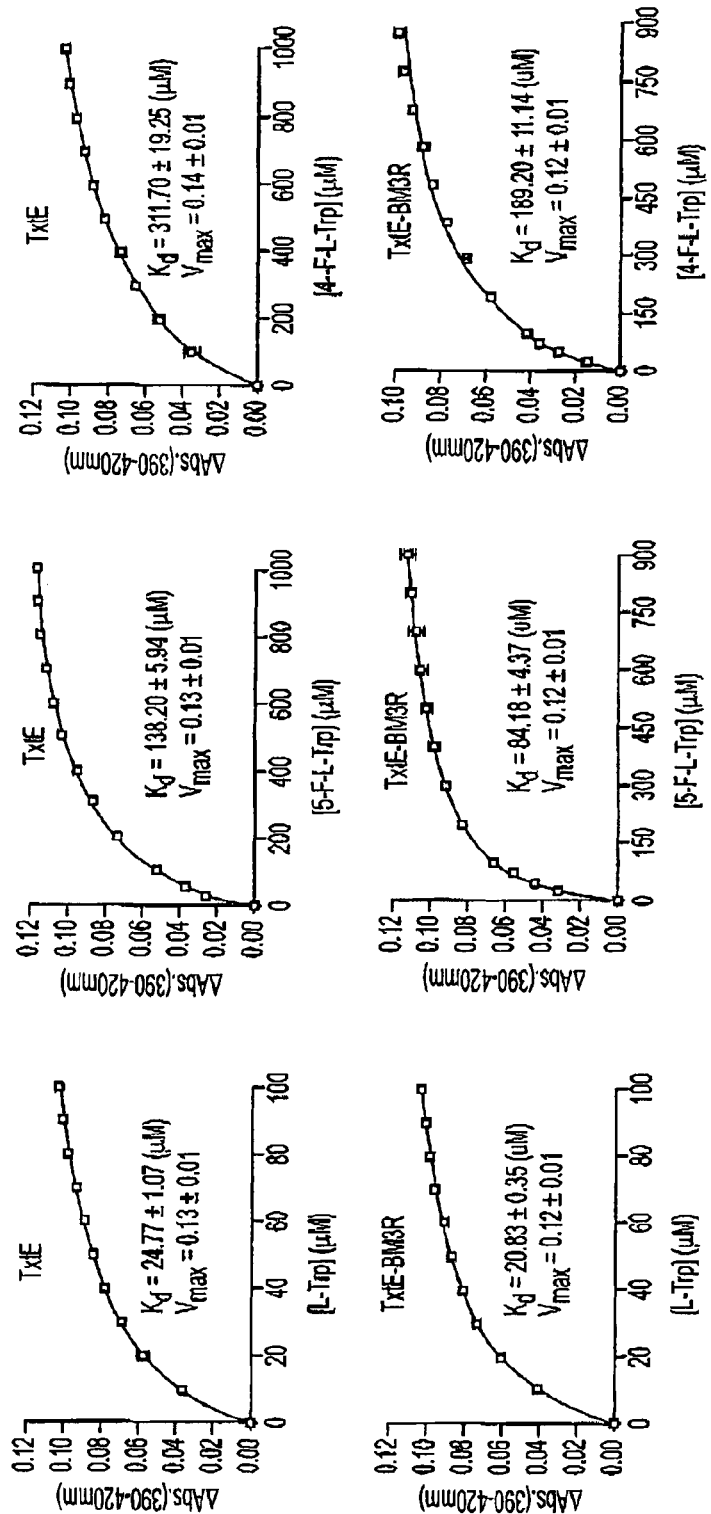

This example describes the use of TxtE-BM3R to produce nitro-tryptophan analogs. In this study, commercially available racemic 4-F-DL-tryptophan and 5-F-L-tryptophan were chosen as unnatural substrates because fluorine substitution is a common strategy used by medicinal chemists to generate drug molecules with improved properties (Ilardi et al. 2014). The binding of both substrates toward TxtE and TxtE-BM3R was studied (FIG. 6). Similar to L-tryptophan, the two fluorinated substrates induced type I spectral changes in both enzyme solutions. Compared with TxtE, the binding affinities between these substrates and TxtE-BM3R were about 60% tighter, indicating the BM3R might facilitate substrate binding (FIG. 6). In previous studies, D-tryptophan was unable to induce spectral changes in TxtE solution (Barry et al. 2012; Dodani et al. 2014). This observation may suggest that 4-F-L-tryptophan of the racemic mixture is the actual ligand bound to TxtE and TxtE-BM3R. With current inaccessibility to optically pure 4-F-L-tryptophan, the total concentration of the racemic mixture to calculate $K_d$ values, which thus underestimated the accurate binding affinities. Nonetheless, compared with native substrate L-tryptophan ($K_d$=20.83±0.35 μM), the binding affinities between TxtE-BM3R and 4-F-DL-tryptophan ($K_d$=189.20±11.14 μM) and 5-F-L-tryptophan ($K_d$=84.18±4.37 μM) were lowered by about 8 and 3 times, respectively, reflecting the binding interferences induced by the F-substitution at different positions. Next, the influences of the fluorination substitution on enzyme activity were examined. Remarkably, both TxtE and TxtE-BM3R slightly preferred 5-F-L-tryptophan over L-tryptophan (1.2:1) in the nitration reaction. In addition, although the $C_4$ in 4-F-L-tryptophan is occupied by a F substitution, both enzymes were able to nitrate this substrate as characterized by HPLC and LC-MS/MS analysis (FIGS. 4A-4C). The overall conversion rate was, however, only about 20% of L-tryptophan.

Figure 7:
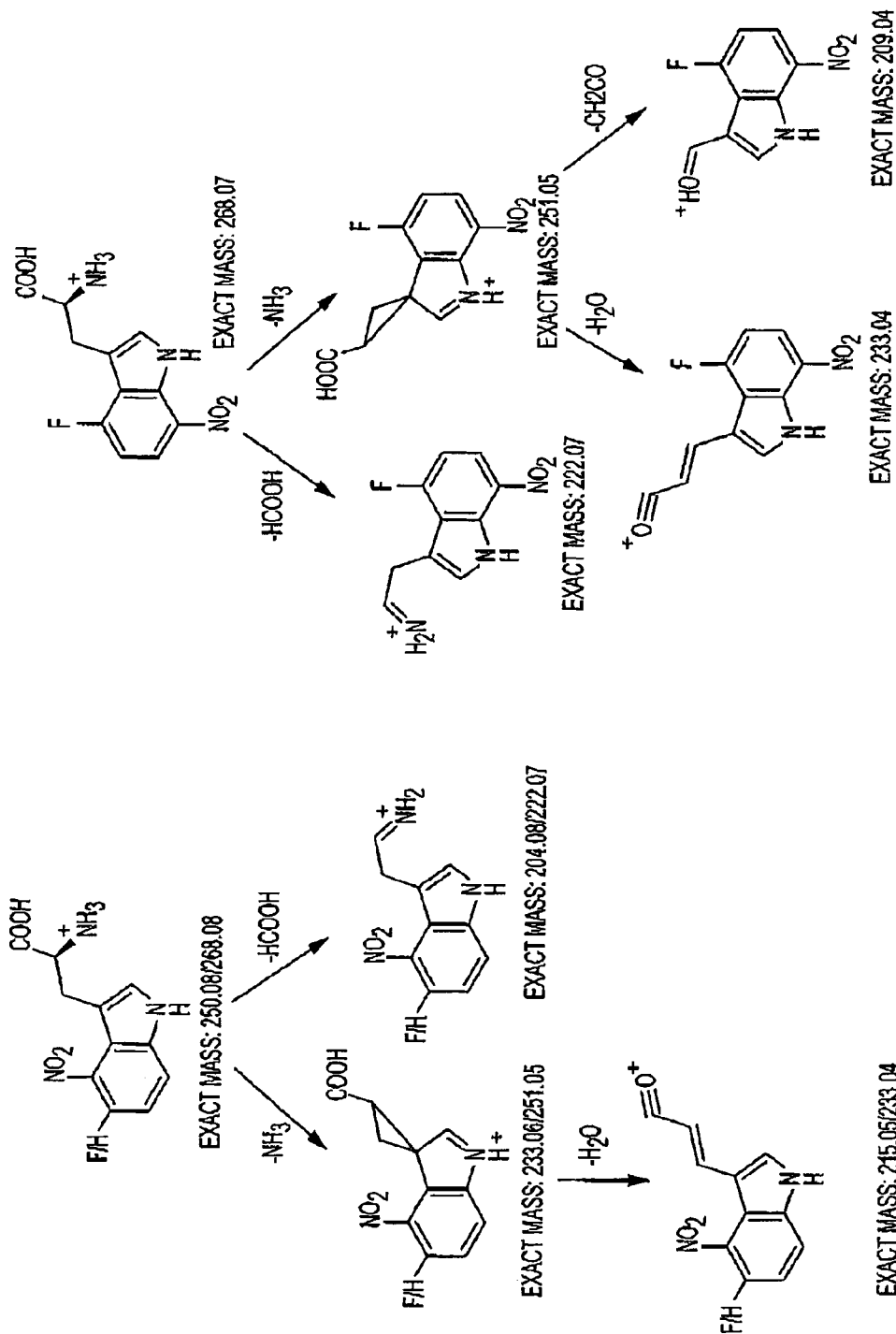

Example 6: Structural Characterization of Fluorinated Nitro-Tryptophan Analogs Structural characterization of nitrated F-tryptophan products were first performed by LC-MS/MS (FIGS. 4A-4C). Nitrated 5-F-L-tryptophan was fragmented in the same pattern as that of 4-nitro-L-tryptophan in MS2 spectra (FIGS. 4A-4B). However, the C5-F substitution not only increased the m/z values of all corresponding ions by 18 Da but also affected the distribution of different ions (FIGS. 4A-4B). The most abundant ion in the MS2 spectrum of 4-nitro-L-tryptophan had the m/z values of 159.0. It was switched to 174.2 in the MS2 spectrum of nitrated 5-F-L-tryptophan, corresponding to the non-fluorinated ion of 156.2. The most abundant ion in the MS2 spectrum of nitrated product with 4-F-DL-tryptophan as the substrate had an m/z value of 209.0 (FIG. 4C). Importantly, its overall fragmentation pattern was notably different with that of nitrated 5-F-L-tryptophan. Putative chemical structures of red-labeled ions in these MS2 spectra are shown in FIG. 7. This result suggested that 5-F-L-tryptophan may be nitrated at the same site, the $C_4$, as L-tryptophan but the nitration site at 4-F-L-tryptophan as the potential real substrate in the racemic mixture is different.

Figure 8A:
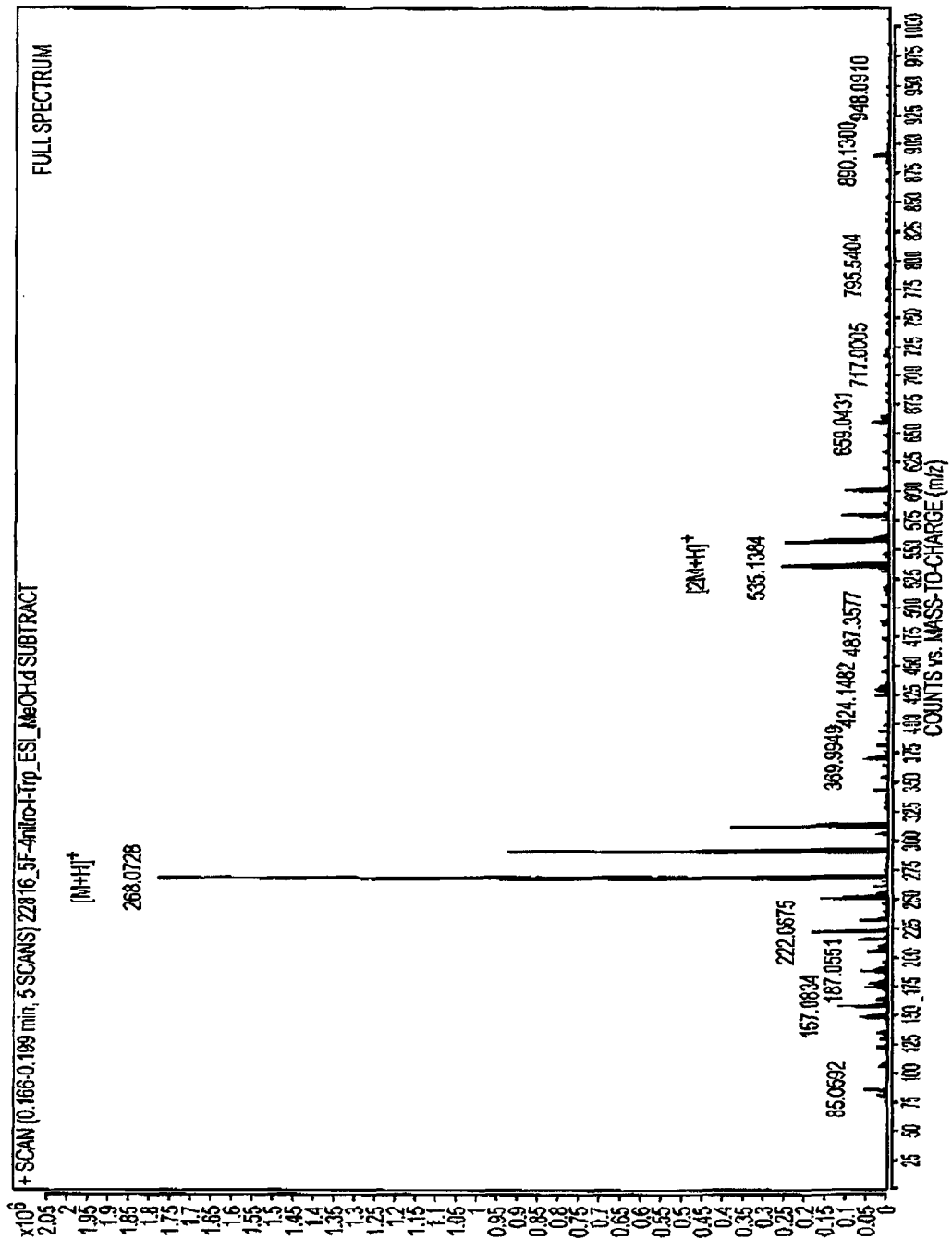
Figure 8B:
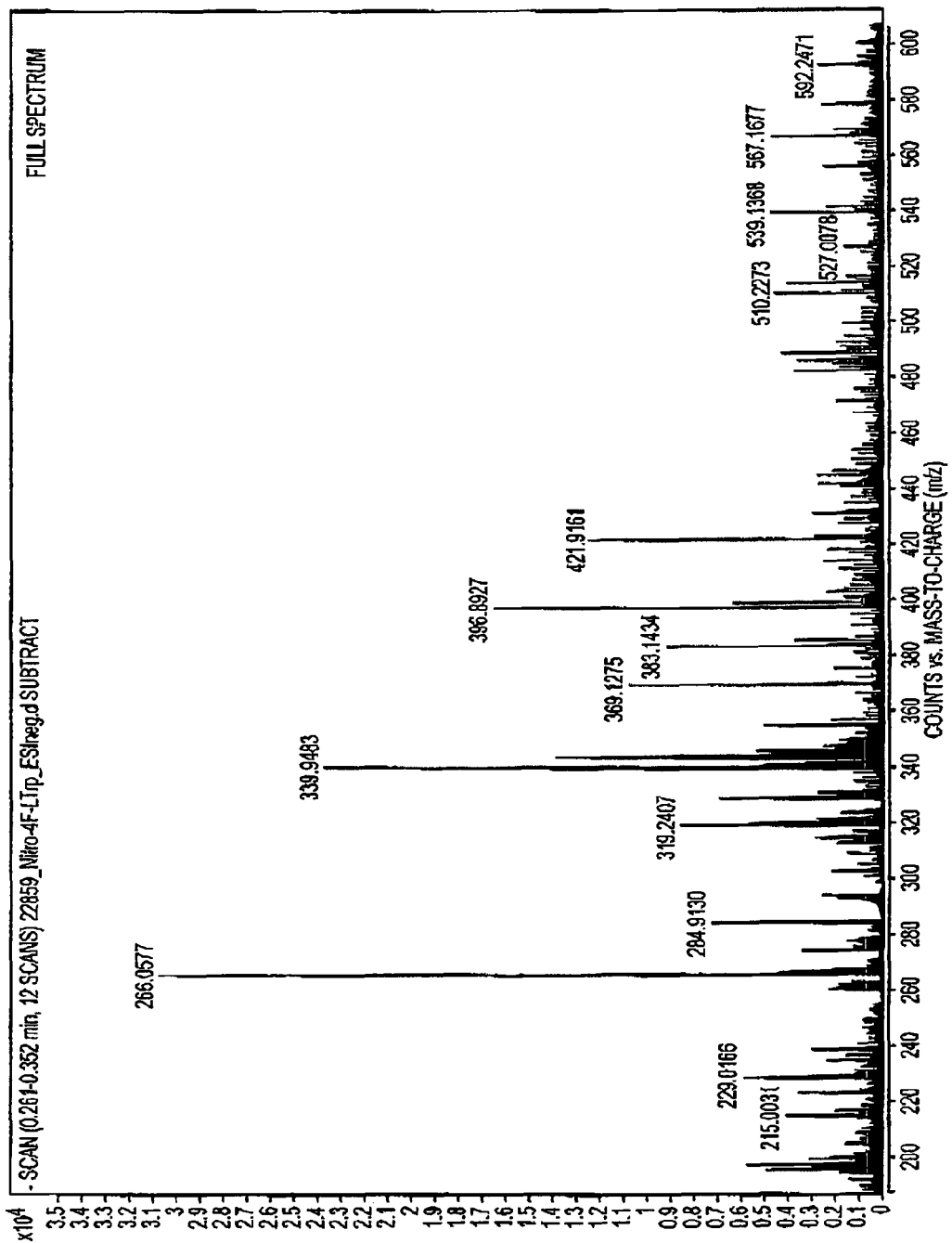
Figure 9A:
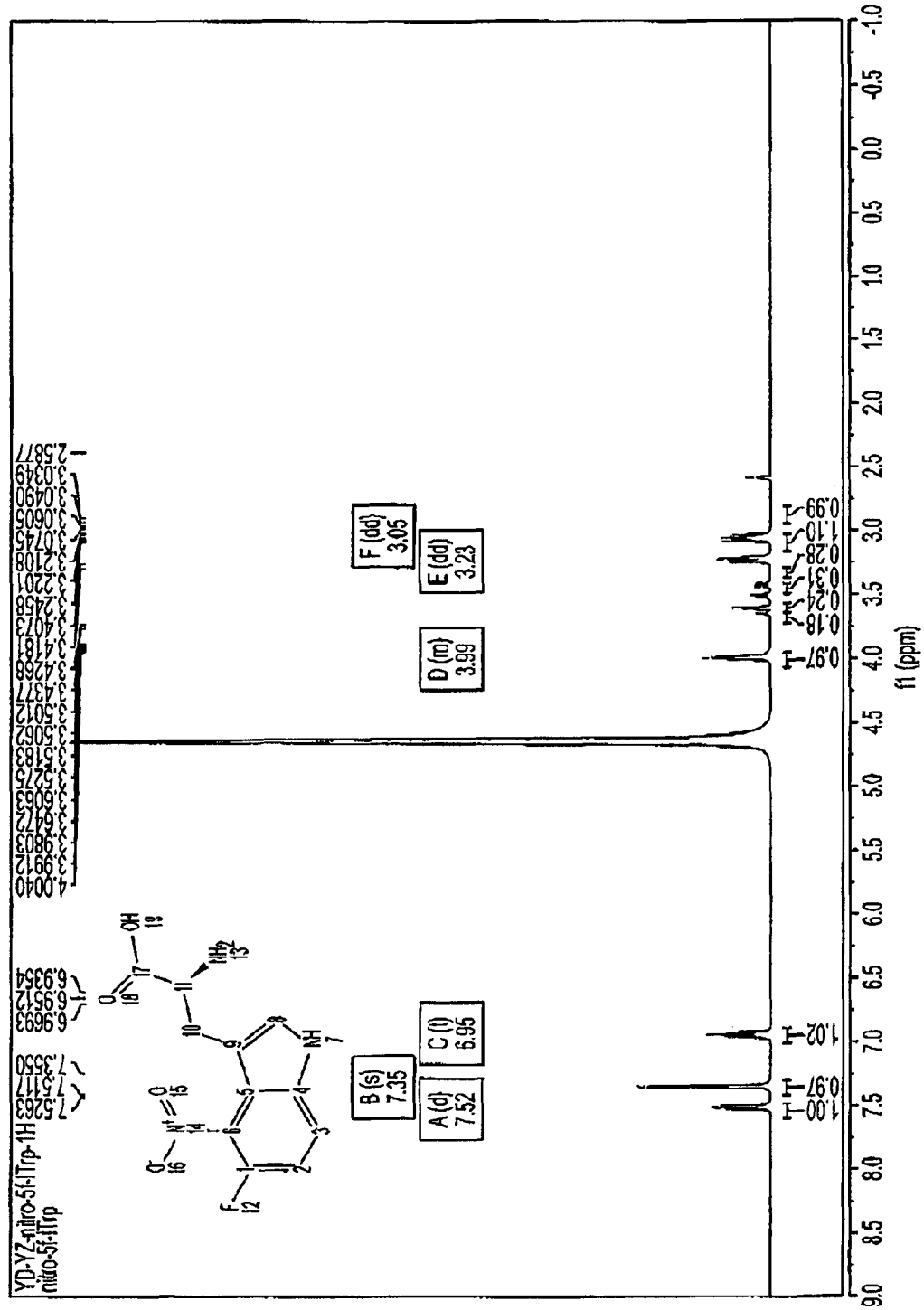
Figure 9B:
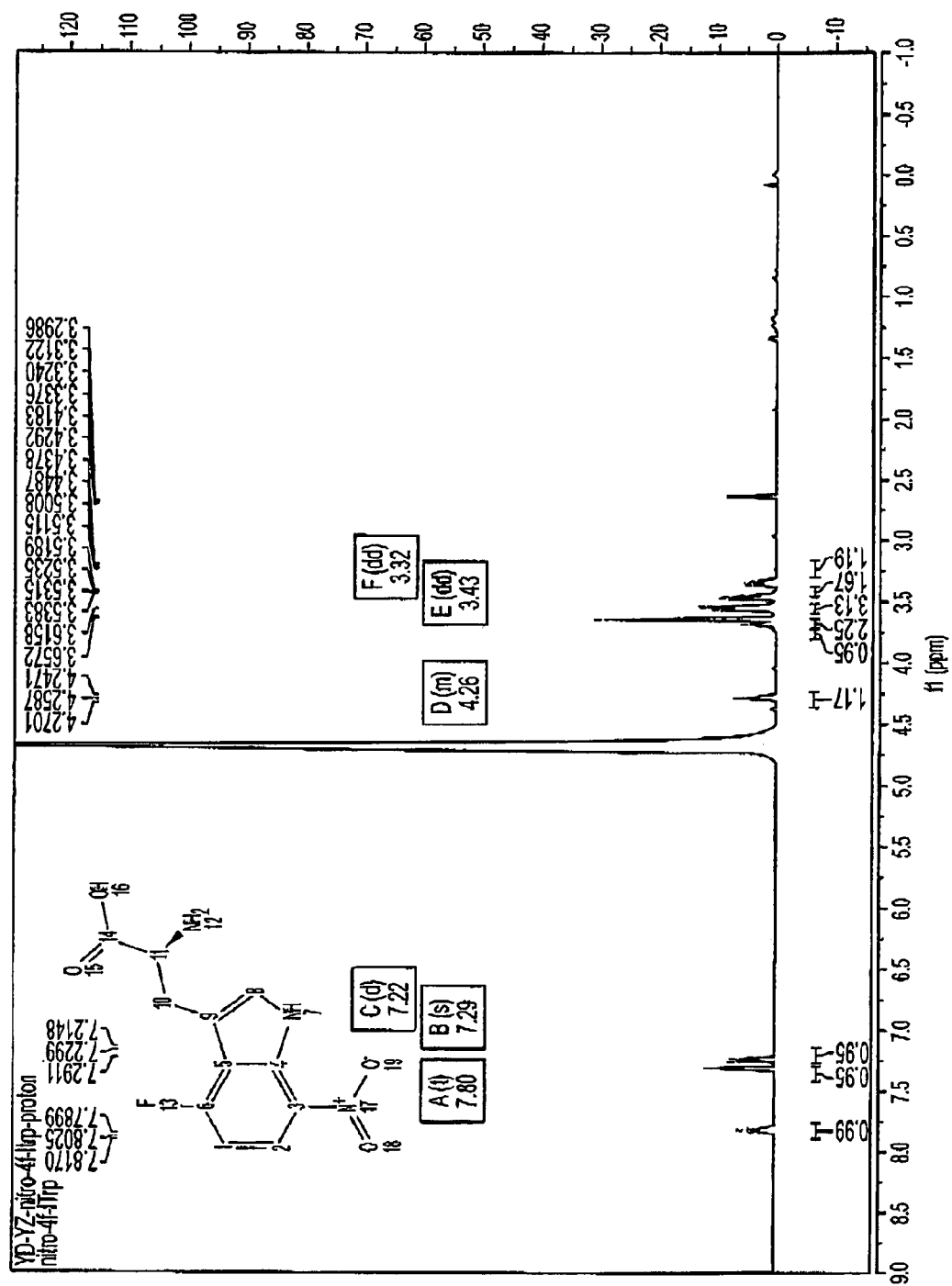
Figure 10A:
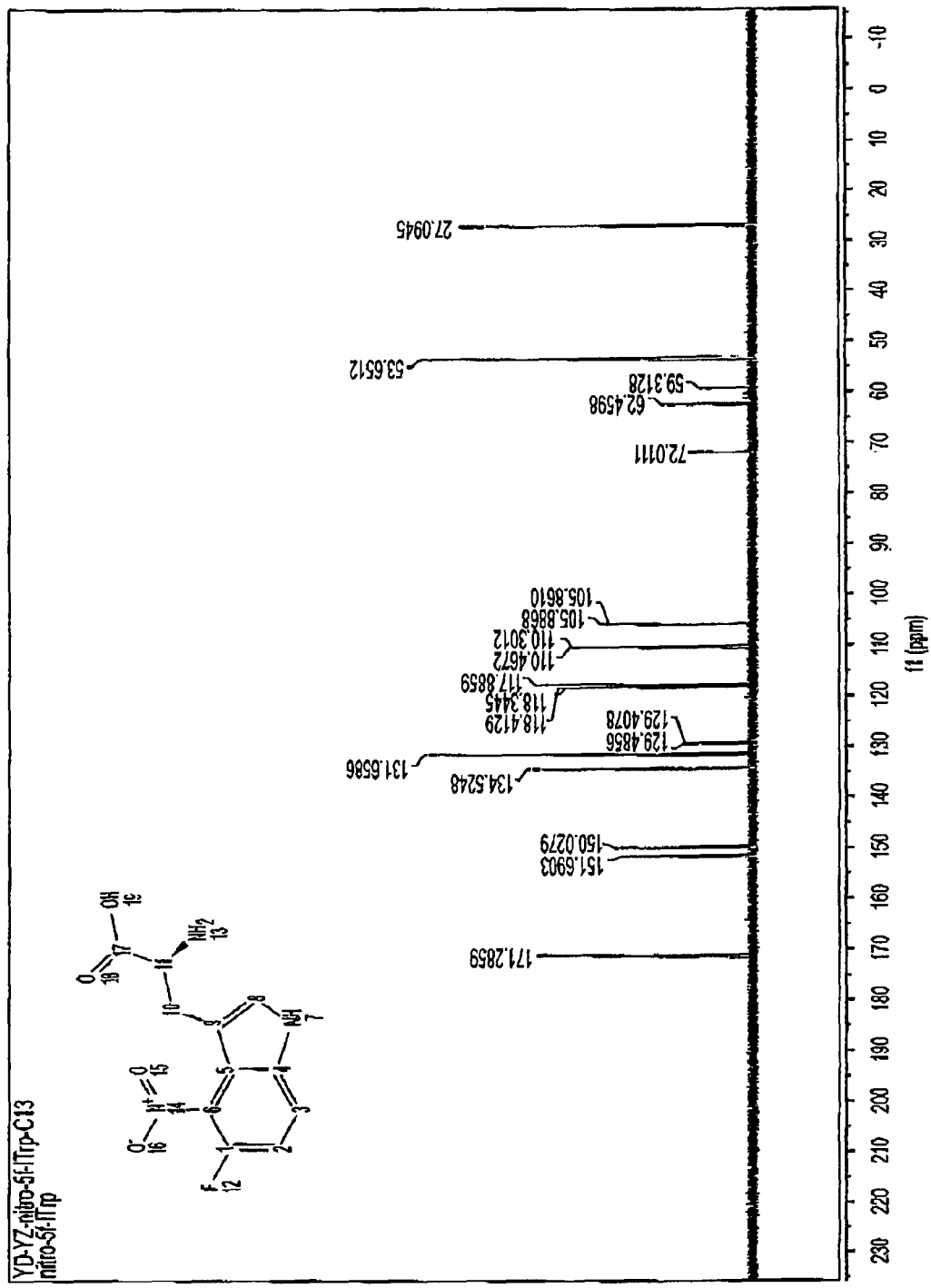
Figure 10B:
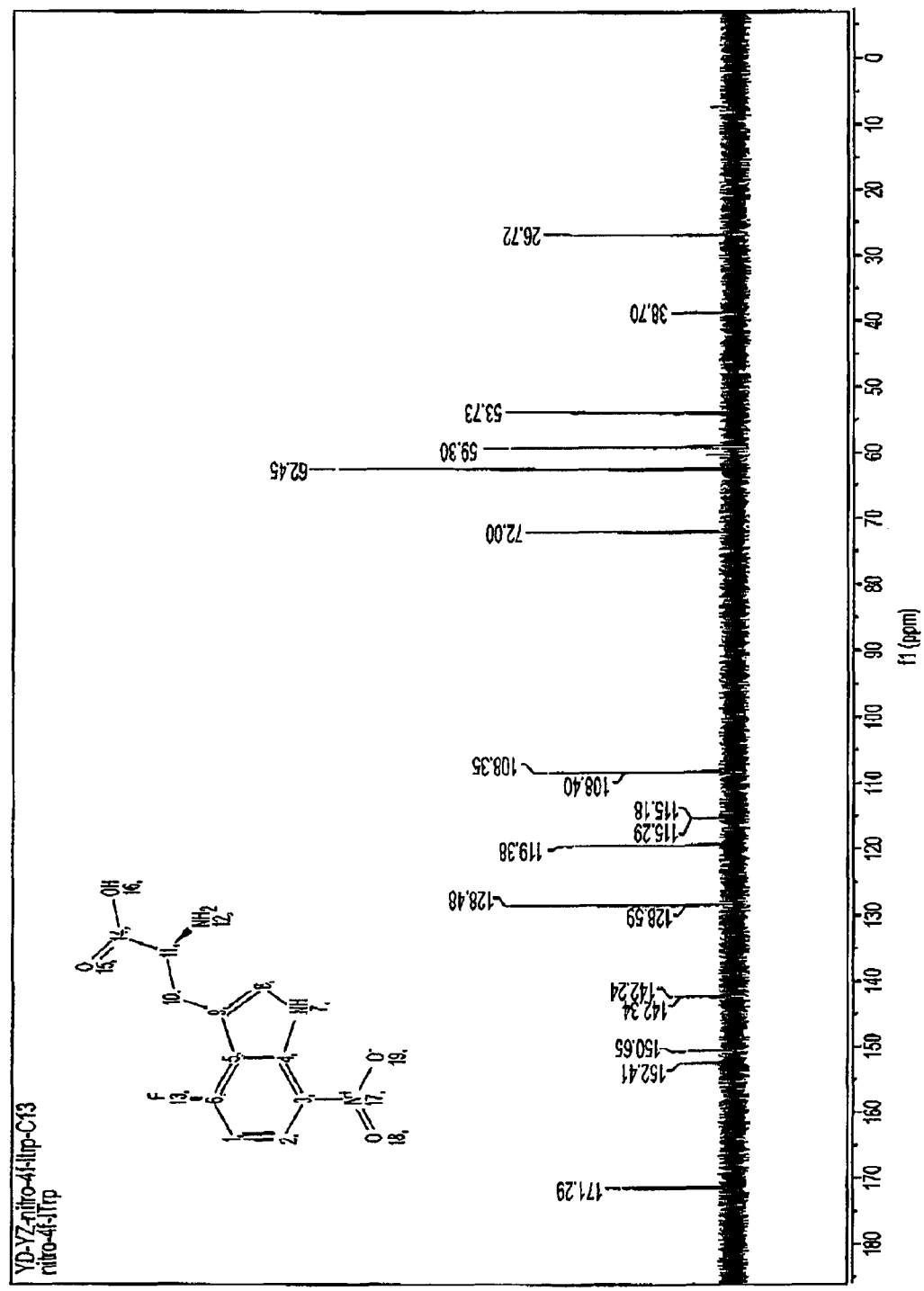
Figure 11A:
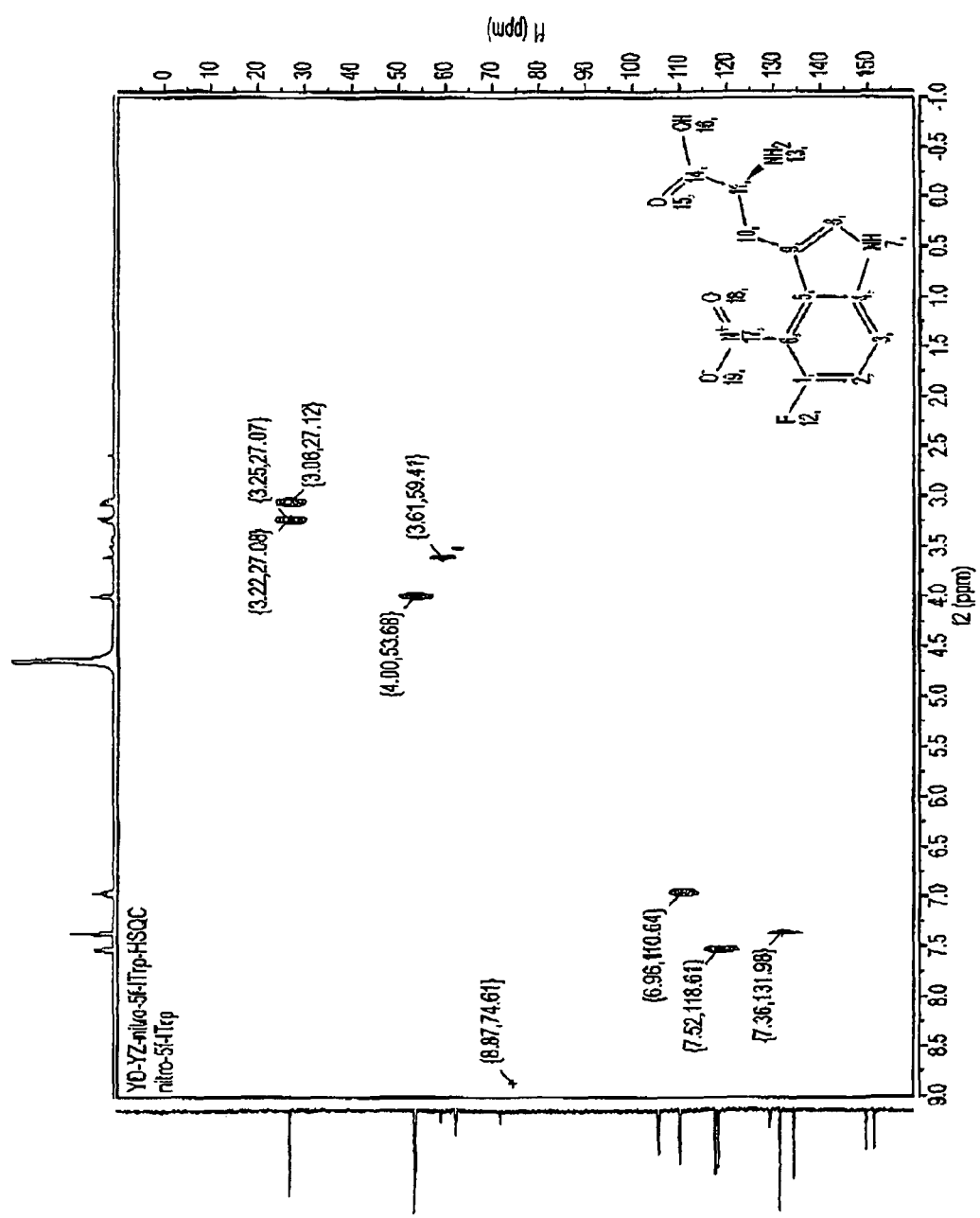
Figure 11B:
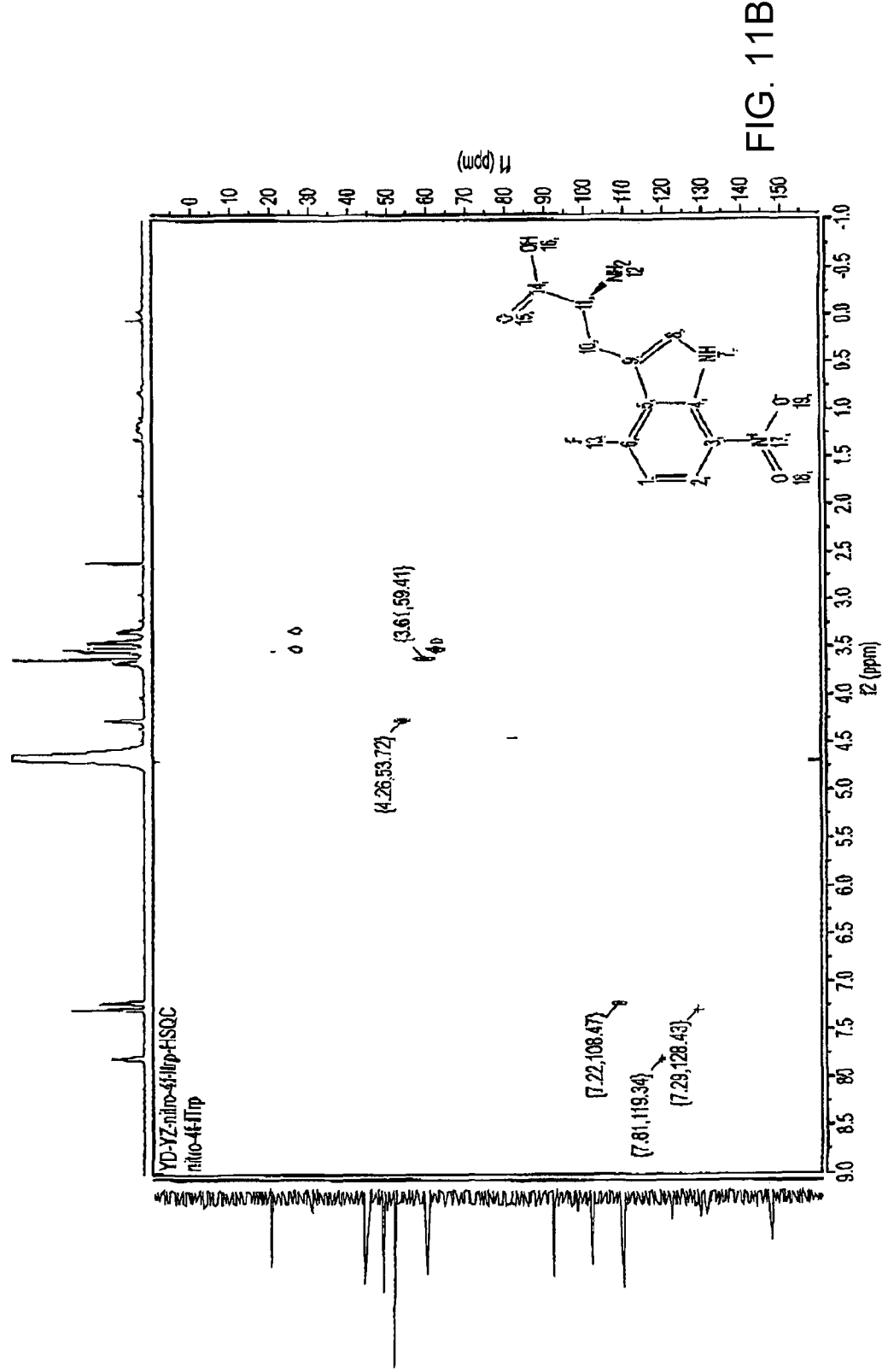
Figure 12A:
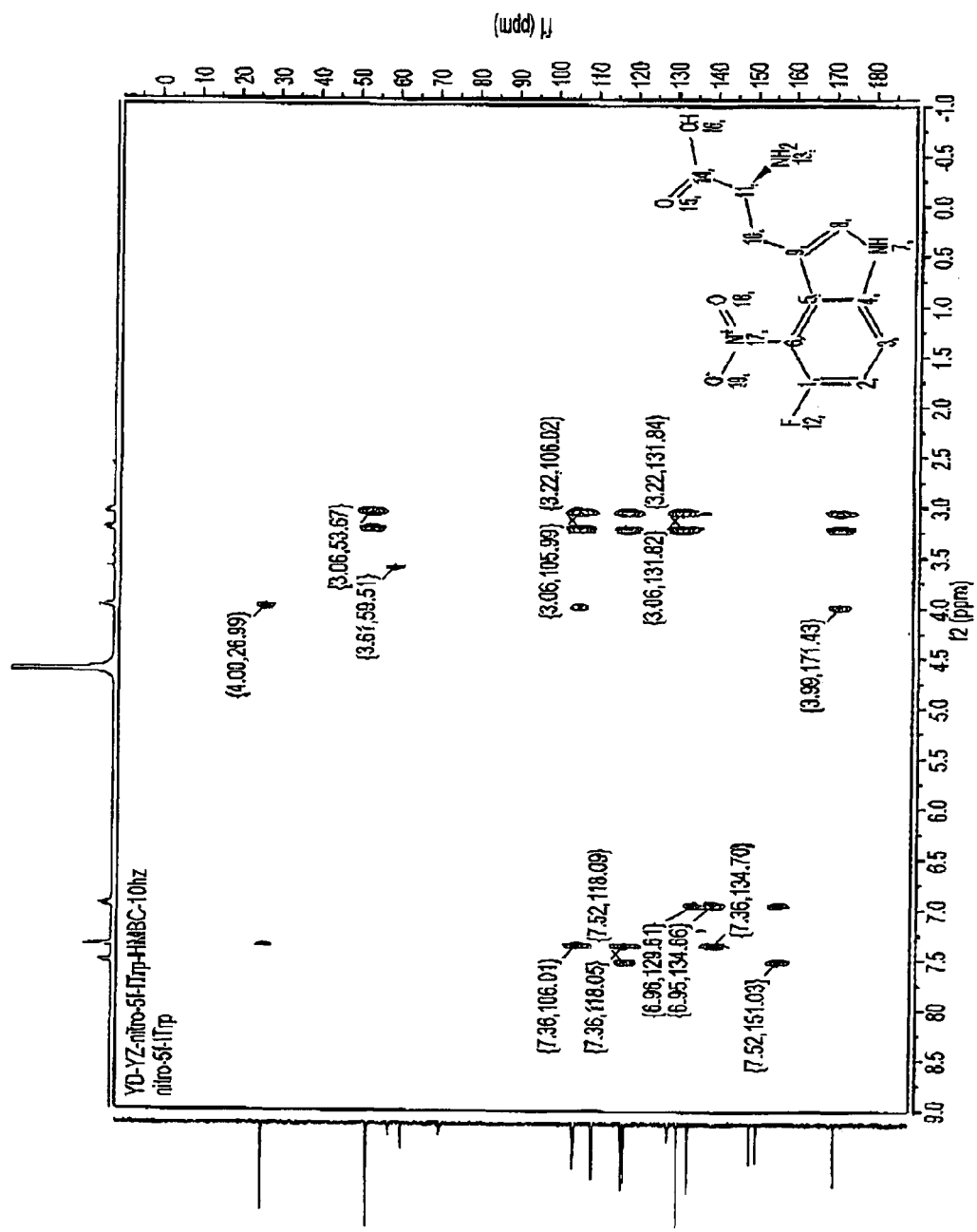
Figure 12B:
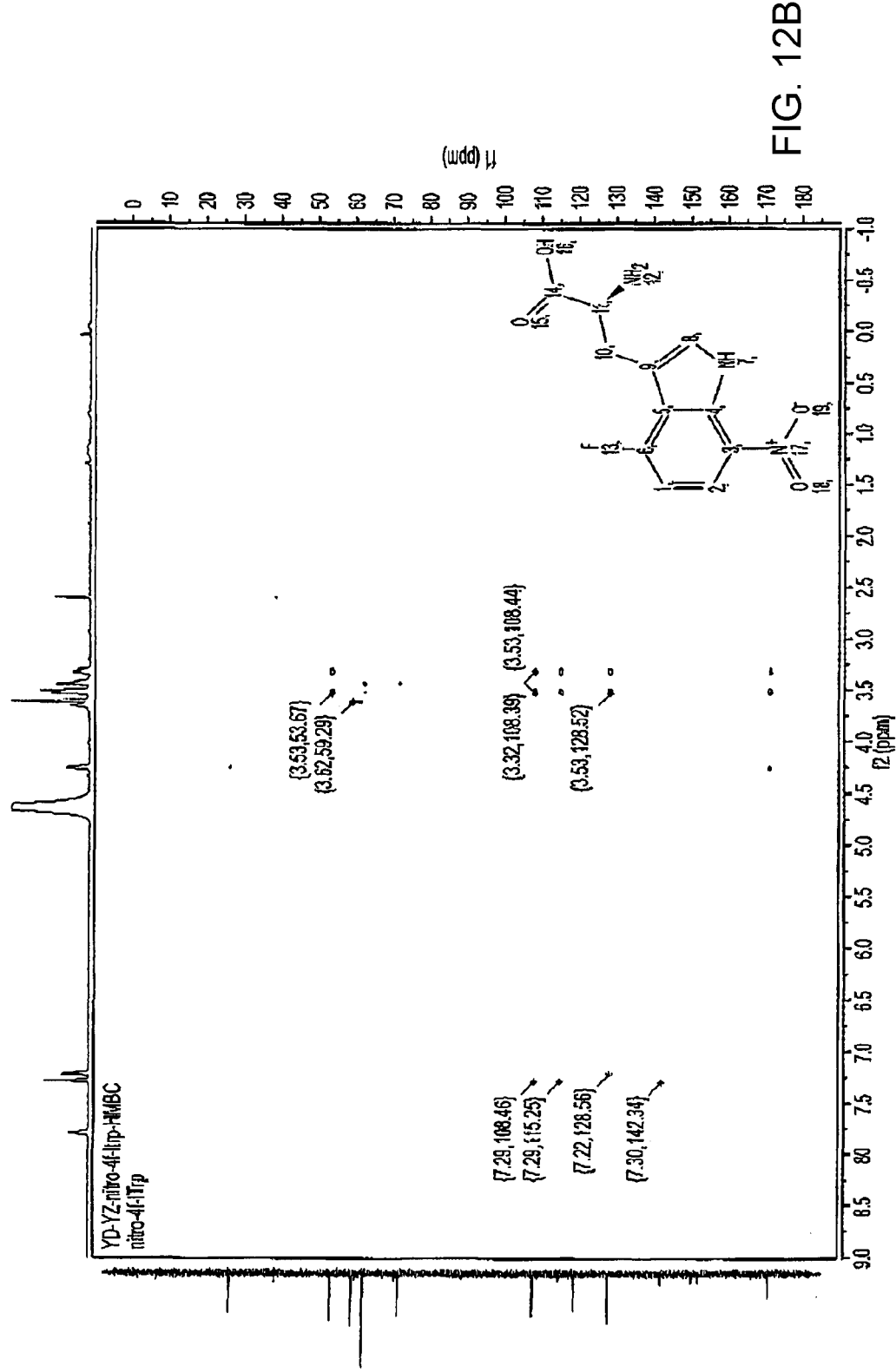

To further elucidate the nitro position in nitrated products, large scale enzymatic reactions were performed. About 90% of 5-F-L-tryptophan was nitrated and about 2 milligrams of the nitro product as a yellow powder were purified by a semi-preparative HPLC. Similarly, less than 0.2 milligrams of putative nitro-4-F-L-tryptophan as a light beige solid was isolated. Both products carried a single nitro group, and their corresponding exact masses were confirmed in HRMS analysis (FIGS. 8A-8B). Isolated products were further structurally characterized by $^1$H and $^{13}$C and 2D NMR analysis (FIGS. 9A, 9B, 10A, 10B, 11A, 11B, 12A, 12B, and Table 2). Examining the NMR data demonstrated that the $C_4$ and the $C_7$ of 5-F-L-tryptophan and 4-F-L-tryptophan, respectively, are nitrated in TxtE-BM3R reactions. From the $^1$H NMR spectrum of the nitro 5-F-L-tryptophan product (FIGS. 9A-9B), the large coupling constant (J=10.2 Hz) of the triplet-like peak at δ 6.95 ppm (C6) suggested a single vicinal coupling with the fluorine atom. Furthermore, a neighboring doublet peak at δ 7.52 ppm (C7) with a coupling constant J=8.8 Hz defined an ortho substitution pattern of the two aromatic protons. The aforementioned multiplicity and coupling constants therefore determined the C4 nitro substitution in the 5-F-L-tryptophan substrate, which was further confirmed by HSQC and HMBC analysis (FIGS. 11A, 11B, 12A, and 12B). From its $^1$H NMR spectrum, a triplet-like peak at δ 7.80 ppm (C5) displayed a doublet of doublet split with two approximately equal coupling constants of 8.1 Hz, suggesting a vicinal coupling with the fluorine atom. An ortho substitution pattern of the two aromatic protons was further defined by a large coupling constant (J=9.1 Hz) of neighboring doublet peak at δ 7.52 ppm (C6). Together, the nitro site was determined to be the C7 of 4-F-L-tryptophan, which was further confirmed by HSQC and HMBC analysis (FIGS. 11A, 11B, 12A, and 12B). These results therefore revealed TxtE as a versatile nitrating biocatalyst with remarkable regio-selectivity and substrate promiscuity.

TABLE 2

$^{13}$C and $^1$H NMR data for 5-fluoro-4-nitro-1-tryptophan and 4-fluoro-7-nitro-1-tryptophan (recorded in 50 mM DCl)

| Atom | 5-F-4-nitro-L-Trp | | 4-F-7-nitro-L-Trp | |
|---|---|---|---|---|
| | $δ_C{}^a$, type | $δ_H{}^b$ (J in Hz) | $δ_C{}^a$, type | $δ_H{}^b$ (J in Hz) |
| 2 | 131.7, CH | 7.35 s | 128.5, CH | 7.29 s |
| 3 | 105.9, C | | 108.3, C | |
| 3a | 117.9, C | | 115.2, C | |
| 4 | 129.5, C | | 151.5, C | |
| 5 | 150.9, C | | 119.4, CH | 7.80 dd (8.1, 8.1) |
| 6 | 110.4, CH | 6.95 dd (10.2,10.2) | 108.4, CH | 7.22 d (9.1) |
| 7 | 118.4, CH | 7.52 d (8.8) | 128.6, C | |
| 7a | 134.5, C | | 142.3, C | |
| 1' | 171.3, C | | 171.3, C | |
| 2' | 53.7, CH | 3.99 m | 53.7, CH | 4.26 m |
| 3' | 27.1, $CH_2$ | 3.23 dd (15.3, 5.6) 3.05 dd (15.3, 8.4) | 26.7, $CH_2$ | 3.43 dd (15.2, 6.5) 3.32 dd (15.2, 8.2) |

Example 7: Artificial Self-Sufficient Cytochrome p450 Enzymes

Figure 13A:
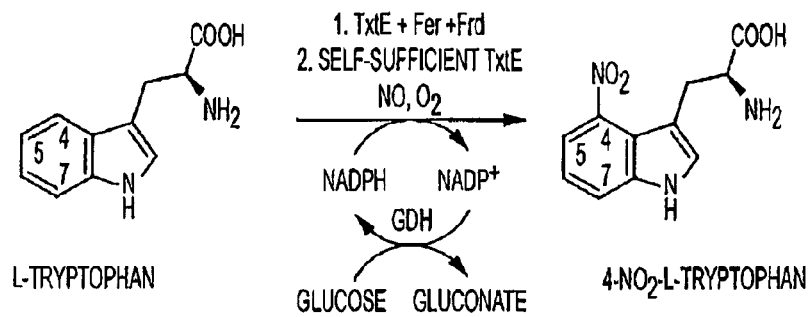
Figure 13B:
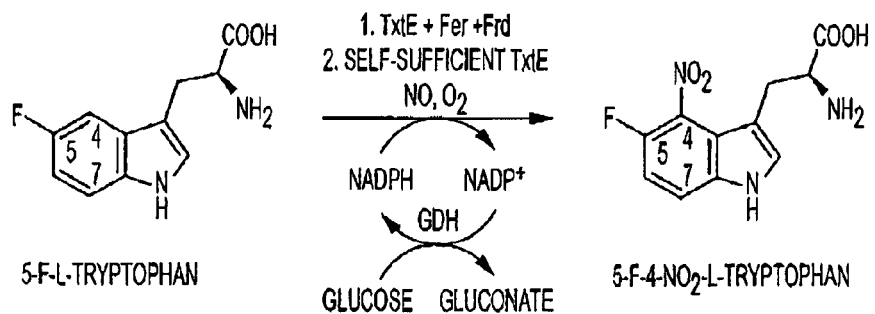
Figure 13C:
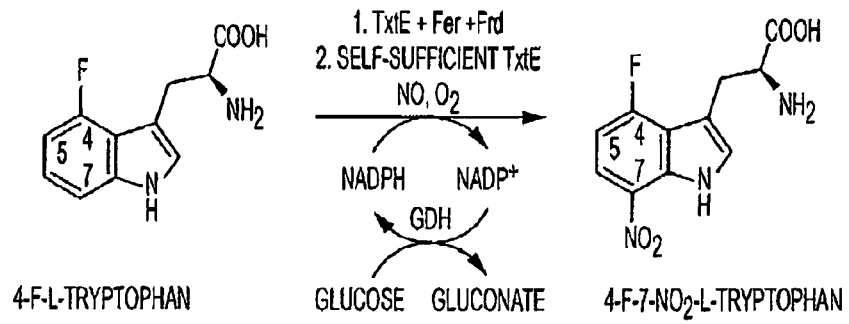

This example describes a direct nitration reaction on the L-tryptophan indole ring with $O_2$ and NO as co-substrates that is catalyzed by the enzyme TxtE (FIG. 13A).

General Chemicals, DNA Sub-Cloning, and Bacterial Strains

Molecular biology reagents and enzymes were supplied by Fisher Scientific. Primers were ordered from Sigma-Aldrich. 4-F-dl-Tryptophan was purchased from MP Biomedicals (Santa Ana, Calif.), while NOC-5 [3-(Aminopropyl)-1-hydroxy-3-isopropyl-2-oxo-1-triazene] was purchased from EMD Millipore. Marfey's reagent was purchased from Fisher Scientific. Other chemicals and solvents were purchased from Fisher Scientific and Sigma-Aldrich. *Escherichia coli* DH5α (Life Technologies) was used for cloning and plasmid harvesting, while *E. coli* BL21-GOLD (DE3) (Agilent) was used for protein overexpression. *E. coli* strains were grown in Luria-Bertani broth or Terrific broth. Preparation and manipulation of plasmid DNA from *E. coli* was accomplished following manufacture protocols from Thermo Scientific or Zymo Research. DNA sequencing was performed at Eurofins. A Shimadzu Prominence UHPLC system (Kyoto, Japan) fitted with an Agilent Poroshell 120 EC-C18 column (2.7 μm, 3.0×50 mm), coupled with a PDA detector was used for HPLC analysis and determination of chemical UV spectra. A 3200 QTRAP (Applied Biosystems) equipped with a Shimadzu UPLC system was used for LC-MS/MS analysis in the studies. All NMR spectra were recorded in $D_2O$ on an Agilent 600 MHz spectrometer using a 1.5 mm High Temperature Superconductor Probe in the AMRIS facility at the University of Florida. The instrument was operated at 600.17 MHz for $^1$H and 150.9 MHz for $^{13}$C. Spectroscopy data were collected using VNMRJ Version-4.0. HRMS data were obtained using an Agilent LC-TOF mass spectrometer equipped with electrospray source detector.

Construction of Self-Sufficient TxtE Variants

TxtE gene (Genbank: FN554889 REGION: 3613916 . . . 3615136) was amplified from genomic DNA of *S. scabies* 87.22 (NRRL B-24449) using a pair of TxtEFN and TxtERH primers (Table 1) in PCR reaction. The PCR mixture (50 μL) contained 50 ng template, 2 μM of each primer, 0.1 mM of dNTP, 3% dimethyl sulfoxide, and 0.5 μl Phusion high fidelity DNA polymerase in 1×GC reaction buffer. Reaction conditions consisted of an initial denaturation step at 98° C. for 30 s followed by 30 cycles of 98° C. for 10 s, 70° C. for 20 s, and 72 OC for 30 s, and a final extension of 72° C. for 5 min. The PCR product was analyzed by agarose gel and extracted with a GeneJET Gel Extraction Kit (Thermo) following a manufacture's protocol. To create the TxtE-P450BM3 reductase (BM3R) domain fusion gene, TxtE gene was amplified using a pair of TxtEFN and TxtEBRR primers while TxtEBRF and BRRS primers were used to amplify BM3R gene (GenBank: J04832.1) from the genome of *B. megaterium* ATCC 14581, which was then followed by an overlapping PCR. Similarly, TxtE-RhFRed and TxtE-RhFRed* fusion genes were generated by fusing TxtE gene with P450RhF reductase domain (RhFRed) gene (GenBank: AF459424.1) amplified from the template of pET21b-RhFRED. Corresponding primers were included in Table 1 Purified PCR products and pET28a were digested with the same sets of restriction enzymes and corresponding linear DNAs were ligated to generate expression constructs. All inserts in the constructs were sequenced to exclude mutations introduced during PCR amplification and gene manipulation.

Heterologous expression and purification of recombinant proteins

Insert validated constructs were transformed into E. coli BL21 (DE3)-GOLD competent cells for protein expression. Cells harboring the constructs were cultured in Terrific Broth medium supplemented with kanamycin (50 µg/ml) and 1× trace metal solution (1000× stock solution: 50 mM $FeCl_3$, 20 mM $CaCl_2$, 10 mM $MnSO_4$, 10 mM $ZnSO_4$, 2 mM $CoSO_4$, 2 mM $CuCl_2$, 2 mM $NiCl_2$, 2 mM $Na_2MoO_4$, and 2 mM $H_3BO_3$). Cultures were grown at 37° C., 250 rpm until $OD_{600}$ reached 0.6. Protein expression was then induced by isopropyl-β-D-thiogalactopyranoside (IPTG) with a final concentration of 0.1 mM. The cultures were further grown at 16° C., 250 rpm for 16 hours. After centrifugation (5,000 g, 10 min, and 4° C.), cell pellets were stored at −80° C. or directly used for protein purification. For protein purification, cell pellets were first resuspended in the suitable volumes of lysis buffer (cell biomass:volume=1:4) [25 mM Tris-HCl, pH 8.0, 100 mM NaCl, 20 mM imidazole, 3 mM β-mercaptoethanol (BME) and 10% glycerol]. Soluble proteins were released by sonication. After centrifugation at 35,000×g at 4° C. for 30 min, the clear supernatants were incubated with pre-equilibrated Ni-NTA agarose resin (Thermo) at 4° C. for 2 h. The resins were washed with 10 volumes of lysis buffer with 30 mM imidazole, and recombinant P450s were then eluted in lysis buffer with 50 to 320 mM imidazole. After SDS-PAGE analysis, elution solution fractions containing P450s were combined and concentrated. The proteins were then exchanged into storage buffer (25 mM Tris-HCl, pH8.0, 100 mM NaCl, 3 mM βME, and 10% glycerol) using a PD-10 column according to the manufacture's protocol, aliquoted and stored at −80° C. until needed. The concentrations of functional P450s were accurately measured by CO difference spectroscopy.

Spectral Analysis of Self-Sufficient TxtE Variants

Purified TxtE and its fusion enzymes were spectrally analyzed following a previous protocol. Briefly, the absorbance spectra (400-600 nm) of TxtE variants (3 µM) in Tris-HCl (25 mM, pH 8) buffer were recorded with a Shimadzu UV2700 dual beam UV-Vis spectrophotometer. The ferric heme of enzymes was then saturated with carbon monoxide (Airgas) through bubbling and the spectra of the saturated enzyme solutions were recorded. Immediately, sodium dithionite solution (30 µL, 0.5 M) was added to reduce ferric ion, and reduced spectra were taken subsequently. CO reduced difference spectra of all enzymes were created by subtracting the CO binding spectra from the reduced spectra. Data were further analyzed by GraphPad Prism 4. Substrate binding affinities to P450s were measured using 1.5 µM of enzyme solutions in 25 mM Tris-HCl, pH 8.0. Not more than 10 µl of substrate stock solutions prepared in the above buffer were added to the sample cuvette with an interval of 0.5 µl, and the spectra were recorded from 300 nm to 500 nm each time. The equal volume of buffer was added to the reference cuvette. The changes in absorbance (ΔA) were determined by subtracting the absorbance at ~420 nm from that at ~390 nm. Data were then fitted to the equation of $\Delta A=\Delta A_{max}[L]/(K_d+[L])$ using GraphPad Prism 4.

Analytical and Semi-Preparative HPLC Analysis

For analytical analysis, the HPLC column kept at 40° C. was eluted first with 1% solvent B (acetonitrile with 0.1% formic acid) for 0.5 min and then with a linear gradient of 1-20% solvent B in 2 min, followed by another linear gradient of 20-99% solvent B in 0.5 min. The solvent A was water with 0.1% formic acid. The column was further cleaned with 99% solvent B for 0.5 min and then re-equilibrated with 1% solvent B for 2 min. The flow rate was set as 1.5 mL/min, and the products were detected at 211 nm with a PDA detector. All enzyme reactions were performed at least in triplicate.

For semi-preparative analysis, the column kept at 40° C. was eluted first with 20% solvent B (acetonitrile with 0.1% formic acid) for 3 min and then with a linear gradient of 20-54% solvent B for 3 min, followed by a linear gradient of 54-77% solvent B for 6 min. The column was then cleaned by 99% solvent B for 1 min and re-equilibrated with 20% solvent B for 1 min. The flow rate was set at 3 mL/min, and the products were detected at 211 nm with a PDA detector. All isolates were combined, concentrated, freeze-dried, and then weighed.

LC-MS/MS and NMR Analysis of Isolated Products

A SHIMADZU Prominence UPLC system fitted with an Agilent Poroshell 120 EC-C18 column (2.7 µm, 3.0×50 mm) coupled with a Linear Ion Trap Quadrupole LC/MS/MS Mass Spectrometer system was used in the studies. The column was eluted with 1% solvent B (acetonitrile with 0.1% formic acid) for 2 min and then with a linear gradient of 1-20% solvent B in 8 min, followed by another linear gradient of 20-99% solvent B in 2.5 min. The column was then cleaned by 99% solvent B for 0.5 min and re-equilibrated with 1% solvent B for 2.5 min. The flow rate was 0.5 mL/min. For MS detection, the turbo spray conditions were identical for all chemicals (curtain gas: 30 psi; ion spray voltage: 5500 V; temperature: 750° C.; ion source gas 1: 60 psi; ion source gas 2: 70 psi). For MS/MS analysis, the collision energy was 20 eV. In NMR analysis, chemical shifts were reported in parts per million (ppm) downfield from tetramethylsilane. Proton coupling patterns were described as singlet (s), doublet (d), double doublet (dd), triplet (t), and multiplet (m). 5-F-4-nitro-l-tryptophan: $^1$H NMR (600 MHz, $D_2O$) δ 7.52 (d, J=8.8 Hz, 1H), 7.35 (s, 1H), 6.95 (t, J=10.2 Hz, 1H), 4.04-3.93 (m, 1H), 3.23 (dd, J=15.3, 5.6 Hz, 2H), 3.05 (dd, J=15.3, 8.4 Hz, 2H); $^{13}$C NMR (151 MHz, $D_2O$) δ 171.29, 151.69, 150.03, 134.52, 131.66, 129.49, 129.41, 118.41, 118.34, 117.89, 110.47, 110.30, 105.89, 105.86, 72.01, 62.46, 59.31, 53.65, 27.09. HRMS (ESI$^+$): calc. for $C_{11}H_{11}FN_3O_4$ [M+H]$^+$: 268.0728, found: 268.0728. 4-F-7-nitro-l-tryptophan: $^1$H NMR (600 MHz, $D_2O$) δ 7.80 (t, J=8.1 Hz, 1H), 7.29 (s, 1H), 7.22 (d, J=9.1 Hz, 1H), 4.29-4.23 (m, 1H), 3.43 (dd, J=11.7, 6.5 Hz, 2H), 3.32 (dd, J=15.2, 8.2 Hz, 1H); $^{13}$C NMR (151 MHz, $D_2O$) δ 171.29, 152.41, 150.65, 142.34, 142.24, 128.59, 128.48, 119.38, 115.29, 115.18, 108.40, 108.35, 72.00, 62.45, 59.30, 53.73, 38.70, 26.72. HRMS (ESI$^-$): calc. for $C_{11}H_{11}FN_3O_4$[M−H]$^-$ 266.0583, found: 266.0577.

Marfey's Derivatization

To determine the stereoisomer of 4-F-dl-tryptophan in the nitration reaction, l-tryptophan, 4-nitro-l-tryptophan, 5-F-l-tryptophan, 5-F-4-nitro-l-tryptophan, 4-F-dl-tryptophan, and nitrated 4-F-dl-tryptophan from enzyme reactions and in purified form were reacted with Marfey's reagent following the manufacture manual (Thermo Scientific). Derivatized products were analyzed by LC-MS with A SHIMADZU Prominence UPLC system fitted with a Waters Symmetry-Shield™ RP-C18 column (3.5 µm, 4.6×100 mm) and a Linear Ion Trap Quadrupole LC/MS/MS Mass Spectrometer system. The column was eluted with 90% solvent A (0.05 M triethylammonium acetate, pH 3.0), 10% solvent B (acetonitrile) for 2 min and then with a linear gradient of 10-50% solvent B in 60 min. The column was then cleaned by 50% solvent B for 5 min and re-equilibrated with 10% solvent B for 2 min. The flow rate was 0.5 mL/min. For MS detection, the turbo spray conditions were the same as described above.

Catalytic Activities of Self-Sufficient TxtE Variants

P450 reactions contained 0.5 mM substrate, 1 mM $NADP^+$, 1 mM glucose, ~10 units/mL self-prepared glucose dehydrogenase crude extract, 1 mM NOC-5 [3-(aminopropyl)-1-hydroxy-3-isopropyl-2-oxo-1-triazene] in 100 μL of Tris-HCl buffer (100 mM, pH 8.0). As the positive control, the TxtE reaction was also re-constructed in the above mixture further supplemented with 0.43 μM spinach Fer and 0.33 μM Frd. The reactions were initiated by adding 1.5 μM P450s, and incubated at 20° C., 300 rpm on a thermostat (Eppendorf) for 2 hours. Methanol (200 μl) was then added to stop the reactions. After centrifugation, 10 μl solutions were analyzed by HPLC. Total turnover number (TTN) was reported as nmol product per nmol P450. The 4-$NO_2$-l-tryptophan was synthesized in a large-scale enzymatic reaction to establish a standard curve for product quantification. To determine the coupling efficiency, NADPH (2 mM) replaced the NADPH regeneration system ($NADP^+$, glucose, glucose dehydrogenase crude extract) in the reaction mixture. NADPH consumption in enzyme reactions was measured at 340 nm ($\varepsilon$=6.22 $mM^{-1} \cdot cm^{-1}$) with a Shimadzu UV2700 dual beam UV-Vis spectrophotometer. Non-enzymatic oxidation of NADPH was subtracted as the background. The quantity of nitrated product was determined by HPLC analysis as described above. Coupling efficiency (%) was determined as product (nmol)/consumed NADPH (nmol)×100. All reactions were independently repeated at least three times.

Biochemical Characterization of Self-Sufficient TxtE Variants.

The stability of NO donor NOC-5 was first examined by incubating it in solutions of different pH values (4.5 to 9.5) and temperatures (4 to 65° C.) for 30 min. NOC-5 was stable at all tested pH values but decomposed quickly and significantly at temperatures higher than 25° C. It was then used as the NO donor in the following experiments. To determine pH effects on the activity of TxtE and TxtEBM3R, enzyme (1.5 μM) reactions were performed in 100 mM Tris-Cl or sodium phosphate at different pH values (4.5 to 9.5) at 20° C., 300 rpm for 30 min. To determine enzyme pH stability, 5 μL of 30 μM enzyme solutions were incubated in buffers with different pH values (4.5 to 9.5). After 15 min, other reaction components (95 μL) were mixed to initiate nitration reactions as described above. To test enzyme thermostability, TxtE and TxtEBM3R were incubated in 100 mM Tris-HCl (pH 8.0) at different temperatures (4° C., 15° C., 20° C., 25° C., 30° C., 35° C., 40° C., 45° C., 55° C., and 65° C.) for 15 min. After cooling on ice for 5 min, enzyme solutions were centrifuged and then used to initiate reactions at 20° C., 300 rpm for 30 min. Products were quantitated by HPLC as described above. Peak area was determined with software installed in the Shimadzu Prominence UHPLC system. Conversion rate (%) was calculated as product (nmol)/product+substrate (nmol)×100 based on the standard curves of Trp and 4-$NO_2$-Trp generated. All experiments were performed at least in triplicate. In this study, the $T_{50}$ is defined as the temperature at which a 15-min incubation of the enzyme causes the loss of one-half of the enzyme activity, relative to a 100% activity reference enzyme that does not undergo incubation.

Large-Scale Enzymatic Synthesis of Nitrated Fluoro-Tryptophan Analogs

To isolate sufficient amounts of nitrated fluoro-tryptophan analogs for structural determination, 18 μM TxtEBM3R was used in a 10-mL reaction mixture containing 1.5 mM fluorinated substrate, 3 mM $NADP^+$, 3 mM glucose, ~30 units/mL self-prepared glucose dehydrogenase crude extract, 3 mM NOC-5 in 100 mM Tris-HCl buffer (pH 8.0). The reactions in a 200-ml flask were incubated at 20° C., 250 rpm overnight, and then terminated by 20 mL methanol addition or acidification to pH 1.0 with 6 M HCl. After centrifugation, the supernatants were concentrated in vacuo and then freeze-dried. The products were redissolved in 3 ml methanol. Semi-preparation was performed with a semi-prep C18 column (Agilent ZORBAX SB-C18, 5 μm, 9.4× 250 mm).

Creation of Properly Folded Self-Sufficient TxtE Variants

Figure 14A:
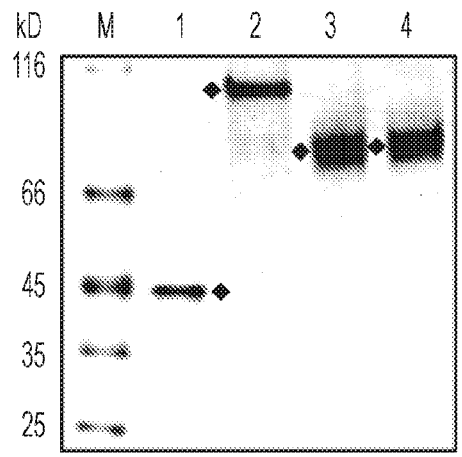
Figure 14C:
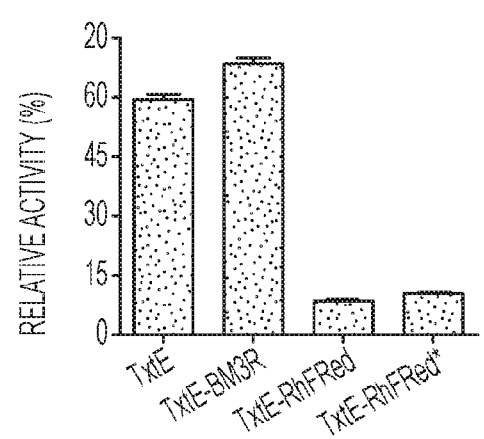
Figure 14B:
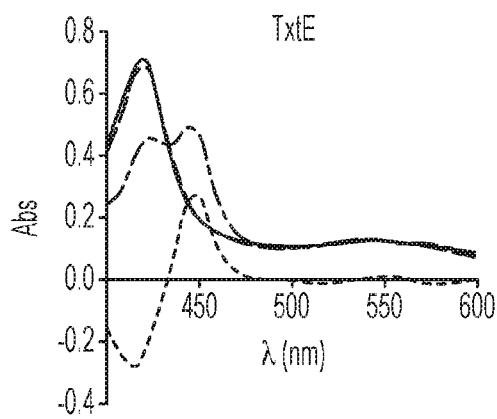
Figure 14B:
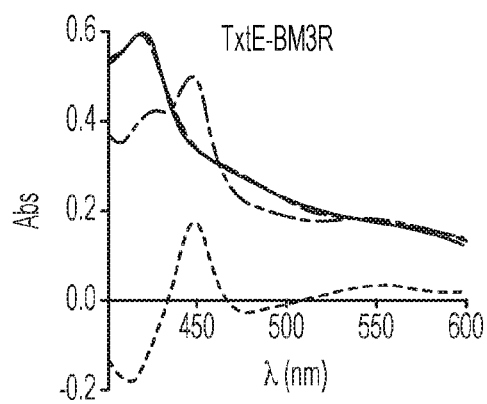
Figure 14B:
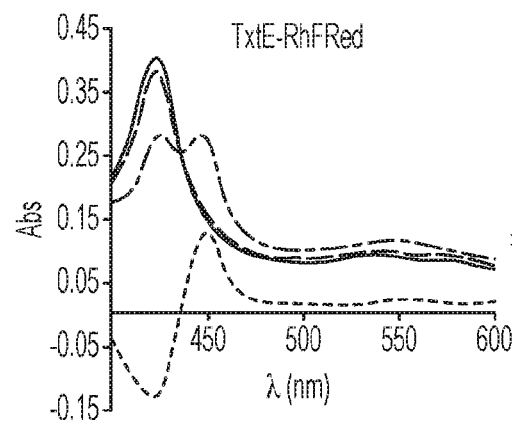
Figure 14B:
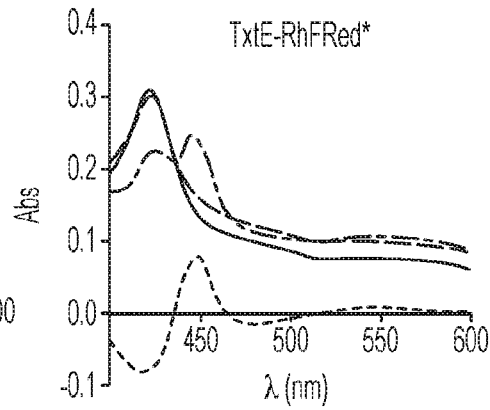

TxtE promotes a regio-selective nitration on the C4 of the l-tryptophan indole ring using $O_2$ and NO as co-substrates and consuming NADPH (FIG. 13A). Although the native redox partners of TxtE remain unidentified, spinach Fer and Frd were able to support the reaction. To use TxtE as a broadly applicable biocatalyst for aromatic nitration, three artificial self-sufficient TxtE fusion enzymes, TxtE-BM3R, TxtE-RhFRed, and TxtE-RhFRed*, were designed by appending NADPH-dependent reductase domains of P450BM3 and of P450RhF to the C-terminus of TxtE. The linker of TxtE-BM3R was predicted from P450BM3 using software Domcut. Due to proven effects of linker lengths on catalytic activities of RhFRed fusion enzymes, two fusion enzymes were created. TxtE-RhFRed contained the native linker length, while TxtE-RhFRed* has eight additional residues: this design offered the highest activities in previous studies. All fusion enzymes were expressed in E. coli and purified to homogeneity with over 85% purity by a single nickel affinity chromatography (FIG. 14A). All recombinant proteins showed calculated molecular weights, 112 kD for TxtE-BM3R and about 82 kD for both TxtE-RhFRed and TxtE-RhFRed*, in SDS-PAGE analysis (FIG. 14A). To assess the functional folding of recombinant fusion proteins, UV/Vis spectroscopy was used to record their absorption spectra (FIG. 14B). The CO-bound oxidized form and reduced form of these enzymes resembled similar features to wild type TxtE and other bacterial CYPs. Soret peaks were shifted from around 419 nm in the oxidized forms to around 449 nm in the reduced-CO difference forms (dotted lines), indicating the proper folding of all fusion enzymes.

Catalytic Performances of Fusion Enzymes

Figure 15:
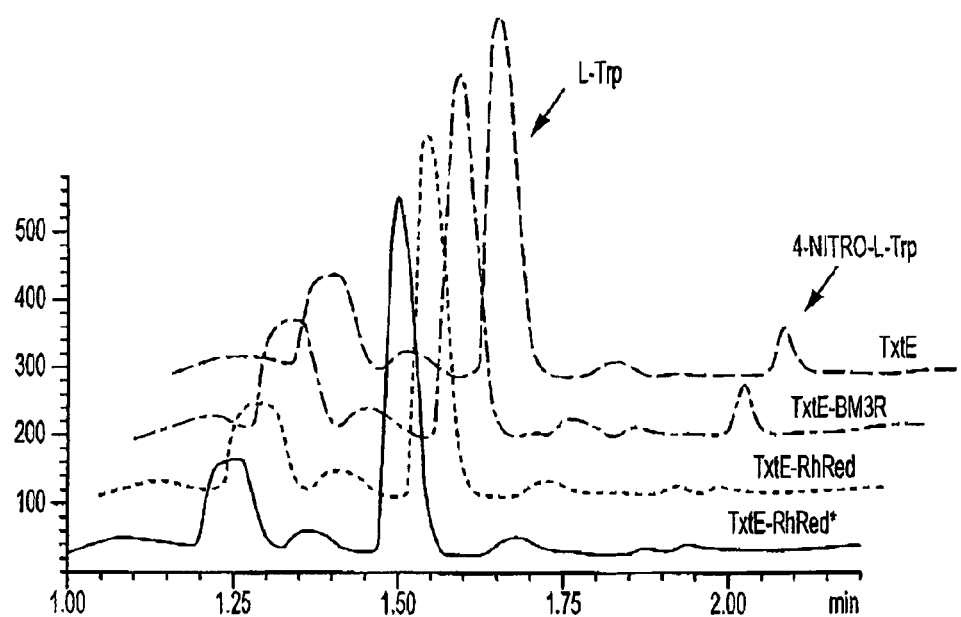
Figure 16A:
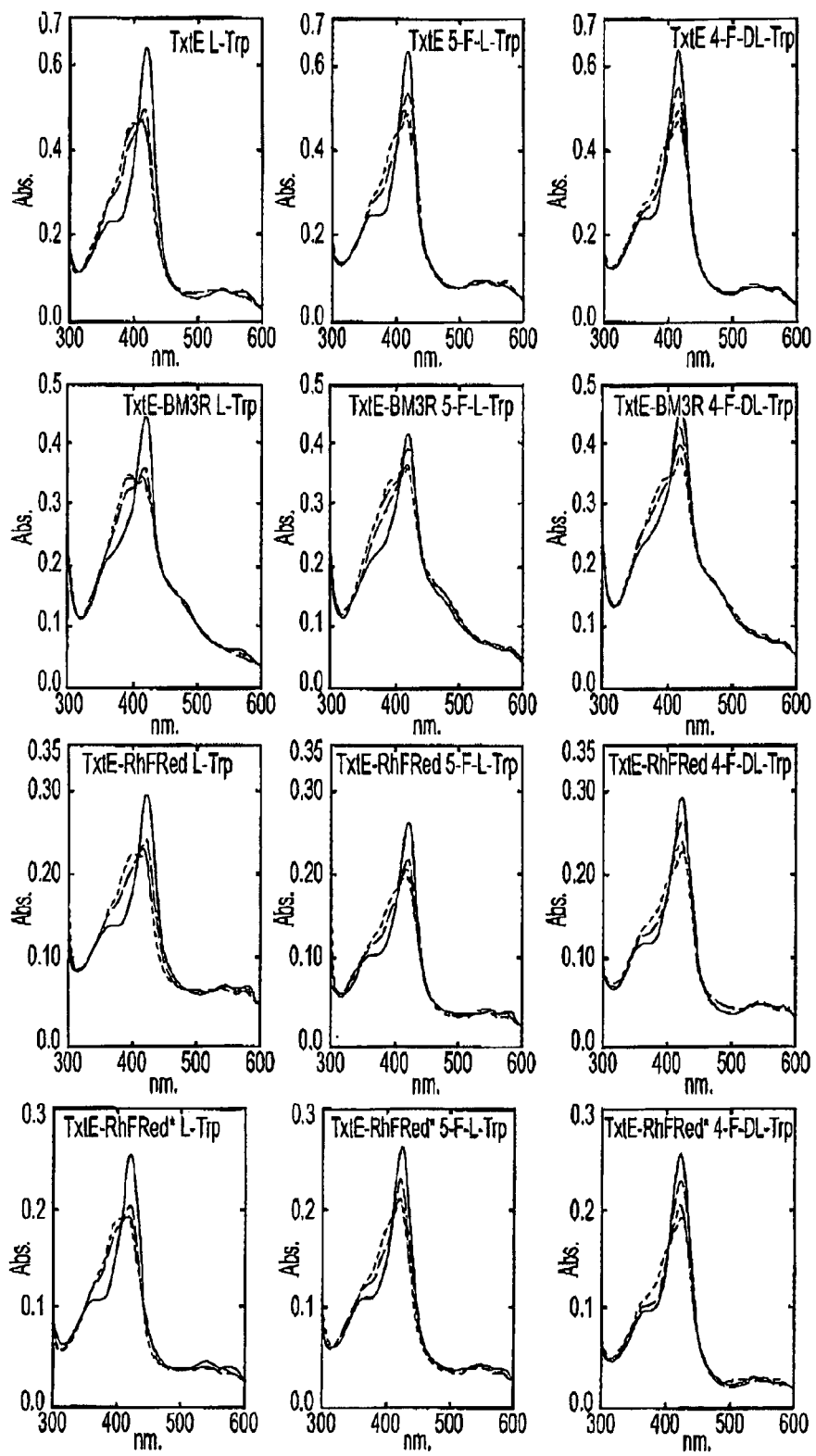
Figure 16B:
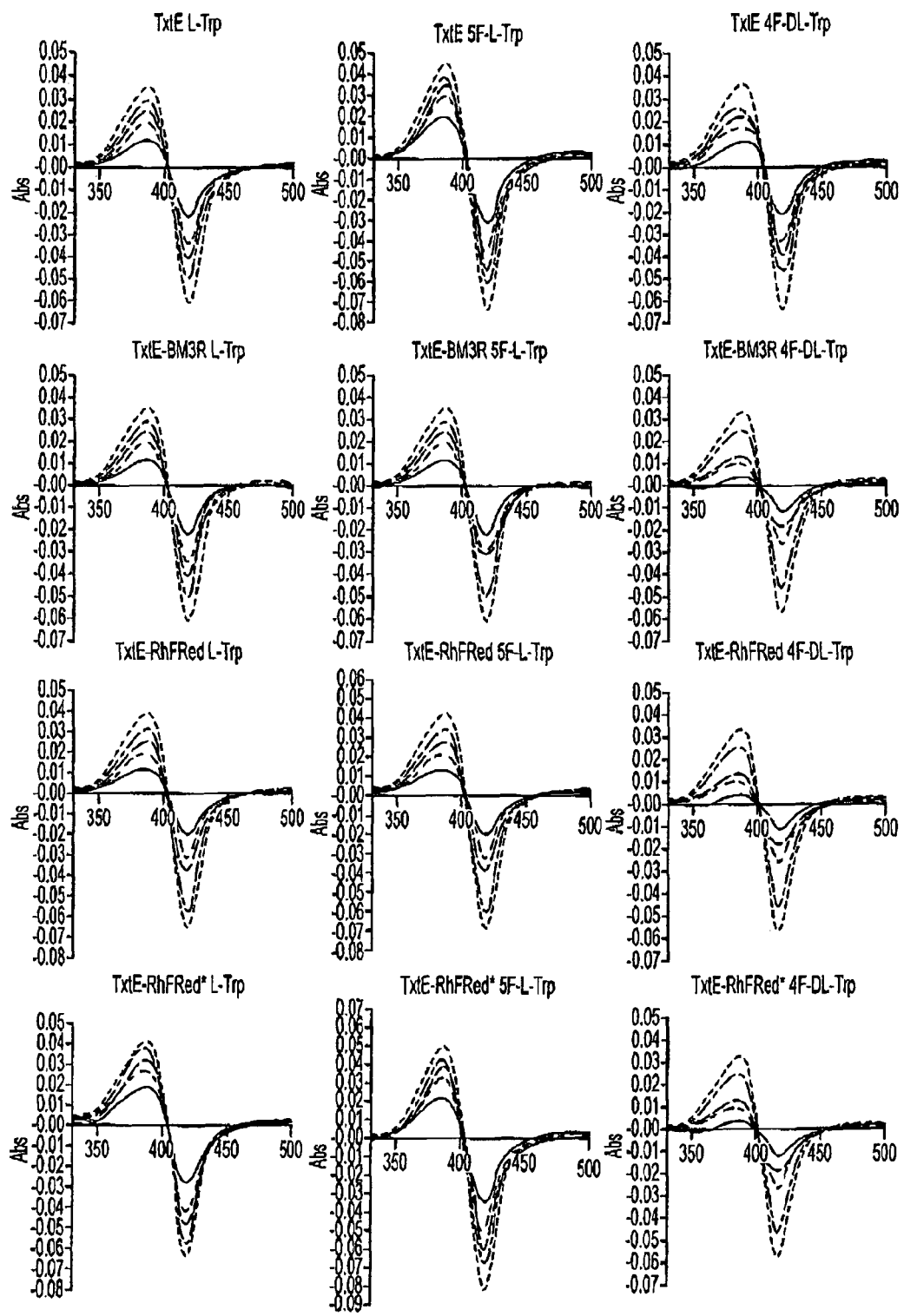

Catalytic activities of all three fusion enzymes were assessed, with the control of wild type TxtE coupled with spinach Fer and Frd. HPLC analysis of reaction mixtures revealed that all fusion enzymes nitrated l-tryptophan to a different extent (FIG. 14C). After 2 hours, TxtE-BM3R exhibited slightly higher conversion (18.1%) than the control (15.9%), while both TxtE-RhFRed and TxtE-RhFRed* only reached 2.1% and 2.8%, respectively (FIG. 15). In consistency with these observations, TTN values of both TxtE-RhFRed and TxtE-RhFRed* were less than 10, while TxtE-BM3R catalyzed over 320 nitration cycles, similar to TxtE (Table 3). To examine the extent to which the fusion arrangement influenced the substrate-enzyme interaction, which might induce the observed variation of enzyme performance, the binding of L-tryptophan toward all fusion enzymes was assessed and the Type I spectral changes were observed (FIGS. 16A-16B). The shift from 420 to 390 nm is expected when a P450 substrate displaces the axial water ligand from the heme iron, which changes the heme's iron from its low-spin state to the high-spin state (FIG. 16A). Binding affinities were then determined by examining the differential UV-Visible spectra with various substrate concentrations (FIG. 16B). TxtE-RhFRed showed the highest binding affinity with the $K_d$ value of 18.2±1.4 µM, followed by TxtE-BM3R ($K_d$=20.8±0.4 µM) and TxtE-RhFRed* ($K_d$=24.3±1.2 µM). These values remained in the same range as wild type TxtE ($K_d$=24.8±1.1 µM), indicating that fusion design had a minimal effect on substrate binding. Coupling efficiency was then determined in order to evaluate electron transfer compatibility of each enzyme during the nitration reaction (Table 3). Coupling efficiency of the TxtE-BM3R was slightly (1.9%) lower than TxtE (2.4%) coupled with Fer and Frd. However, TxtE-RhFRed and TxtE-RhFRed* showed 8- and 24-folds decreased coupling efficiency, respectively, in comparison with TxtE. Therefore, the fusion organization between TxtE and RhFRed impaired proper electron transfer. Nonetheless, TxtE-BM3R was comparable with TxtE in term of catalytic performance.

Figures 29A, 29B:
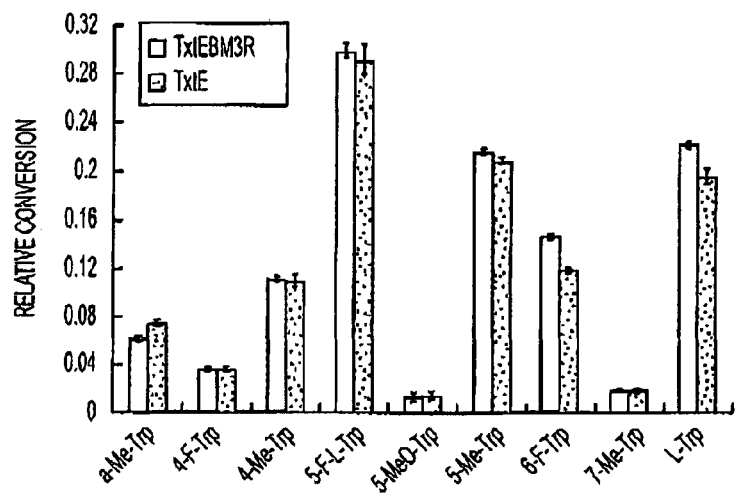
FIGS. 29A-29B show: binding affinities (FIG. 29A); and relative nitration conversions (FIG. 29B) for L-tryptophan and substituted tryptophan analogs

Binding affinities and relative nitration conversions for L-tryptophan and several substituted tryptophan analogs were also assessed (FIGS. 29A-29B). Substrates with changes on the amine or carboxylate moieties (e.g., L-tryptophanol; α-Me-Trp; indole-3-pyruvate) showed significantly weakened interactions while compounds with substitution on the indole ring maintained binding affinity (FIG. 29A). Furthermore, the nitration activity of TxtE and TxtEBM3R was assessed. In addition to substrate, enzyme reactions typically contained NADP+, an NADPH regeneration system (glucose and glucose dehydrogenase, GDH), spinach ferredoxin (Fer) and ferredoxin reductase (Frd) as redox partners, and 3-[2-hydroxy-1-(1-methylethyl)-2-nitrosohydrazinyl]-1-propanamine (NOC-5) as an NO donor. Reverse-phase UHPLC coupled with a PDA detector and liquid chromatography-mass spectrometry (LC-MS, ESI positive) was employed to detect the nitrated products (FIG. 29B).

Biochemical Characterization of TxtE and TxtE-BM3R

Figure 17A:
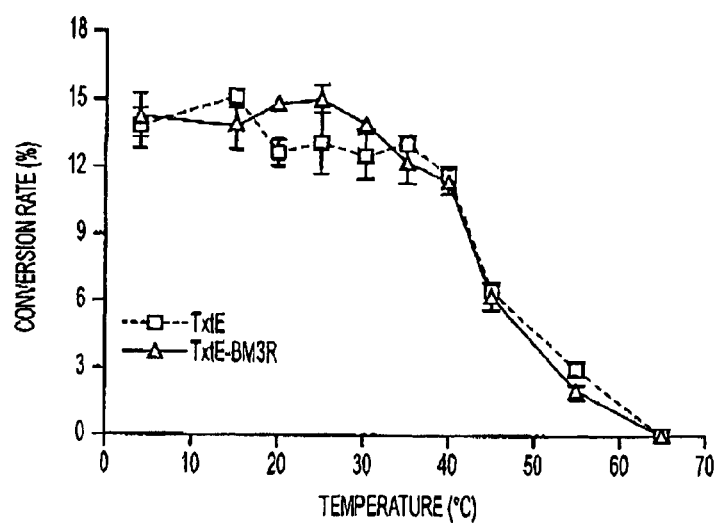
Figure 17B:
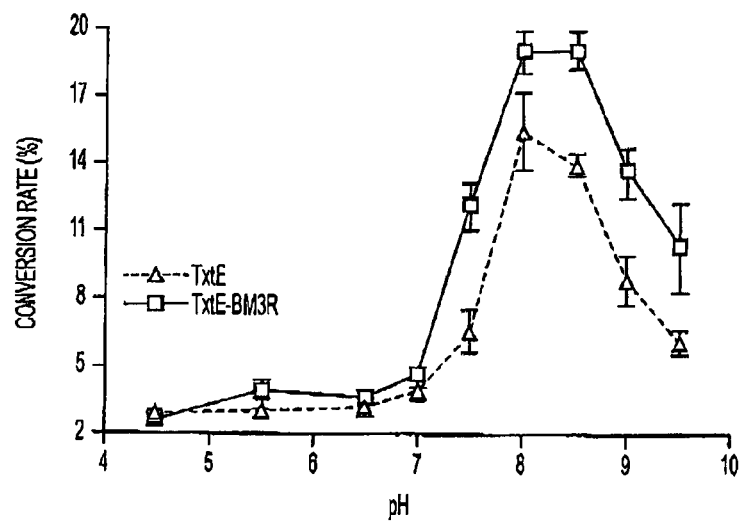
Figure 18:
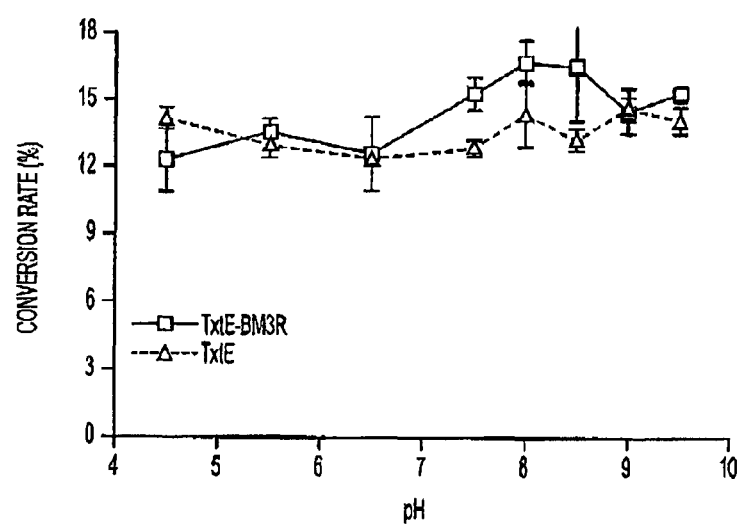

To investigate biochemical properties of nitration biocatalysts, thermostability of both TxtE and TxtE-BM3R was examined (FIGS. 17A-17B). These enzymes were incubated at different temperatures (4 to 65° C.) for 15 min and then used in the L-tryptophan nitration reaction at 20° C. Both enzymes showed a similar level of thermostability with a $T_{50}$ of around 45° C. (FIG. 17A). After incubation at 65° C. for 15 min, their activity was completely lost, indicating irreversible conformational changes at high temperature. Next, the pH dependence of TxtE and TxtE-BM3R was examined using NOC-5 as the NO donor (FIG. 17B). This reagent is stable over a broad pH range (data not shown). Both enzymes remained <5% activity in buffers with pH below 7.0. TxtE-BM3R showed over 50% activity from pH 7.5 to pH 9.5 and an optimal pH range of 8.0 to 8.5. TxtE's activity depended on a narrower pH range with optimal activity at pH 8.0. The extent to which the stability of both enzymes were affected by buffers with different pH values was examined. After incubation in these buffers for 15 min, enzymes were then used to nitrate l-tryptophan at pH 8.0, 20° C. (FIG. 18). HPLC analysis revealed that enzyme activities were only minimally affected by the incubation in different buffers. This result suggested that the pH dependence of enzyme activity (FIG. 17B) was not associated with enzyme pH stability.

Enzymatic Production of Fluorinated Nitro-Tryptophan Analogs

Figure 19:
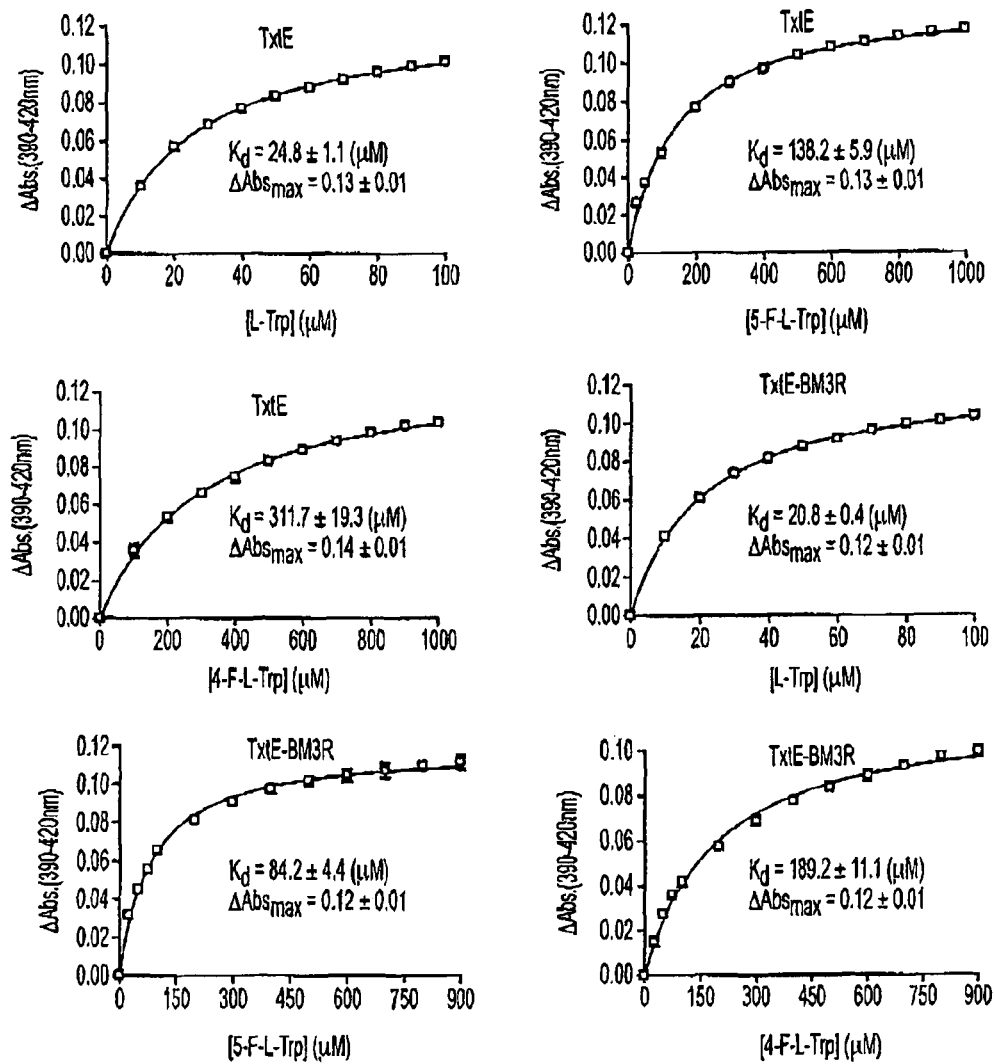
Figure 20A:
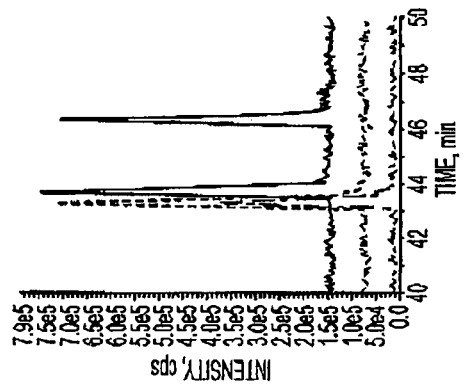
Figure 20B:
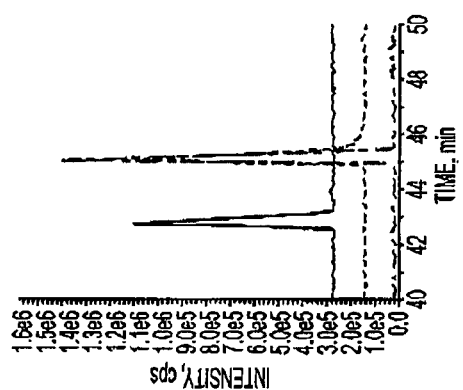
Figure 20C:
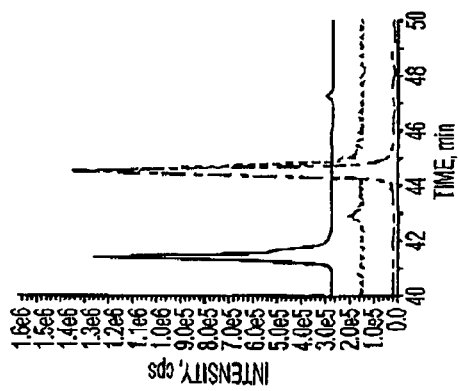
Figure 21A:
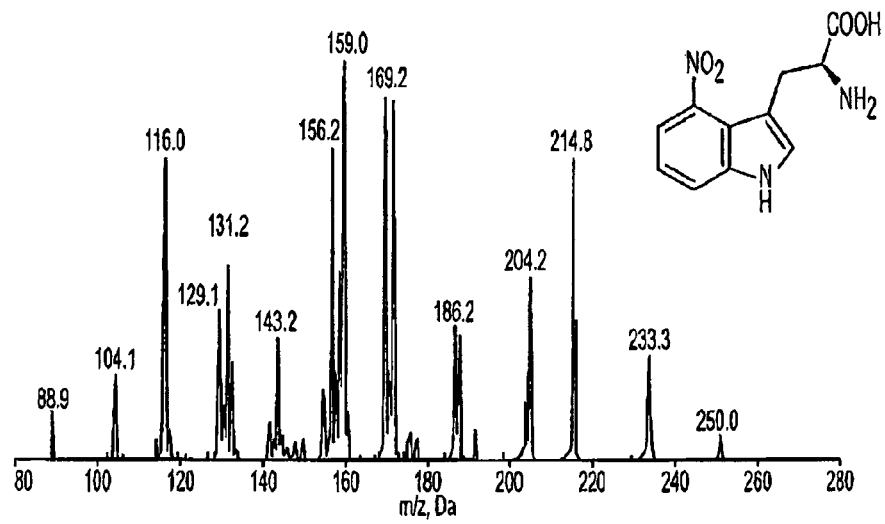
Figure 21B:
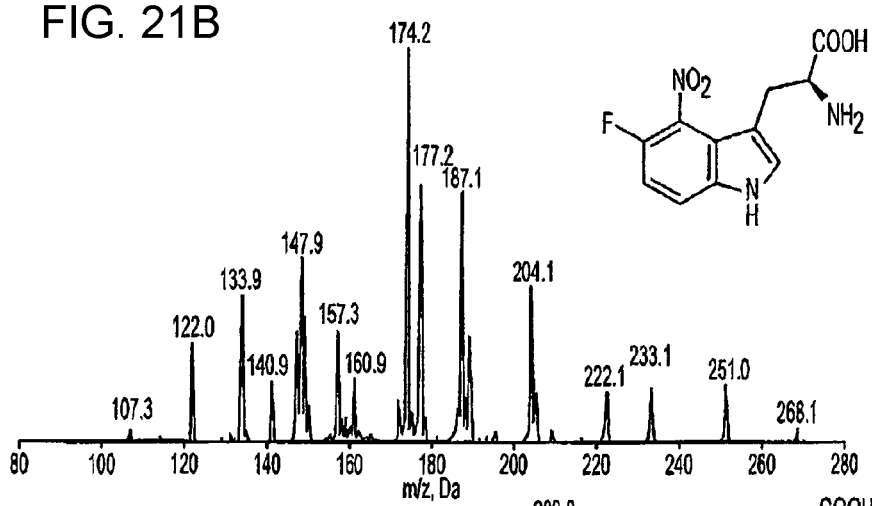
Figure 21C:
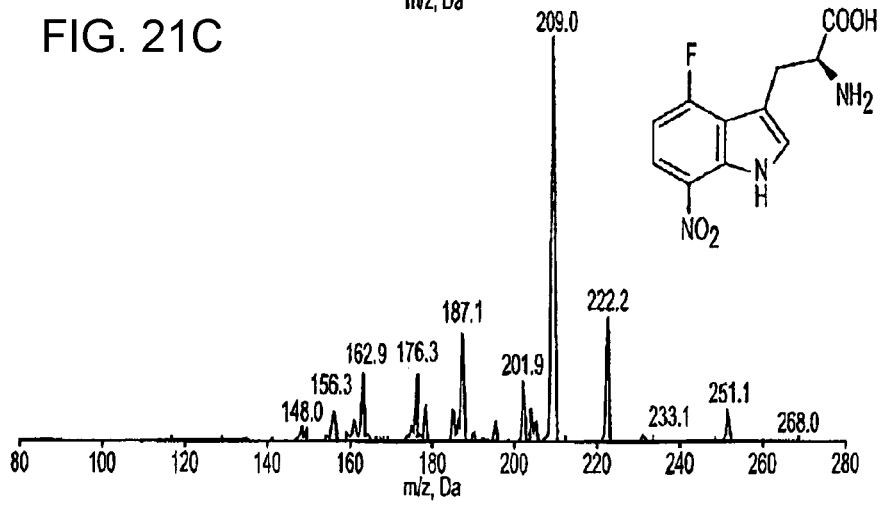
Figure 22:
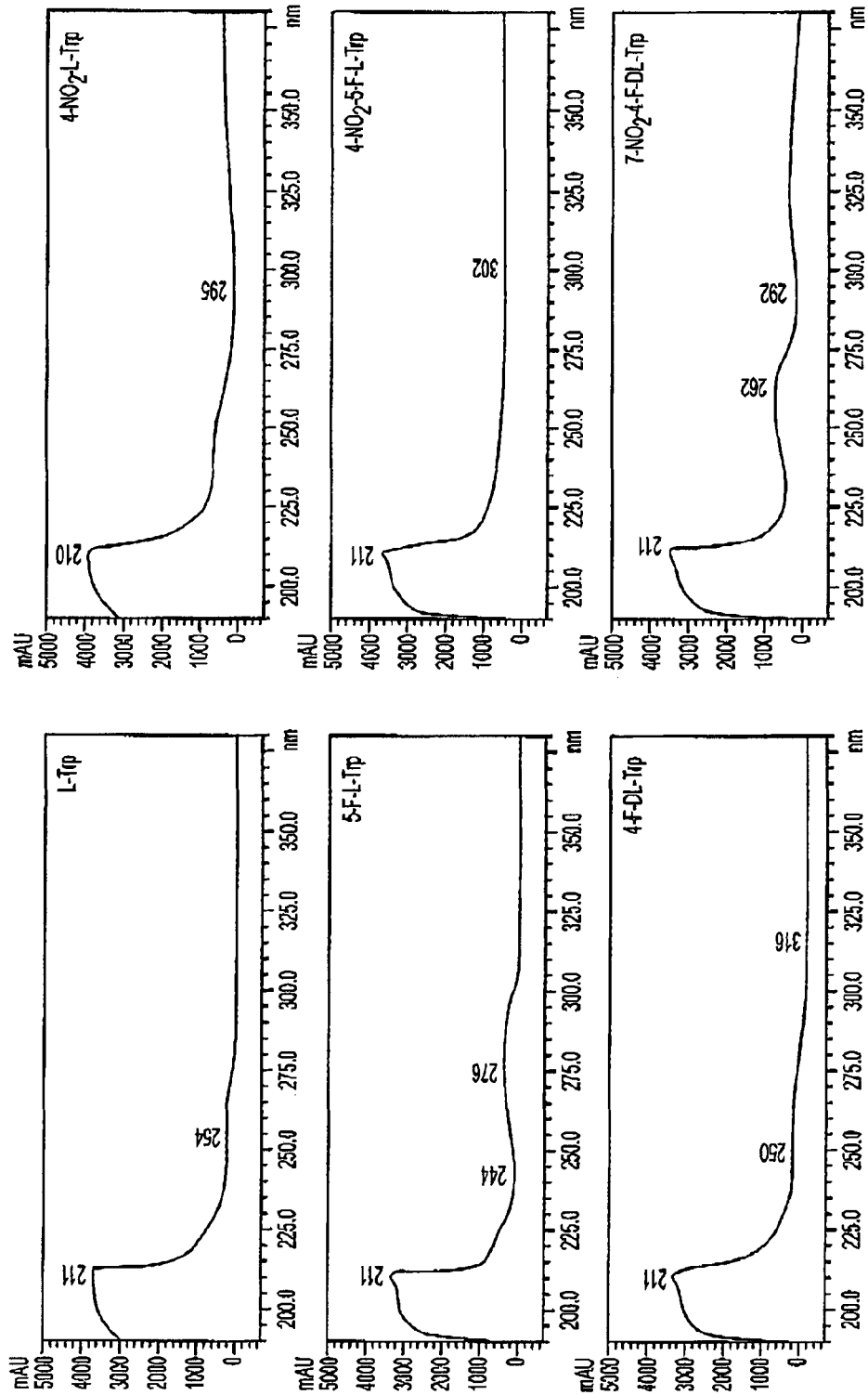
FIG. 22 shows UV spectra of all three substrates and their corresponding nitrated products as determined by Shimadzu PDA detector coupled with UHPLC system. All compounds have the same maximal absorbance wavelength at 211 nm.

To expand the applications of TxtE-BM3R in nitration, the enzyme was used to nitrate two unnatural substrates, commercially available racemic 4-F-dl-tryptophan and 5-F-l-tryptophan. Fluorine substitution is a common strategy used by medicinal chemists to generate drug molecules with improved properties. The two fluorinated substrates induced type I spectral changes in solutions of TxtE and TxtE-BM3R (FIGS. 16A-16B). Similarly, they bound to TxtE-RhFRed and TxtE-RhFRed*. The binding affinity between each substrate and TxtE-BM3R was about 60% higher than to TxtE, indicating that BM3R might facilitate substrate binding (FIG. 19). In previous studies, d-tryptophan is unable to induce spectral changes in TxtE solution. Next, derivatized l-tryptophan, 5-F-l-tryptophan, 4-F-dl-tryptophan, and their nitrated products were produced in the enzyme reactions and also produced in purified form with Marfey's reagent. LC-MS analysis identified only one derivatized product from nitrated 4-F-dl-tryptophan and suggested to be nitro-4-F-l-tryptophan (FIGS. 20A-20C). With current inaccessibility to optically pure 4-F-l-tryptophan, the total concentration of the racemic mixture was used to calculate $K_d$ values, which thus underestimated the accurate binding affinities. Nonetheless, compared with the native substrate l-tryptophan ($K_d$=20.8±0.4 µM), the binding affinities between TxtE-BM3R and 4-F-dl-tryptophan ($K_d$=189.2±11.1 µM) and 5-F-l-tryptophan ($K_d$=84.2±4.4 µM) were lowered by about 8 and 3 times, respectively, reflecting the binding interferences induced by the F-substitution. Next, the influences of the fluorination substitution on enzyme activity were examined. Remarkably, both TxtE and TxtE-BM3R slightly preferred 5-F-l-tryptophan over l-tryptophan (1.2:1) in the nitration reaction. In addition, although the C4 in 4-F-l-tryptophan is occupied by an F substitution, both enzymes were able to nitrate this substrate as characterized by HPLC and LC-MS/MS analysis (FIGS. 21A-21C). The overall conversion rate was, however, only about 20% of l-tryptophan. The F substitution did not induce any significant change on the UV spectra of substrates and nitrated products (FIG. 22).

Structural Characterization of Fluorinated Nitro-Tryptophan Analogs

Figure 23:
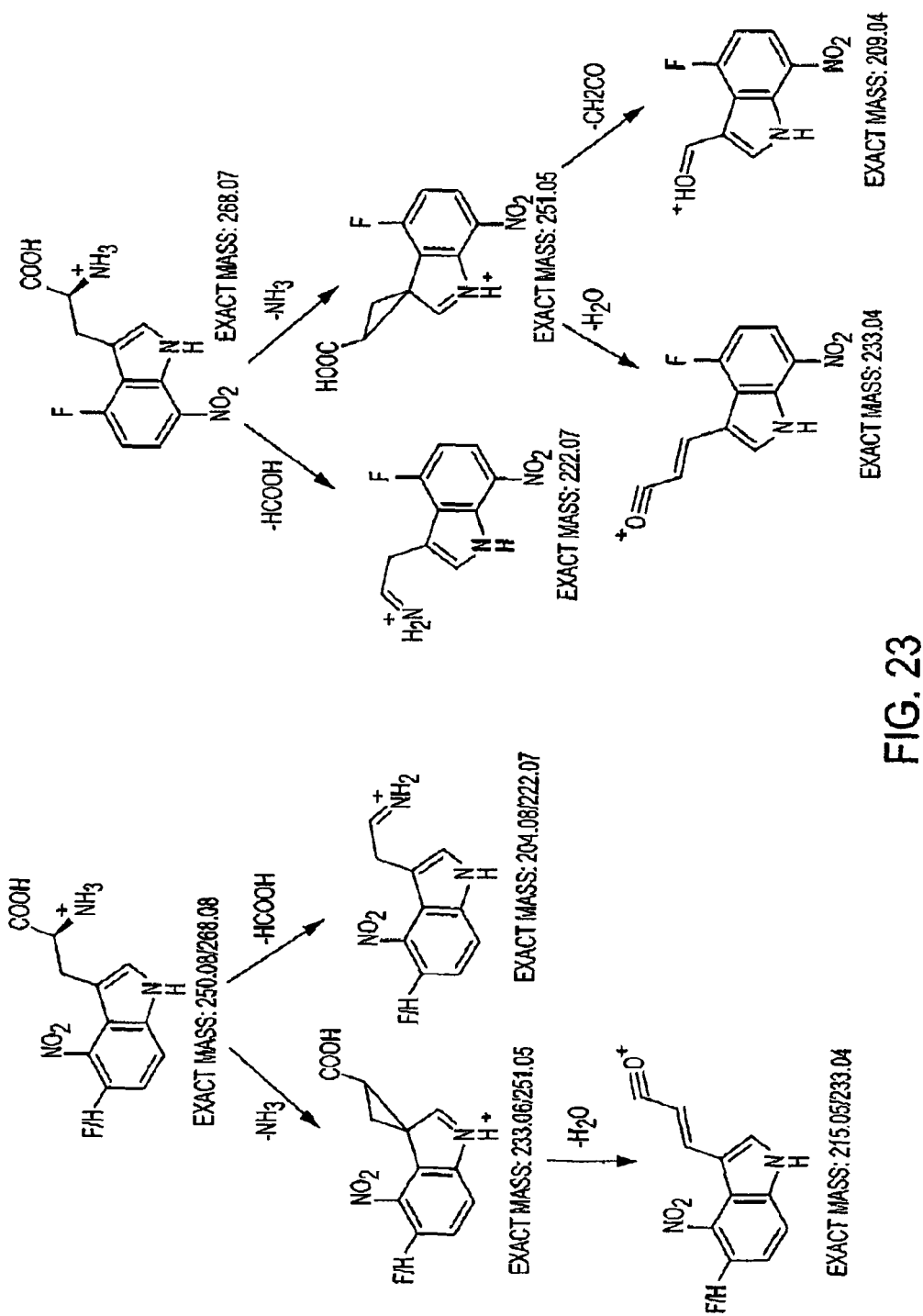
FIG. 23 shows Putative fragmentation pathways of 4-nitro-l-tryptophan, 4-nitro-5-F-l-tryptophan, and 7-nitro-4-F-l-tryptophan. Exact masses of all putative ions were shown.

Structural characterization of nitrated F-tryptophan products were first performed by LC-MS/MS (FIGS. 21A-21C). Nitrated 5-F-l-tryptophan was fragmented in the same pattern as that of 4-nitro-l-tryptophan in MS2 spectra (FIG. 21A-21B). The C5-F substitution increased the m/z values of all corresponding ions by 18 Da and affected the distribution of different fragments. The most abundant ion in the MS2 spectrum of 4-nitro-l-tryptophan had the m/z values of 159.0. It was switched to 174.2 in the MS2 spectrum of nitrated 5-F-l-tryptophan, corresponding to the non-fluorinated ion of 156.2. The most abundant ion in the MS2 spectrum of nitro-4-F-l-tryptophan had an m/z value of 209.0 (FIG. 21C). Importantly, its overall fragmentation pattern was notably different with that of nitrated 5-F-l-tryptophan. Putative chemical structures of red-labeled ions in these MS2 spectra are shown in FIG. 23. This result suggested that 5-F-l-tryptophan may be nitrated at the same site, the C4, as l-tryptophan but the nitration site at 4-F-l-tryptophan is different.

Figure 24A:
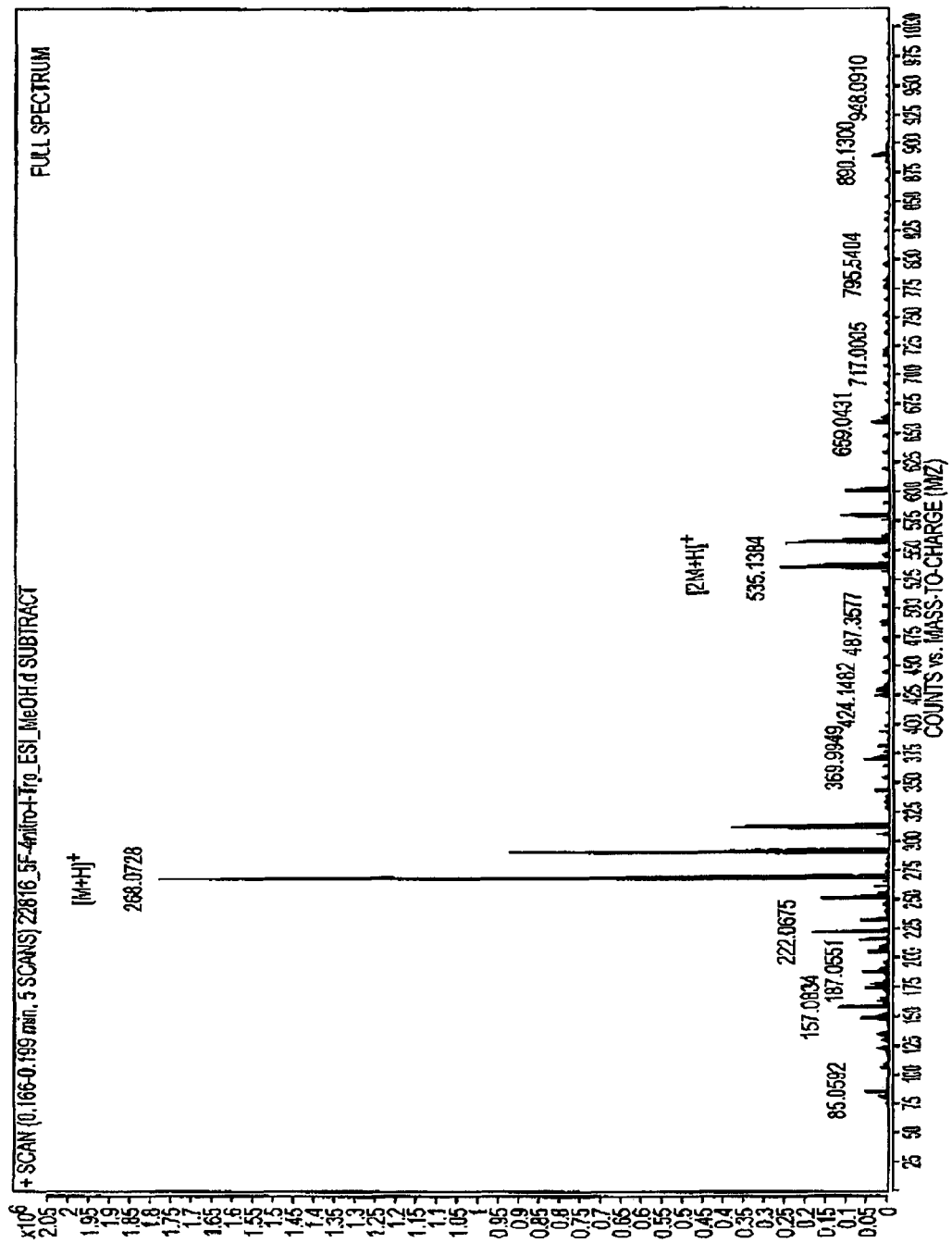
FIGS. 24A-24B show HRMS spectra of nitrated products in TxtE-BM3R reactions.
Figure 24B:
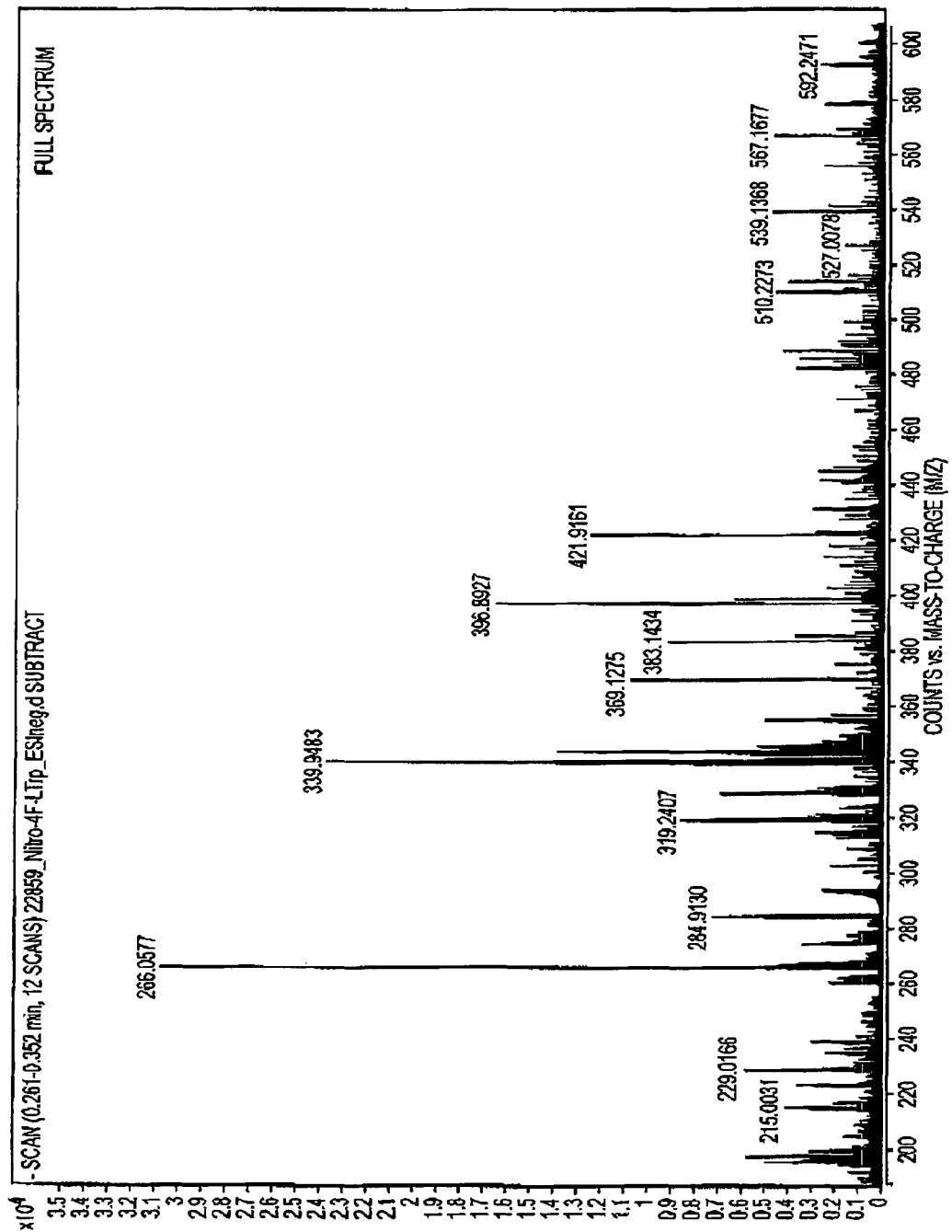
Figure 25A:
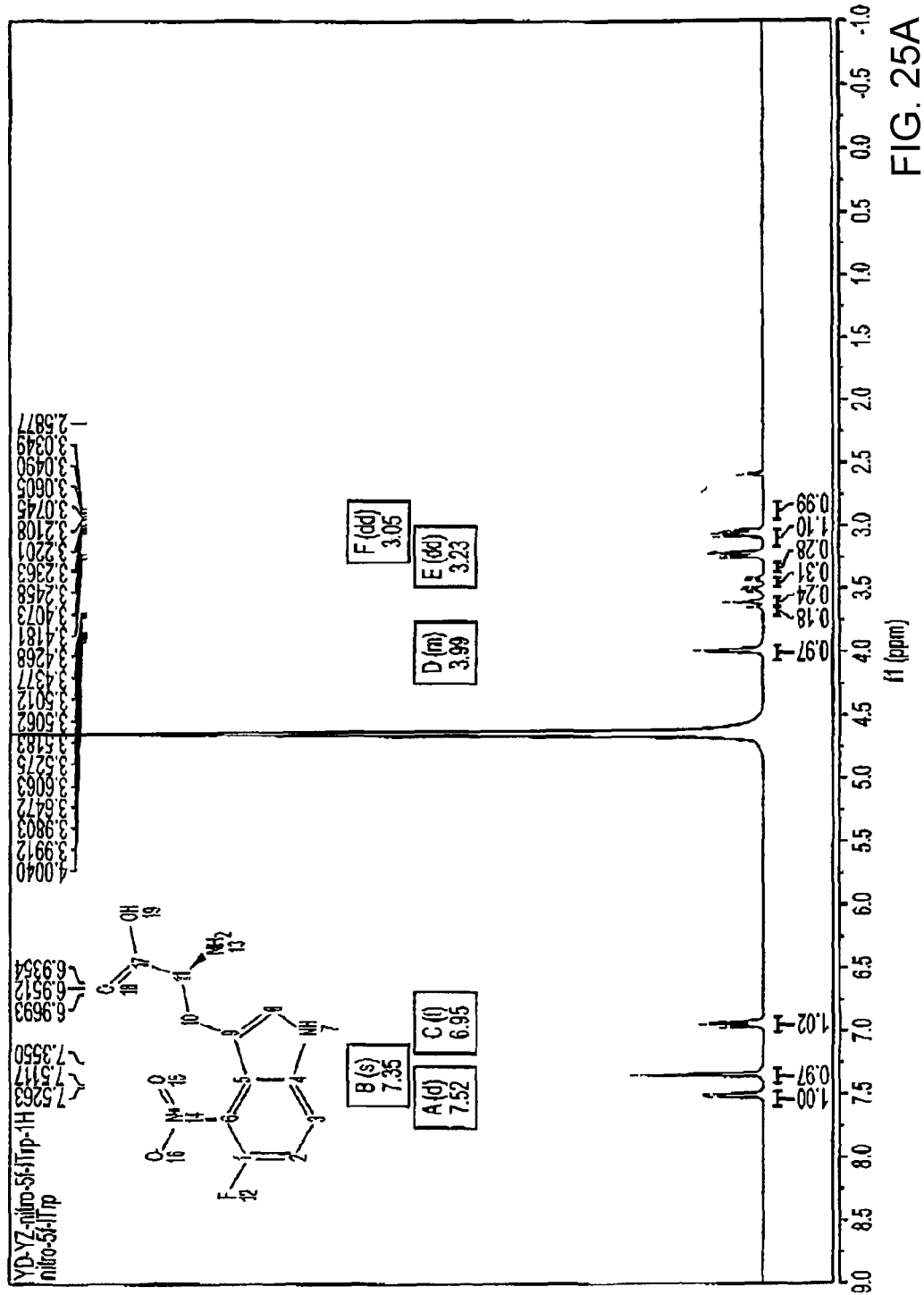
FIGS. 25A-25B show $^1$H NMR spectra of nitrated F-tryptophan products.
Figure 25B:
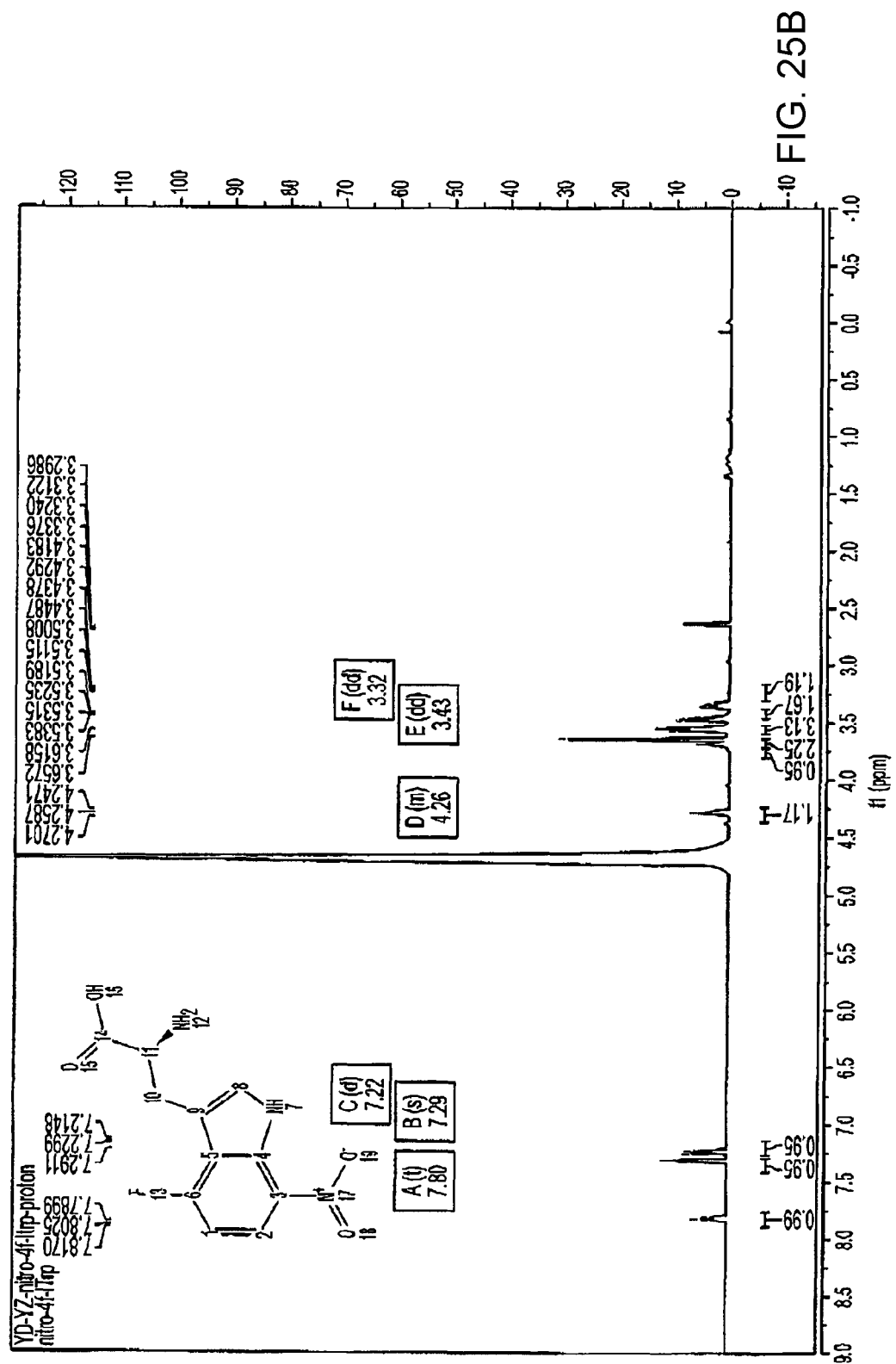
Figure 26A:
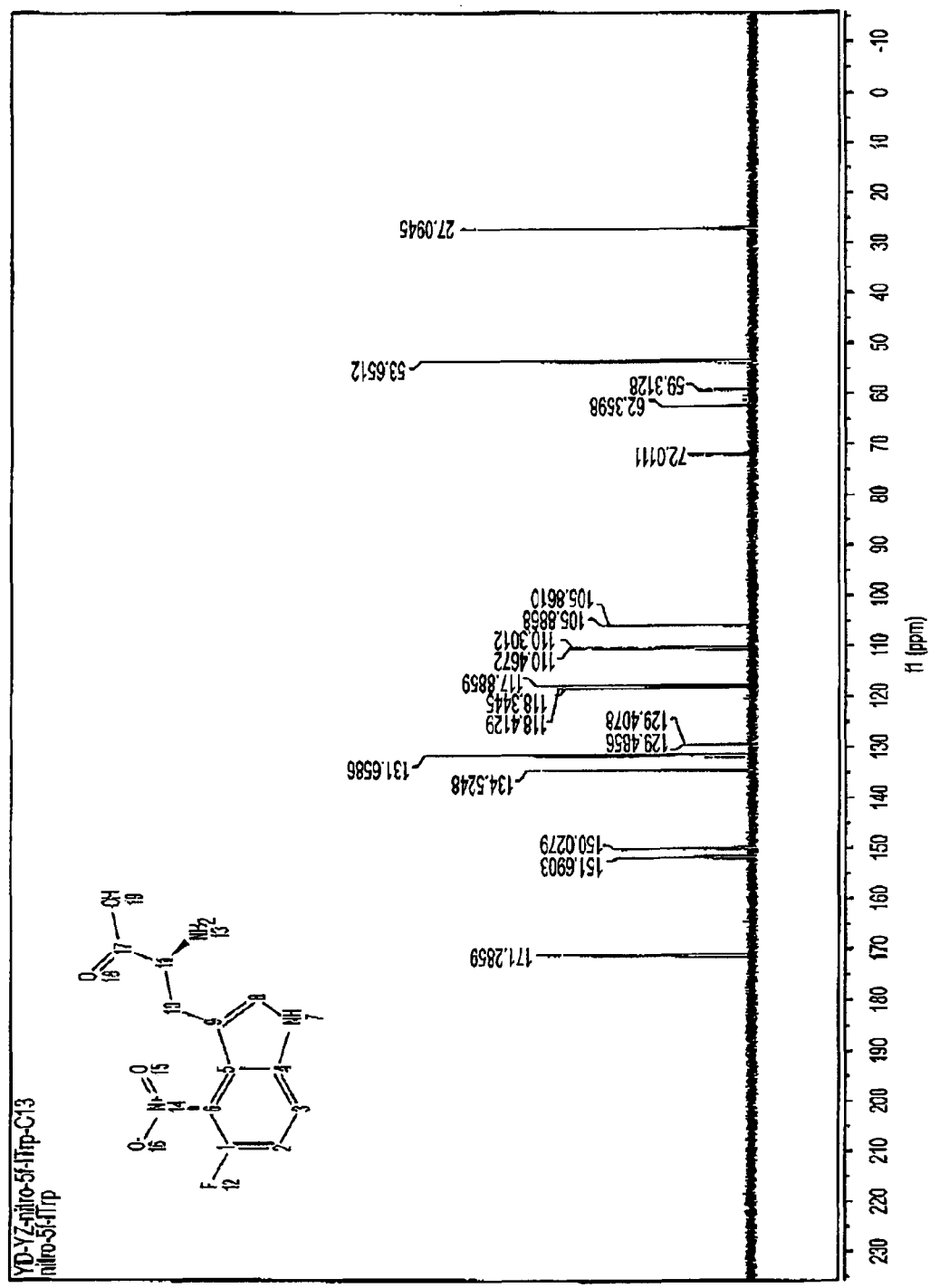
FIGS. 26A-26B show $^{13}$C NMR spectra of nitrated F-tryptophan products.
Figure 26B:
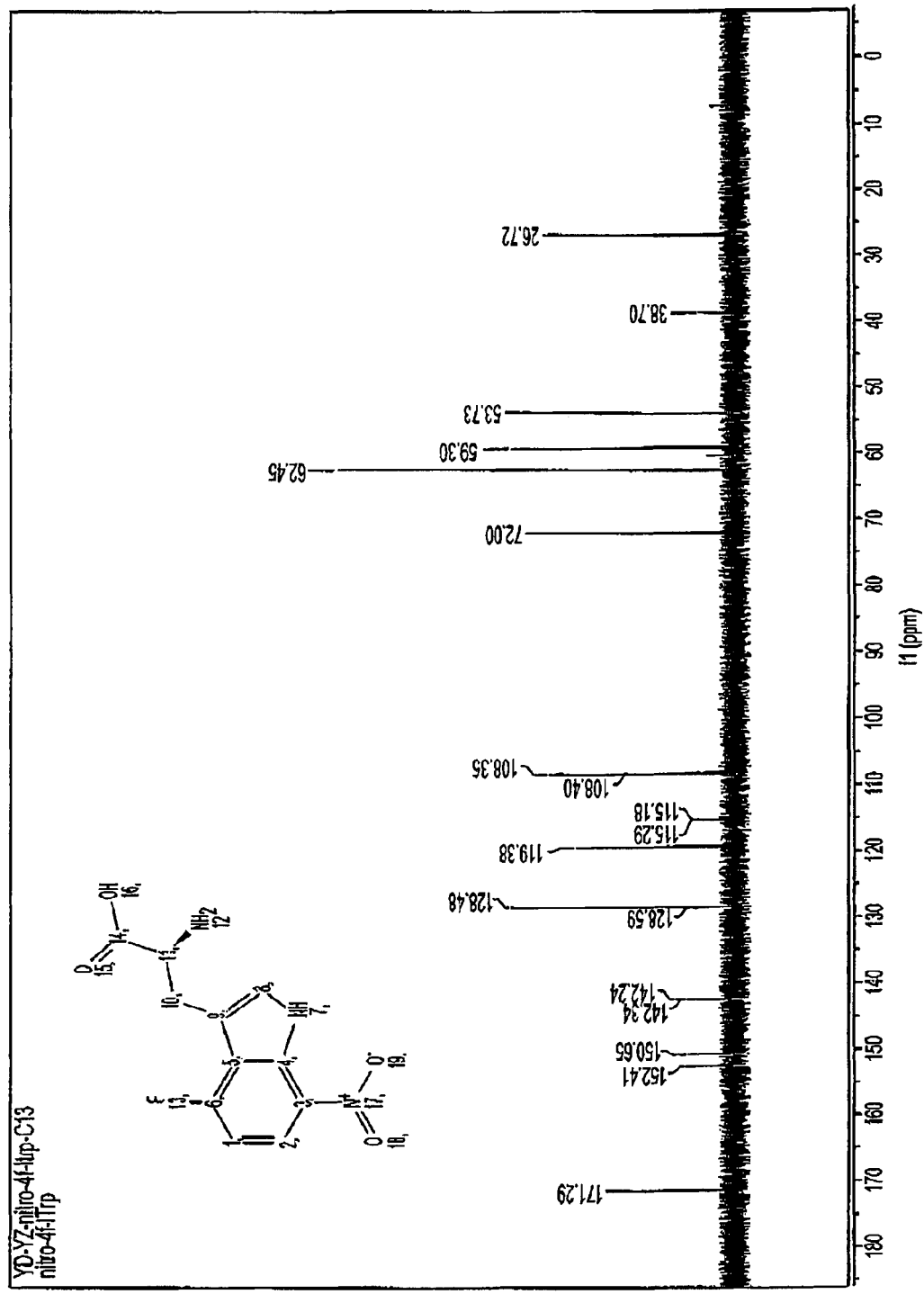
Figure 27A:
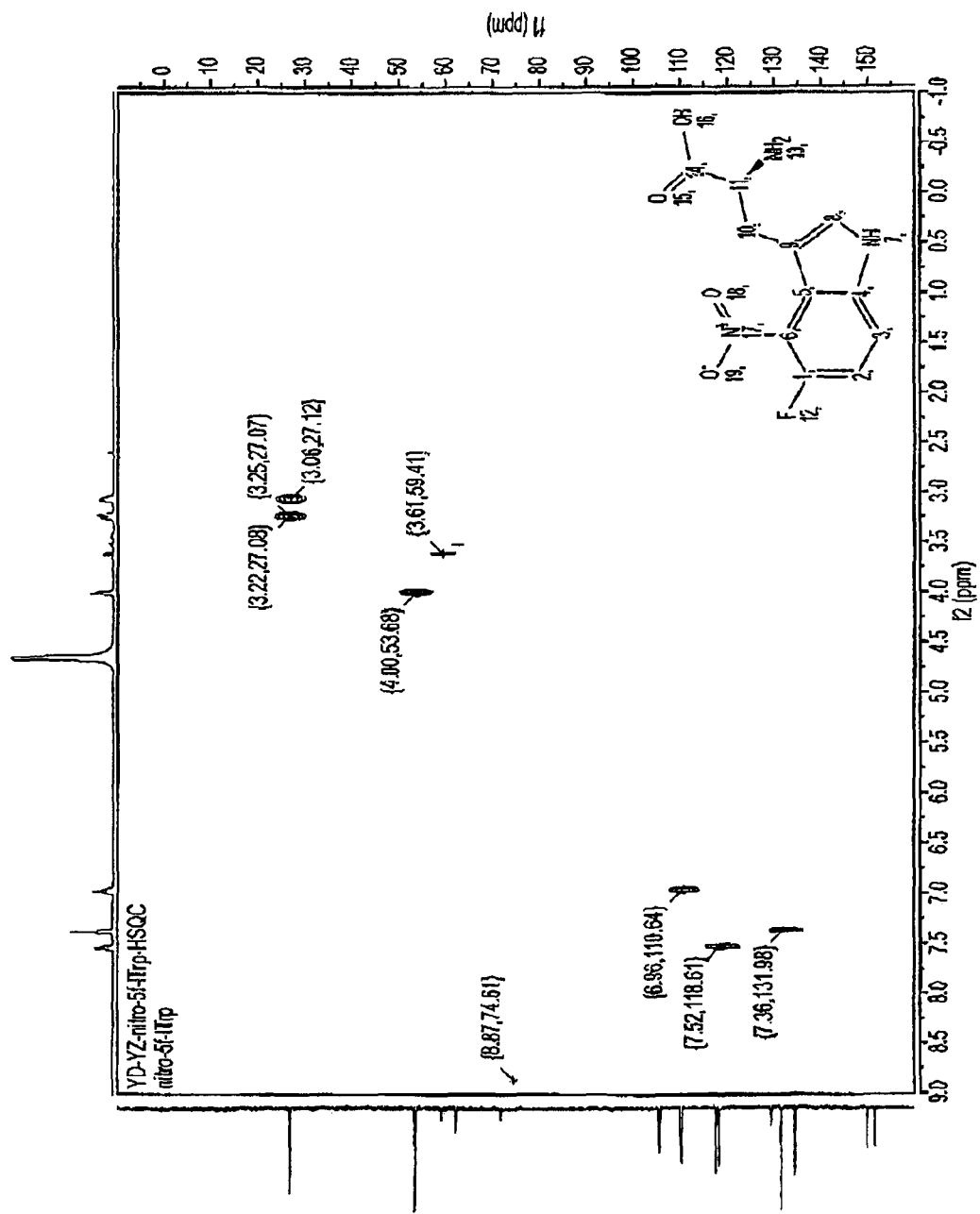
FIGS. 27A-27B show HSQC NMR spectra of nitrated F-tryptophan products.
Figure 27B:
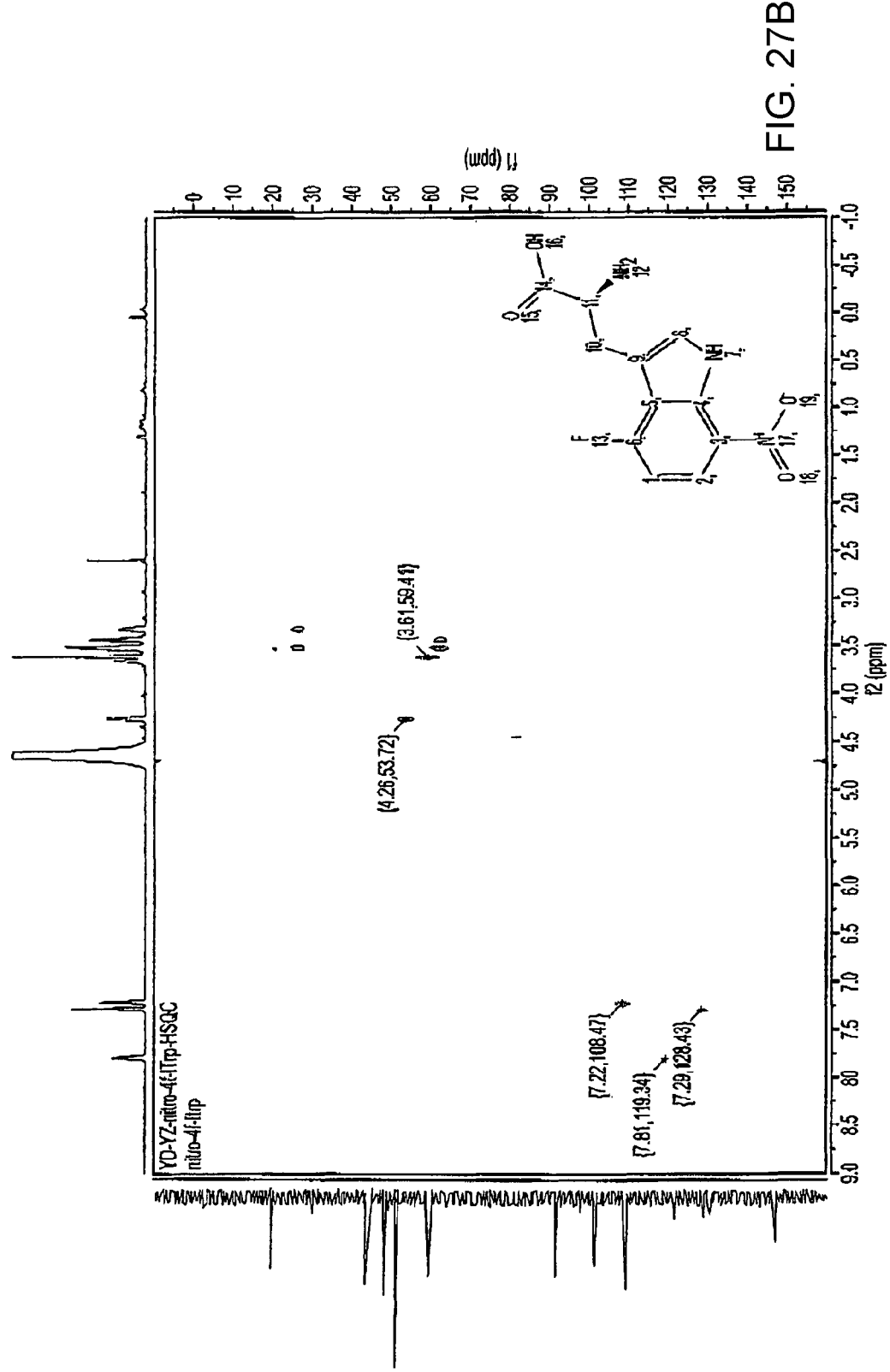
Figure 28A:
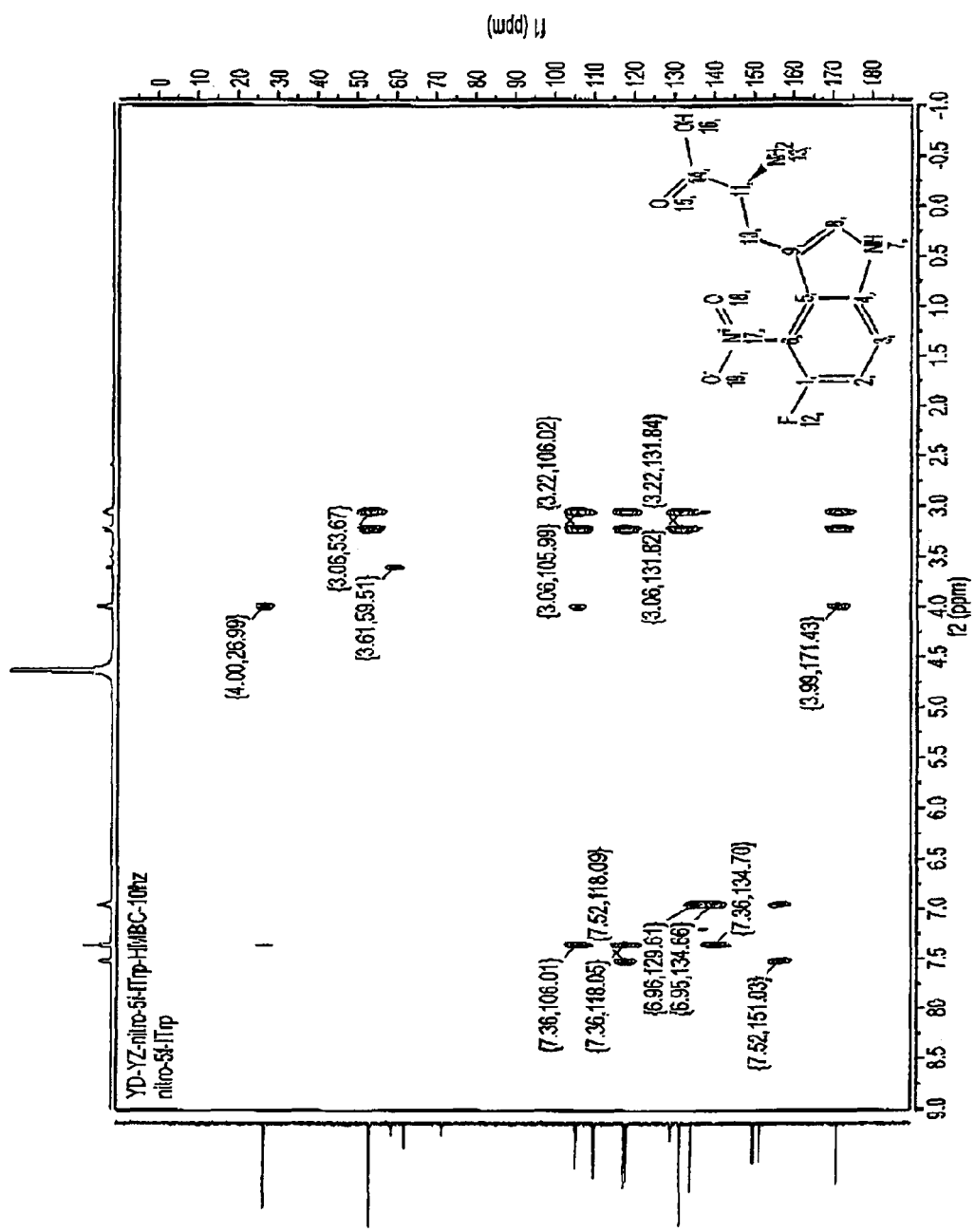
FIGS. 28A-28B show HMBC NMR spectra of nitrated F-tryptophan products.
Figure 28B:
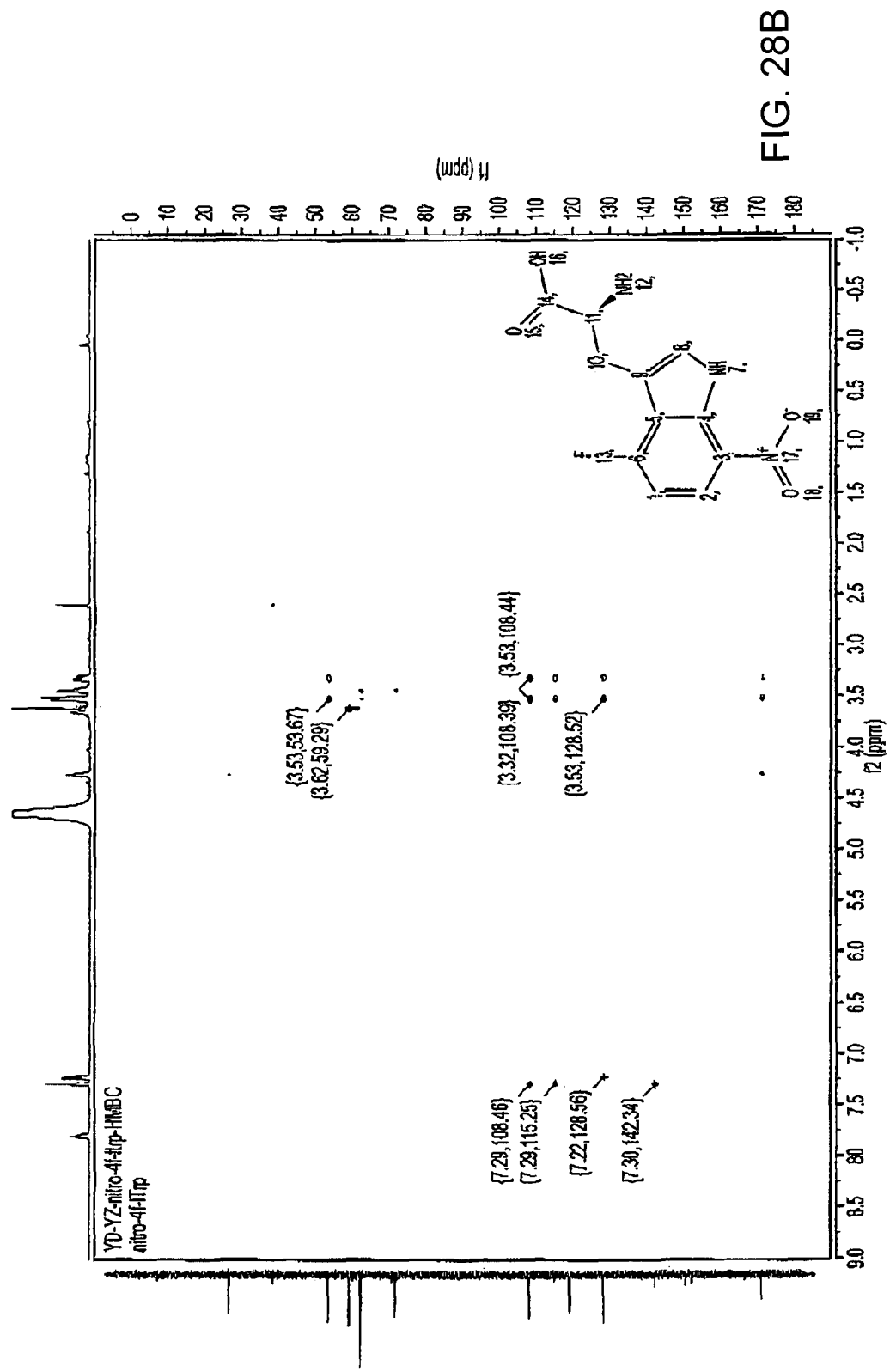

To further elucidate the nitro position in nitrated products, large scale enzymatic reactions were performed. About 90% of 5-F-l-tryptophan was nitrated to produce 2 mg of the nitro product as a yellow powder after purification by semi-preparative HPLC. In contrast, less than 0.2 mg of putative nitro-4-F-l-tryptophan as a light beige solid was isolated. Both products carried a single nitro group as revealed in HRMS analysis (FIGS. 24A-24B). Isolated products were further structurally characterized by $^1$H and $^{13}$C and 2D NMR analysis (FIGS. 25A, 25B, 26A, 26B, 27A, 27B, 28A, and 28B) (Table 2). Examining the NMR data suggested that the C4 and the C7 of 5-F-l-tryptophan and 4-F-l-tryptophan, respectively, were nitrated in TxtE-BM3R reactions. From the $^1$H NMR spectrum of the nitro 5-F-l-tryptophan product (FIGS. 24A-24B), the large coupling constant (J=10.2 Hz) of the triplet-like peak at δ 6.95 ppm (C6) suggested a single vicinal coupling with the fluorine atom. Furthermore, a neighboring doublet peak at δ 7.52 ppm (C7) with a coupling constant J=8.8 Hz defined an ortho substitution pattern of the two aromatic protons. The aforementioned multiplicity and coupling constants therefore determined the C4 nitro substitution in the 5-F-l-tryptophan substrate (FIG. 14B), which was further confirmed by HSQC and HMBC analysis (FIGS. 27A, 27B, 28A, and 28B). Although <0.2 mg of nitro-4-F-l-tryptophan were isolated, interpretation of the nitro position in this product was significantly eased using a 1.5 mm High Temperature Superconductor Probe. From its $^1$H NMR spectrum, a triplet-like peak at δ 7.80 ppm (C5) displayed a doublet of doublet split with two approximately equal coupling constant of 8.1 Hz, suggesting a vicinal coupling with the fluorine atom. An ortho substitution pattern of the two aromatic protons was further defined by a large coupling constant (J=9.1 Hz) of the neighboring doublet peak at δ 7.52 ppm (C6). Together, the nitro site was determined to be the C7 of 4-F-l-tryptophan (FIG. 14C), which was further confirmed by HSQC and HMBC analysis (FIGS. 27A, 27B, 28A, and 28B). These results therefore revealed TxtE as a versatile nitrating biocatalyst with remarkable substrate promiscuity and substrate-tuned regioselectivity.

TABLE 3

Determination of total turnover number and coupling efficiency of TxtE and three fusion enzymes. All reactions were independently repeated at least three times.

| P450s | TTN | Coupling efficiency (%) |
|---|---|---|
| TxtE | 385 ± 17 | 2.4 ± 0.3 |
| TxtE-BM3R | 321 ± 12 | 1.9 ± 0.2 |
| TxtE-RhFRed | 5 ± 0.3 | 0.1 ± 0.02 |
| TxtE-RhFRed* | 7 ± 0.6 | 0.3 ± 0.09 |

The following nitro-tryptophan analogs can be synthesized using any of the methods delineated herein, including the processes presented in Examples 1-7.

Example 8: Preparation of (S)-2-amino-3-(5-methyl-4-nitro-1H-indol-3-yl)propanoic acid (8)

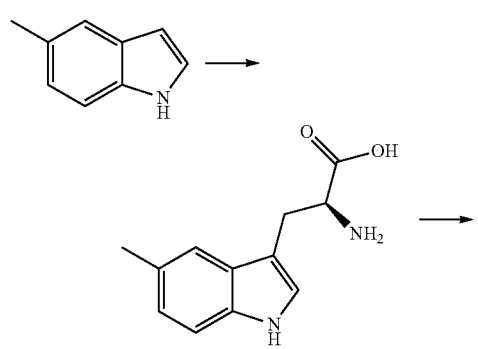

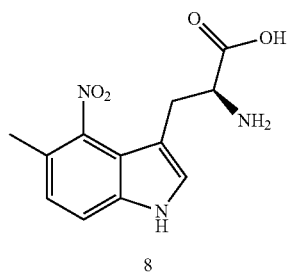

8

Example 8 can be prepared from 5-methylindole as shown above and in a similar manner as described in Examples 1-7.

Example 9: Preparation of (S)-2-amino-3-(6-methyl-4-nitro-1H-indol-3-yl)propanoic acid (9)

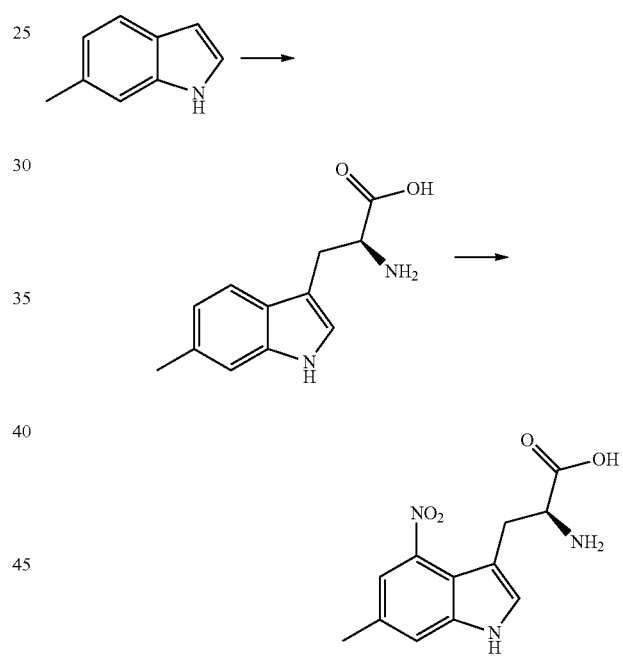

9

Example 9 can be prepared from 6-methylindole as shown above and in a similar manner as described in Examples 1-7.

Example 10: Preparation of (S)-2-amino-3-(7-methyl-4-nitro-1H-indol-3-yl)propanoic acid (10)

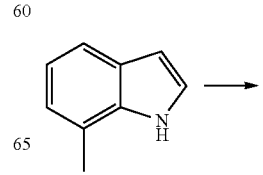

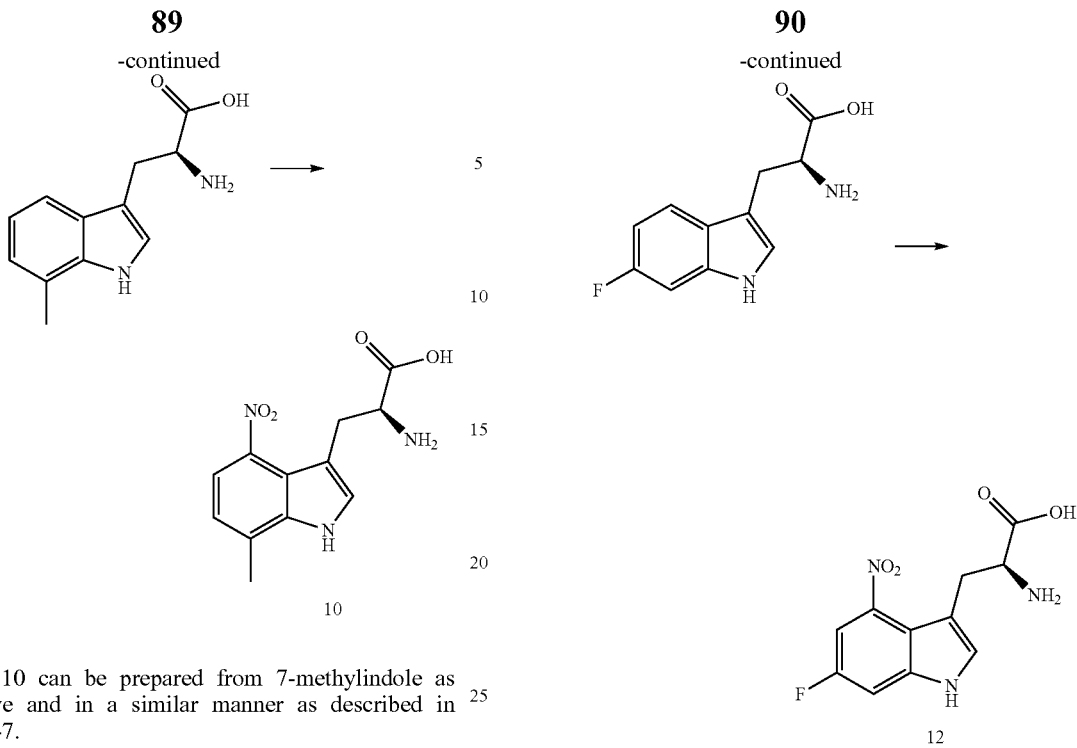

Example 10 can be prepared from 7-methylindole as shown above and in a similar manner as described in Examples 1-7.

Example 11: Preparation of (S)-2-amino-3-(4-methyl-7-nitro-1H-indol-3-yl)propanoic acid (11)

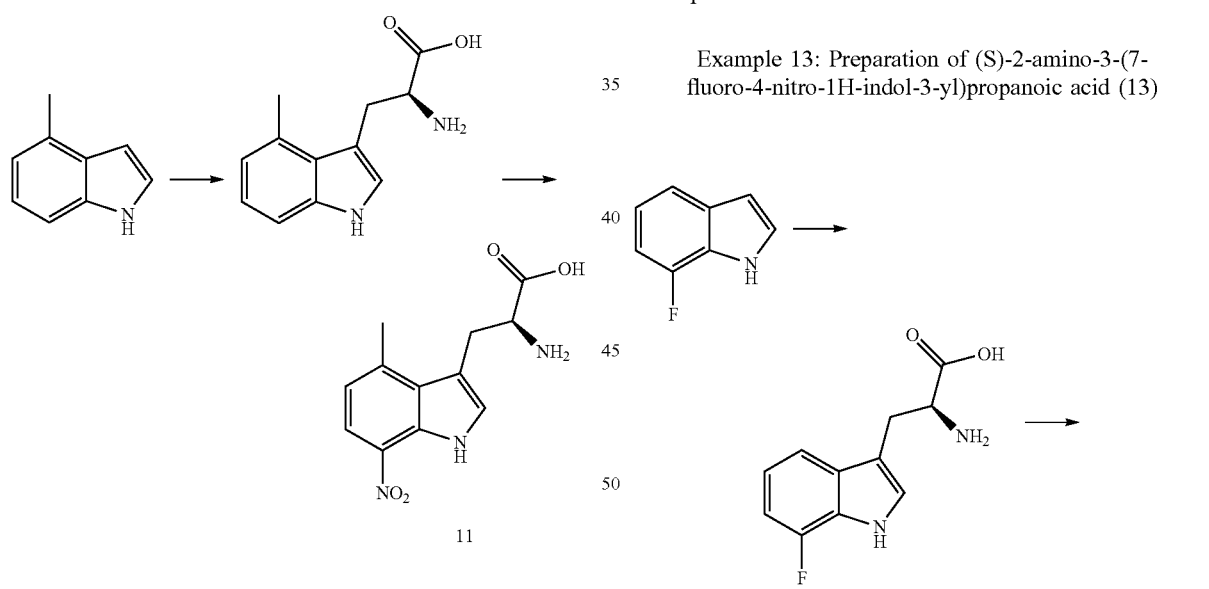

Example 11 can be prepared from 4-methylindole as shown above and in a similar manner as described in Examples 1-7.

Example 12: Preparation of (S)-2-amino-3-(6-fluoro-4-nitro-1H-indol-3-yl)propanoic acid (12)

Example 12 can be prepared from 6-fluoroindole as shown above and in a similar manner as described in Examples 1-7.

Example 13: Preparation of (S)-2-amino-3-(7-fluoro-4-nitro-1H-indol-3-yl)propanoic acid (13)

Example 13 can be prepared from 7-fluoroindole as shown above and in a similar manner as described in Examples 1-7.

Example 14: Preparation of (S)-2-amino-3-(S-chloro-4-nitro-1H-indol-3-yl)propanoic acid (14)

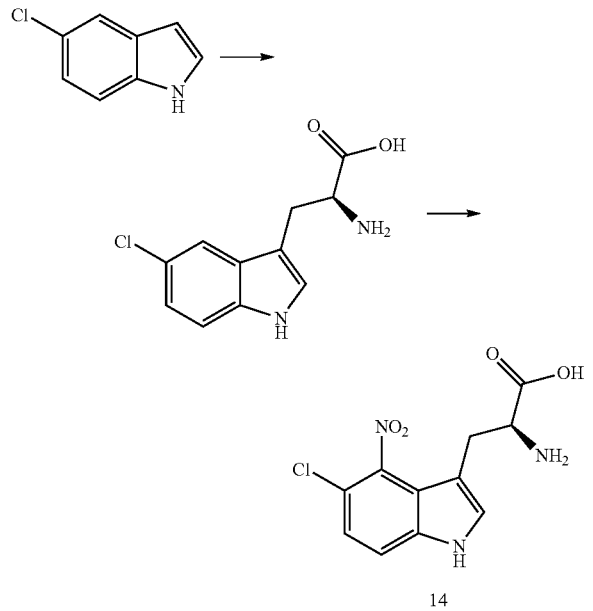

14

Example 14 can be prepared from 5-chloroindole as shown above and in a similar manner as described in Examples 1-7.

Example 15: Preparation of (S)-2-amino-3-(6-chloro-4-nitro-1H-indol-3-yl)propanoic acid (15)

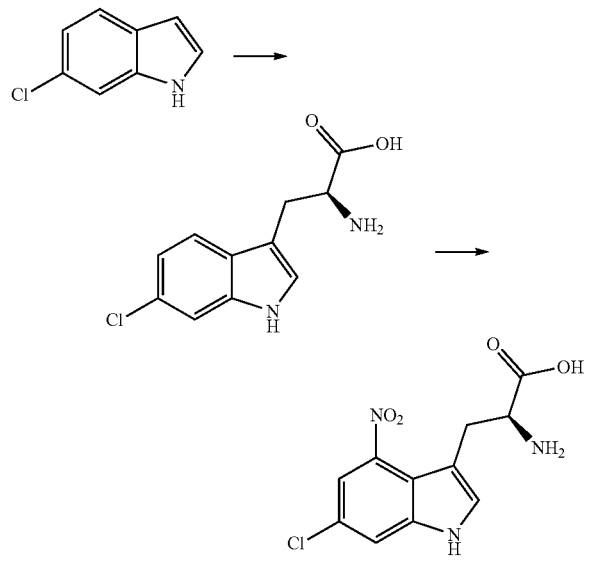

15

Example 15 can be prepared from 6-chloroindole as shown above and in a similar manner as described in Examples 1-7.

Example 16: Preparation of (S)-2-amino-3-(7-chloro-4-nitro-1H-indol-3-yl)propanoic acid (16)

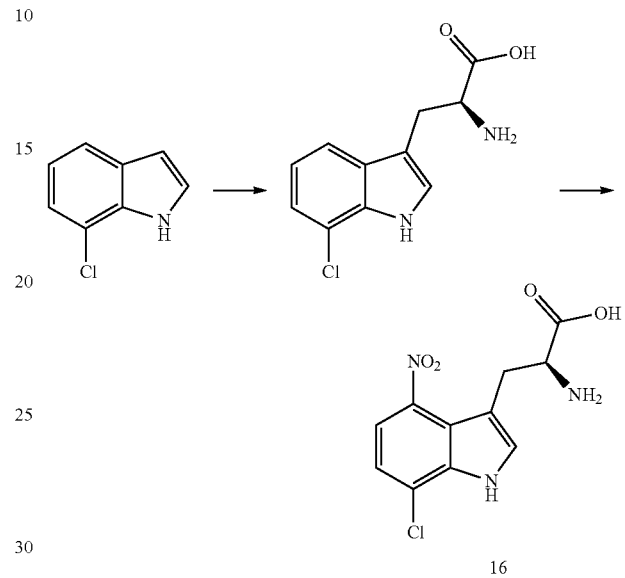

16

Example 16 can be prepared from 7-chloroindole as shown above and in a similar manner as described in Examples 1-7.

Example 17: Preparation of (S)-2-amino-3-(4-chloro-7-nitro-1H-indol-3-yl)propanoic acid (17)

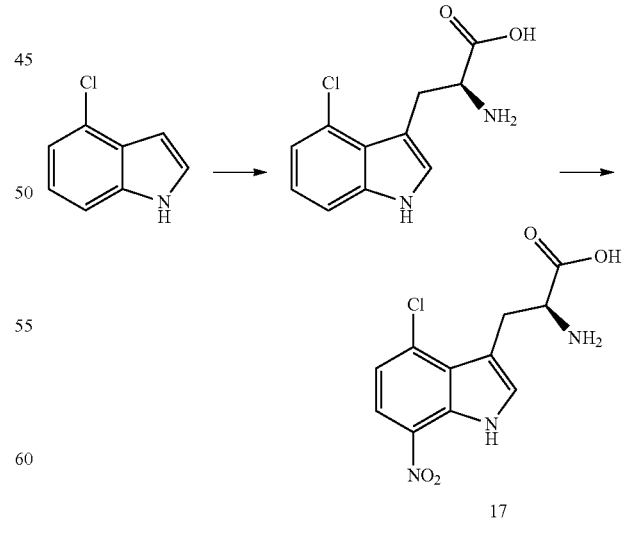

17

Example 17 can be prepared from 4-chloroindole as shown above and in a similar manner as described in Examples 1-7.

Example 18: Preparation of (S)-2-amino-3-(5-bromo-4-nitro-1H-indol-3-yl)propanoic acid (18)

Example 20: Preparation of (S)-2-amino-3-(7-bromo-4-nitro-1H-indol-3-yl)propanoic acid (20)

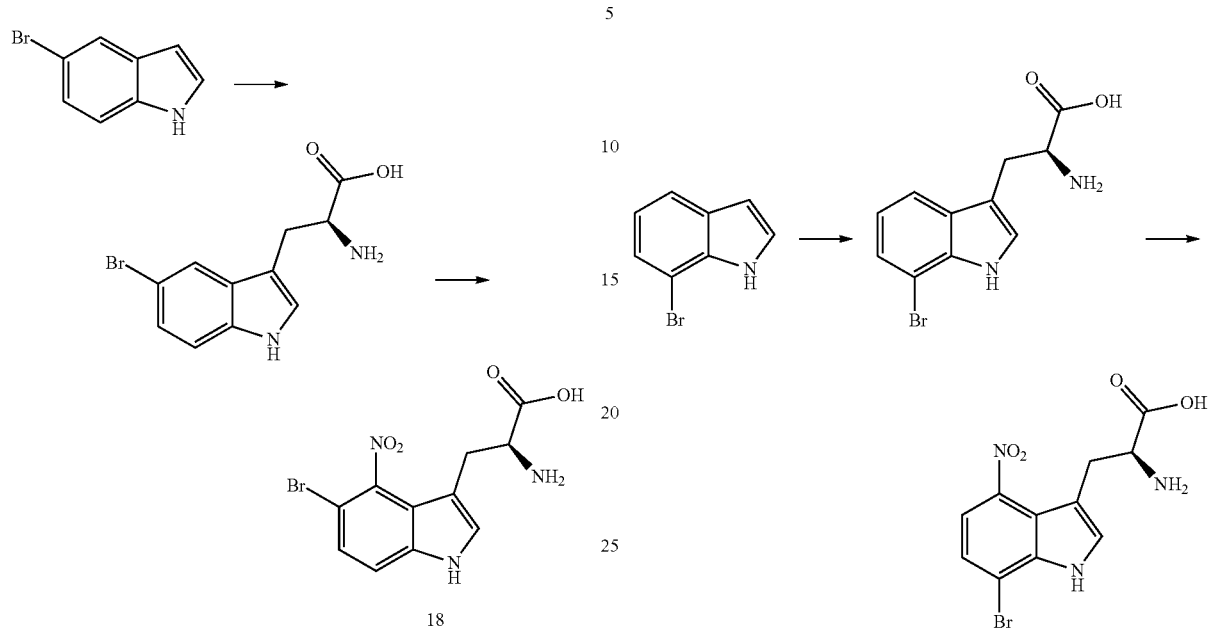

Example 18 can be prepared from 5-bromoindole as shown above and in a similar manner as described in Examples 1-7.

Example 20 can be prepared from 7-bromoindole as shown above and in a similar manner as described in Examples 1-7.

Example 19: Preparation of (S)-2-amino-3-(6-bromo-4-nitro-1H-indol-3-yl)propanoic acid (19)

Example 21: Preparation of (S)-2-amino-3-(4-bromo-7-nitro-1H-indol-3-yl)propanoic acid (21)

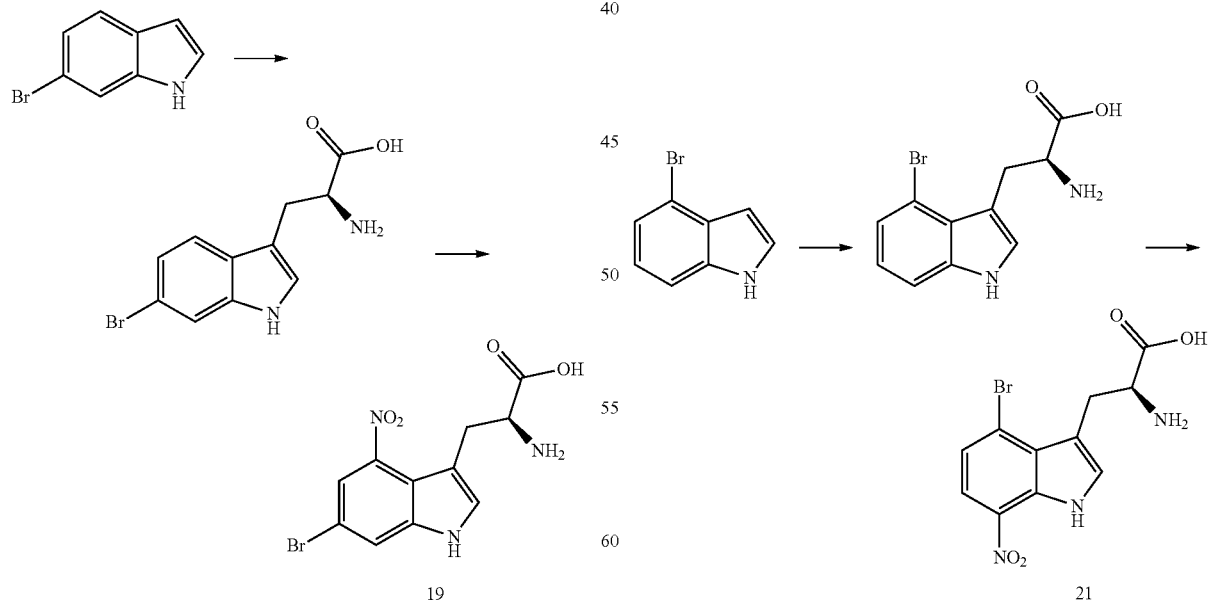

Example 19 can be prepared from 6-bromoindole as shown above and in a similar manner as described in Examples 1-7.

Example 21 can be prepared from 4-bromoindole as shown above and in a similar manner as described in Examples 1-7.

Example 22: Preparation of (S)-2-amino-3-(5-methoxy-4-nitro-1H-indol-3-yl)propanoic acid (22)

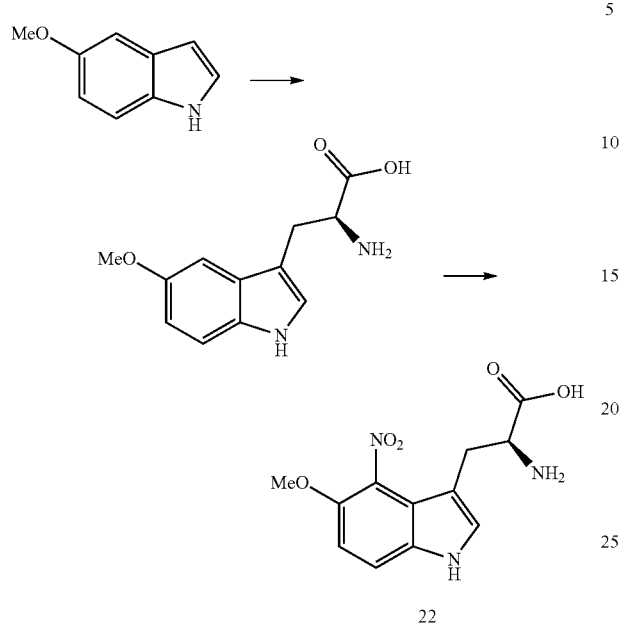

22

Example 22 can be prepared from 5-methoxyindole as shown above and in a similar manner as described in Examples 1-7.

Example 23: Preparation of (S)-2-amino-3-(6-methoxy-4-nitro-1H-indol-3-yl)propanoic acid (23)

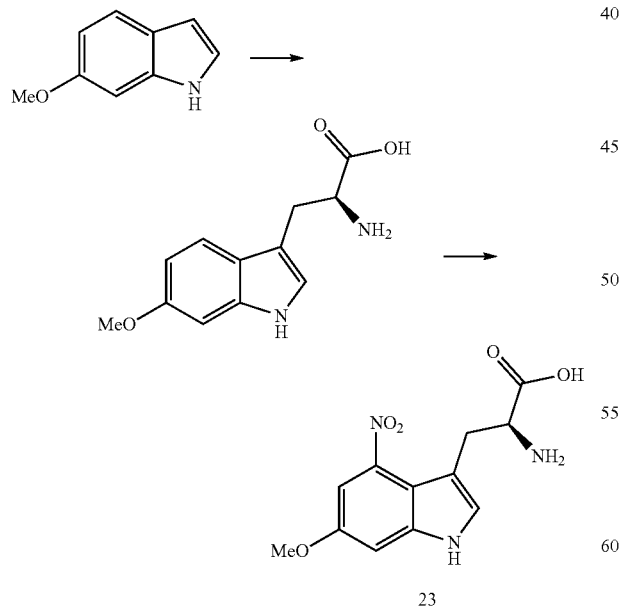

23

Example 23 can be prepared from 6-methoxyindole as shown above and in a similar manner as described in Examples 1-7.

Example 24: Preparation of (S)-2-amino-3-(7-methoxy-4-nitro-1H-indol-3-yl)propanoic acid (24)

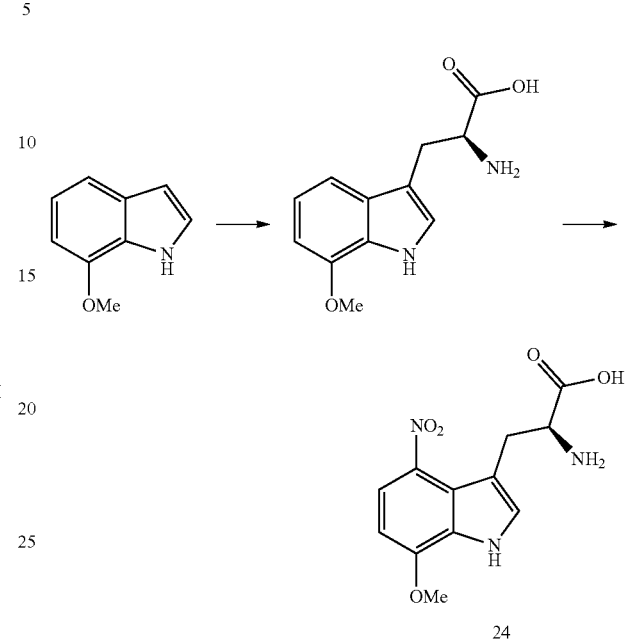

24

Example 24 can be prepared from 7-methoxyindole as shown above and in a similar manner as described in Examples 1-7.

Example 25: Preparation of (S)-2-amino-3-(4-methoxy-7-nitro-1H-indol-3-yl)propanoic acid (25)

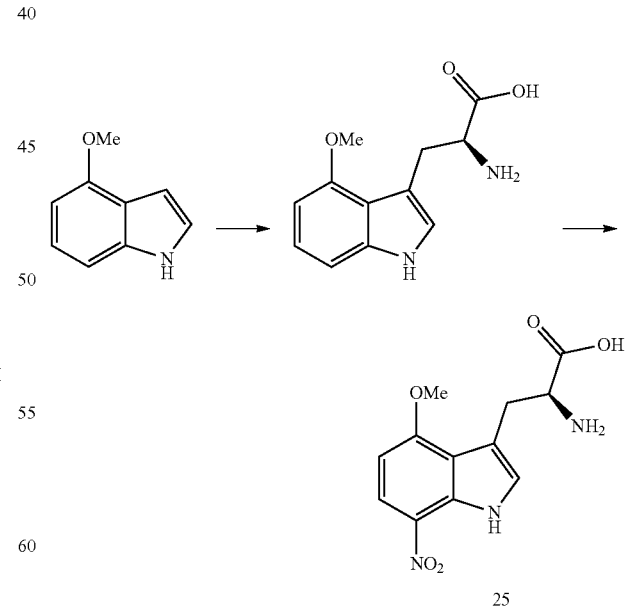

25

Example 25 can be prepared from 4-methoxyindole as shown above and in a similar manner as described in Examples 1-7.

Example 26: Preparation of (S)-2-amino-3-(5-amino-4-nitro-1H-indol-3-yl)propanoic acid (26)

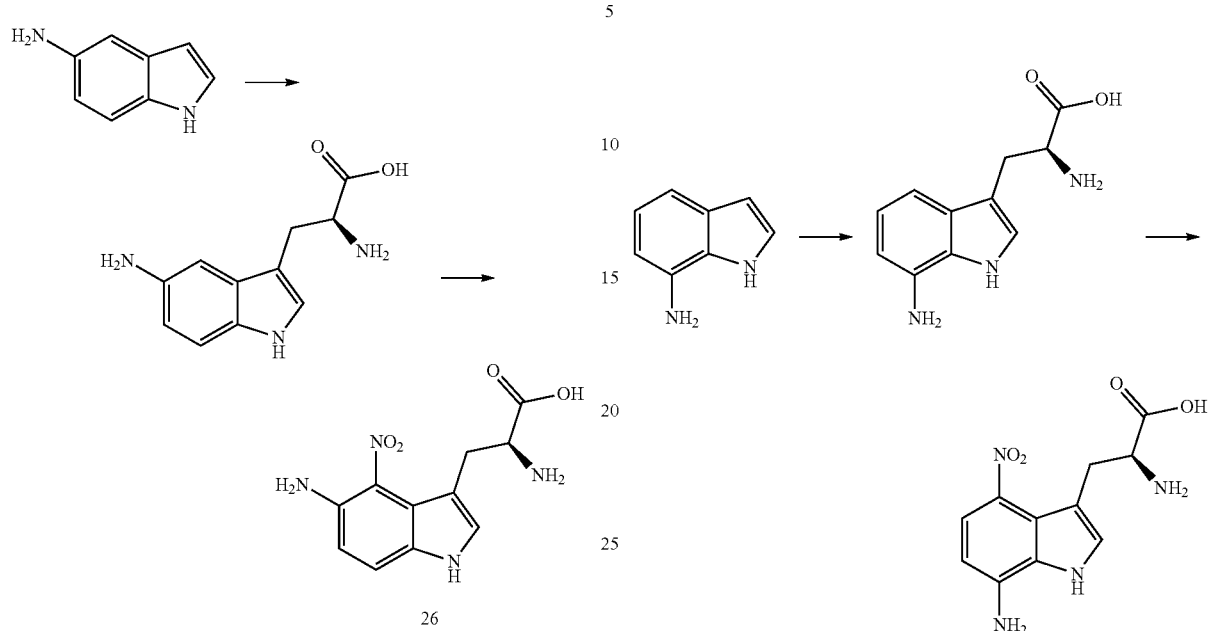

26

Example 26 can be prepared from 5-aminoindole as shown above and in a similar manner as described in Examples 1-7.

Example 27: Preparation of (S)-2-amino-3-(6-amino-4-nitro-1H-indol-3-yl)propanoic acid (27)

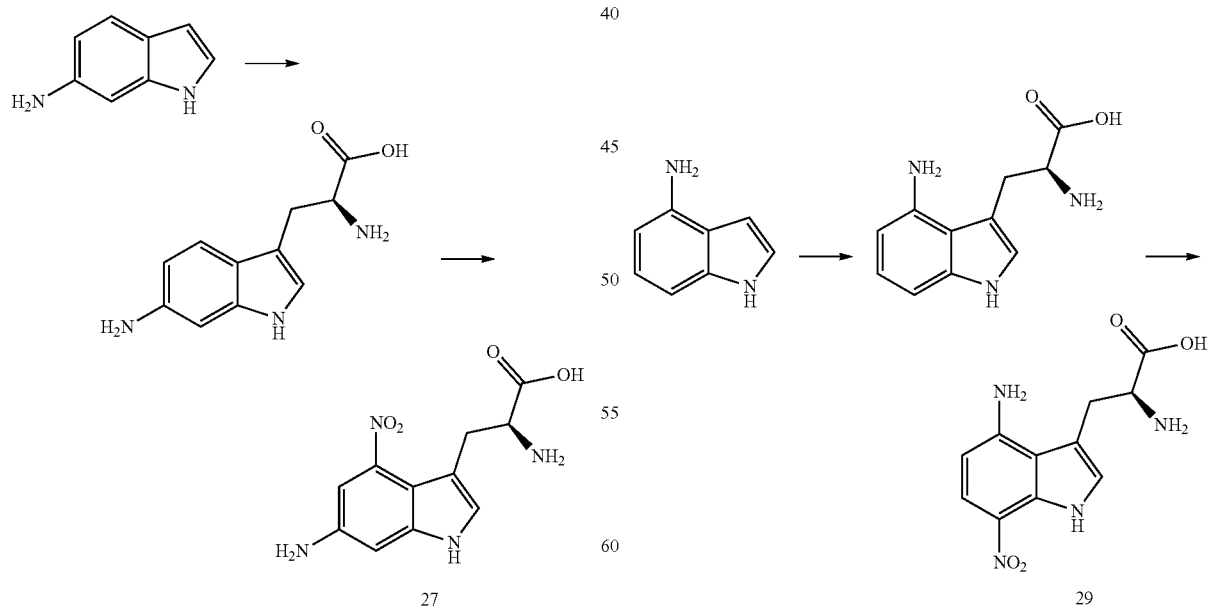

27

Example 27 can be prepared from 6-aminoindole as shown above and in a similar manner as described in Examples 1-7.

Example 28: Preparation of (S)-2-amino-3-(7-amino-4-nitro-1H-indol-3-yl)propanoic acid (28)

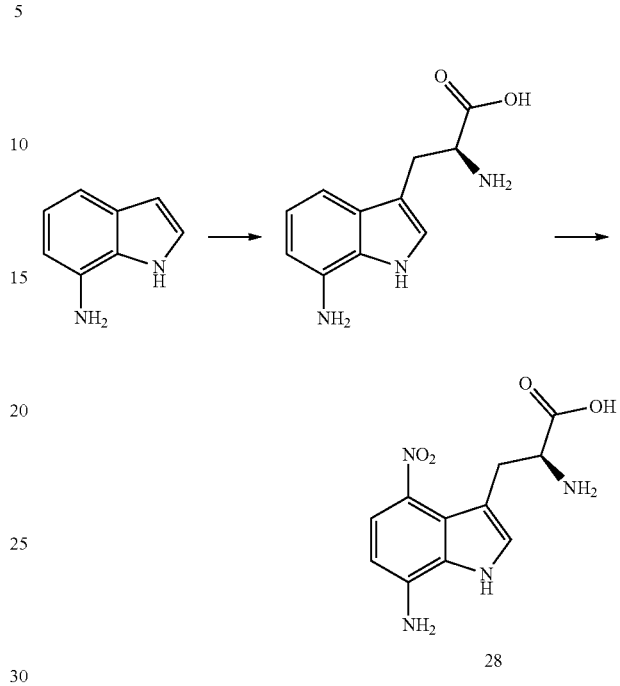

28

Example 28 can be prepared from 7-aminoindole as shown above and in a similar manner as described in Examples 1-7.

Example 29: Preparation of (S)-2-amino-3-(4-amino-7-nitro-1H-indol-3-yl)propanoic acid (29)

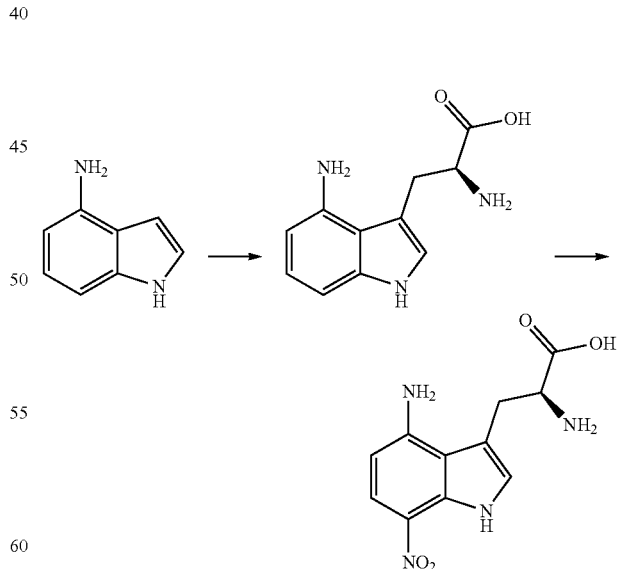

29

Example 29 can be prepared from 4-aminoindole as shown above and in a similar manner as described in Examples 1-7.

Example 30: Preparation of (S)-2-amino-3-(5-hydroxy-4-nitro-1H-indol-3-yl)propanoic acid (30)

Example 32: Preparation of (S)-2-amino-3-(7-hydroxy-4-nitro-1H-indol-3-yl)propanoic acid (32)

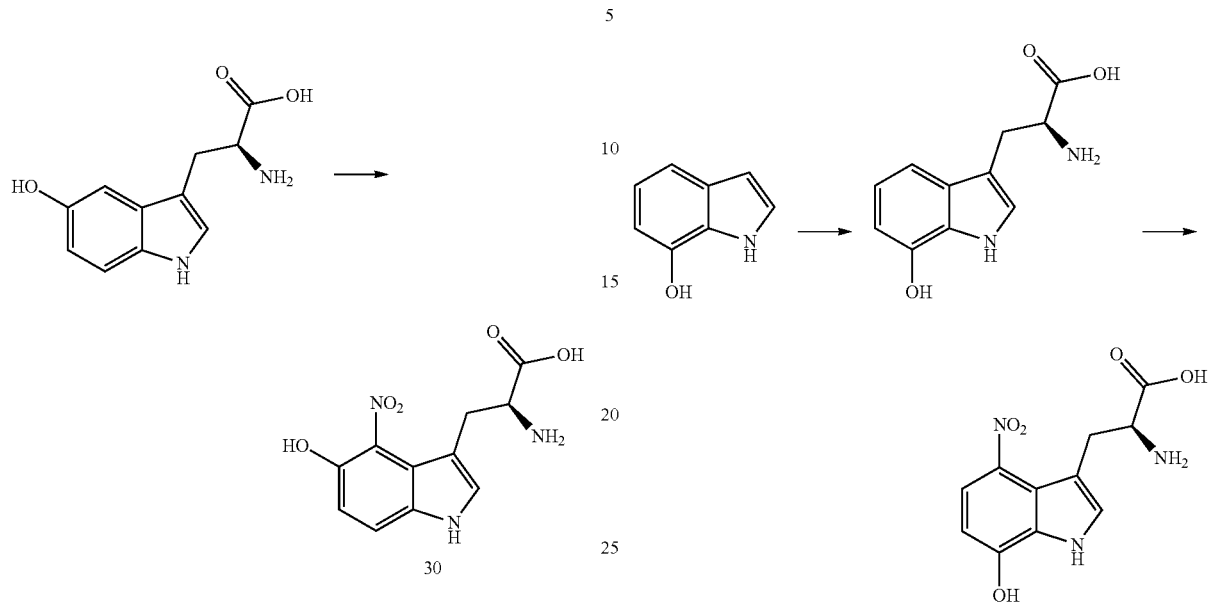

Example 30 was prepared from (S)-2-amino-3-(5-hydroxy-1H-indol-3-yl)propanoic acid as shown above and in a similar manner as described in Examples 1-7.

Example 31: Preparation of (S)-2-amino-3-(6-hydroxy-4-nitro-1H-indol-3-yl)propanoic acid (31)

Example 32 can be prepared from 7-hydroxyindole as shown above and in a similar manner as described in Examples 1-7.

Example 33: Preparation of (S)-2-amino-3-(4-hydroxy-7-nitro-1H-indol-3-yl)propanoic acid (33)

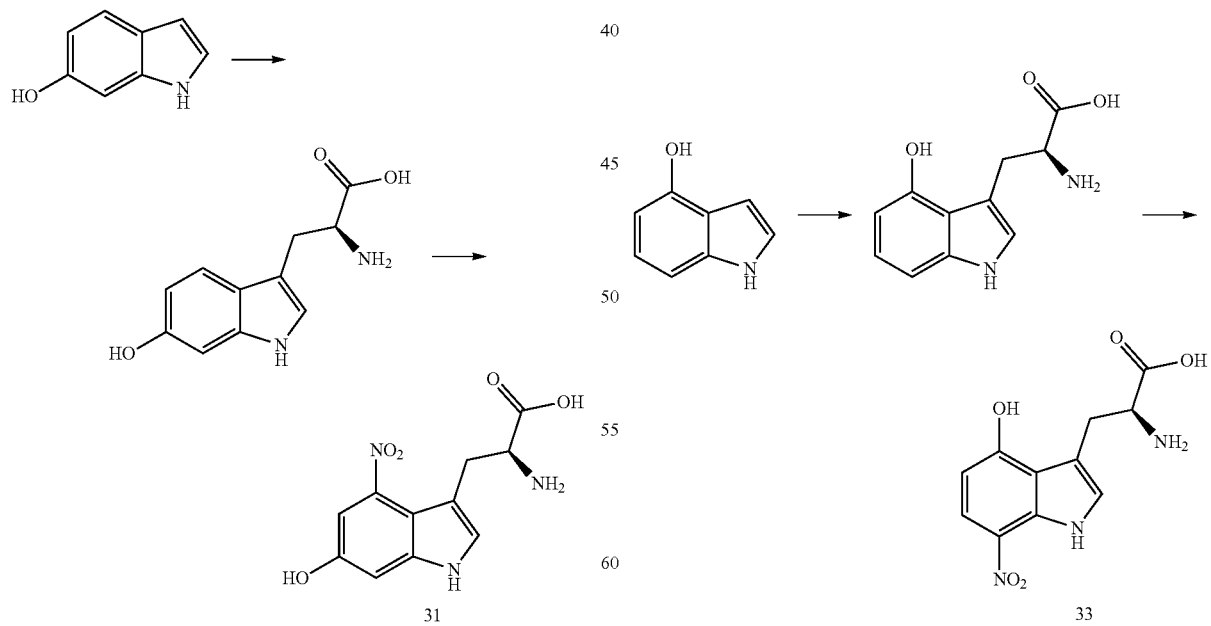

Example 31 can be prepared from 6-hydroxyindole as shown above and in a similar manner as described in Examples 1-7.

Example 33 can be prepared from 4-hydroxyindole as shown above and in a similar manner as described in Examples 1-7.

Example 34: Preparation of (S)-2-amino-3-(4-nitro-5-phenyl-1H-indol-3-yl)propanoic acid (34)

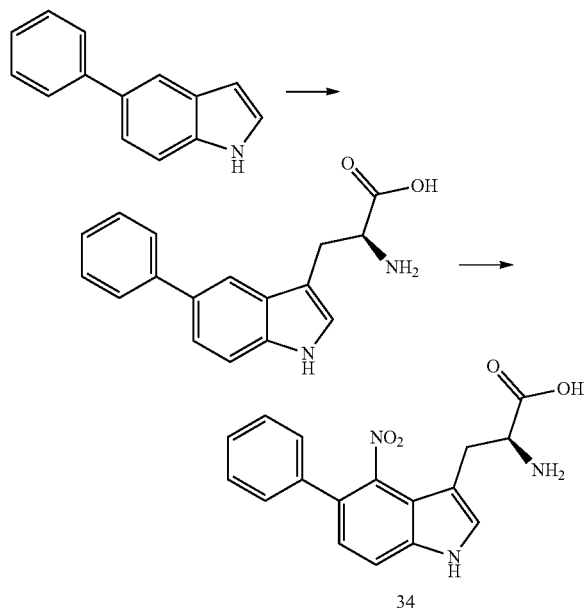

Example 34 can be prepared from 5-phenylindole as shown above and in a similar manner as described in Examples 1-7.

Example 35: Preparation of (S)-2-amino-3-(4-nitro-6-phenyl-1H-indol-3-yl)propanoic acid (35)

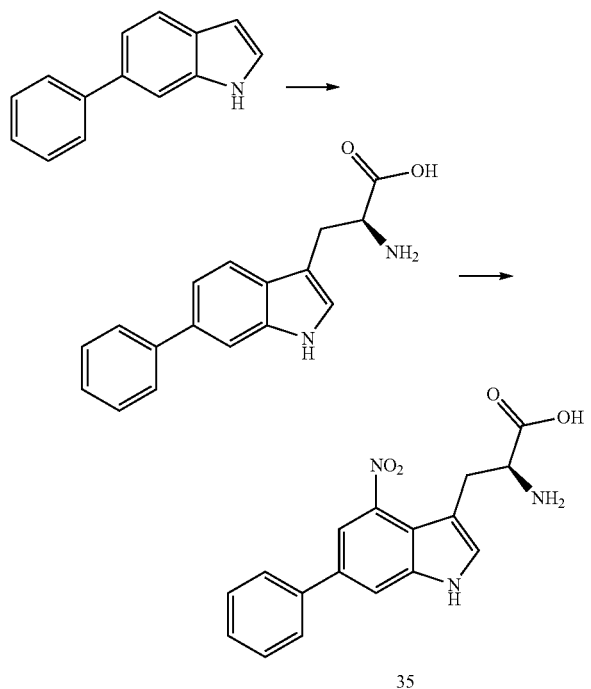

Example 35 can be prepared from 6-phenylindole as shown above and in a similar manner as described in Examples 1-7.

Example 36: Preparation of (S)-2-amino-3-(4-nitro-7-phenyl-1H-indol-3-yl)propanoic acid (36)

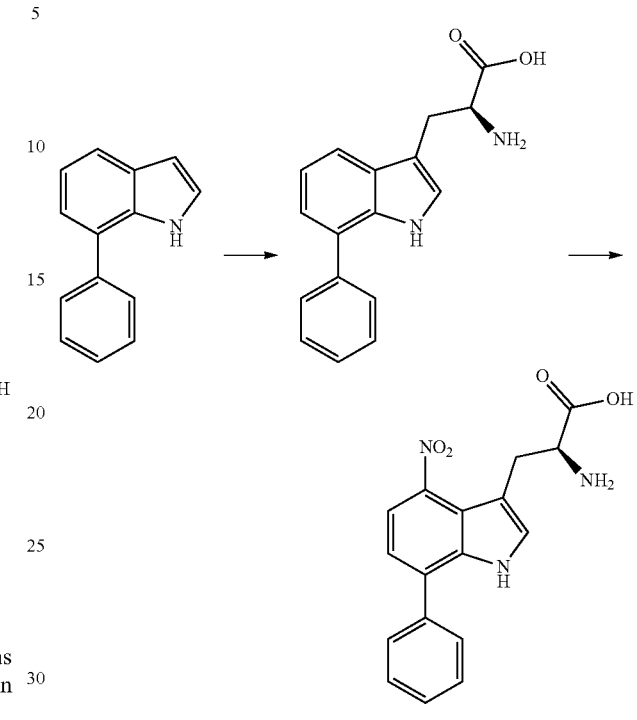

Example 36 can be prepared from 7-phenylindole as shown above and in a similar manner as described in Examples 1-7.

Example 37: Preparation of (S)-2-amino-3-(7-nitro-4-phenyl-1H-indol-3-yl)propanoic acid (37)

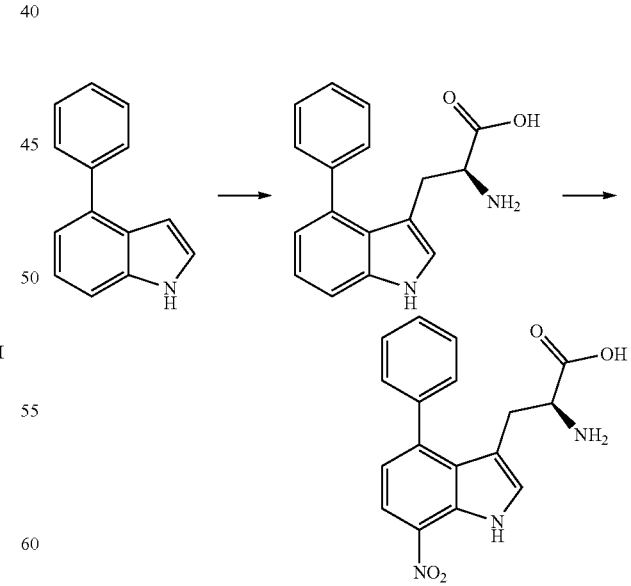

Example 37 can be prepared from 4-phenylindole as shown above and in a similar manner as described in Examples 1-7.

Example 38: Preparation of (S)-2-amino-3-(5-cyclopropyl-4-nitro-1H-indol-3-yl)propanoic acid (38)

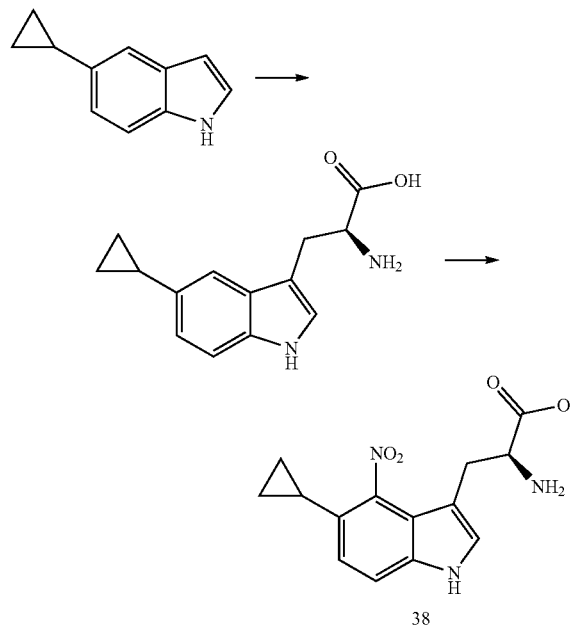

Example 38 can be prepared from 5-cyclopropylindole as shown above and in a similar manner as described in Examples 1-7.

Example 39: Preparation of (S)-2-amino-3-(6-cyclopropyl-4-nitro-1H-indol-3-yl)propanoic acid (39)

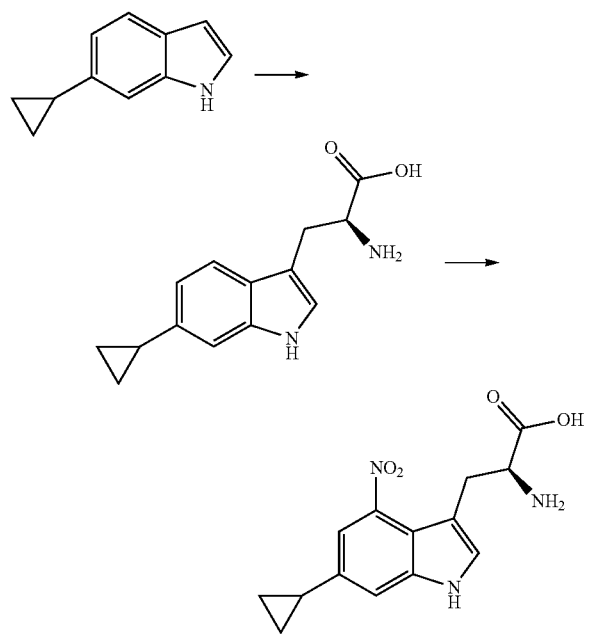

Example 39 can be prepared from 6-cyclopropylindole as shown above and in a similar manner as described in Examples 1-7.

Example 40: Preparation of (S)-2-amino-3-(7-cyclopropyl-4-nitro-1H-indol-3-yl)propanoic acid (40)

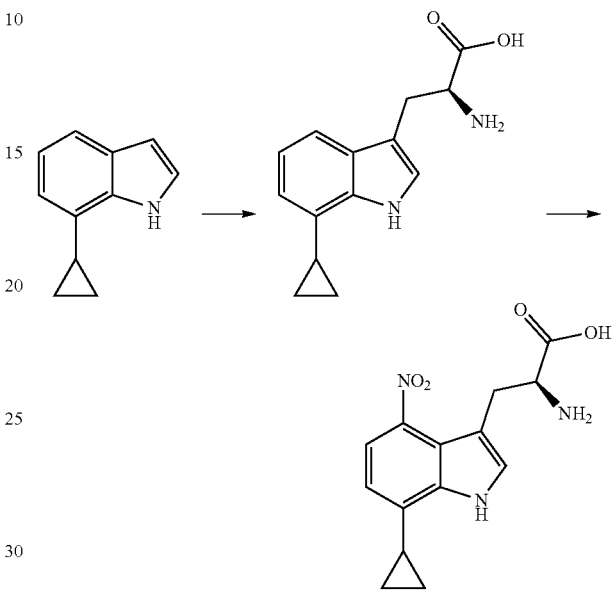

Example 40 can be prepared from 7-cyclopropylindole as shown above and in a similar manner as described in Examples 1-7.

Example 41: Preparation of (S)-2-amino-3-(4-cyclopropyl-7-nitro-1H-indol-3-yl)propanoic acid (41)

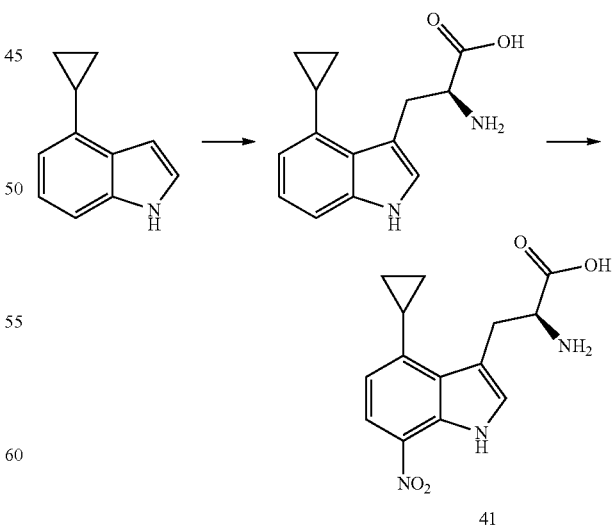

Example 41 can be prepared from 4-cyclopropylindole as shown above and in a similar manner as described in Examples 1-7.

Example 42: Preparation of (S)-2-amino-3-(4-nitro-5-vinyl-1H-indol-3-yl)propanoic acid (42)

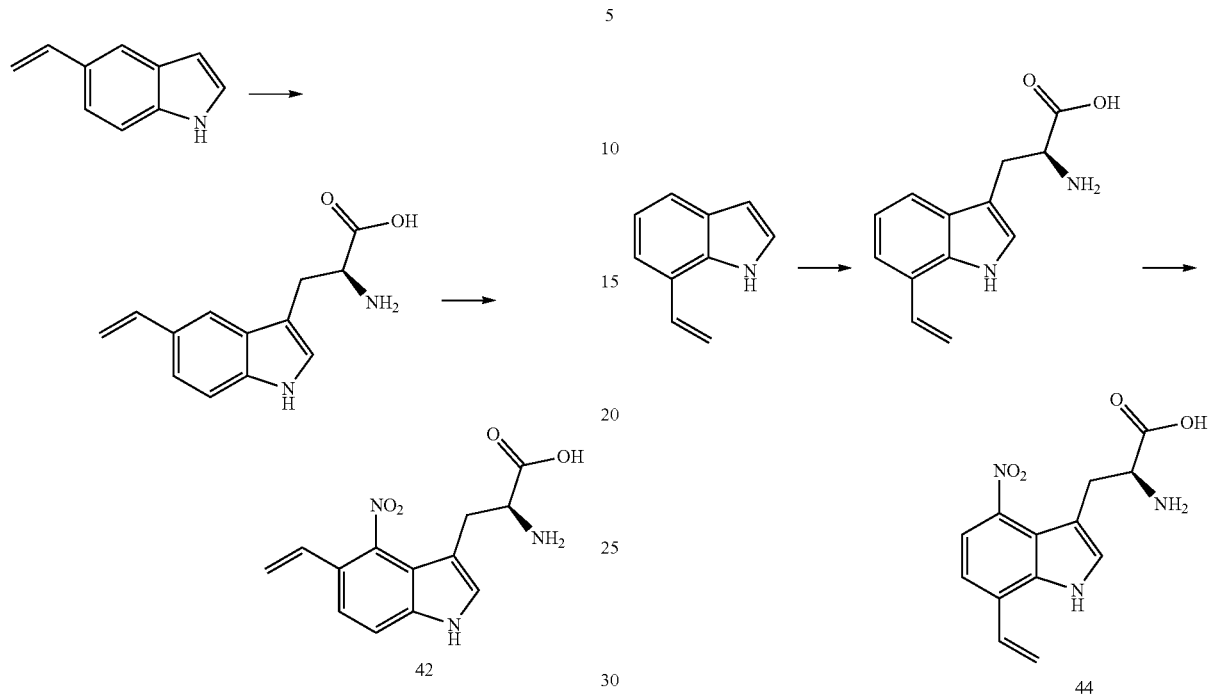

Example 42 can be prepared from 5-vinylindole as shown above and in a similar manner as described in Examples 1-7.

Example 43: Preparation of (S)-2-amino-3-(4-nitro-6-vinyl-1H-indol-3-yl)propanoic acid (43)

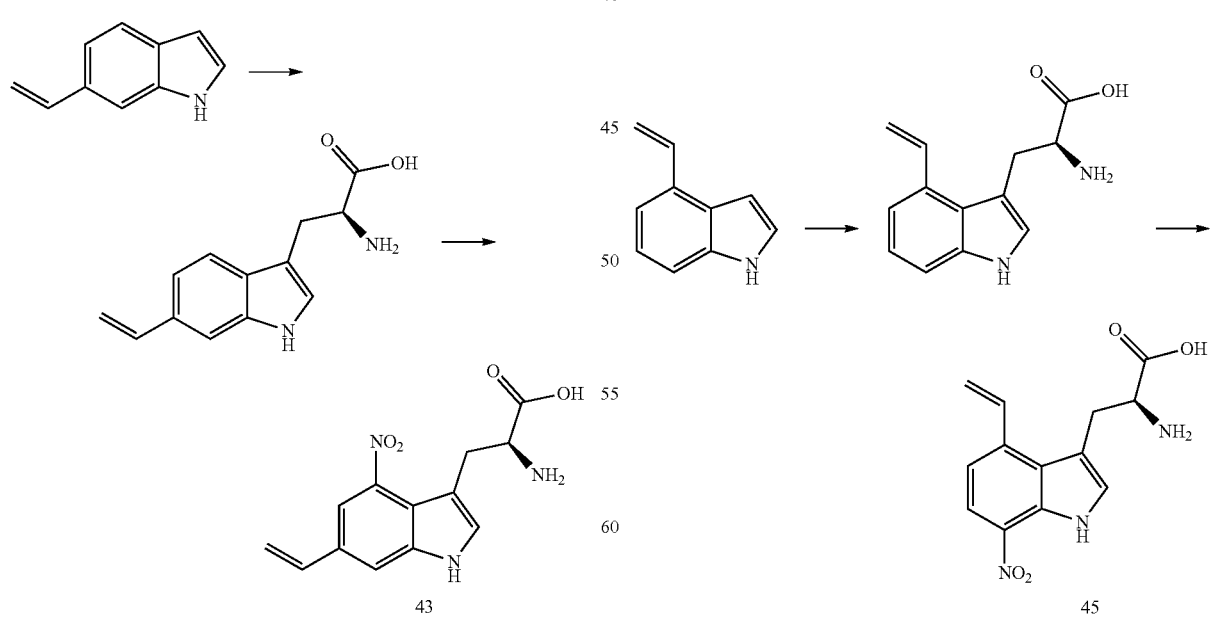

Example 43 can be prepared from 6-vinylindole as shown above and in a similar manner as described in Examples 1-7.

Example 44: Preparation of (S)-2-amino-3-(4-nitro-7-vinyl-1H-indol-3-yl)propanoic acid (44)

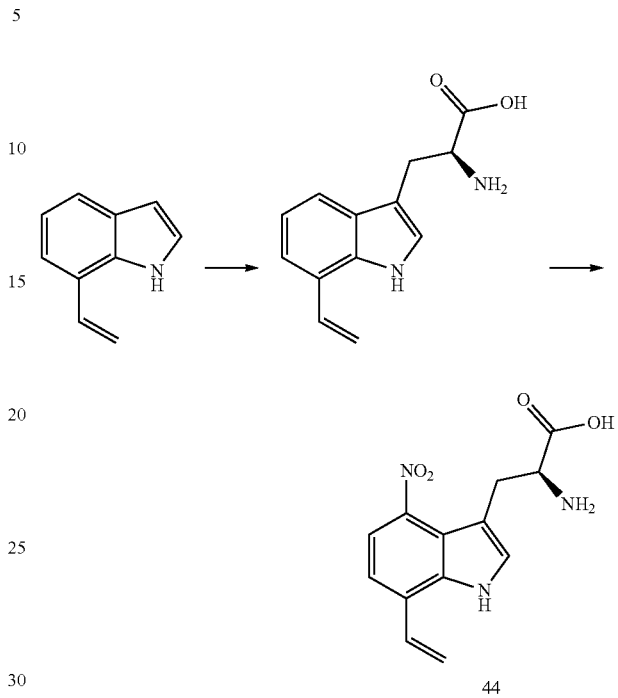

Example 44 can be prepared from 7-vinylindole as shown above and in a similar manner as described in Examples 1-7.

Example 45: Preparation of (S)-2-amino-3-(7-nitro-4-vinyl-1H-indol-3-yl)propanoic acid (45)

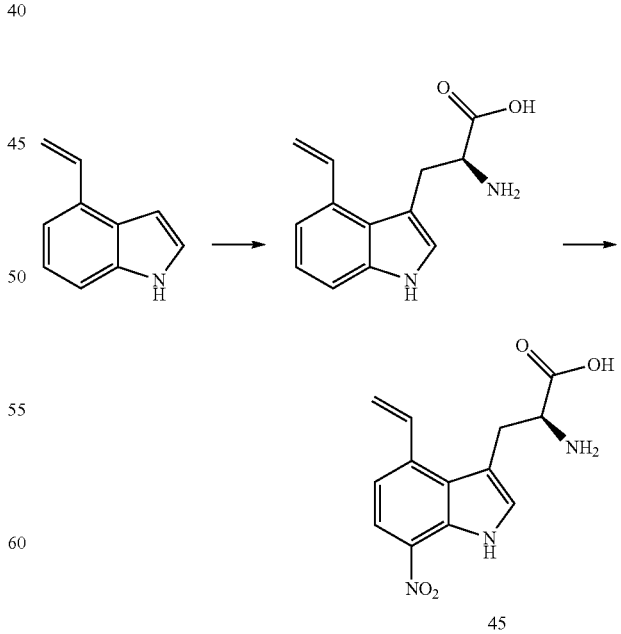

Example 45 can be prepared from 4-vinylindole as shown above and in a similar manner as described in Examples 1-7.

Example 46: Preparation of (S)-2-amino-3-(5-ethynyl-4-nitro-1H-indol-3-yl)propanoic acid (46)

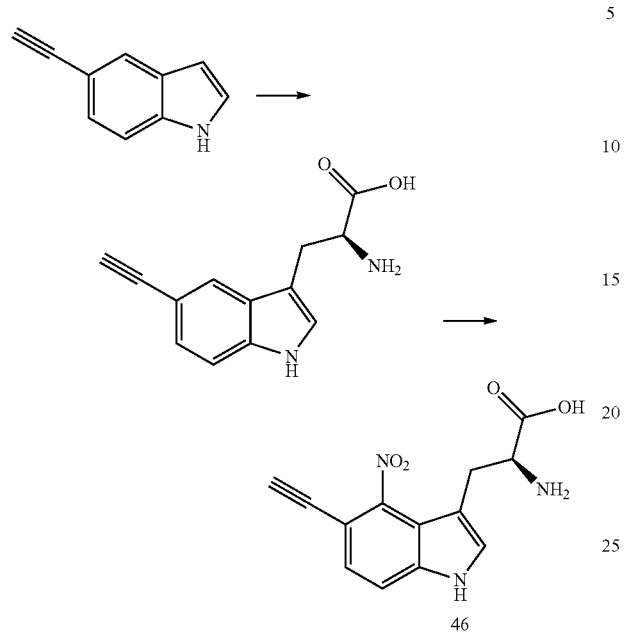

Example 46 can be prepared from 5-ethynylindole as shown above and in a similar manner as described in Examples 1-7.

Example 47: Preparation of (S)-2-amino-3-(6-ethynyl-4-nitro-1H-indol-3-yl)propanoic acid (47)

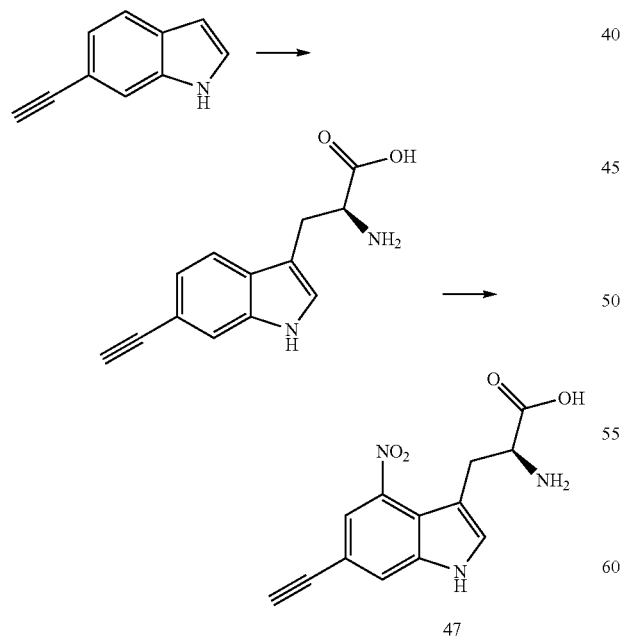

Example 47 can be prepared from 6-ethynylindole as shown above and in a similar manner as described in Examples 1-7.

Example 48: Preparation of (S)-2-amino-3-(7-ethynyl-4-nitro-1H-indol-3-yl)propanoic acid (48)

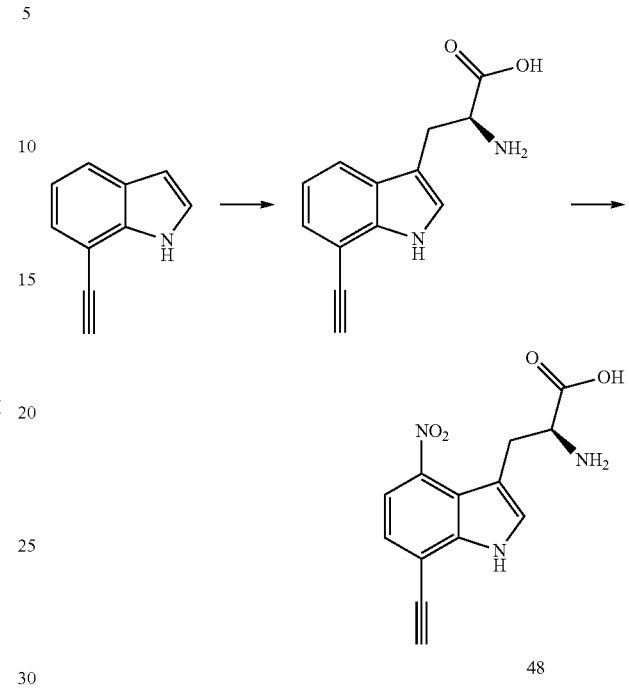

Example 48 can be prepared from 7-ethynylindole as shown above and in a similar manner as described in Examples 1-7.

Example 49: Preparation of (S)-2-amino-3-(4-ethynyl-7-nitro-1H-indol-3-yl)propanoic acid (49)

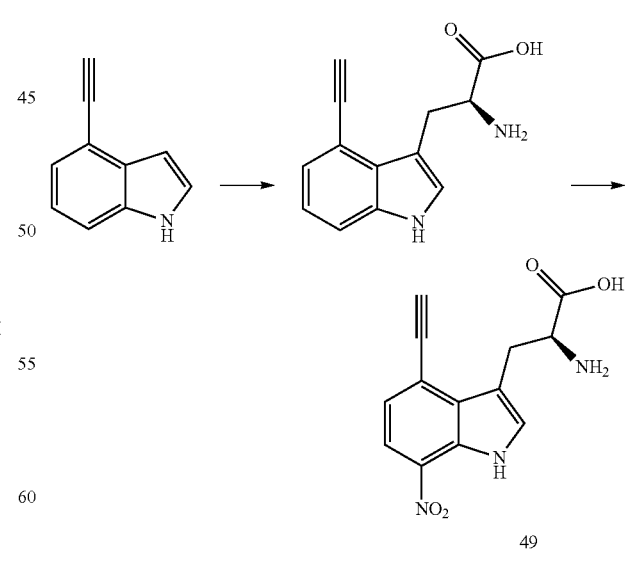

Example 49 can be prepared from 4-ethynylindole as shown above and in a similar manner as described in Examples 1-7.

Example 50: Preparation of (S)-2-amino-3-(5-morpholino-4-nitro-1H-indol-3-yl)propanoic acid (50)

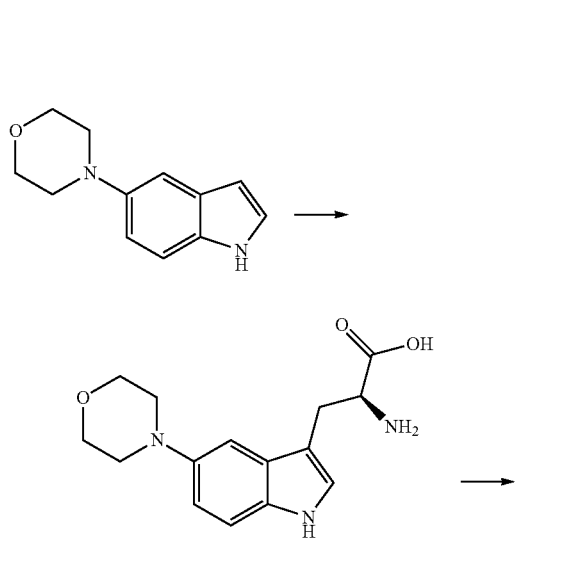

Example 50 can be prepared from 5-morpholinoindole as shown above and in a similar manner as described in Examples 1-7.

Example 51: Preparation of (S)-2-amino-3-(6-morpholino-4-nitro-1H-indol-3-yl)propanoic acid (51)

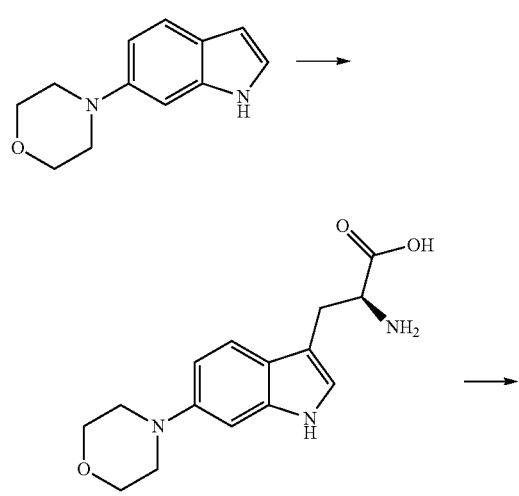

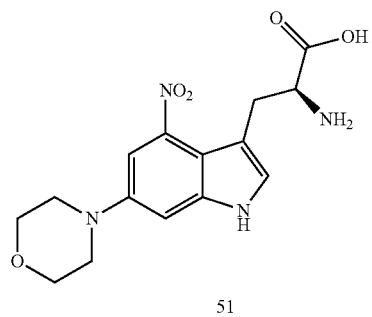

Example 51 can be prepared from 6-morpholinoindole as shown above and in a similar manner as described in Examples 1-7.

Example 52: Preparation of (S)-2-amino-3-(7-morpholino-4-nitro-1H-indol-3-yl)propanoic acid (52)

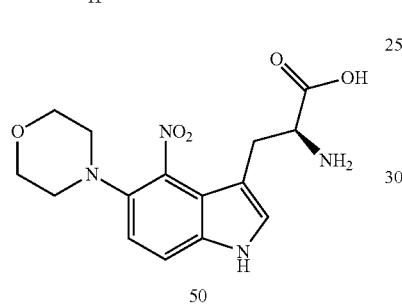

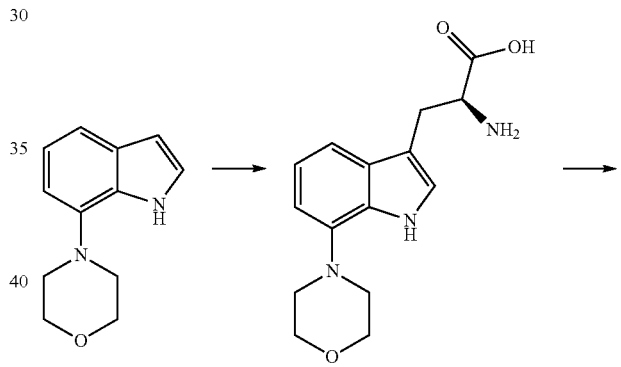

Example 52 can be prepared from 7-morpholinoindole as shown above and in a similar manner as described in Examples 1-7.

Example 53: Preparation of (S)-2-amino-3-(4-morpholino-7-nitro-1H-indol-3-yl)propanoic acid (53)

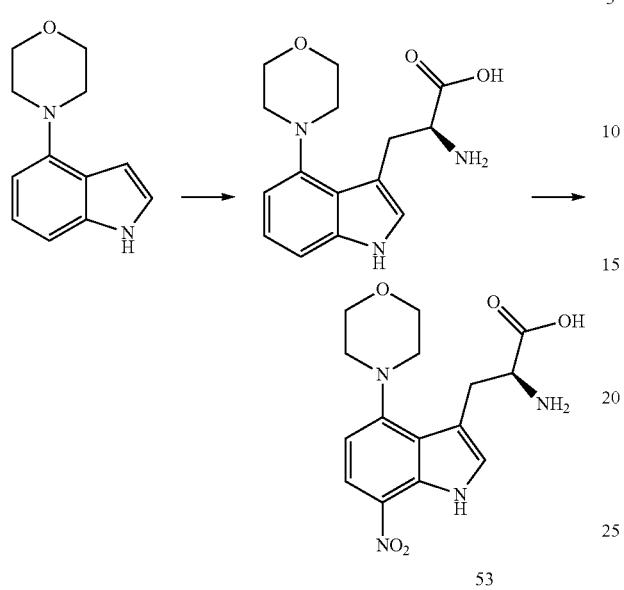

53

Example 53 can be prepared from 4-morpholinoindole as shown above and in a similar manner as described in Examples 1-7.

Example 54: Preparation of (S)-2-amino-3-(5-(methylthio)-4-nitro-1H-indol-3-yl)propanoic acid (54)

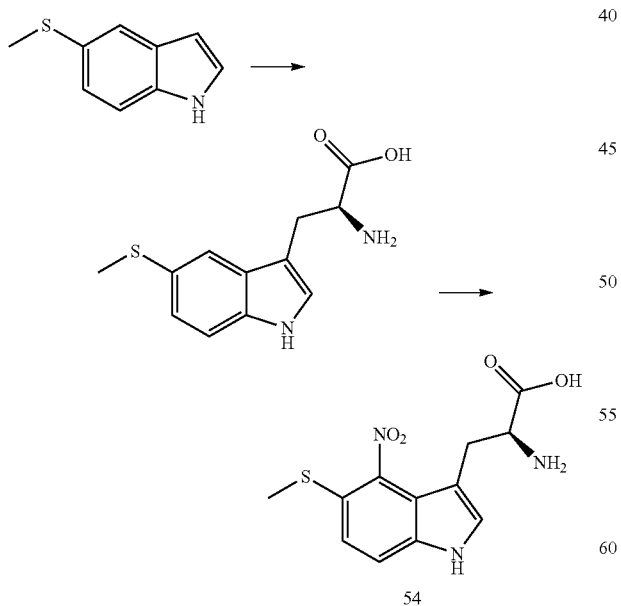

54

Example 54 can be prepared from 5-(methylthio)indole as shown above and in a similar manner as described in Examples 1-7.

Example 55: Preparation of (S)-2-amino-3-(6-(methylthio)-4-nitro-1H-indol-3-yl)propanoic acid (55)

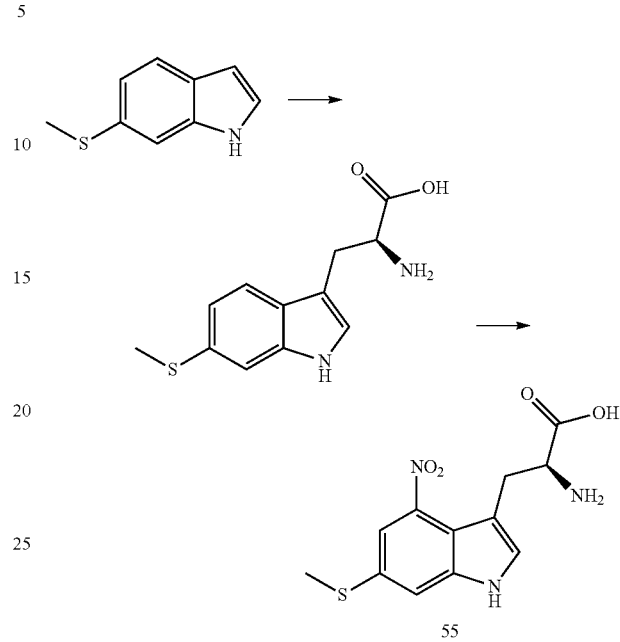

55

Example 55 can be prepared from 6-(methylthio)indole as shown above and in a similar manner as described in Examples 1-7.

Example 56: Preparation of (S)-2-amino-3-(7-(methylthio)-4-nitro-1H-indol-3-yl)propanoic acid (56)

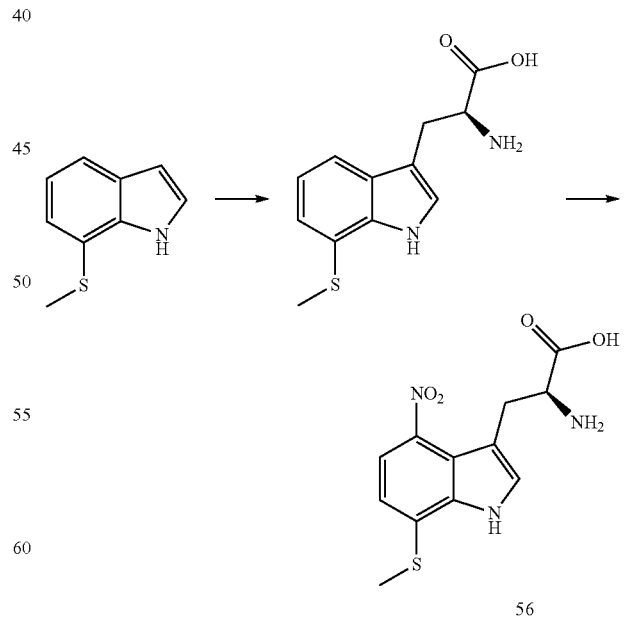

56

Example 56 can be prepared from 7-(methylthio)indole as shown above and in a similar manner as described in Examples 1-7.

Example 57: Preparation of (S)-2-amino-3-(4-(methylthio)-7-nitro-1H-indol-3-yl)propanoic acid (57)

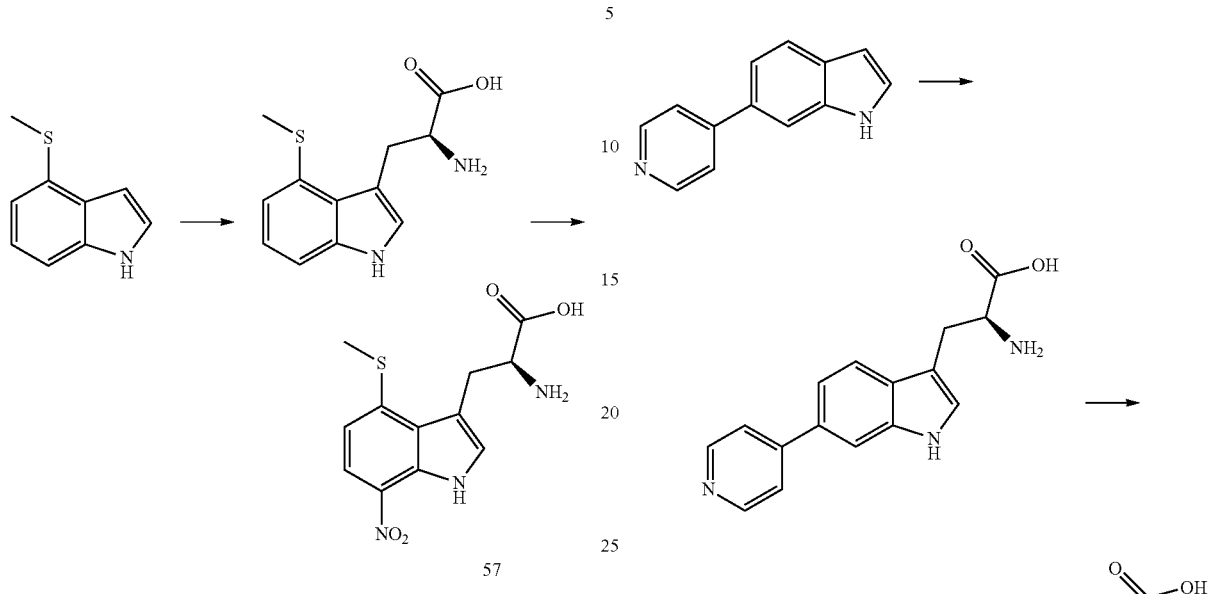

Example 57 can be prepared from 4-(methylthio)indole as shown above and in a similar manner as described in Examples 1-7.

Example 58: Preparation of (S)-2-amino-3-(4-nitro-5-(pyridin-4-yl)-1H-indol-3-yl)propanoic acid (58)

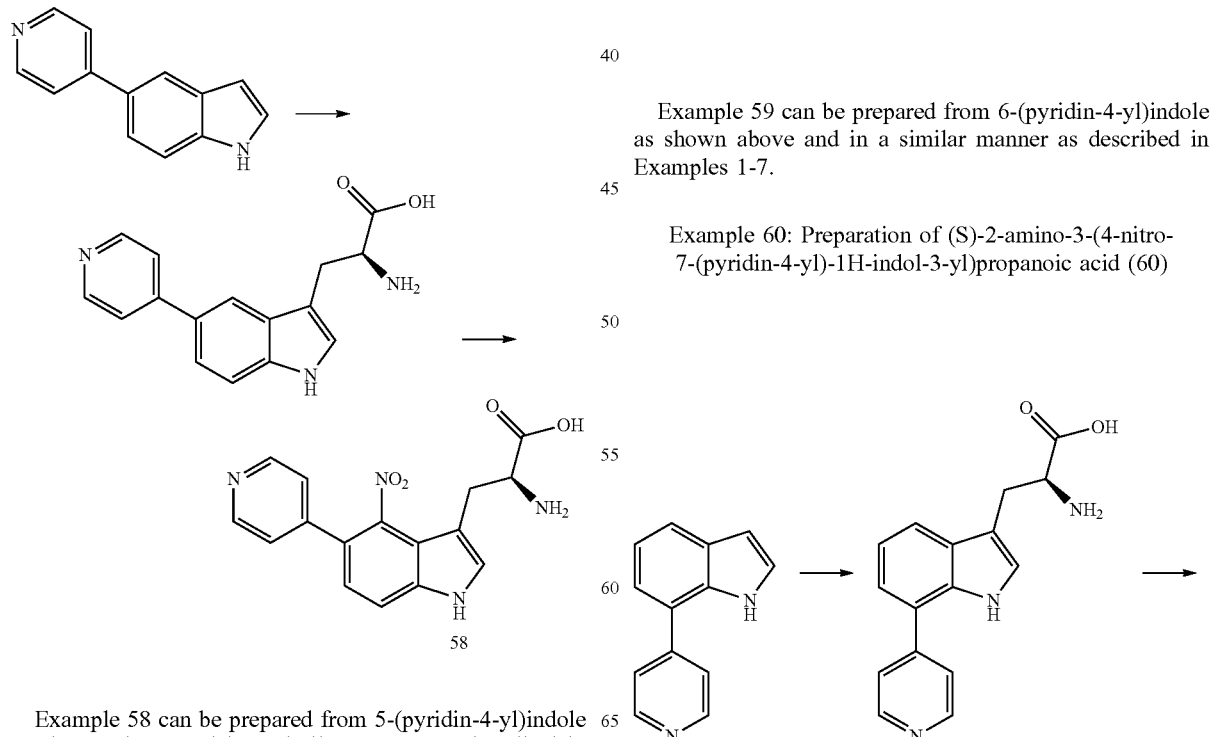

Example 58 can be prepared from 5-(pyridin-4-yl)indole as shown above and in a similar manner as described in Examples 1-7.

Example 59: Preparation of (S)-2-amino-3-(4-nitro-6-(pyridin-4-yl)-1H-indol-3-yl)propanoic acid (59)

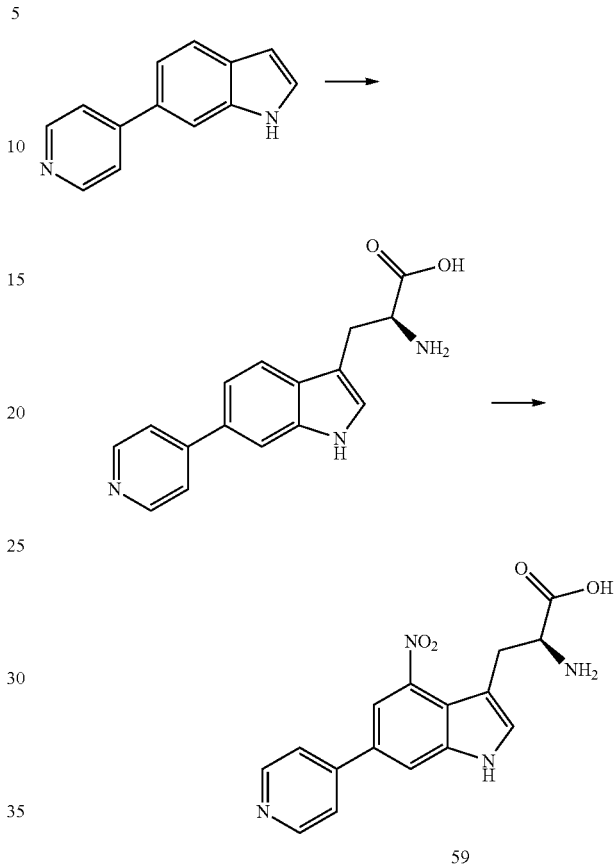

Example 59 can be prepared from 6-(pyridin-4-yl)indole as shown above and in a similar manner as described in Examples 1-7.

Example 60: Preparation of (S)-2-amino-3-(4-nitro-7-(pyridin-4-yl)-1H-indol-3-yl)propanoic acid (60)

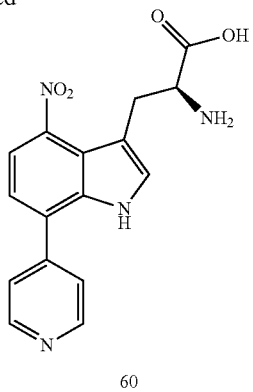

60

Example 60 can be prepared from 7-(pyridin-4-yl)indole as shown above and in a similar manner as described in Examples 1-7.

Example 61: Preparation of (S)-2-amino-3-(7-nitro-4-(pyridin-4-yl)-1H-indol-3-yl)propanoic acid (61)

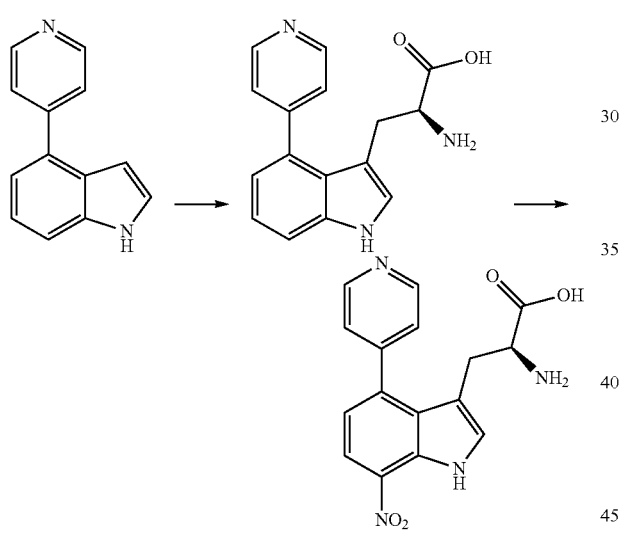

61

Example 61 can be prepared from 4-(pyridin-4-yl)indole as shown above and in a similar manner as described in Examples 1-7.

Example 62: Preparation of 2-amino-3-(5-methyl-4-nitro-1H-indol-3-yl)propanoic acid (62)

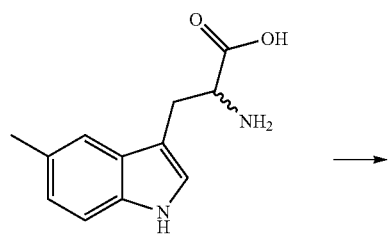

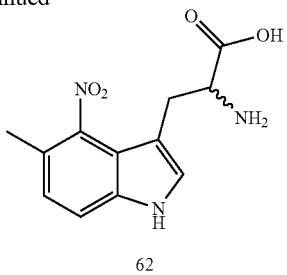

62

Example 62 was prepared from 2-amino-3-(5-methyl-1H-indol-3-yl)propanoic acid as shown above and in a similar manner as described in Examples 1-7.

Example 63: Preparation of 2-amino-3-(6-methyl-4-nitro-1H-indol-3-yl)propanoic acid (63)

63

Example 63 can be prepared from 6-methylindole as shown above and in a similar manner as described in Examples 1-7.

Example 64: Preparation of 2-amino-3-(7-methyl-4-nitro-1H-indol-3-yl)propanoic acid (64)

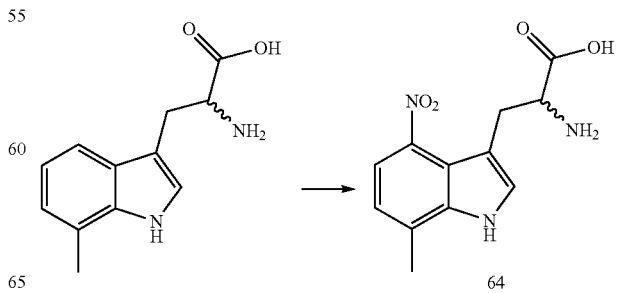

64

Example 64 was prepared from 2-amino-3-(7-methyl-1H-indol-3-yl)propanoic acid as shown above and in a similar manner as described in Examples 1-7.

Example 65: Preparation of 2-amino-3-(4-methyl-7-nitro-1H-indol-3-yl)propanoic acid (65)

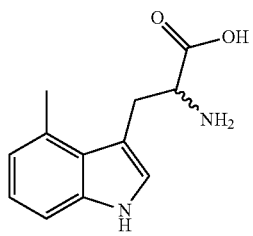

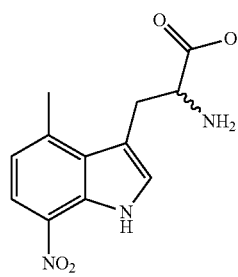

65

Example 65 was prepared from 2-amino-3-(4-methyl-1H-indol-3-yl)propanoic acid as shown above and in a similar manner as described in Examples 1-7.

Example 66: Preparation of 2-amino-3-(6-fluoro-4-nitro-1H-indol-3-yl)propanoic acid (66)

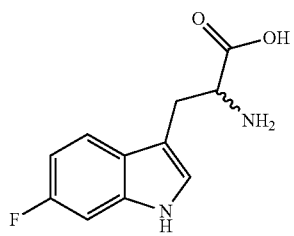

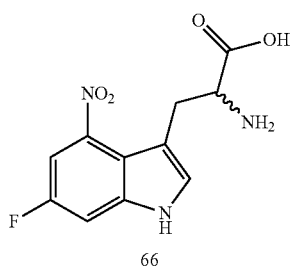

66

Example 66 was prepared from 2-amino-3-(6-fluoro-1H-indol-3-yl)propanoic acid as shown above and in a similar manner as described in Examples 1-7.

Example 67: Preparation of 2-amino-3-(7-fluoro-4-nitro-1H-indol-3-yl)propanoic acid (67)

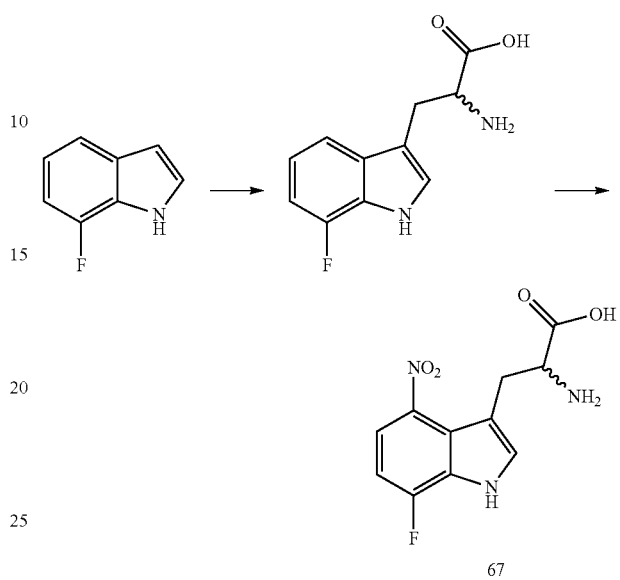

67

Example 67 can be prepared from 7-fluoroindole as shown above and in a similar manner as described in Examples 1-7.

Example 68: Preparation of 2-amino-3-(4-fluoro-7-nitro-1H-indol-3-yl)propanoic acid (68)

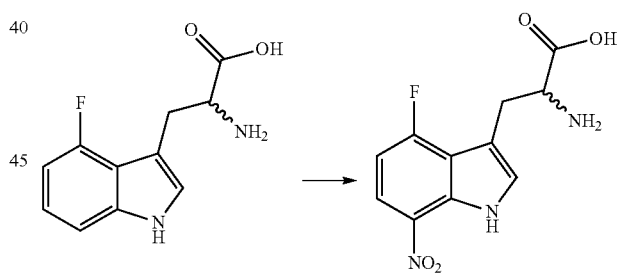

68

Example 68 was prepared from 2-amino-3-(4-fluoro-1H-indol-3-yl)propanoic acid as shown above and in a similar manner as described in Examples 1-7.

Example 69: Preparation of 2-amino-3-(5-chloro-4-nitro-1H-indol-3-yl)propanoic acid (69)

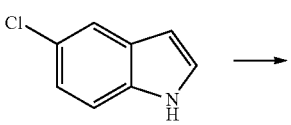

-continued

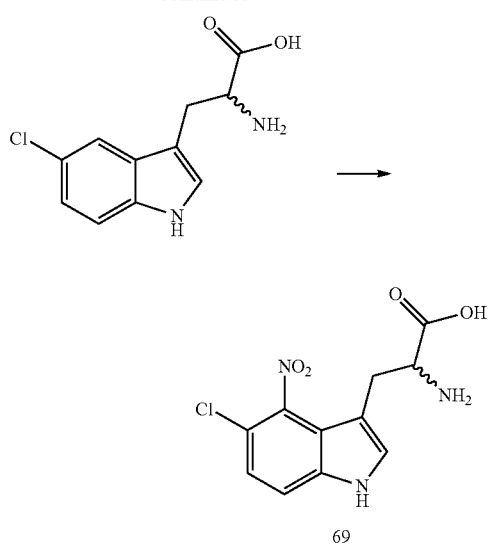

69

Example 69 can be prepared from 5-chloroindole as shown above and in a similar manner as described in Examples 1-7.

Example 70: Preparation of 2-amino-3-(6-chloro-4-nitro-1H-indol-3-yl)propanoic acid (70)

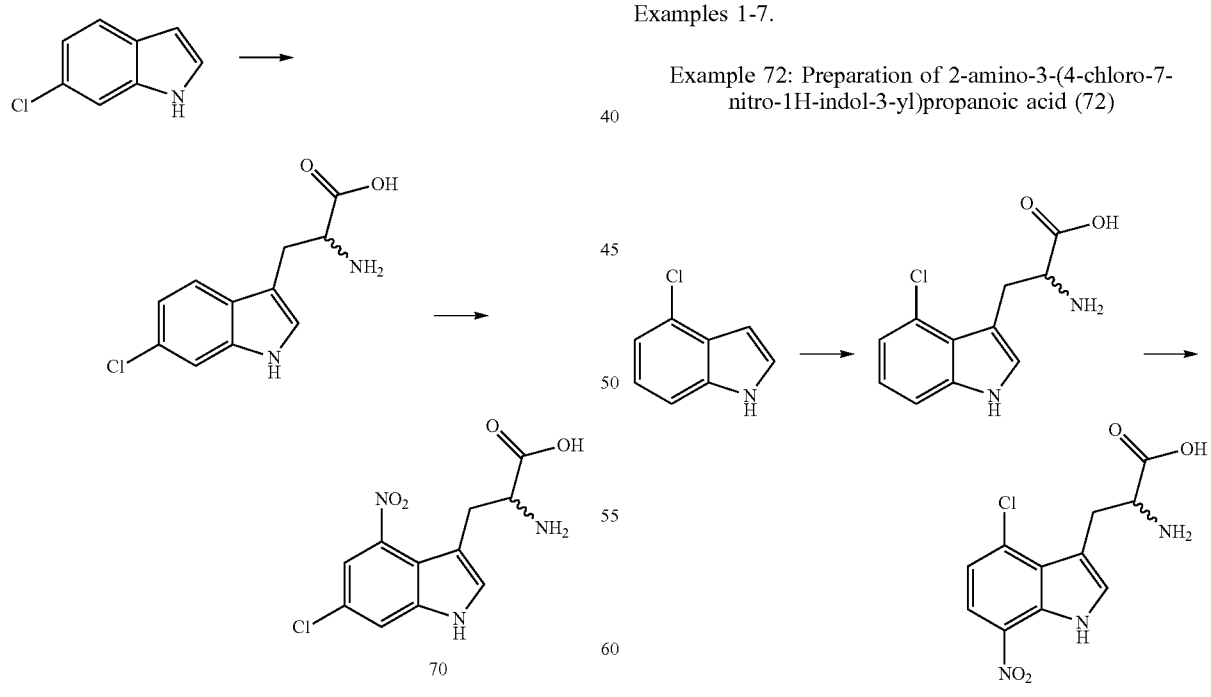

70

Example 70 can be prepared from 6-chloroindole as shown above and in a similar manner as described in Examples 1-7.

Example 71: Preparation of 2-amino-3-(7-chloro-4-nitro-1H-indol-3-yl)propanoic acid (71)

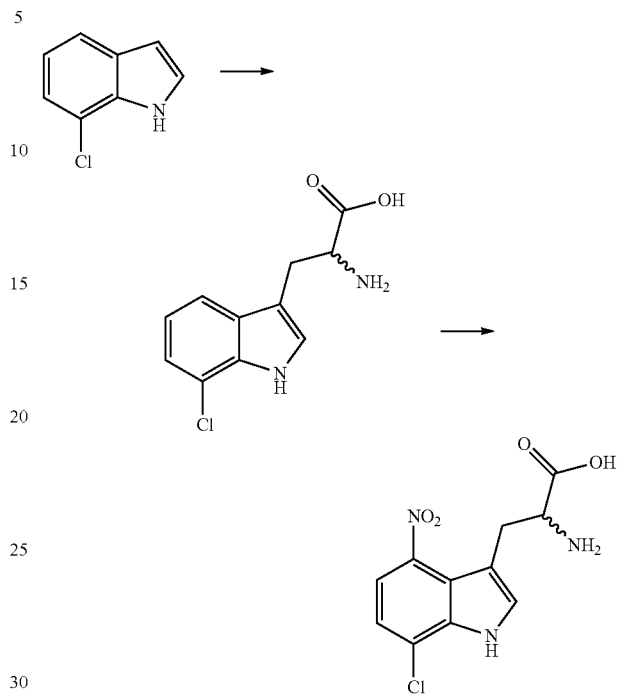

71

Example 71 can be prepared from 7-chloroindole as shown above and in a similar manner as described in Examples 1-7.

Example 72: Preparation of 2-amino-3-(4-chloro-7-nitro-1H-indol-3-yl)propanoic acid (72)

72

Example 72 can be prepared from 4-chloroindole as shown above and in a similar manner as described in Examples 1-7.

Example 73: Preparation of 2-amino-3-(5-bromo-4-nitro-1H-indol-3-yl)propanoic acid (73)

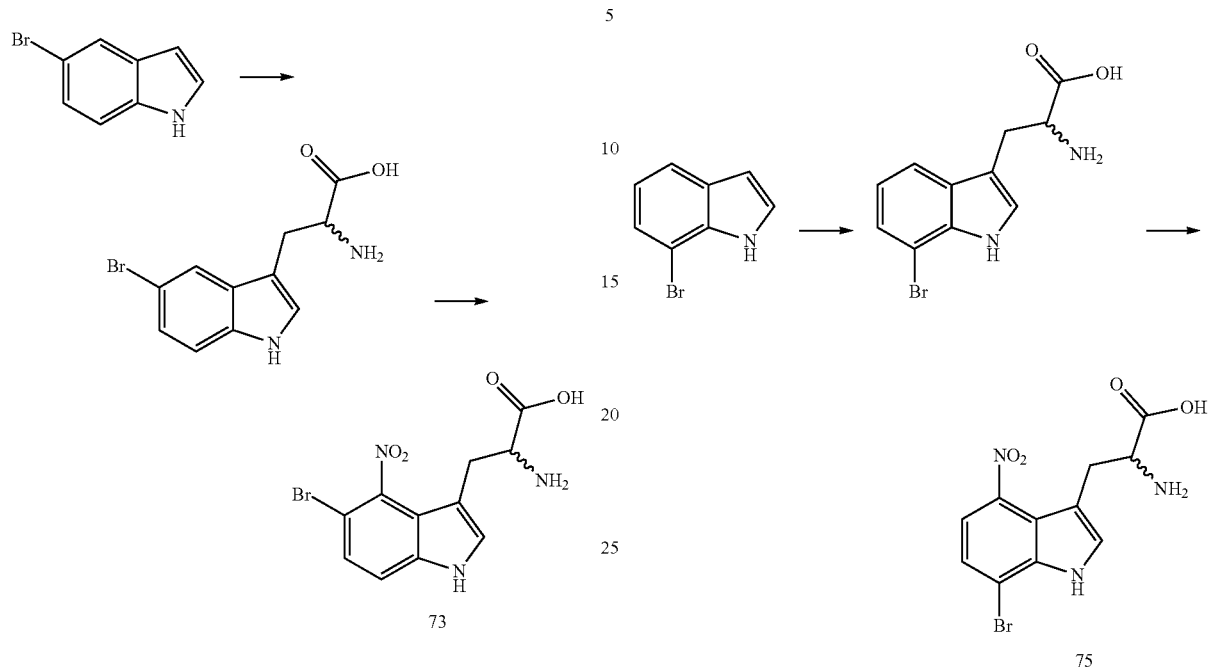

Example 73 can be prepared from 5-bromoindole as shown above and in a similar manner as described in Examples 1-7.

Example 74: Preparation of 2-amino-3-(6-bromo-4-nitro-1H-indol-3-yl)propanoic acid (74)

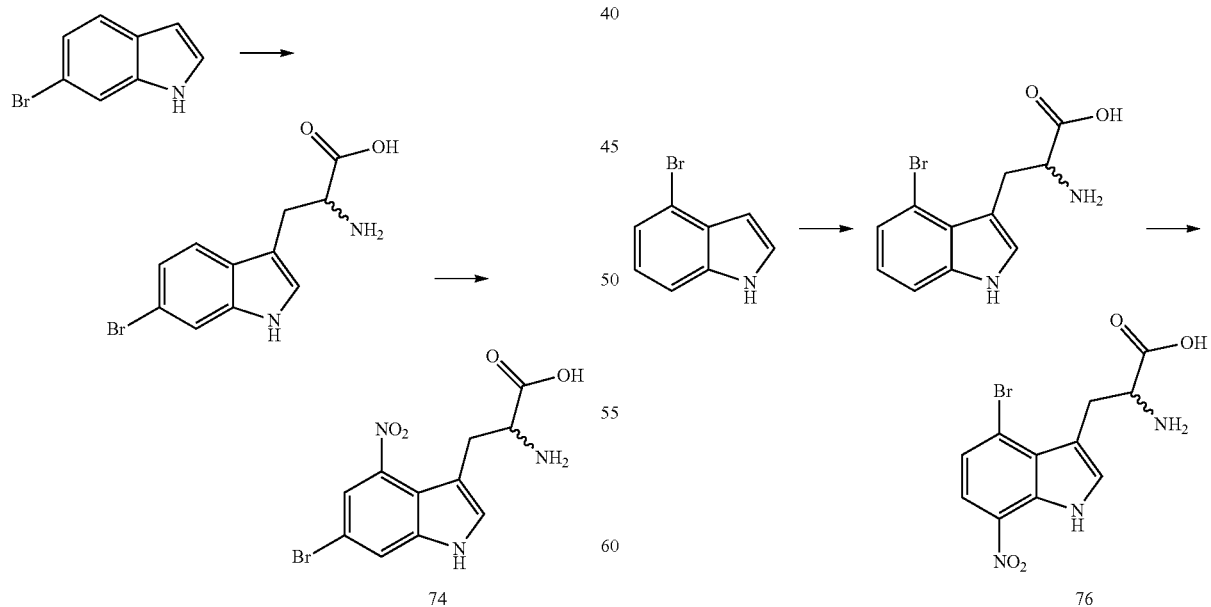

Example 74 can be prepared from 6-bromoindole as shown above and in a similar manner as described in Examples 1-7.

Example 75: Preparation of 2-amino-3-(7-bromo-4-nitro-1H-indol-3-yl)propanoic acid (75)

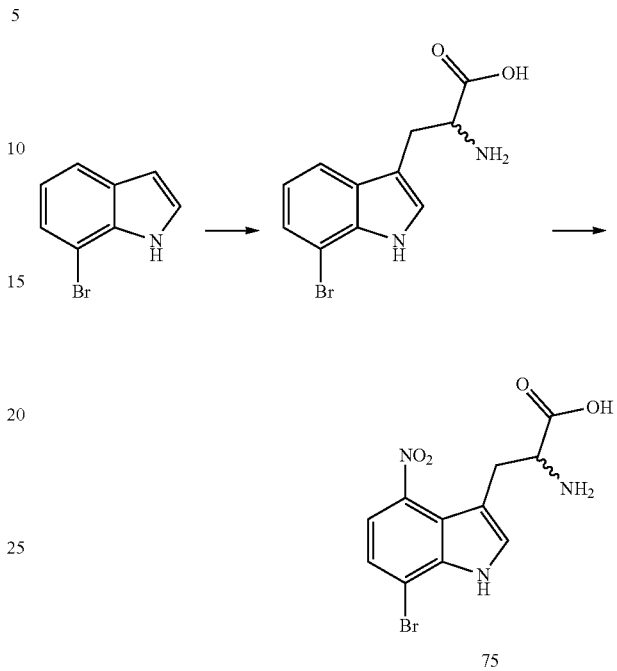

Example 75 can be prepared from 7-bromoindole as shown above and in a similar manner as described in Examples 1-7.

Example 76: Preparation of 2-amino-3-(4-bromo-7-nitro-1H-indol-3-yl)propanoic acid (76)

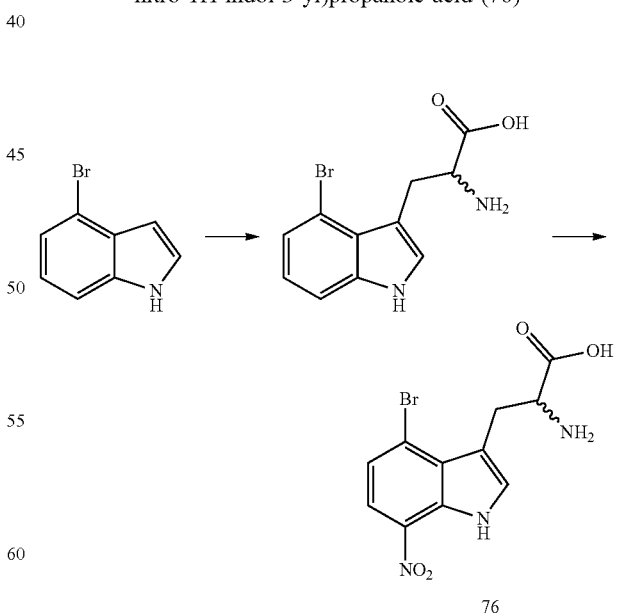

Example 76 can be prepared from 4-bromoindole as shown above and in a similar manner as described in Examples 1-7.

Example 77: Preparation of 2-amino-3-(5-methoxy-4-nitro-1H-indol-3-yl)propanoic acid (77)

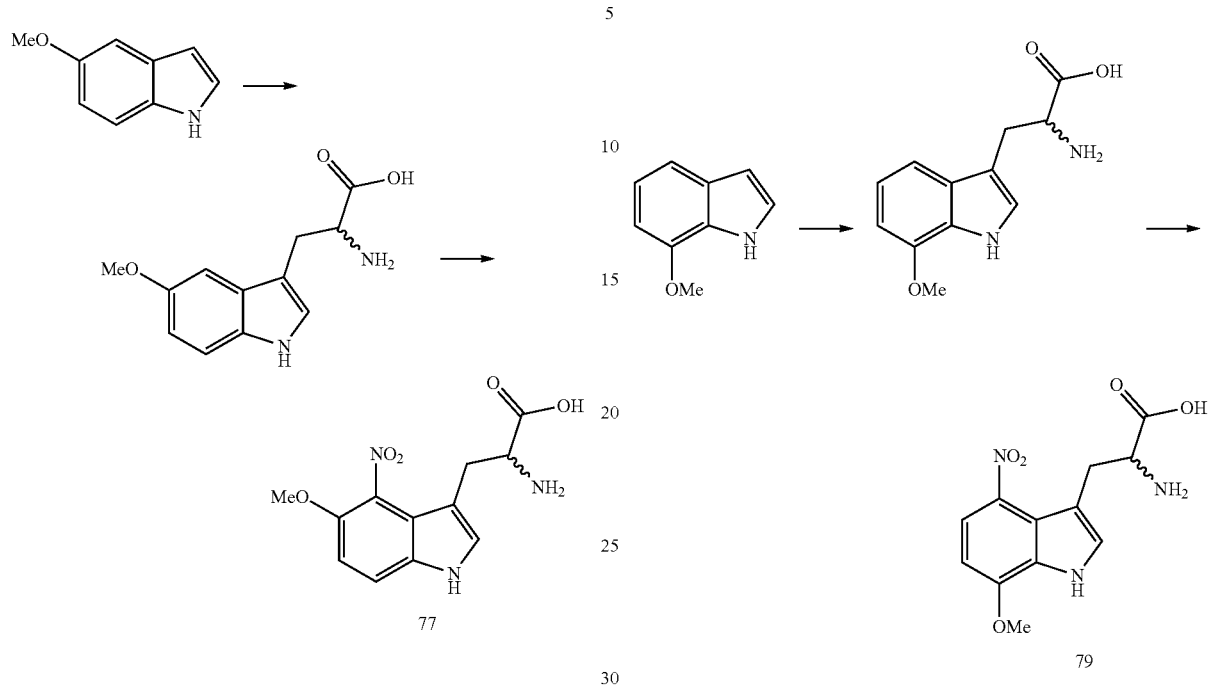

Example 77 can be prepared from 5-methoxyindole as shown above and in a similar manner as described in Examples 1-7.

Example 78: Preparation of 2-amino-3-(6-methoxy-4-nitro-1H-indol-3-yl)propanoic acid (78)

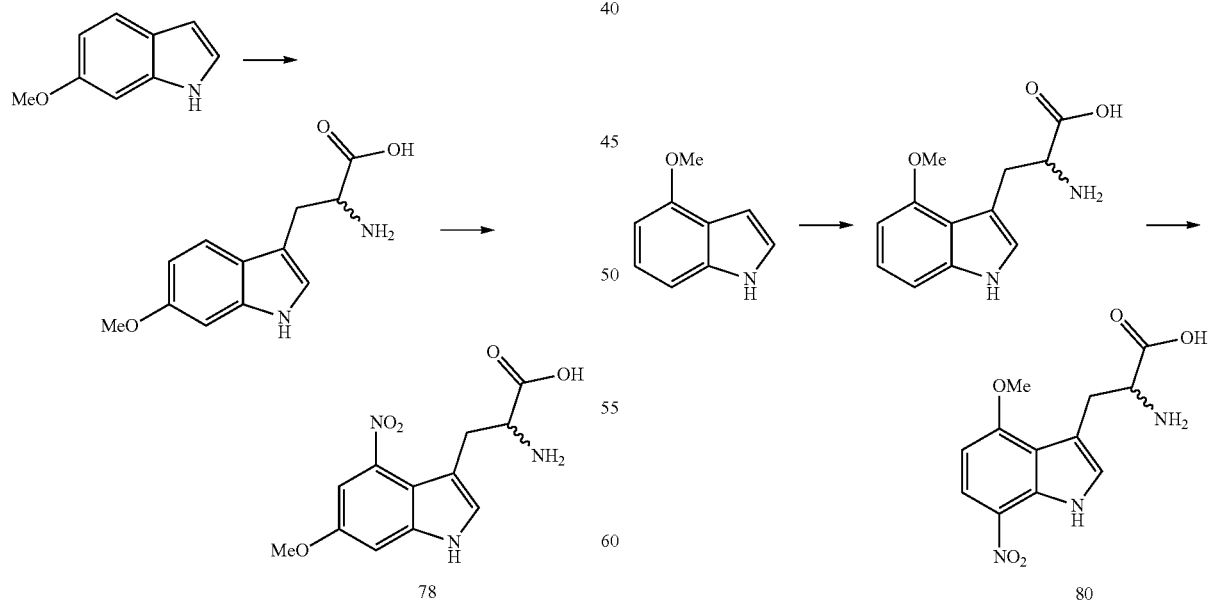

Example 78 can be prepared from 6-methoxyindole as shown above and in a similar manner as described in Examples 1-7.

Example 79: Preparation of 2-amino-3-(7-methoxy-4-nitro-1H-indol-3-yl)propanoic acid (79)

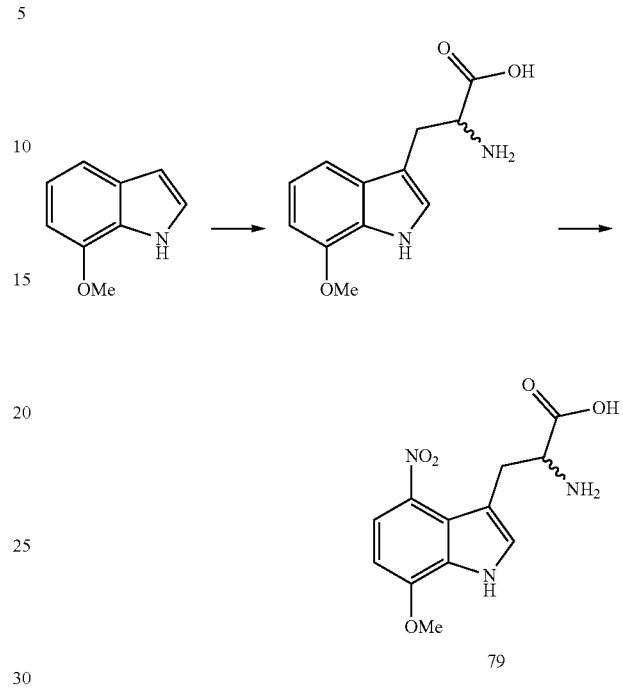

Example 79 can be prepared from 7-methoxyindole as shown above and in a similar manner as described in Examples 1-7.

Example 80: Preparation of 2-amino-3-(4-methoxy-7-nitro-1H-indol-3-yl)propanoic acid (80)

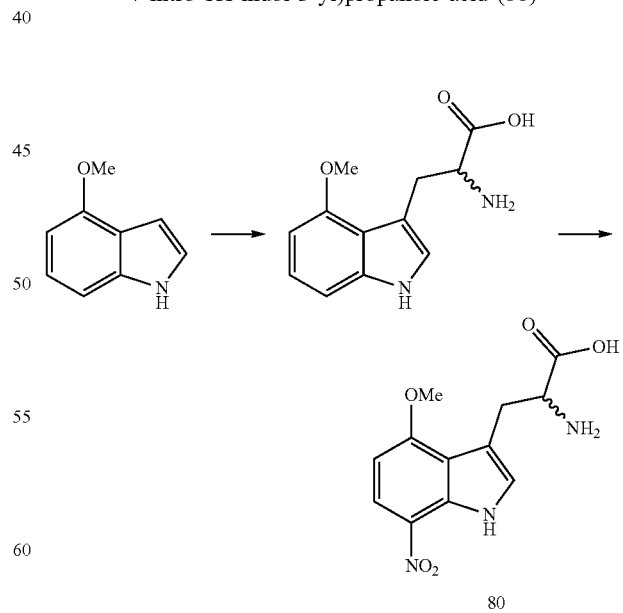

Example 80 can be prepared from 4-methoxyindole as shown above and in a similar manner as described in Examples 1-7.

Example 81: Preparation of 2-amino-3-(5-amino-4-nitro-1H-indol-3-yl)propanoic acid (81)

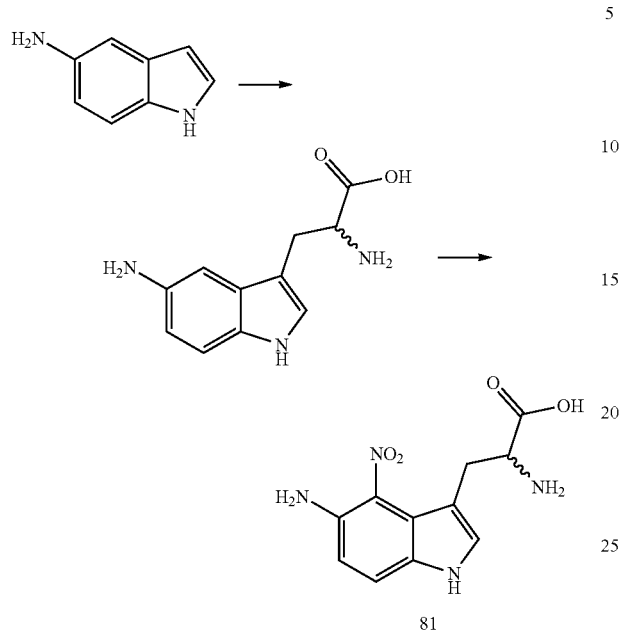

Example 81 can be prepared from 5-aminoindole as shown above and in a similar manner as described in Examples 1-7.

Example 82: Preparation of 2-amino-3-(6-amino-4-nitro-1H-indol-3-yl)propanoic acid (82)

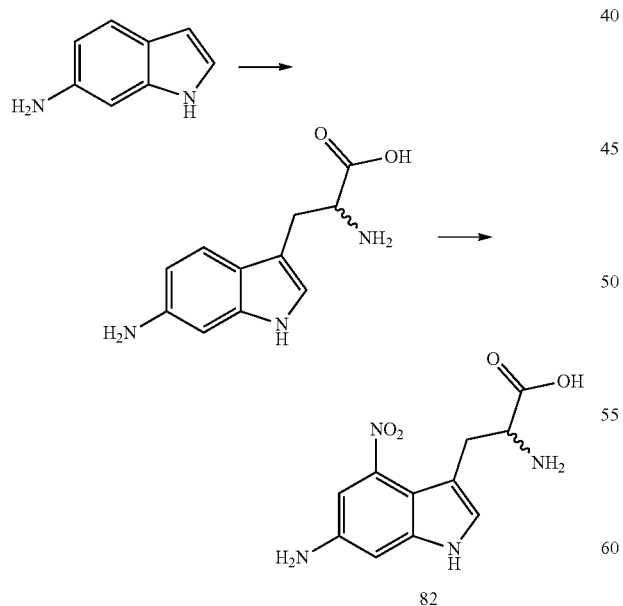

Example 82 can be prepared from 6-aminoindole as shown above and in a similar manner as described in Examples 1-7.

Example 83: Preparation of 2-amino-3-(7-amino-4-nitro-1H-indol-3-yl)propanoic acid (83)

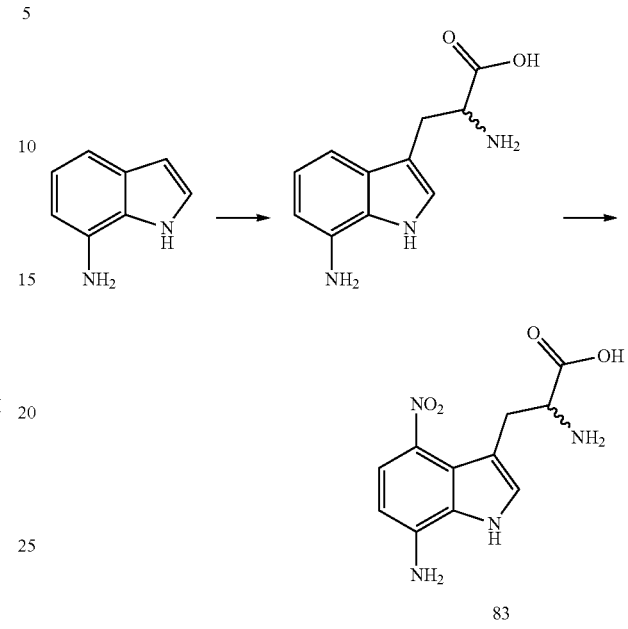

Example 83 can be prepared from 7-aminoindole as shown above and in a similar manner as described in Examples 1-7.

Example 84: Preparation of 2-amino-3-(4-amino-7-nitro-1H-indol-3-yl)propanoic acid (84)

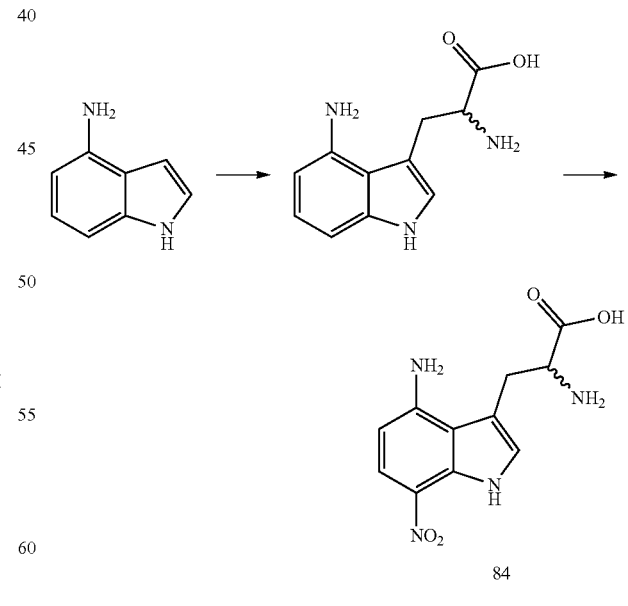

Example 84 can be prepared from 4-aminoindole as shown above and in a similar manner as described in Examples 1-7.

Example 85: Preparation of 2-amino-3-(5-hydroxy-4-nitro-1H-indol-3-yl)propanoic acid (85)

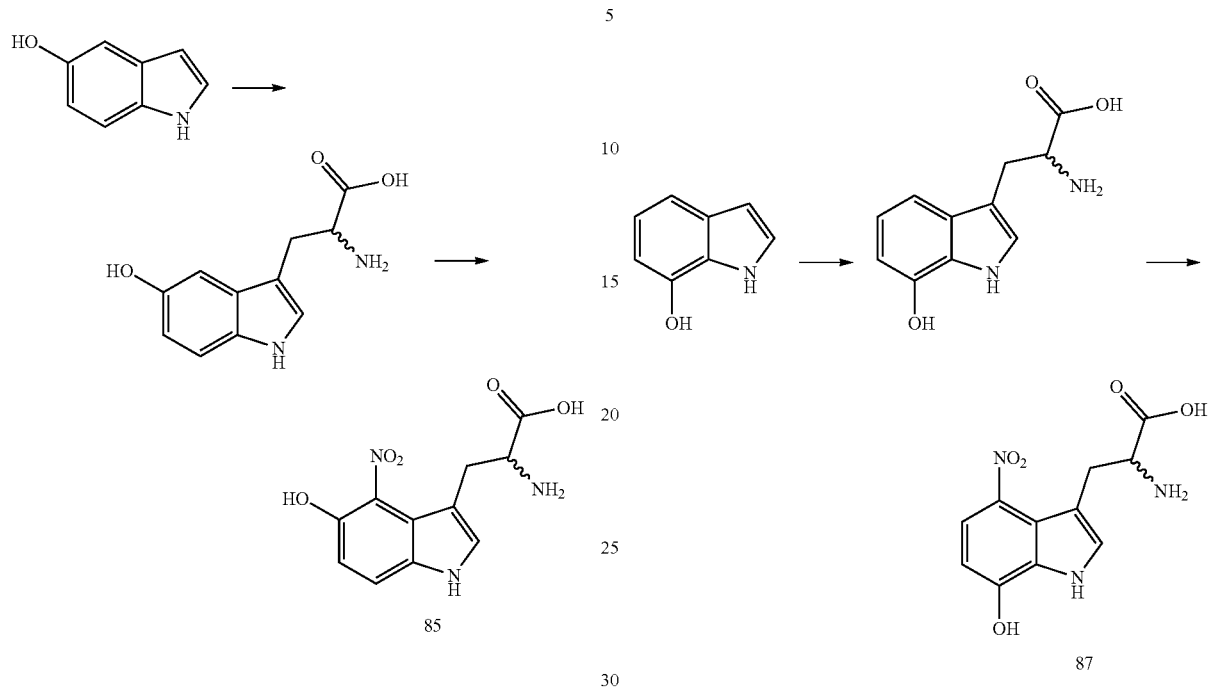

Example 85 can be prepared from 5-hydroxyindole as shown above and in a similar manner as described in Examples 1-7.

Example 86: Preparation of 2-amino-3-(6-hydroxy-4-nitro-1H-indol-3-yl)propanoic acid (86)

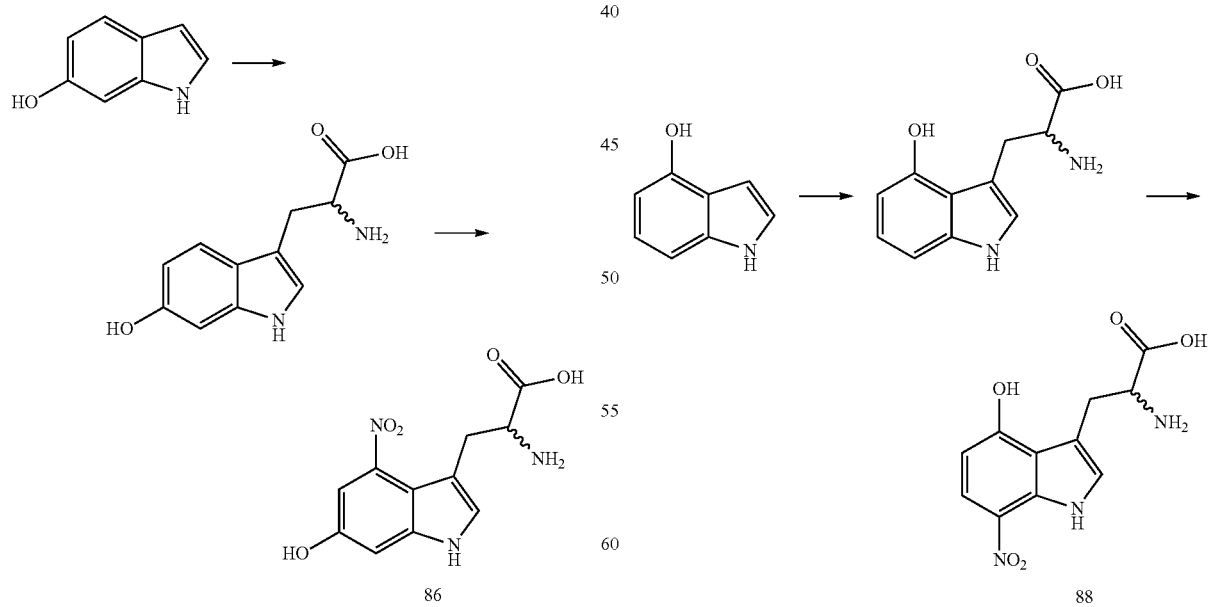

Example 86 can be prepared from 6-hydroxyindole as shown above and in a similar manner as described in Examples 1-7.

Example 87: Preparation of 2-amino-3-(7-hydroxy-4-nitro-1H-indol-3-yl)propanoic acid (87)

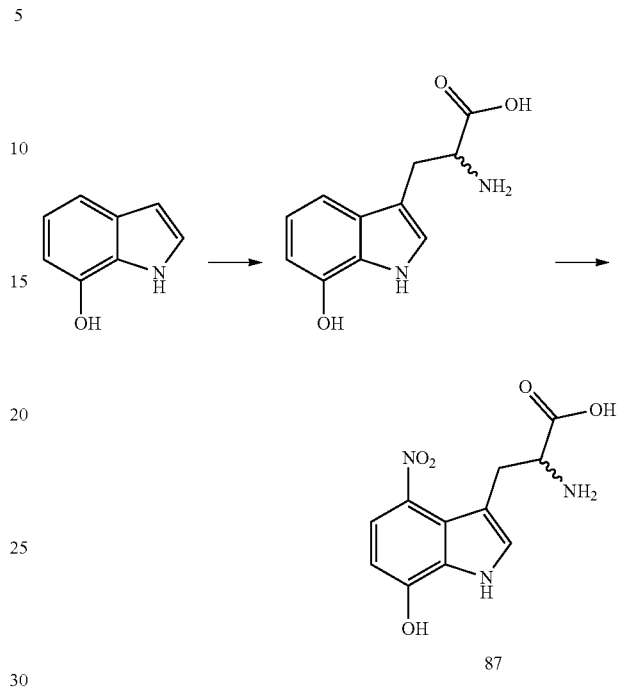

Example 87 can be prepared from 7-hydroxyindole as shown above and in a similar manner as described in Examples 1-7.

Example 88: Preparation of 2-amino-3-(4-hydroxy-7-nitro-1H-indol-3-yl)propanoic acid (88)

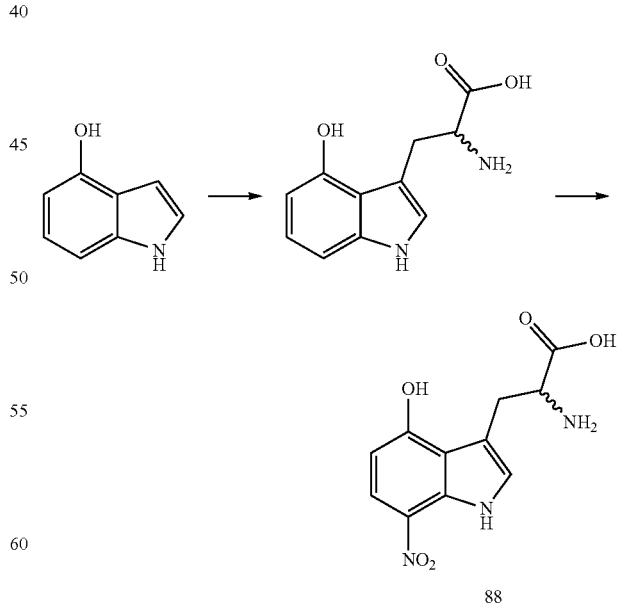

Example 88 can be prepared from 4-hydroxyindole as shown above and in a similar manner as described in Examples 1-7.

Example 89: Preparation of 2-amino-3-(4-nitro-5-phenyl-1H-indol-3-yl)propanoic acid (89)

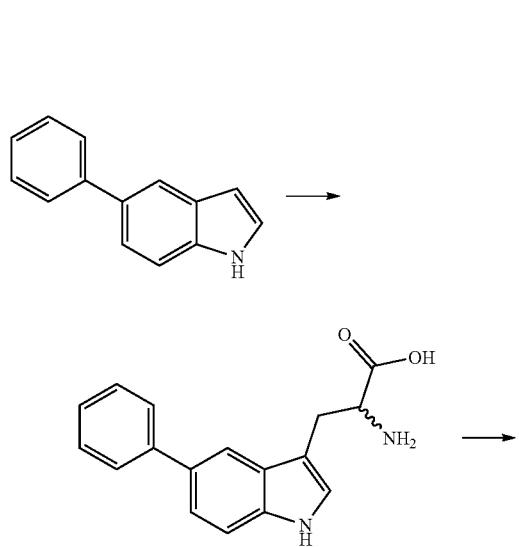

Example 89 can be prepared from 5-phenylindole as shown above and in a similar manner as described in Examples 1-7.

Example 90: Preparation of 2-amino-3-(4-nitro-6-phenyl-1H-indol-3-yl)propanoic acid (90)

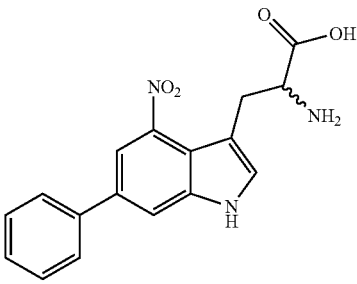

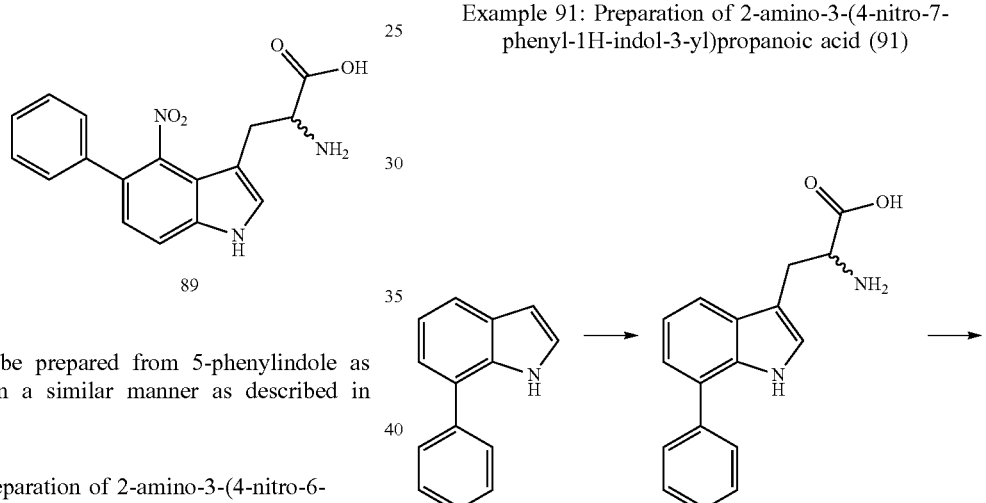

Example 90 can be prepared from 6-phenylindole as shown above and in a similar manner as described in Examples 1-7.

Example 91: Preparation of 2-amino-3-(4-nitro-7-phenyl-1H-indol-3-yl)propanoic acid (91)

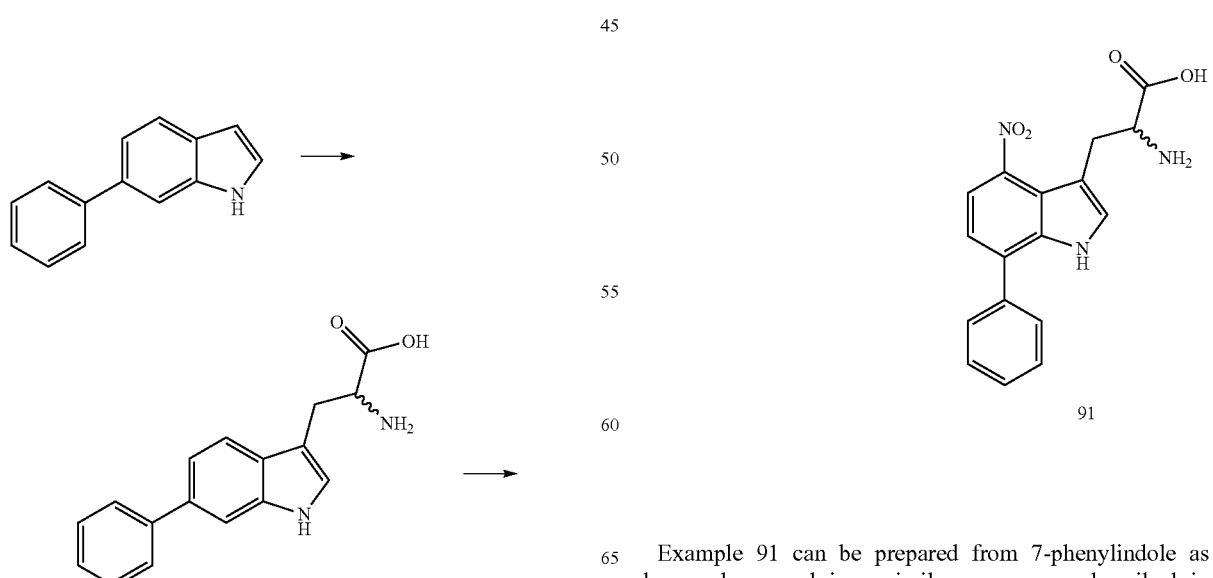

Example 91 can be prepared from 7-phenylindole as shown above and in a similar manner as described in Examples 1-7.

Example 92: Preparation of 2-amino-3-(7-nitro-4-phenyl-1H-indol-3-yl)propanoic acid (92)

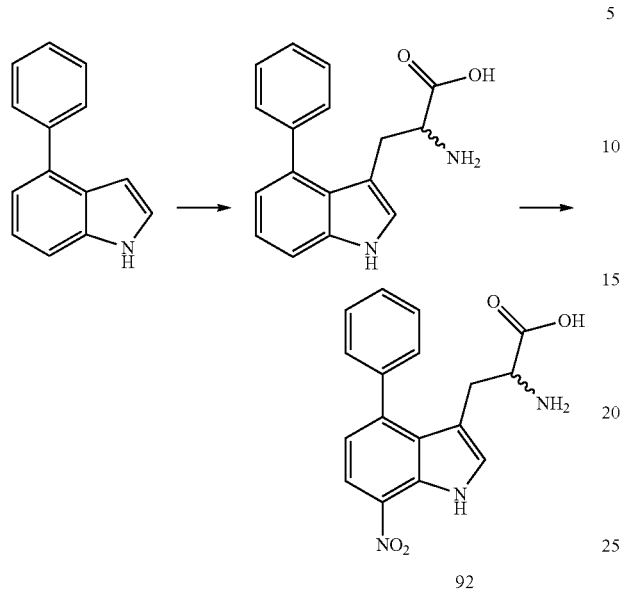

Example 92 can be prepared from 4-phenylindole as shown above and in a similar manner as described in Examples 1-7.

Example 93: Preparation of 2-amino-3-(5-cyclopropyl-4-nitro-1H-indol-3-yl)propanoic acid (93)

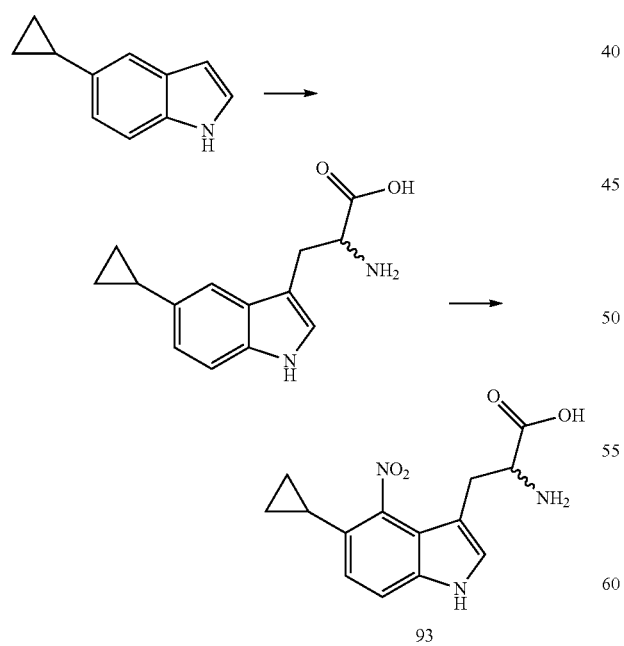

Example 93 can be prepared from 5-cyclopropylindole as shown above and in a similar manner as described in Examples 1-7.

Example 94: Preparation of 2-amino-3-(6-cyclopropyl-4-nitro-1H-indol-3-yl)propanoic acid (94)

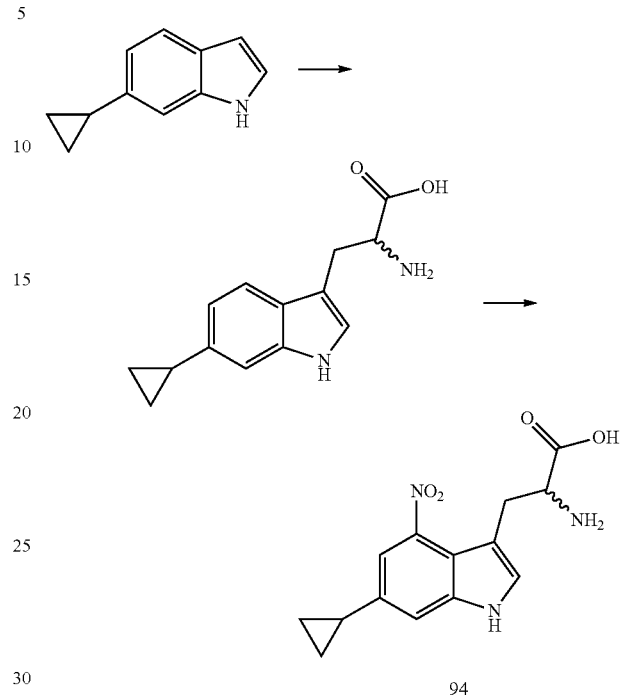

Example 94 can be prepared from 6-cyclopropylindole as shown above and in a similar manner as described in Examples 1-7.

Example 95: Preparation of 2-amino-3-(7-cyclopropyl-4-nitro-1H-indol-3-yl)propanoic acid (95)

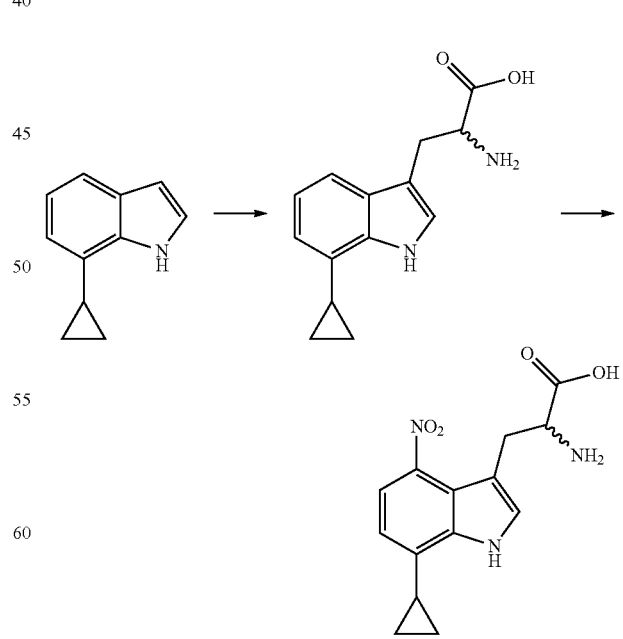

Example 95 can be prepared from 7-cyclopropylindole as shown above and in a similar manner as described in Examples 1-7.

Example 96: Preparation of 2-amino-3-(4-cyclopropyl-7-nitro-1H-indol-3-yl)propanoic acid (96)

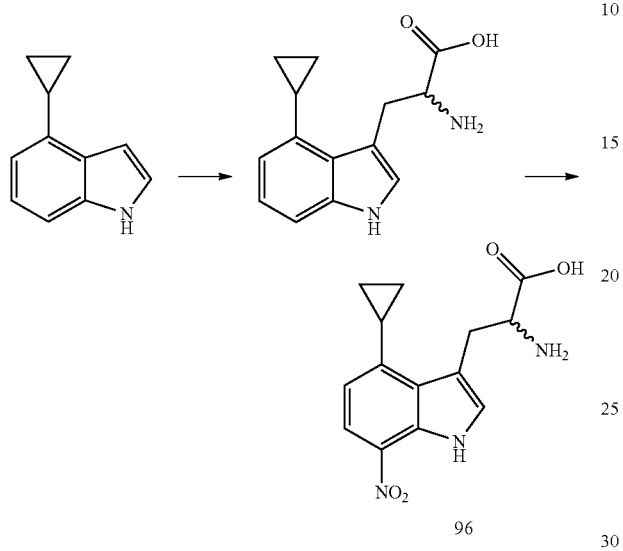

Example 96 can be prepared from 4-cyclopropylindole as shown above and in a similar manner as described in Examples 1-7.

Example 97: Preparation of 2-amino-3-(4-nitro-5-vinyl-1H-indol-3-yl)propanoic acid (97)

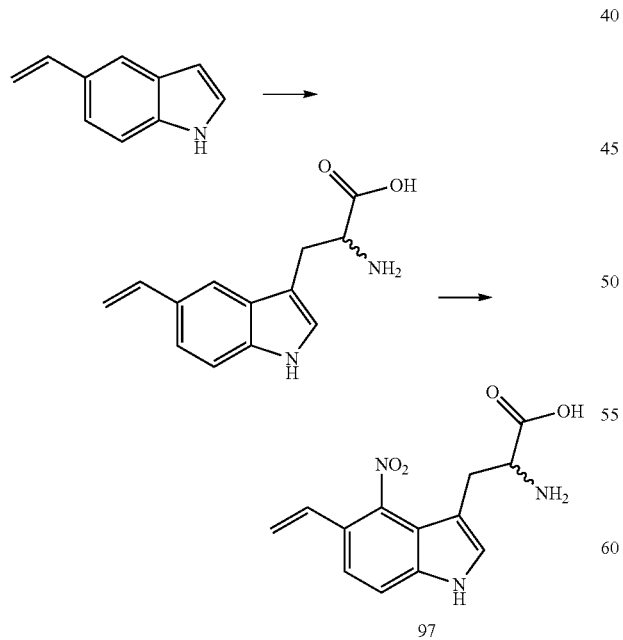

Example 97 can be prepared from 5-vinylindole as shown above and in a similar manner as described in Examples 1-7.

Example 98: Preparation of 2-amino-3-(4-nitro-6-vinyl-1H-indol-3-yl)propanoic acid (98)

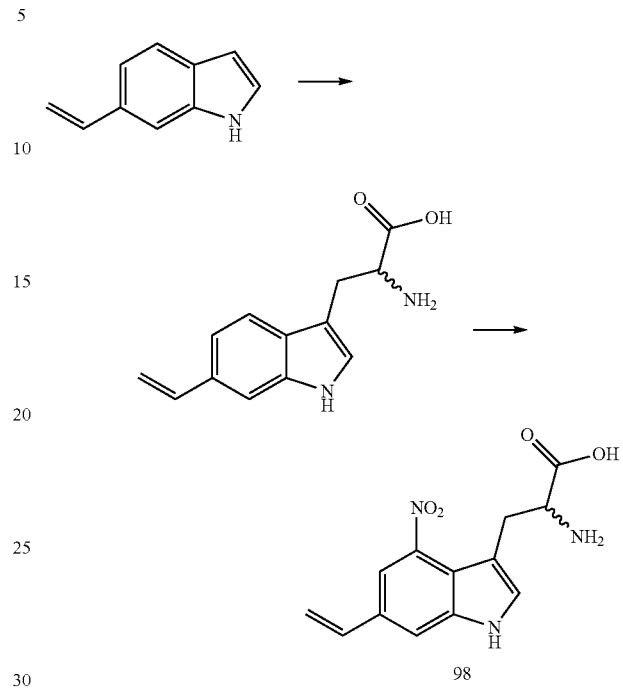

Example 98 can be prepared from 6-vinylindole as shown above and in a similar manner as described in Examples 1-7.

Example 99: Preparation of 2-amino-3-(4-nitro-7-vinyl-1H-indol-3-yl)propanoic acid (99)

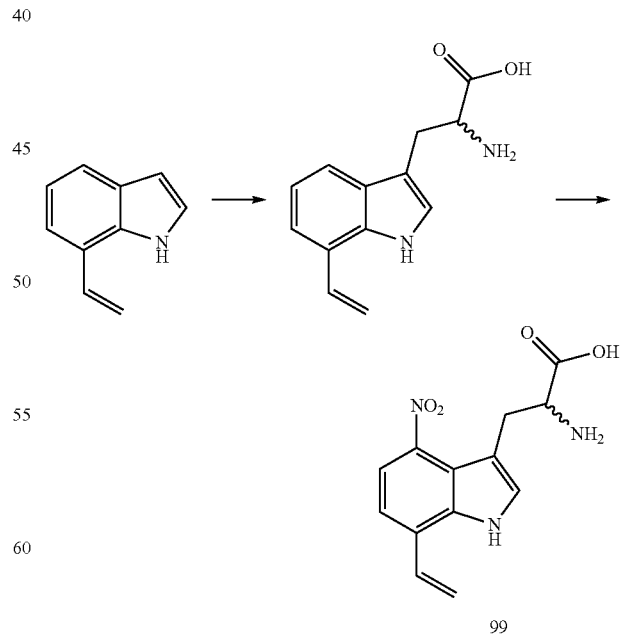

Example 99 can be prepared from 7-vinylindole as shown above and in a similar manner as described in Examples 1-7.

Example 100: Preparation of 2-amino-3-(7-nitro-4-vinyl-1H-indol-3-yl)propanoic acid (100)

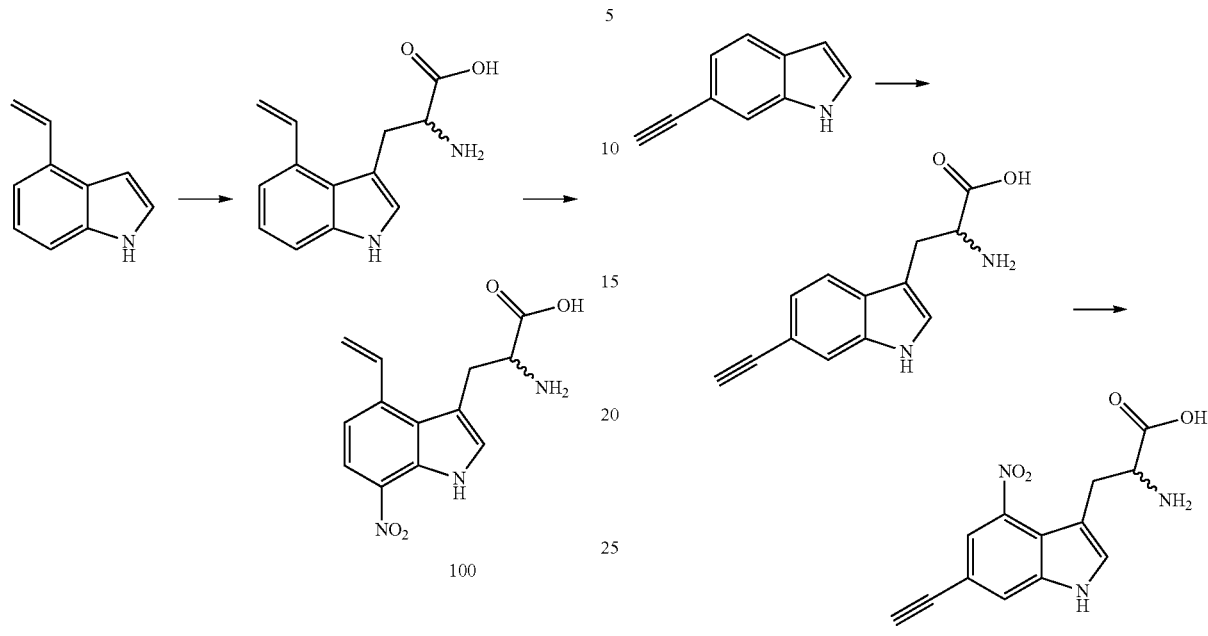

100

Example 100 can be prepared from 4-vinylindole as shown above and in a similar manner as described in Examples 1-7.

Example 101: Preparation of 2-amino-3-(5-ethynyl-4-nitro-1H-indol-3-yl)propanoic acid (101)

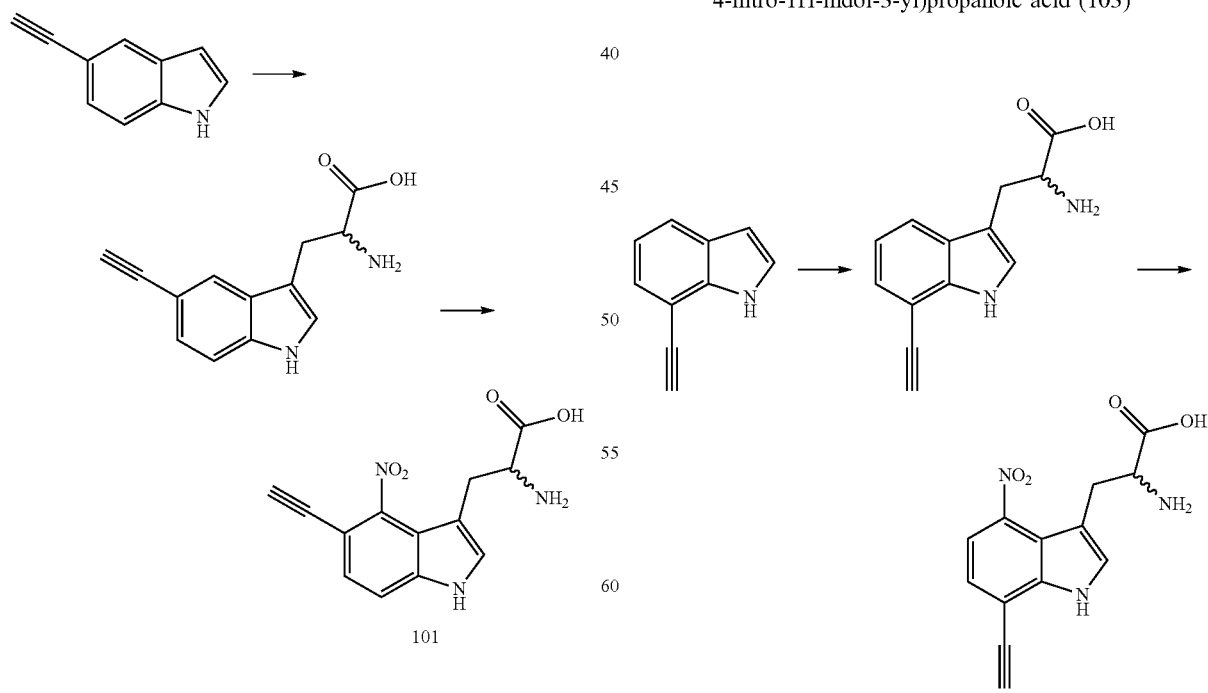

101

Example 101 can be prepared from 5-ethynylindole as shown above and in a similar manner as described in Examples 1-7.

Example 102: Preparation of 2-amino-3-(6-ethynyl-4-nitro-1H-indol-3-yl)propanoic acid (102)

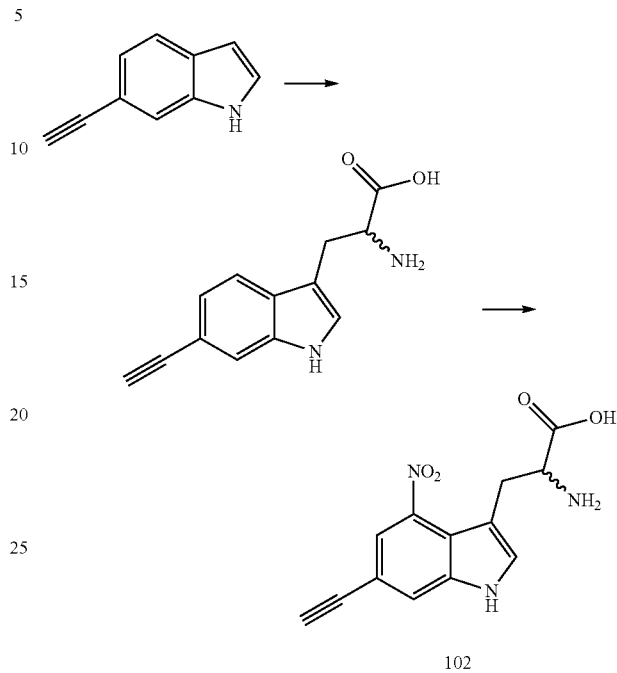

102

Example 102 can be prepared from 6-ethynylindole as shown above and in a similar manner as described in Examples 1-7.

Example 103: Preparation of 2-amino-3-(7-ethynyl-4-nitro-1H-indol-3-yl)propanoic acid (103)

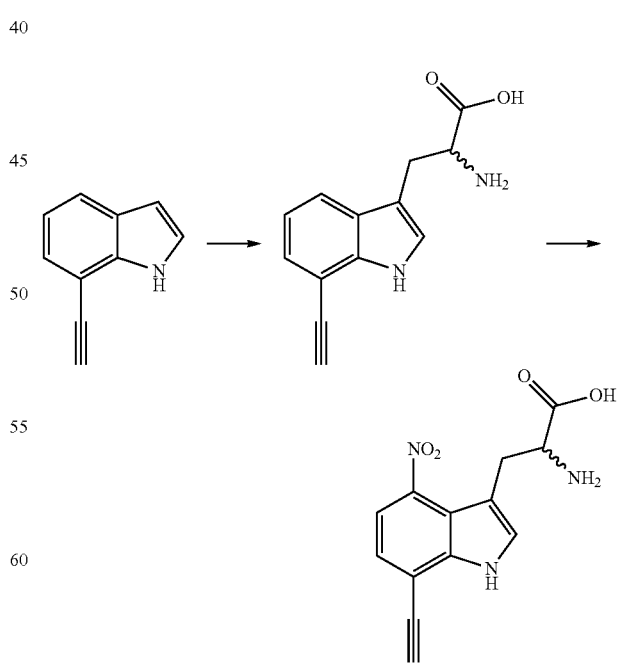

103

Example 103 can be prepared from 7-ethynylindole as shown above and in a similar manner as described in Examples 1-7.

Example 104: Preparation of 2-amino-3-(4-ethynyl-7-nitro-1H-indol-3-yl)propanoic acid (104)

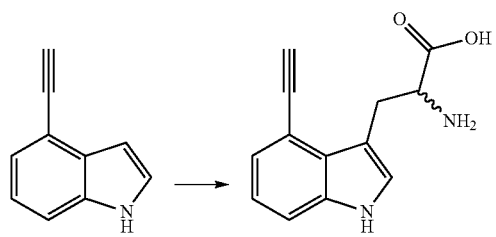

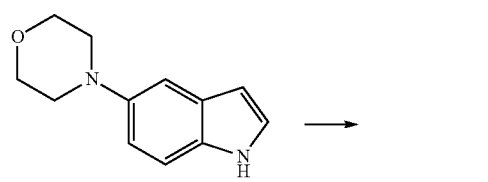

Example 104 can be prepared from 4-ethynylindole as shown above and in a similar manner as described in Examples 1-7.

Example 105: Preparation of 2-amino-3-(5-morpholino-4-nitro-1H-indol-3-yl)propanoic acid (105)

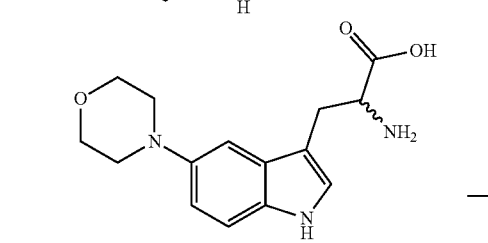

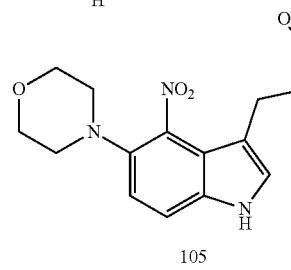

Example 105 can be prepared from 5-morpholinoindole as shown above and in a similar manner as described in Examples 1-7.

Example 106: Preparation of 2-amino-3-(6-morpholino-4-nitro-1H-indol-3-yl)propanoic acid (106)

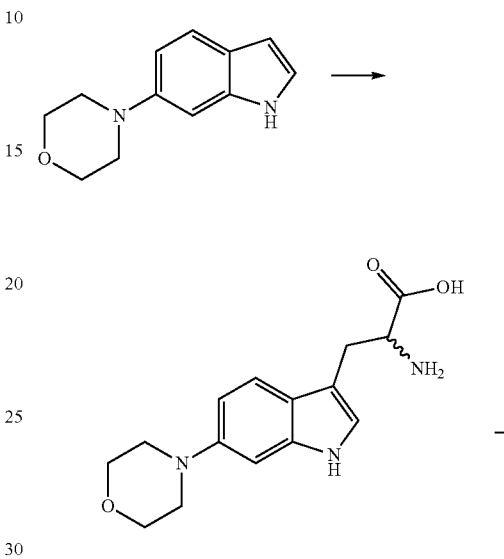

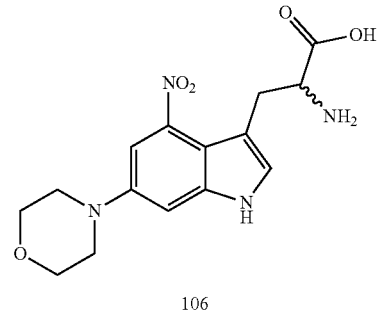

Example 106 can be prepared from 6-morpholinoindole as shown above and in a similar manner as described in Examples 1-7.

Example 107: Preparation of 2-amino-3-(7-morpholino-4-nitro-1H-indol-3-yl)propanoic acid (107)

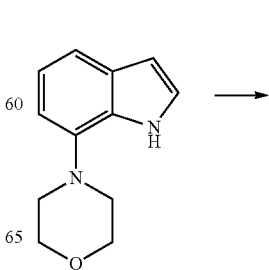

-continued

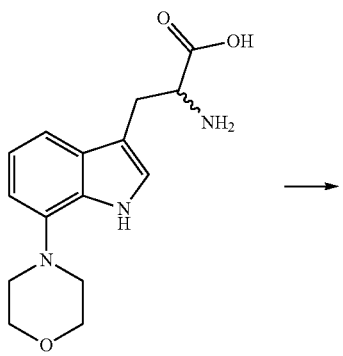

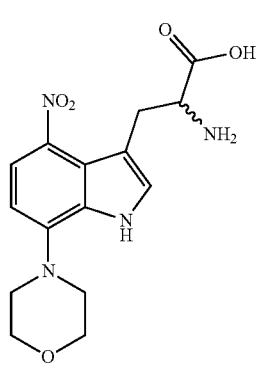

107

Example 107 can be prepared from 7-morpholinoindole as shown above and in a similar manner as described in Examples 1-7.

Example 108: Preparation of 2-amino-3-(4-morpholino-7-nitro-1H-indol-3-yl)propanoic acid (108)

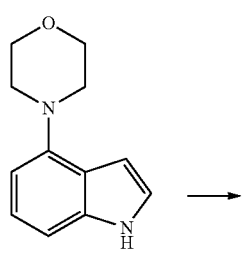

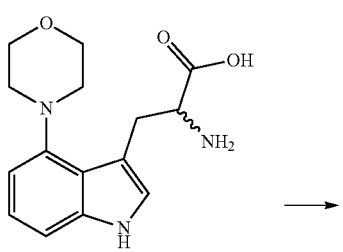

-continued

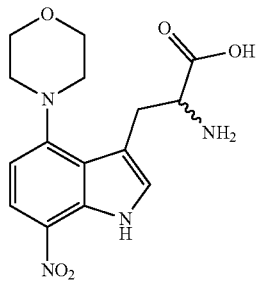

108

Example 108 can be prepared from 4-morpholinoindole as shown above and in a similar manner as described in Examples 1-7.

Example 109: Preparation of 2-amino-3-(5-(methylthio)-4-nitro-1H-indol-3-yl)propanoic acid (109)

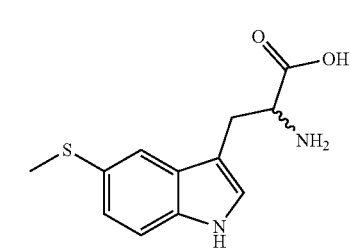

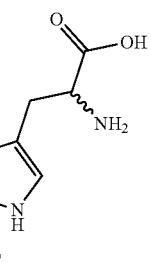

109

Example 109 can be prepared from 5-(methylthio)indole as shown above and in a similar manner as described in Examples 1-7.

Example 110: Preparation of 2-amino-3-(6-(methylthio)-4-nitro-1H-indol-3-yl)propanoic acid (110)

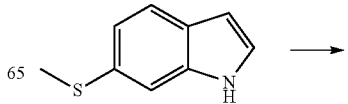

-continued

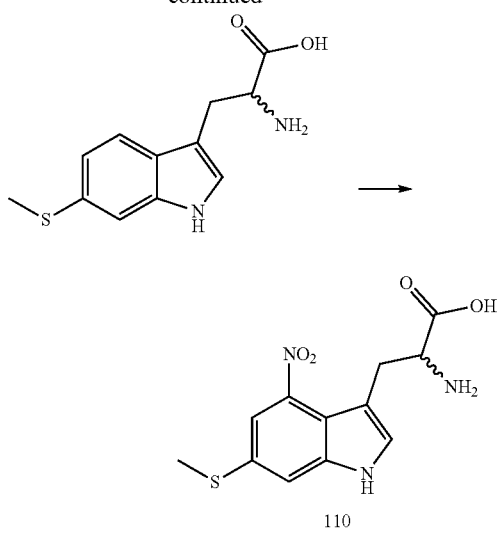

110

Example 110 can be prepared from 6-(methylthio)indole as shown above and in a similar manner as described in Examples 1-7.

Example 111: Preparation of 2-amino-3-(7-(methylthio)-4-nitro-1H-indol-3-yl)propanoic acid (111)

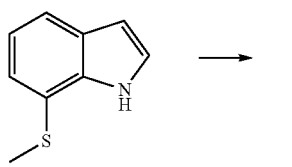

111

Example 111 can be prepared from 7-(methylthio)indole as shown above and in a similar manner as described in Examples 1-7.

Example 112: Preparation of 2-amino-3-(4-(methylthio)-7-nitro-1H-indol-3-yl)propanoic acid (112)

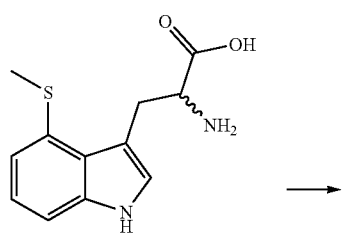

112

Example 112 can be prepared from 4-(methylthio)indole as shown above and in a similar manner as described in Examples 1-7.

Example 113: Preparation of 2-amino-3-(4-nitro-5-(pyridin-4-yl)-1H-indol-3-yl)propanoic acid (113)

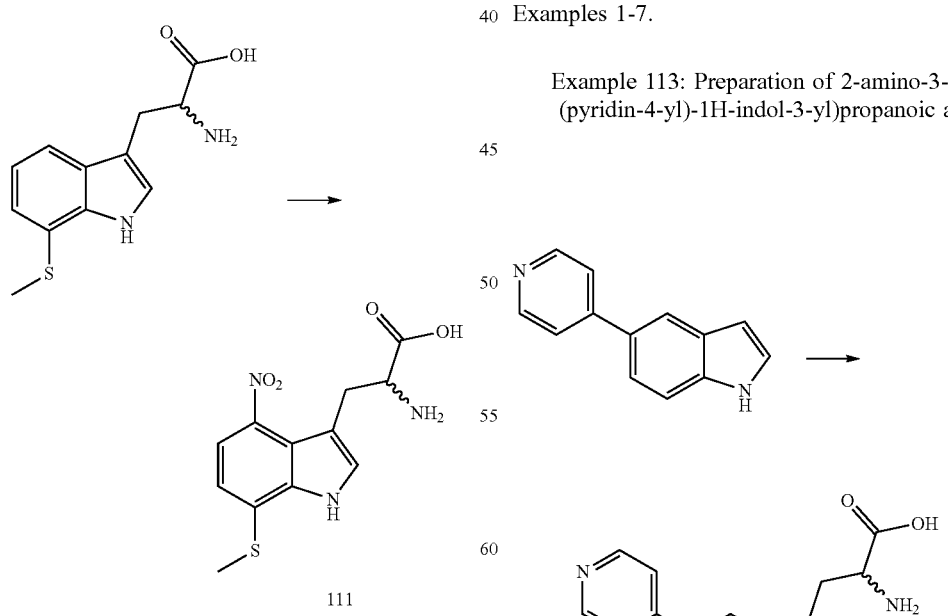

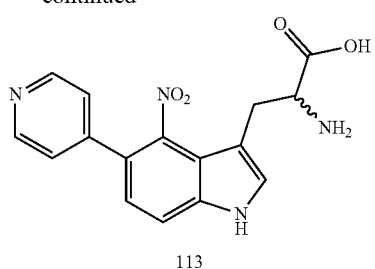

113

Example 113 can be prepared from 5-(pyridin-4-yl)indole as shown above and in a similar manner as described in Examples 1-7.

Example 114: Preparation of 2-amino-3-(4-nitro-6-(pyridin-4-yl)-1H-indol-3-yl)propanoic acid (114)

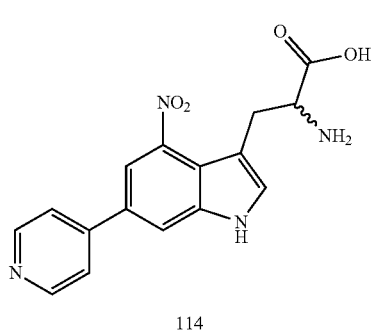

114

Example 114 can be prepared from 6-(pyridin-4-yl)indole as shown above and in a similar manner as described in Examples 1-7.

Example 115: Preparation of 2-amino-3-(4-nitro-7-(pyridin-4-yl)-1H-indol-3-yl)propanoic acid (115)

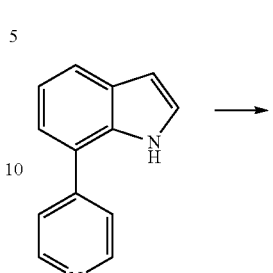

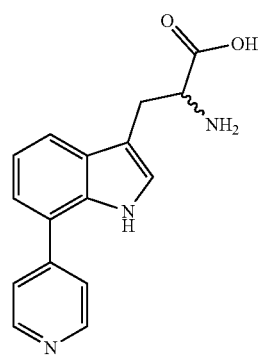

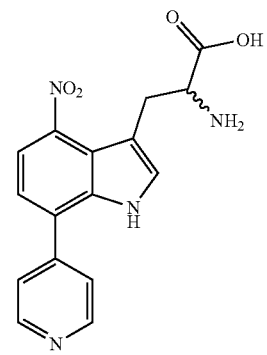

115

Example 115 can be prepared from 7-(pyridin-4-yl)indole as shown above and in a similar manner as described in Examples 1-7.

Example 116: Preparation of 2-amino-3-(7-nitro-4-(pyridin-4-yl)-1H-indol-3-yl)propanoic acid (116)

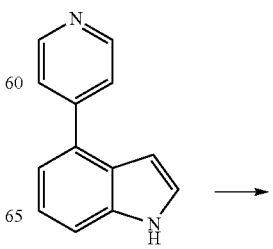

-continued

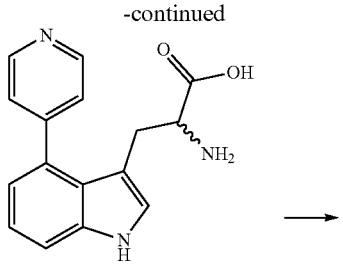

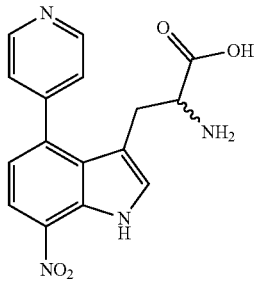

116

Example 116 can be prepared from 4-(pyridin-4-yl)indole as shown above and in a similar manner as described in Examples 1-7.

Example 117: Preparation of 2-amino-3-(1,5-dimethyl-4-nitro-1H-indol-3-yl)propanoic acid (117)

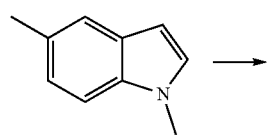

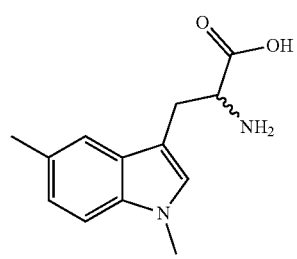

117

Example 117 can be prepared from 1,5-dimethyl-1H-indole as shown above and in a similar manner as described in Examples 1-7.

Example 118: Preparation of 2-amino-3-(1,6-dimethyl-4-nitro-1H-indol-3-yl)propanoic acid (118)

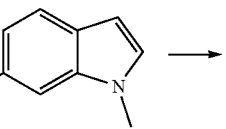

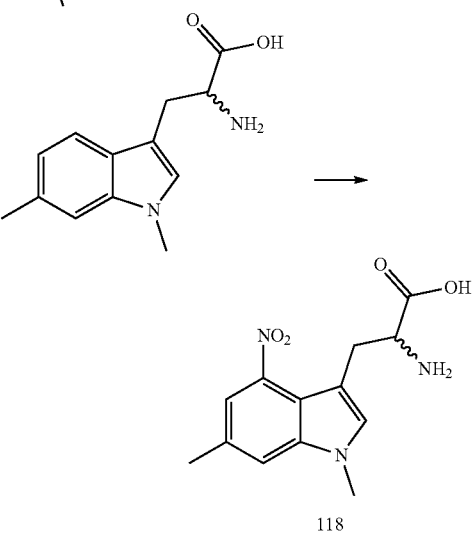

118

Example 118 can be prepared from 1,6-dimethyl-1H-indole as shown above and in a similar manner as described in Examples 1-7.

Example 119: Preparation of 2-amino-3-(1,7-dimethyl-4-nitro-1H-indol-3-yl)propanoic acid (119)

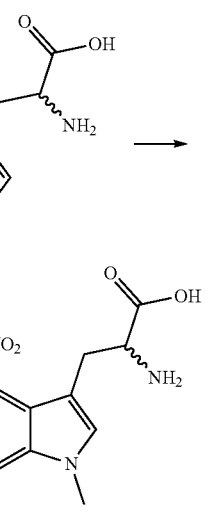

119

Example 119 can be prepared from 1,7-dimethyl-1H-indole as shown above and in a similar manner as described in Examples 1-7.

Example 120: Preparation of 2-amino-3-(1,4-dimethyl-7-nitro-1H-indol-3-yl)propanoic acid (120)

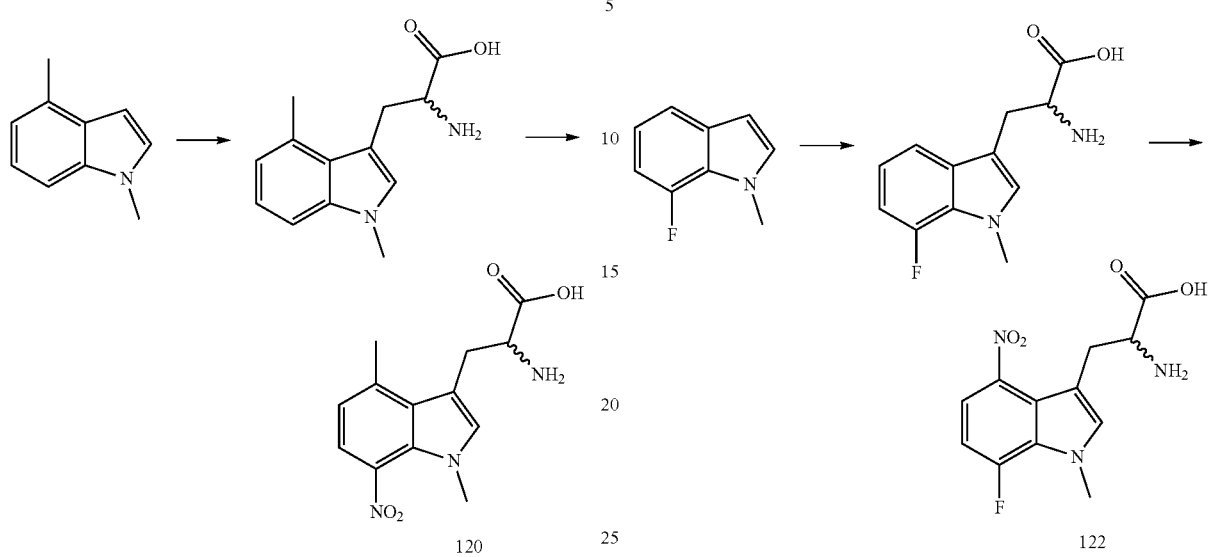

Example 120 can be prepared from 1,4-dimethyl-1H-indole as shown above and in a similar manner as described in Examples 1-7.

Example 121: Preparation of 2-amino-3-(6-fluoro-1-methyl-4-nitro-1H-indol-3-yl)propanoic acid (121)

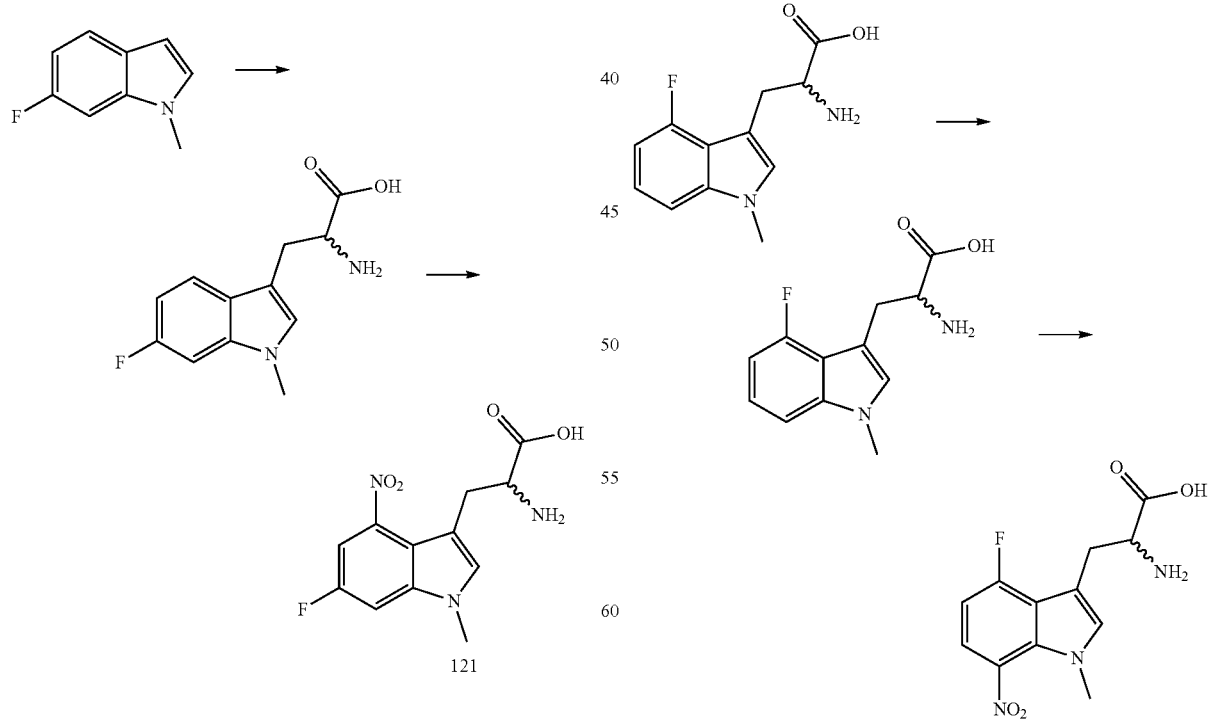

Example 121 can be prepared from 6-fluoro-1-methyl-1H-indole as shown above and in a similar manner as described in Examples 1-7.

Example 122: Preparation of 2-amino-3-(7-fluoro-1-methyl-4-nitro-1H-indol-3-yl)propanoic acid (122)

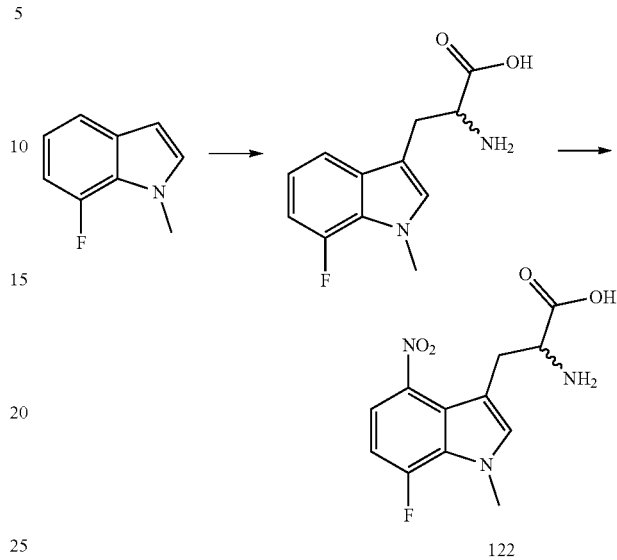

Example 122 can be prepared from 7-fluoro-1-methyl-indole as shown above and in a similar manner as described in Examples 1-7.

Example 123: Preparation of 2-amino-3-(4-fluoro-1-methyl-7-nitro-1H-indol-3-yl)propanoic acid (123)

149

Example 123 can be prepared from 4-fluoro-1-methyl-indole as shown above and in a similar manner as described in Examples 1-7.

Example 124: Preparation of 2-amino-3-(5-chloro-1-methyl-4-nitro-1H-indol-3-yl)propanoic acid (124)

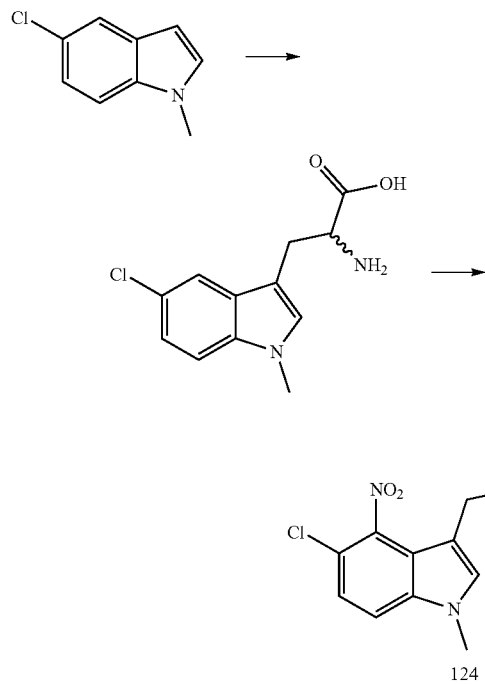

124

Example 124 can be prepared from 5-chloro-1-methyl-indole as shown above and in a similar manner as described in Examples 1-7.

Example 125: Preparation of 2-amino-3-(6-chloro-1-methyl-4-nitro-1H-indol-3-yl)propanoic acid (125)

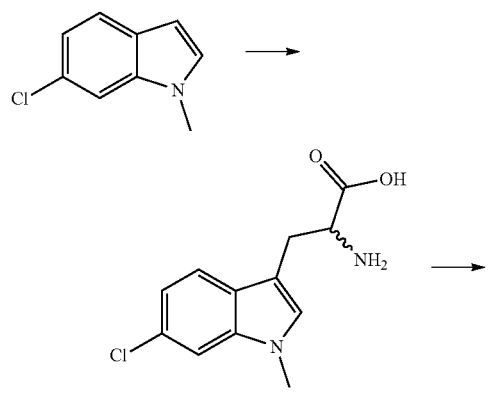

150

-continued

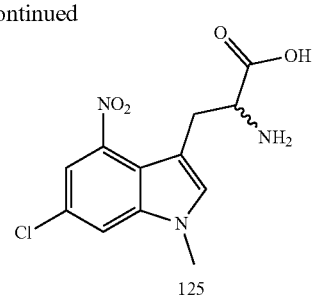

125

Example 125 can be prepared from 6-chloro-1-methyl-indole as shown above and in a similar manner as described in Examples 1-7.

Example 126: Preparation of 2-amino-3-(7-chloro-1-methyl-4-nitro-1H-indol-3-yl)propanoic acid (126)

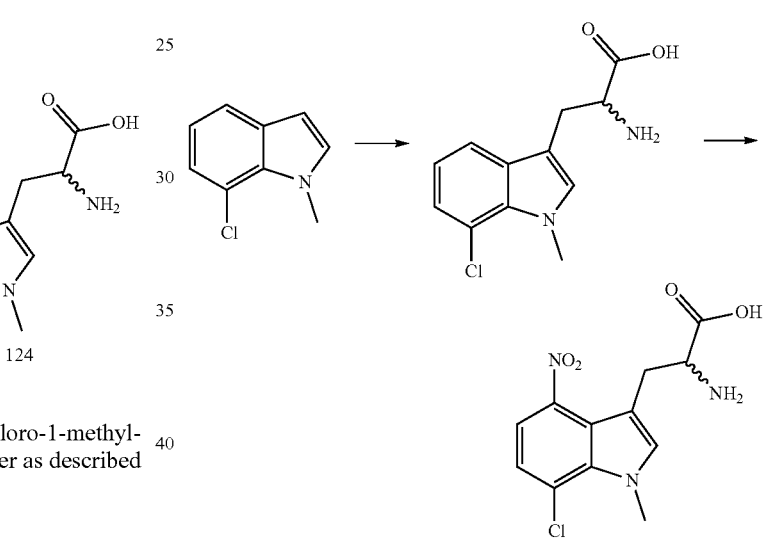

126

Example 126 can be prepared from 7-chloro-1-methyl-indole as shown above and in a similar manner as described in Examples 1-7.

Example 127: Preparation of 2-amino-3-(4-chloro-1-methyl-7-nitro-1H-indol-3-yl)propanoic acid (127)

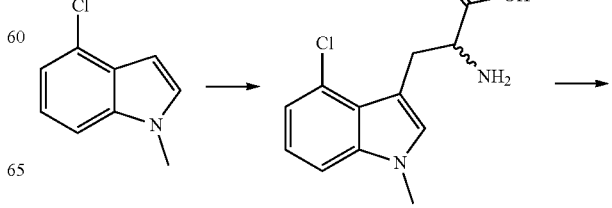

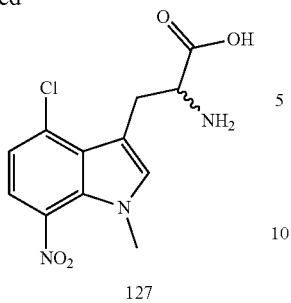

127

Example 127 can be prepared from 4-chloro-1-methyl-indole as shown above and in a similar manner as described in Examples 1-7.

Example 128: Preparation of 2-amino-3-(5-bromo-1-methyl-4-nitro-1H-indol-3-yl)propanoic acid (128)

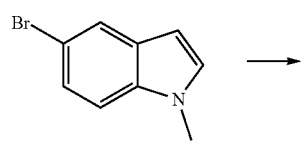

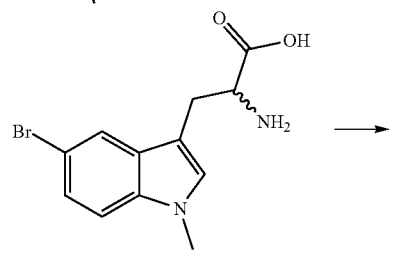

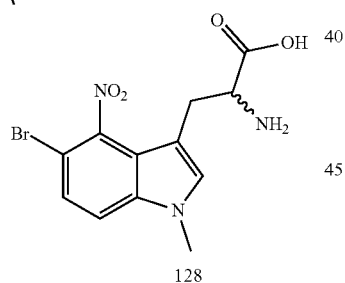

128

Example 128 can be prepared from 5-bromo-1-methyl-indole as shown above and in a similar manner as described in Examples 1-7.

Example 129: Preparation of 2-amino-3-(6-bromo-1-methyl-4-nitro-1H-indol-3-yl)propanoic acid (129)

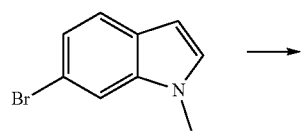

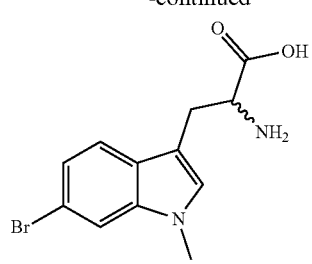

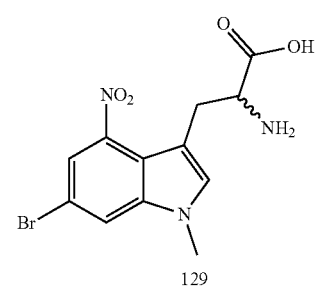

129

Example 129 can be prepared from 6-bromo-1-methyl-indole as shown above and in a similar manner as described in Examples 1-7.

Example 130: Preparation of 2-amino-3-(7-bromo-1-methyl-4-nitro-1H-indol-3-yl)propanoic acid (130)

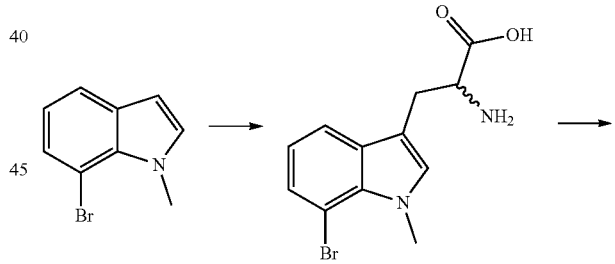

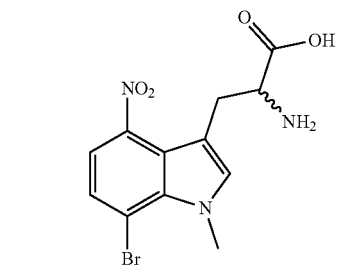

130

Example 130 can be prepared from 7-bromo-1-methyl-indole as shown above and in a similar manner as described in Examples 1-7.

Example 131: Preparation of 2-amino-3-(4-bromo-1-methyl-7-nitro-1H-indol-3-yl)propanoic acid (131)

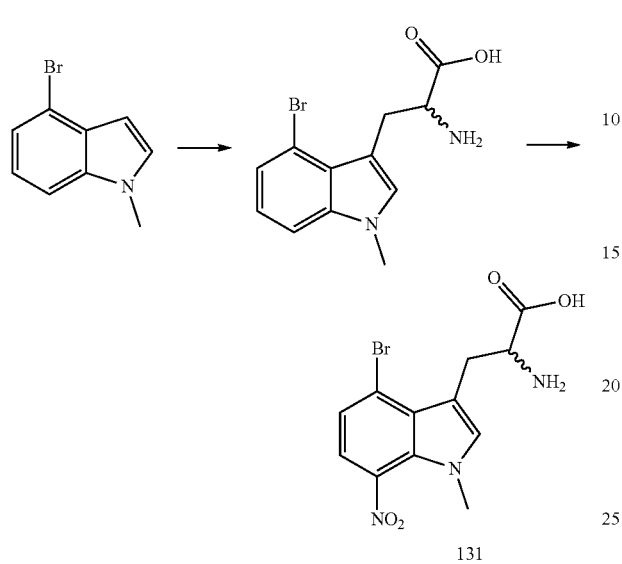

Example 131 can be prepared from 4-bromo-1-methyl-indole as shown above and in a similar manner as described in Examples 1-7.

Example 132: Preparation of 2-amino-3-(5-methoxy-1-methyl-4-nitro-1H-indol-3-yl)propanoic acid (132)

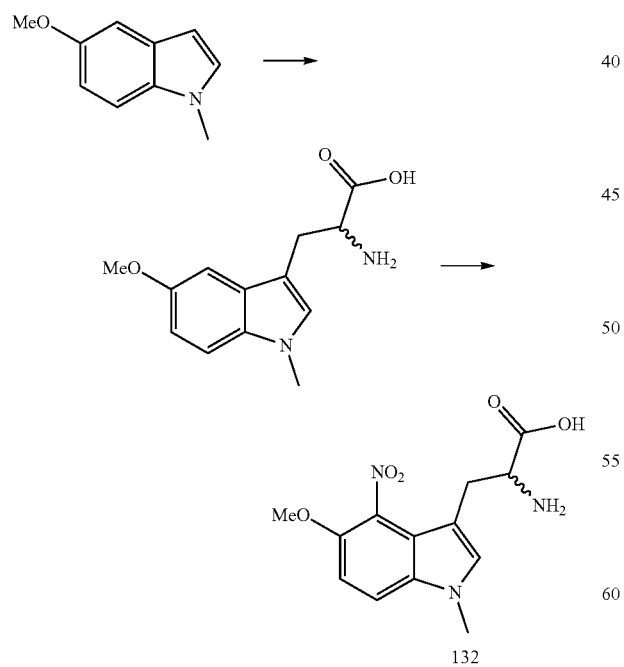

Example 132 can be prepared from 5-methoxy-1-methyl-indole as shown above and in a similar manner as described in Examples 1-7.

Example 133: Preparation of 2-amino-3-(6-methoxy-1-methyl-4-nitro-1H-indol-3-yl)propanoic acid (133)

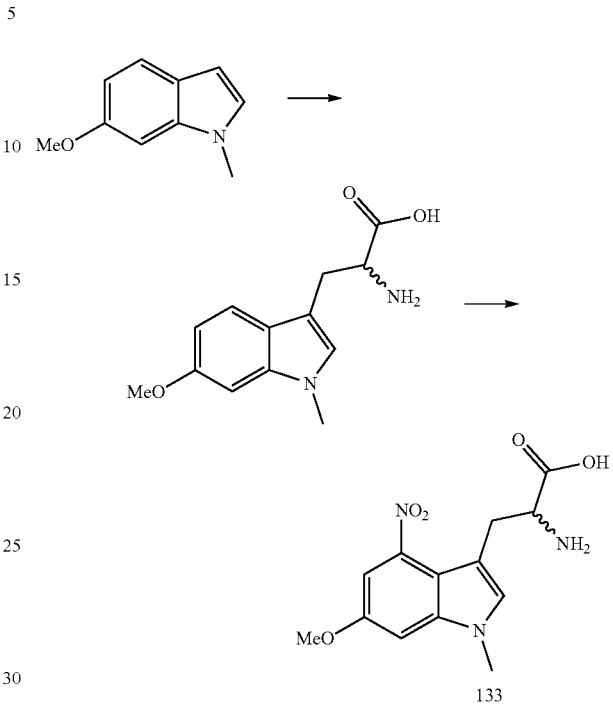

Example 133 can be prepared from 6-methoxy-1-methyl-indole as shown above and in a similar manner as described in Examples 1-7.

Example 134: Preparation of 2-amino-3-(7-methoxy-1-methyl-4-nitro-1H-indol-3-yl)propanoic acid (134)

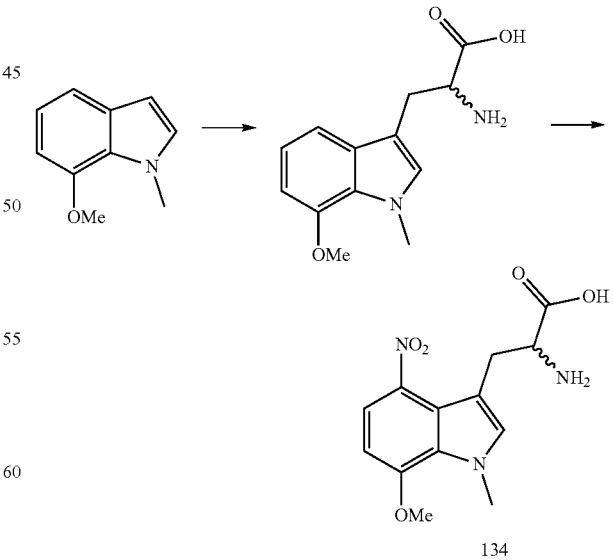

Example 134 can be prepared from 7-methoxy-1-methyl-indole as shown above and in a similar manner as described in Examples 1-7.

Example 135: Preparation of 2-amino-3-(4-methoxy-1-methyl-7-nitro-1H-indol-3-yl)propanoic acid (135)

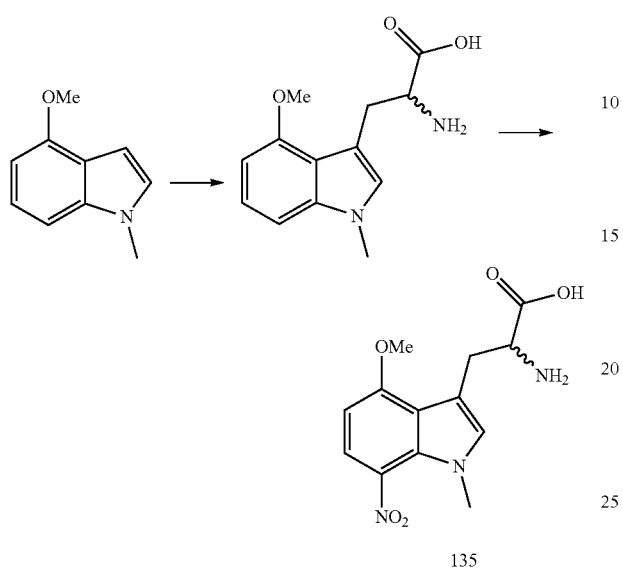

135

Example 135 can be prepared from 4-methoxy-1-methyl-indole as shown above and in a similar manner as described in Examples 1-7.

Example 136: Preparation of 2-amino-3-(5-amino-1-methyl-4-nitro-1H-indol-3-yl)propanoic acid (136)

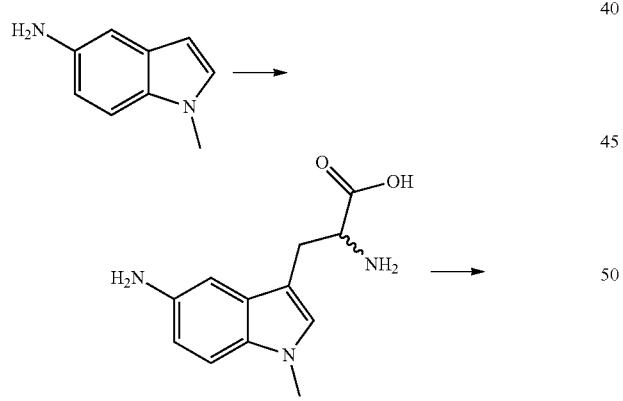

136

Example 136 can be prepared from 5-amino-1-methyl-indole as shown above and in a similar manner as described in Examples 1-7.

Example 137: Preparation of 2-amino-3-(6-amino-1-methyl-4-nitro-1H-indol-3-yl)propanoic acid (137)

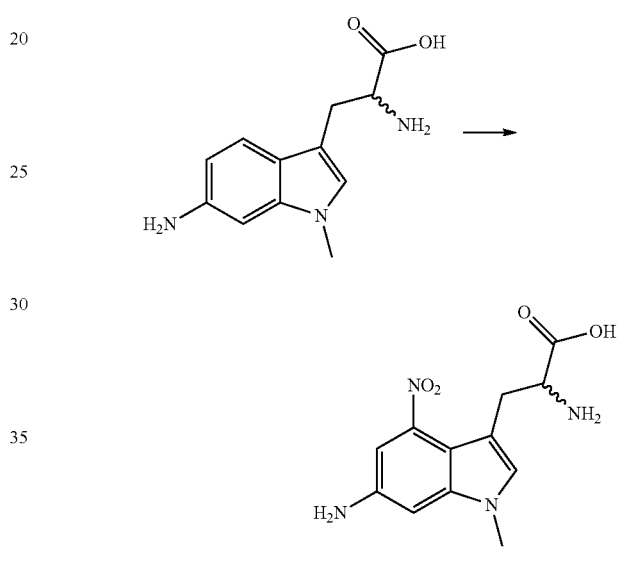

137

Example 137 can be prepared from 6-amino-1-methyl-indole as shown above and in a similar manner as described in Examples 1-7.

Example 138: Preparation of 2-amino-3-(7-amino-1-methyl-4-nitro-1H-indol-3-yl)propanoic acid (138)

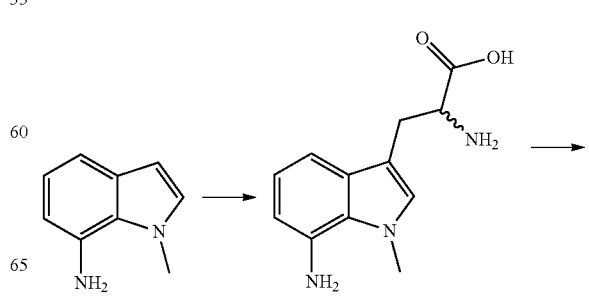

157

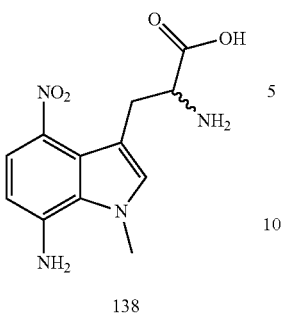
138

Example 138 can be prepared from 7-amino-1-methyl-indole as shown above and in a similar manner as described in Examples 1-7.

Example 139: Preparation of 2-amino-3-(4-amino-1-methyl-7-nitro-1H-indol-3-yl)propanoic acid (139)

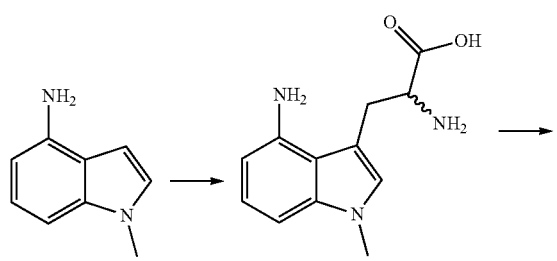
139

Example 139 can be prepared from 4-amino-1-methyl-indole as shown above and in a similar manner as described in Examples 1-7.

Example 140: Preparation of 2-amino-3-(5-hydroxy-1-methyl-4-nitro-1H-indol-3-yl)propanoic acid (140)

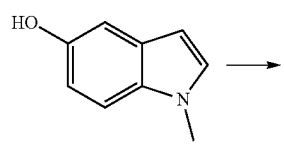

158

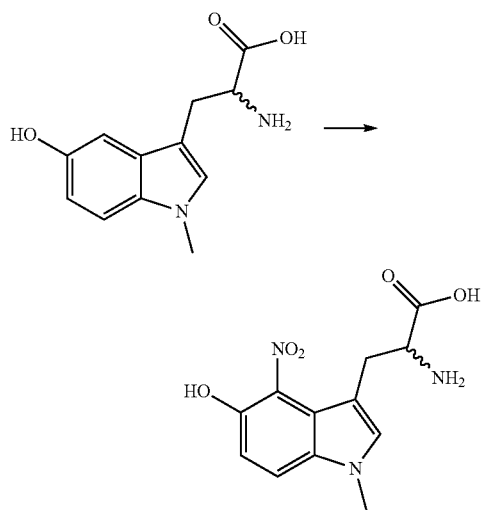
140

Example 140 can be prepared from 5-hydroxy-1-methyl-indole as shown above and in a similar manner as described in Examples 1-7.

Example 141: Preparation of 2-amino-3-(6-hydroxy-1-methyl-4-nitro-1H-indol-3-yl)propanoic acid (141)

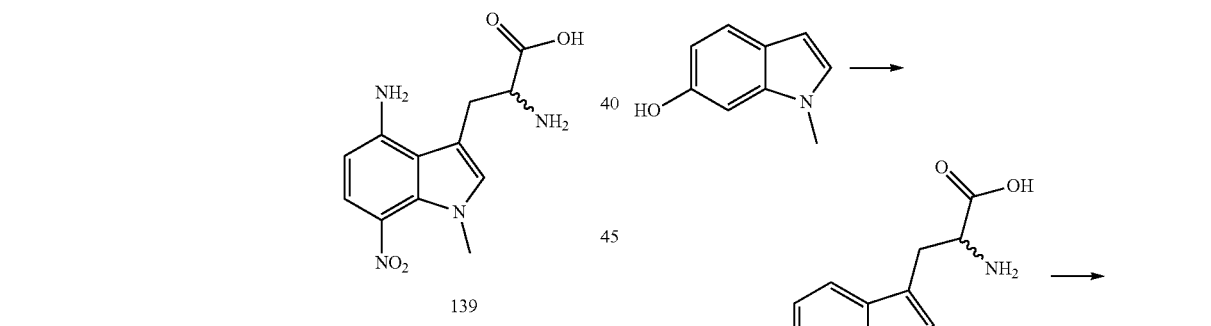
141

Example 141 can be prepared from 6-hydroxy-1-methyl-indole as shown above and in a similar manner as described in Examples 1-7.

Example 142: Preparation of 2-amino-3-(7-hydroxy-1-methyl-4-nitro-1H-indol-3-yl)propanoic acid (142)

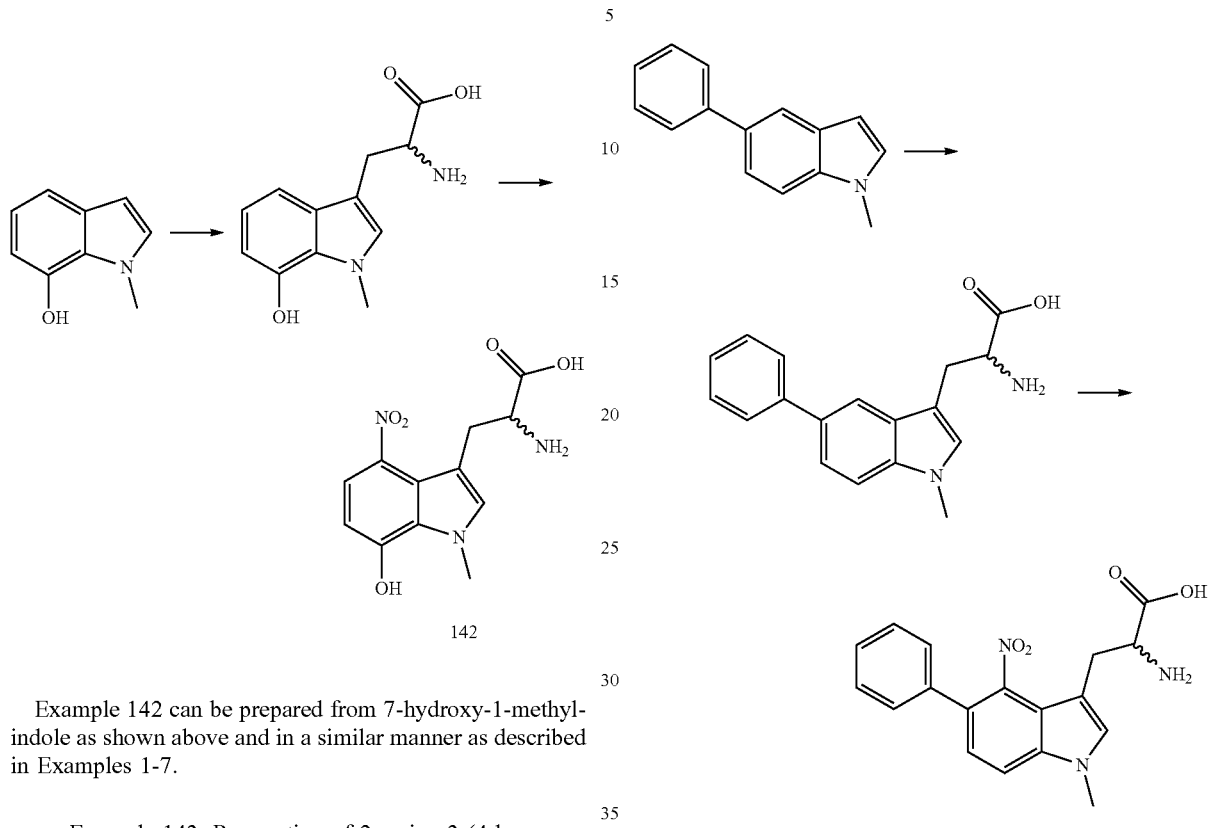

142

Example 142 can be prepared from 7-hydroxy-1-methyl-indole as shown above and in a similar manner as described in Examples 1-7.

Example 143: Preparation of 2-amino-3-(4-hydroxy-1-methyl-7-nitro-1H-indol-3-yl)propanoic acid (143)

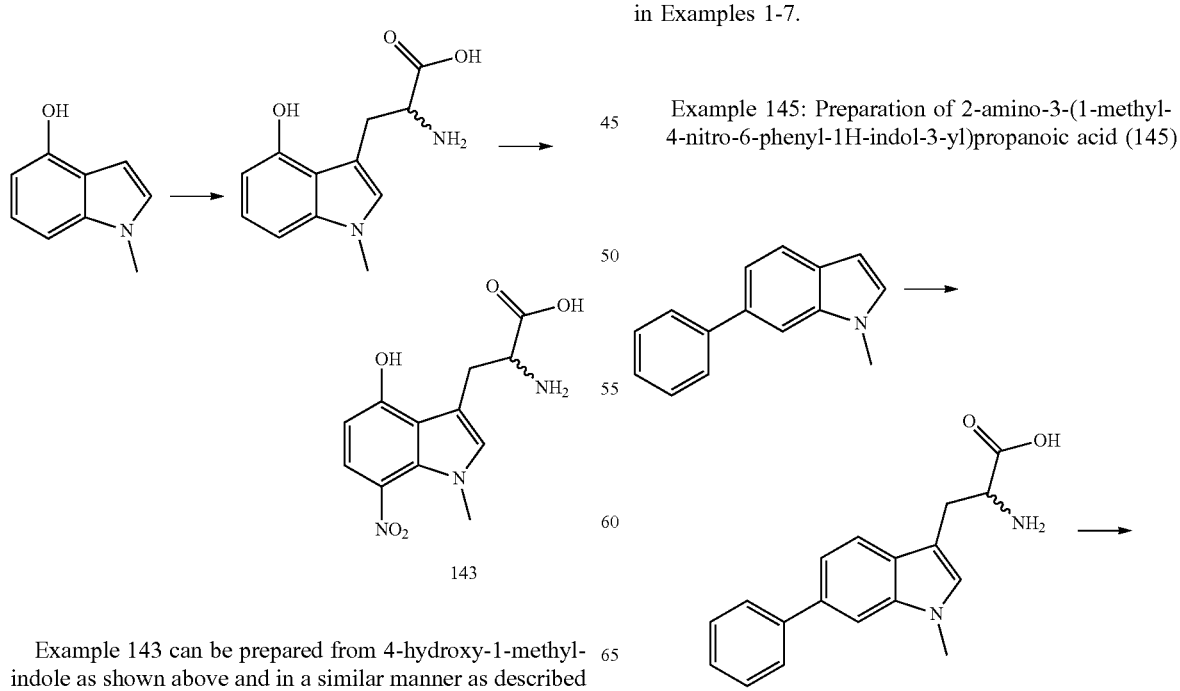

143

Example 143 can be prepared from 4-hydroxy-1-methyl-indole as shown above and in a similar manner as described in Examples 1-7.

Example 144: Preparation of 2-amino-3-(1-methyl-4-nitro-5-phenyl-1H-indol-3-yl)propanoic acid (144)

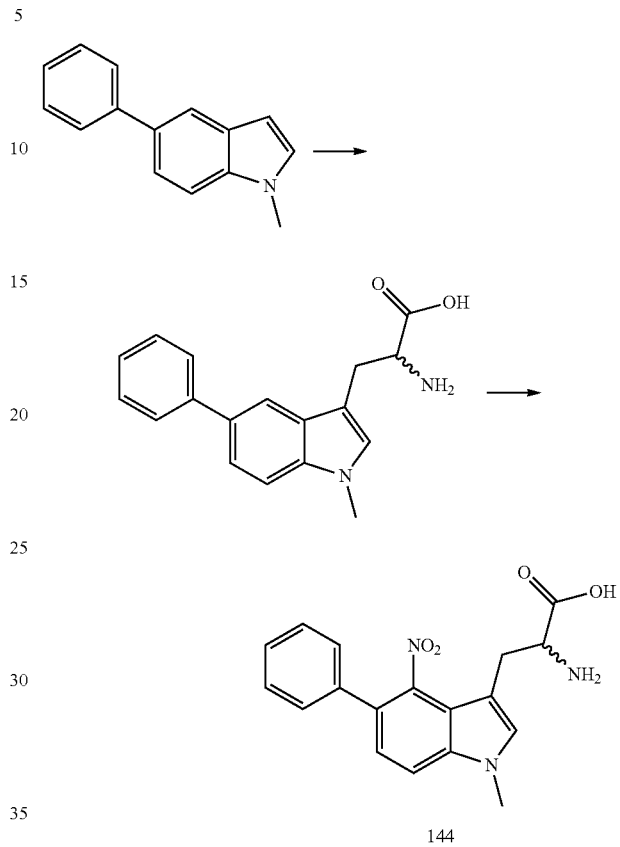

144

Example 144 can be prepared from 5-phenyl-1-methyl-indole as shown above and in a similar manner as described in Examples 1-7.

Example 145: Preparation of 2-amino-3-(1-methyl-4-nitro-6-phenyl-1H-indol-3-yl)propanoic acid (145)

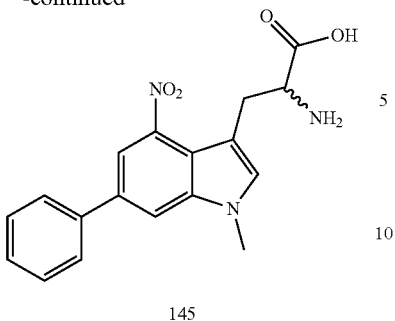

145

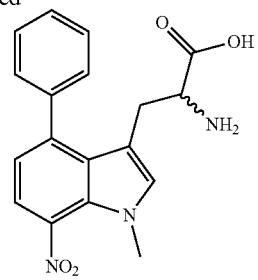

147

Example 145 can be prepared from 6-phenyl-1-methyl-indole as shown above and in a similar manner as described in Examples 1-7.

Example 146: Preparation of 2-amino-3-(1-methyl-4-nitro-7-phenyl-1H-indol-3-yl)propanoic acid (146)

Example 147 can be prepared from 4-phenyl-1-methyl-indole as shown above and in a similar manner as described in Examples 1-7.

Example 148: Preparation of 2-amino-3-(5-cyclopropyl-1-methyl-4-nitro-1H-indol-3-yl)propanoic acid (148)

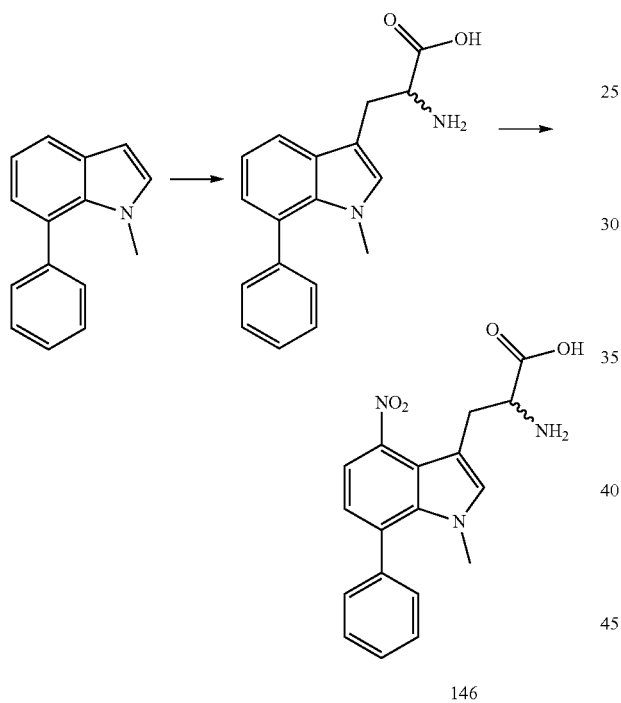

146

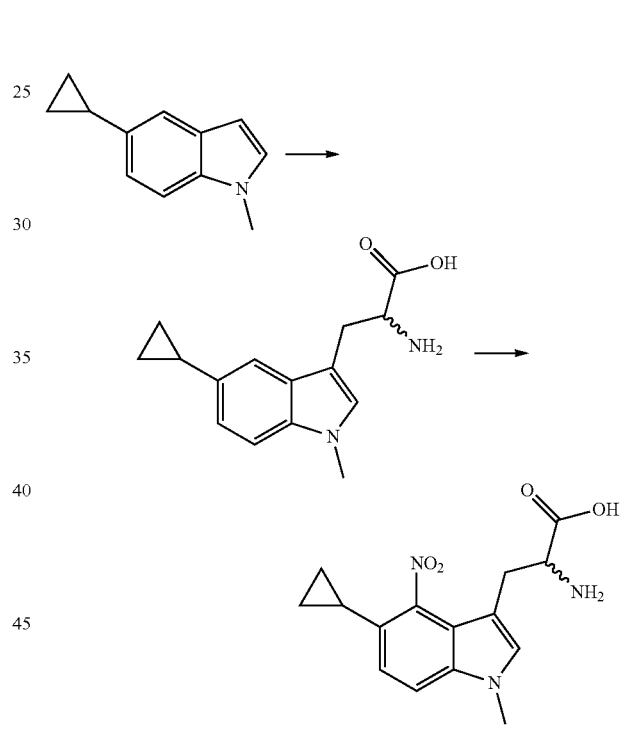

148

Example 146 can be prepared from 7-phenyl-1-methyl-indole as shown above and in a similar manner as described in Examples 1-7.

Example 147: Preparation of 2-amino-3-(1-methyl-7-nitro-4-phenyl-1H-indol-3-yl)propanoic acid (147)

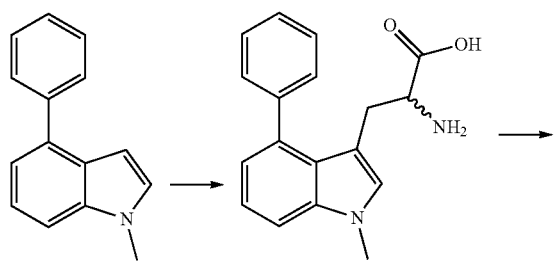

Example 148 can be prepared from 5-cyclopropyl-1-methyl-indole as shown above and in a similar manner as described in Examples 1-7.

Example 149: Preparation of 2-amino-3-(6-cyclopropyl-1-methyl-4-nitro-1H-indol-3-yl)propanoic acid (149)

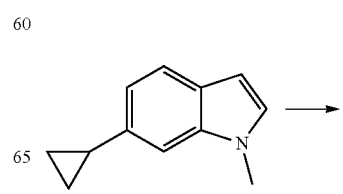

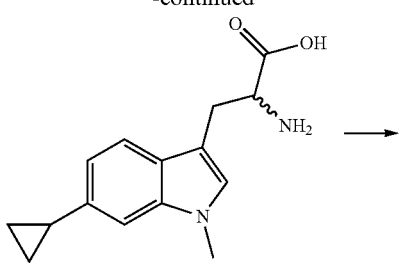

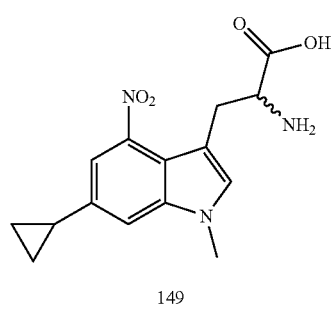

149

Example 149 can be prepared from 6-cyclopropyl-1-methyl-indole as shown above and in a similar manner as described in Examples 1-7.

Example 150: Preparation of 2-amino-3-(7-cyclopropyl-1-methyl-4-nitro-1H-indol-3-yl)propanoic acid (150)

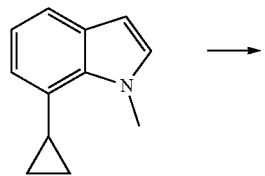

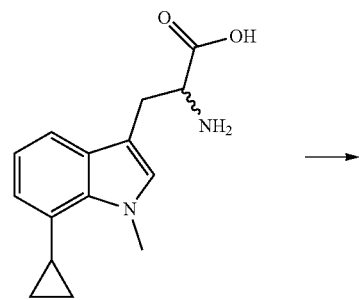

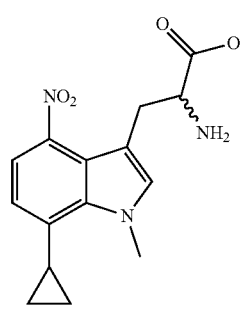

150

Example 150 can be prepared from 7-cyclopropyl-1-methyl-indole as shown above and in a similar manner as described in Examples 1-7.

Example 151: Preparation of 2-amino-3-(4-cyclopropyl-1-methyl-7-nitro-1H-indol-3-yl)propanoic acid (151)

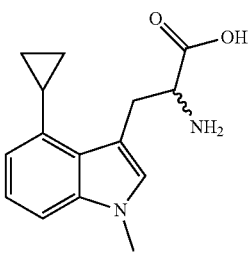

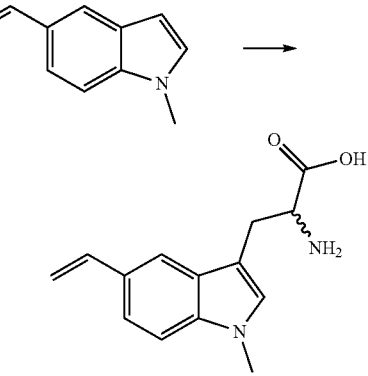

151

Example 151 can be prepared from 4-cyclopropyl-1-methyl-indole as shown above and in a similar manner as described in Examples 1-7.

Example 152: Preparation of 2-amino-3-(1-methyl-4-nitro-5-vinyl-1H-indol-3-yl)propanoic acid (152)

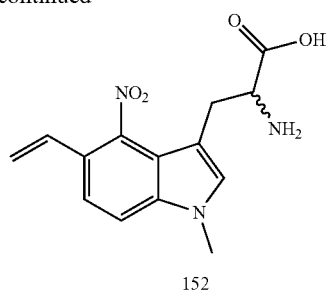

152

Example 152 can be prepared from 5-vinyl-1-methyl-indole as shown above and in a similar manner as described in Examples 1-7.

Example 153: Preparation of 2-amino-3-(1-methyl-4-nitro-6-vinyl-1H-indol-3-yl)propanoic acid (153)

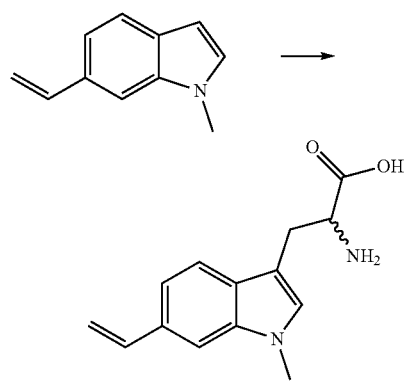

153

Example 153 can be prepared from 6-vinyl-1-methyl-indole as shown above and in a similar manner as described in Examples 1-7.

Example 154: Preparation of 2-amino-3-(1-methyl-4-nitro-7-vinyl-1H-indol-3-yl)propanoic acid (154)

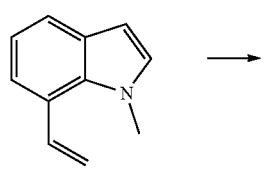

154

Example 154 can be prepared from 7-vinyl-1-methyl-indole as shown above and in a similar manner as described in Examples 1-7.

Example 155: Preparation of 2-amino-3-(1-methyl-7-nitro-4-vinyl-1H-indol-3-yl)propanoic acid (155)

155

Example 155 can be prepared from 4-vinyl-1-methyl-indole as shown above and in a similar manner as described in Examples 1-7.

Example 156: Preparation of 2-amino-3-(5-ethynyl-1-methyl-4-nitro-1H-indol-3-yl)propanoic acid (156)

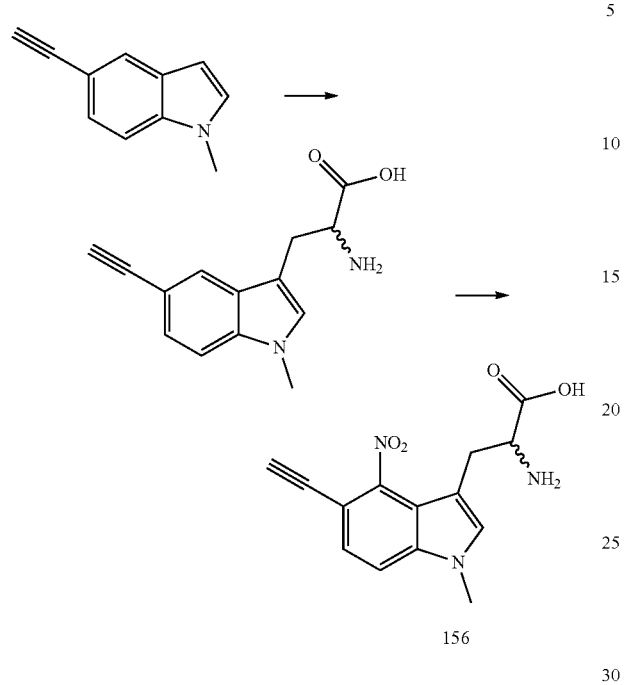

156

Example 156 can be prepared from 5-ethynyl-1-methyl-indole as shown above and in a similar manner as described in Examples 1-7.

Example 157: Preparation of 2-amino-3-(6-ethynyl-1-methyl-4-nitro-1H-indol-3-yl)propanoic acid (157)

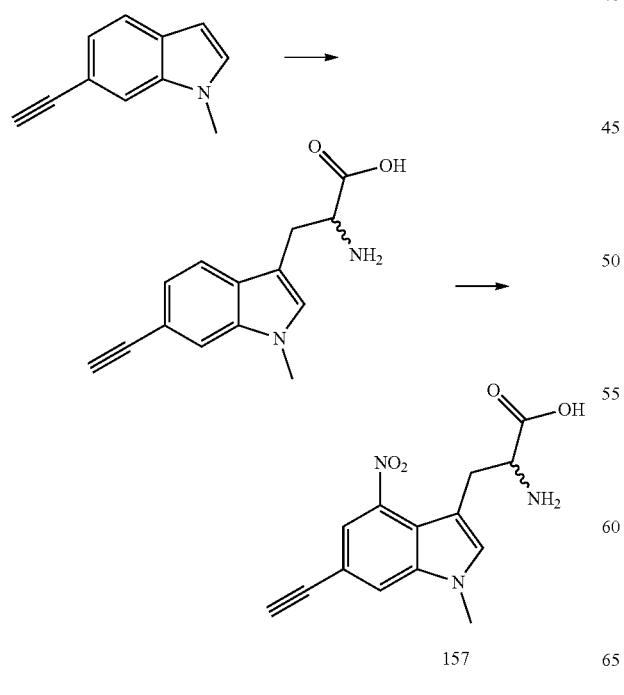

157

Example 157 can be prepared from 6-ethynyl-1-methyl-indole as shown above and in a similar manner as described in Examples 1-7.

Example 158: Preparation of 2-amino-3-(7-ethynyl-1-methyl-4-nitro-1H-indol-3-yl)propanoic acid (158)

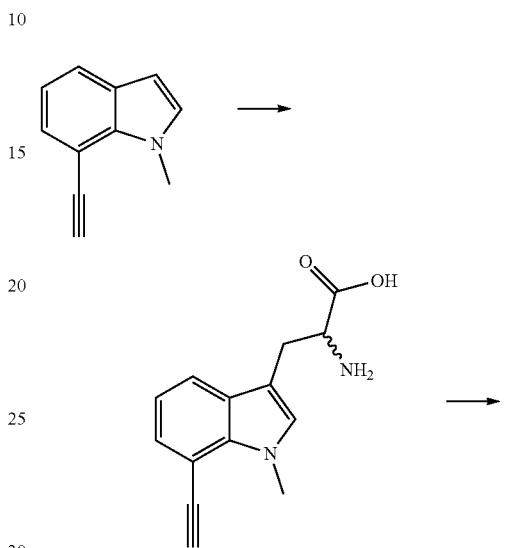

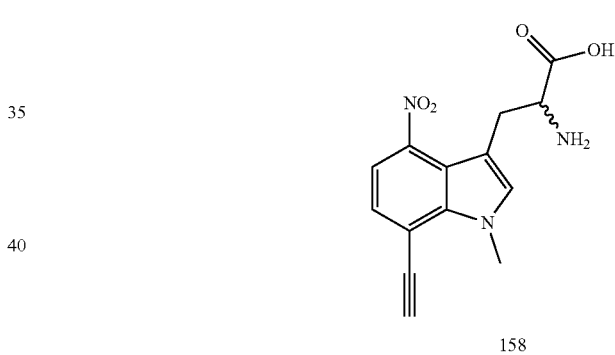

158

Example 158 can be prepared from 7-ethynyl-1-methyl-indole as shown above and in a similar manner as described in Examples 1-7.

Example 159: Preparation of 2-amino-3-(4-ethynyl-1-methyl-7-nitro-1H-indol-3-yl)propanoic acid (159)

-continued

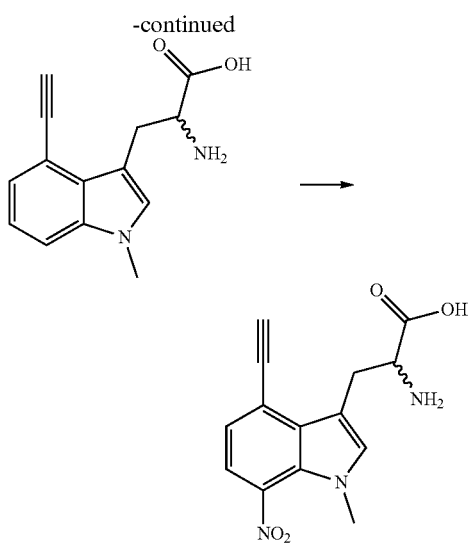

159

Example 159 can be prepared from 4-ethynyl-1-methyl-indole as shown above and in a similar manner as described in Examples 1-7.

Example 160: Preparation of 2-amino-3-(1-methyl-5-morpholino-4-nitro-1H-indol-3-yl)propanoic acid (160)

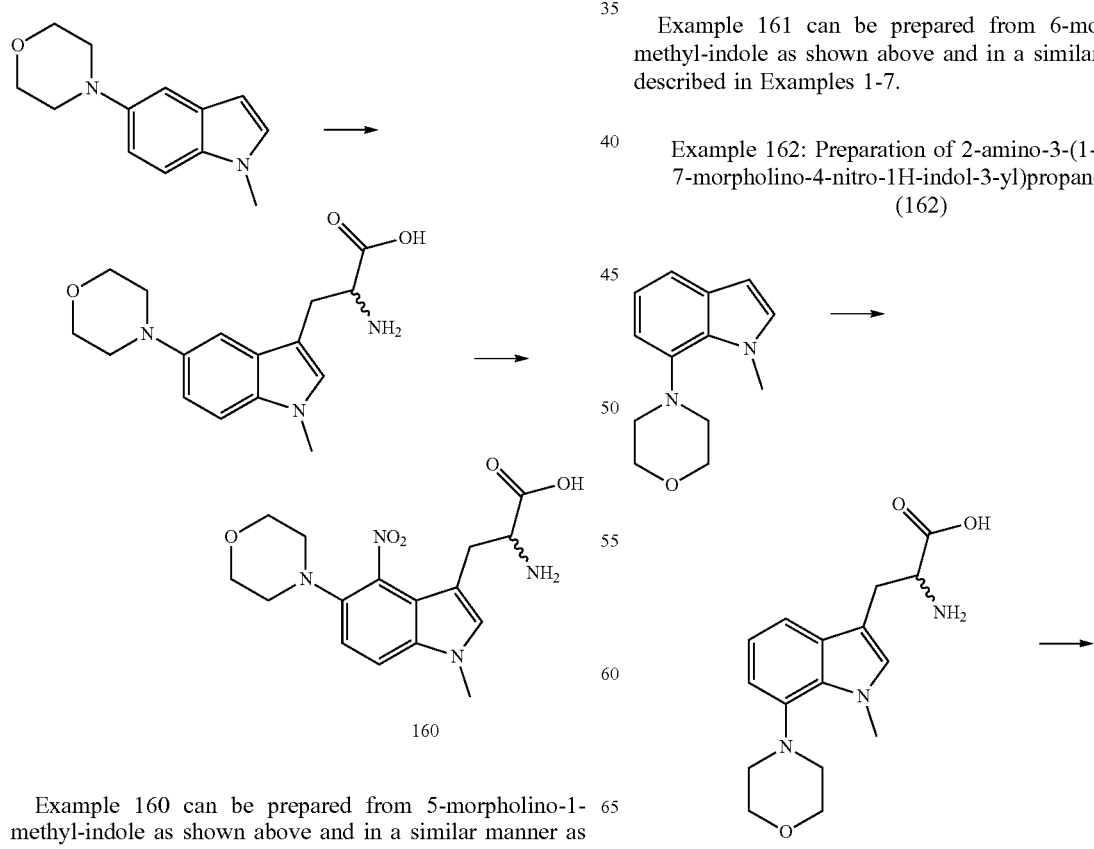

160

Example 160 can be prepared from 5-morpholino-1-methyl-indole as shown above and in a similar manner as described in Examples 1-7.

Example 161: Preparation of 2-amino-3-(1-methyl-6-morpholino-4-nitro-1H-indol-3-yl)propanoic acid (161)

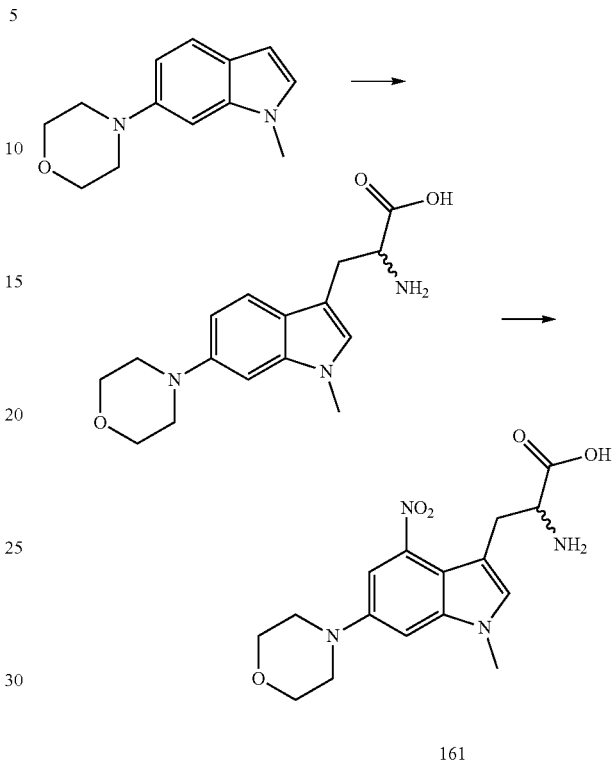

161

Example 161 can be prepared from 6-morpholino-1-methyl-indole as shown above and in a similar manner as described in Examples 1-7.

Example 162: Preparation of 2-amino-3-(1-methyl-7-morpholino-4-nitro-1H-indol-3-yl)propanoic acid (162)

-continued

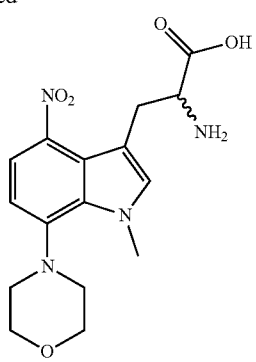
162

Example 162 can be prepared from 7-morpholino-1-methyl-indole as shown above and in a similar manner as described in Examples 1-7.

Example 163: Preparation of 2-amino-3-(1-methyl-4-morpholino-7-nitro-1H-indol-3-yl)propanoic acid (163)

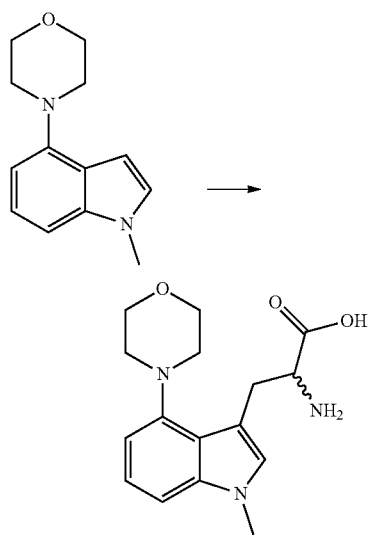
163

Example 163 can be prepared from 4-morpholino-1-methyl-indole as shown above and in a similar manner as described in Examples 1-7.

Example 164: Preparation of 2-amino-3-(1-methyl-5-(methylthio)-4-nitro-1H-indol-3-yl)propanoic acid (164)

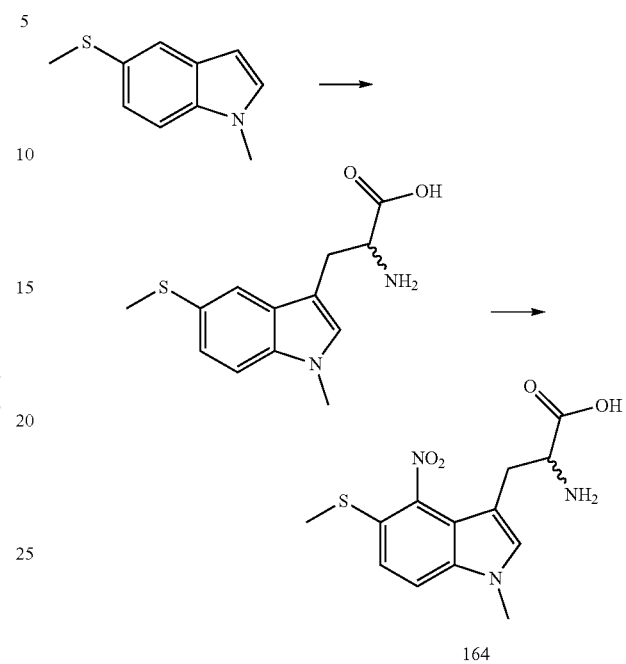
164

Example 164 can be prepared from 5-(methylthio)-1-methyl-indole as shown above and in a similar manner as described in Examples 1-7.

Example 165: Preparation of 2-amino-3-(1-methyl-6-(methylthio)-4-nitro-1H-indol-3-yl)propanoic acid (165)

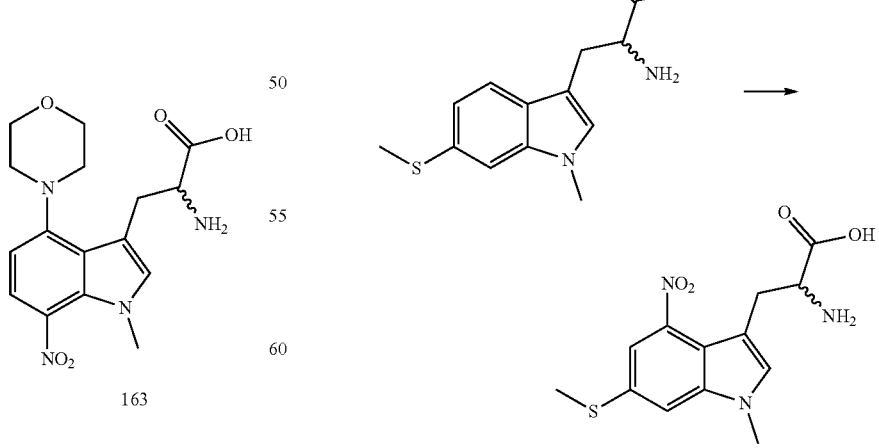
165

Example 165 can be prepared from 6-(methylthio)-1-methyl-indole as shown above and in a similar manner as described in Examples 1-7.

Example 166: Preparation of 2-amino-3-(1-methyl-7-(methylthio)-4-nitro-1H-indol-3-yl)propanoic acid (166)

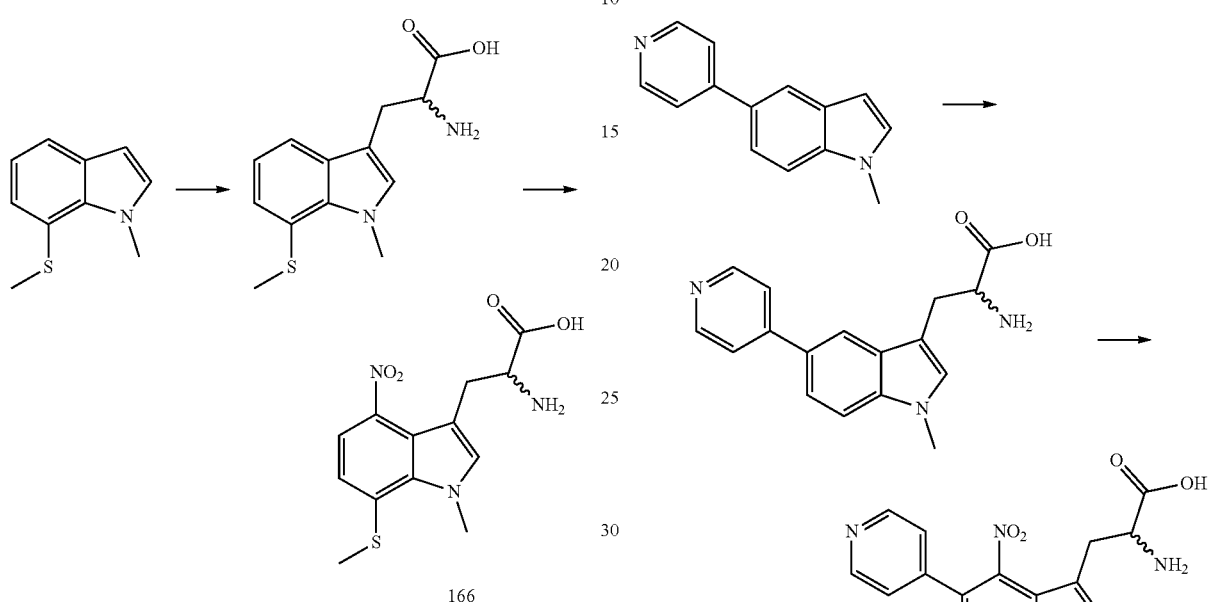

166

Example 166 can be prepared from 7-(methylthio)-1-methyl-indole as shown above and in a similar manner as described in Examples 1-7.

Example 167: Preparation of 2-amino-3-(1-methyl-4-(methylthio)-7-nitro-1H-indol-3-yl)propanoic acid (167)

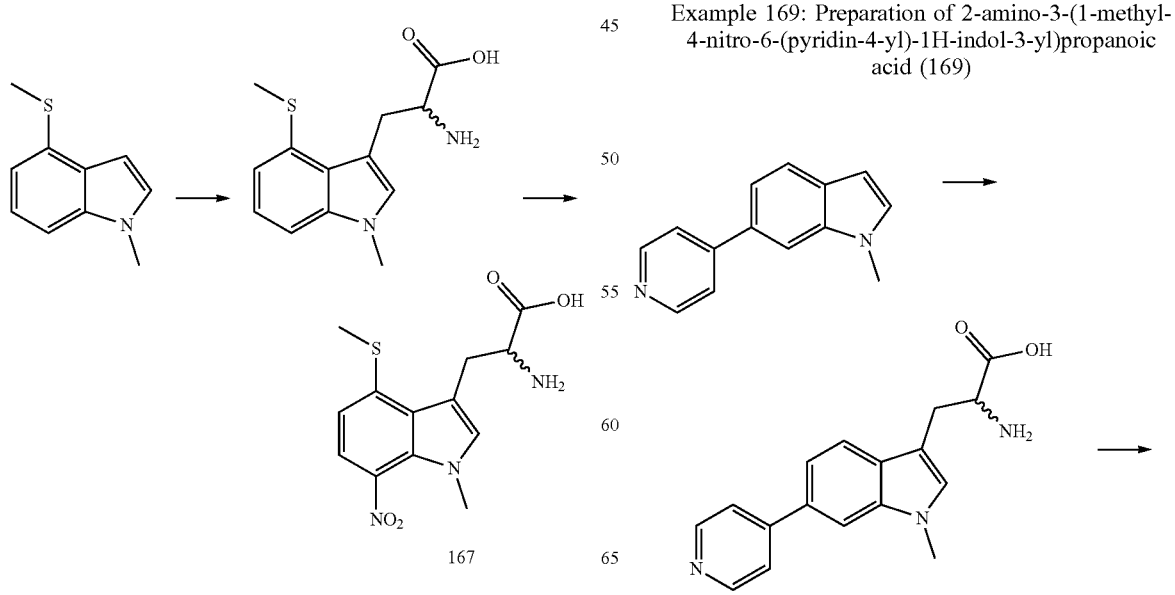

167

Example 167 can be prepared from 4-(methylthio)-1-methyl-indole as shown above and in a similar manner as described in Examples 1-7.

Example 168: Preparation of 2-amino-3-(1-methyl-4-nitro-5-(pyridin-4-yl)-1H-indol-3-yl)propanoic acid (168)

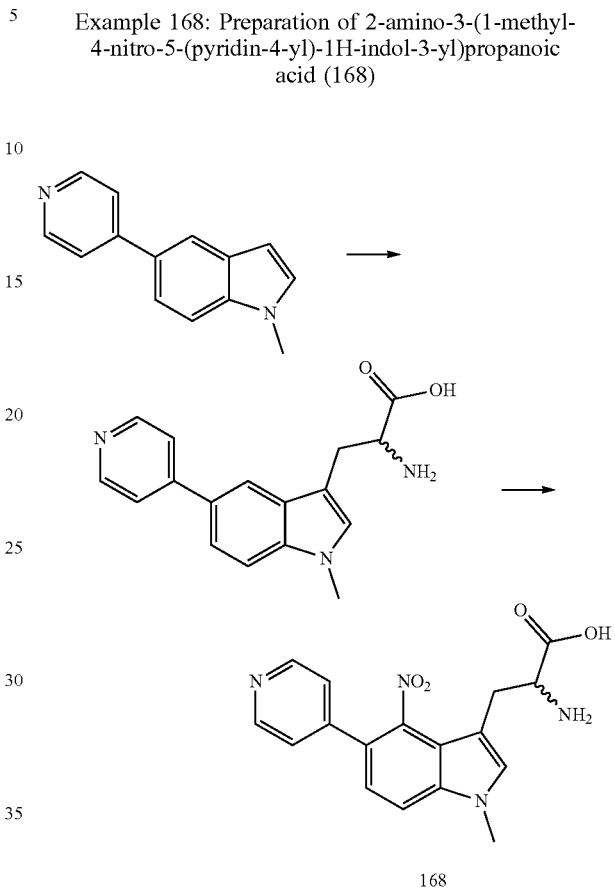

168

Example 168 can be prepared from 5-(pyridin-4-yl)-1-methyl-indole as shown above and in a similar manner as described in Examples 1-7.

Example 169: Preparation of 2-amino-3-(1-methyl-4-nitro-6-(pyridin-4-yl)-1H-indol-3-yl)propanoic acid (169)

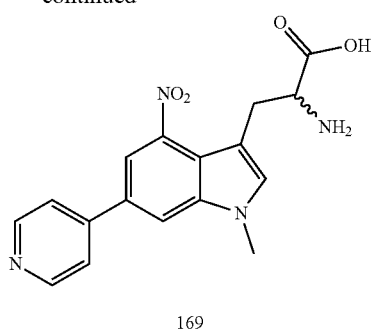

169

Example 169 can be prepared from 6-(pyridin-4-yl)-1-methyl-indole as shown above and in a similar manner as described in Examples 1-7.

Example 170: Preparation of 2-amino-3-(1-methyl-4-nitro-7-(pyridin-4-yl)-1H-indol-3-yl)propanoic acid (170)

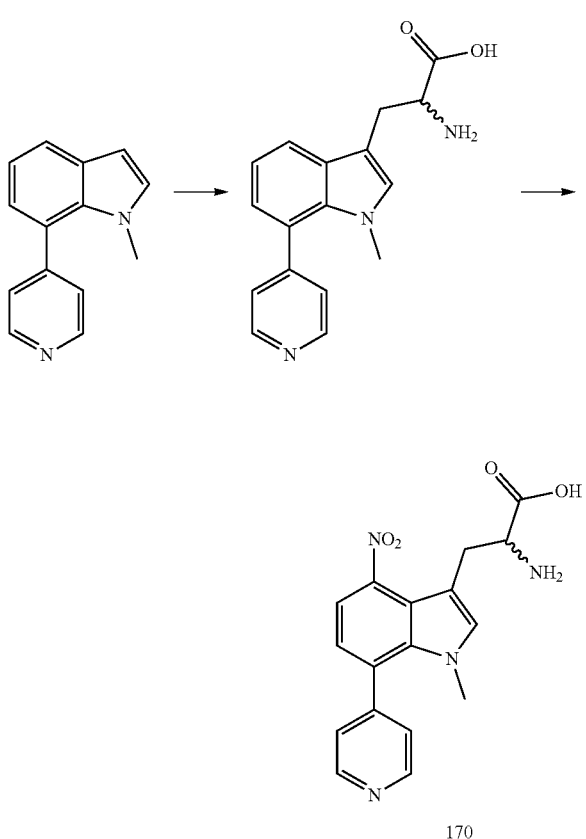

170

Example 170 can be prepared from 7-(pyridin-4-yl)-1-methyl-indole as shown above and in a similar manner as described in Examples 1-7.

Example 171: Preparation of 2-amino-3-(1-methyl-7-nitro-4-(pyridin-4-yl)-1H-indol-3-yl)propanoic acid (171)

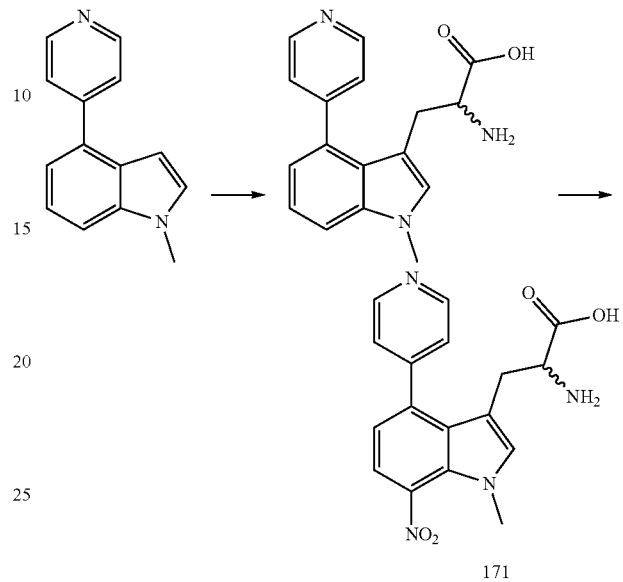

171

Example 171 can be prepared from 4-(pyridin-4-yl)-1-methyl-indole as shown above and in a similar manner as described in Examples 1-7.

Example 172: Preparation of 2-amino-3-(2,5-dimethyl-4-nitro-1H-indol-3-yl)propanoic acid (172)

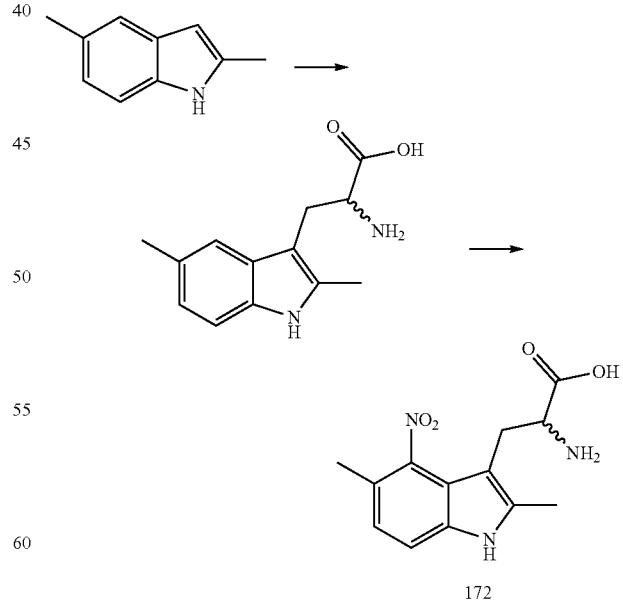

172

Example 172 can be prepared from 2,5-dimethyl-1H-indole as shown above and in a similar manner as described in Examples 1-7.

Example 173: Preparation of 2-amino-3-(2,6-dimethyl-4-nitro-1H-indol-3-yl)propanoic acid (173)

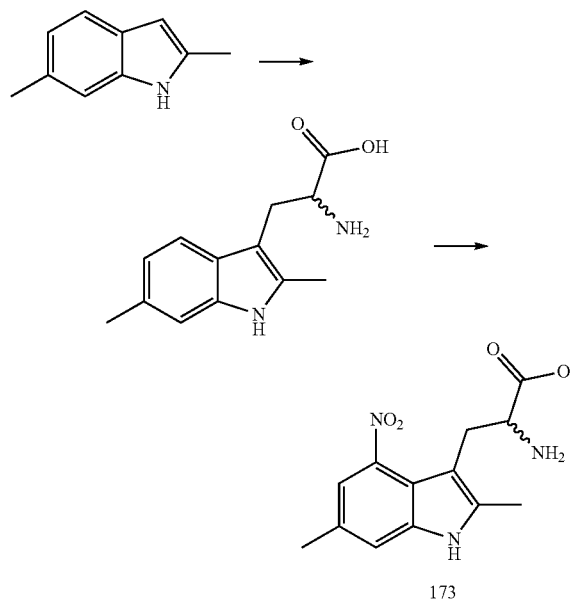

173

Example 173 can be prepared from 2,6-dimethyl-1H-indole as shown above and in a similar manner as described in Examples 1-7.

Example 174: Preparation of 2-amino-3-(2,7-dimethyl-4-nitro-1H-indol-3-yl)propanoic acid (174)

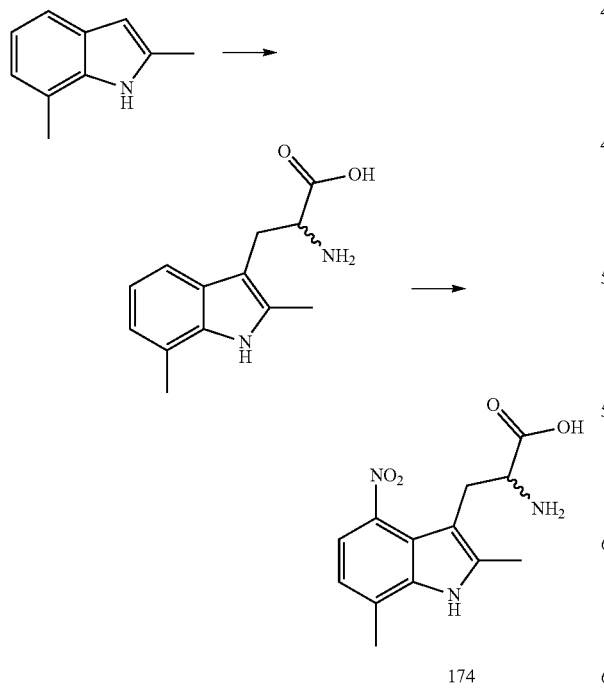

174

Example 174 can be prepared from 2,7-dimethyl-1H-indole as shown above and in a similar manner as described in Examples 1-7.

Example 175: Preparation of 2-amino-3-(2,4-dimethyl-7-nitro-1H-indol-3-yl)propanoic acid (175)

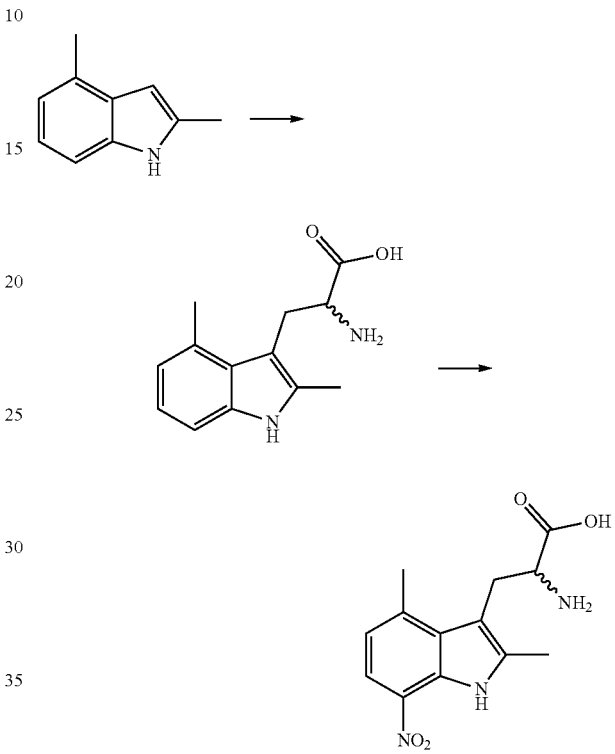

175

Example 175 can be prepared from 2,4-dimethyl-1H-indole as shown above and in a similar manner as described in Examples 1-7.

Example 176: Preparation of 2-amino-3-(6-fluoro-2-methyl-4-nitro-1H-indol-3-yl)propanoic acid (176)

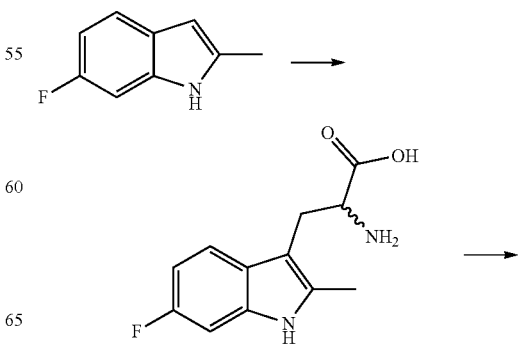

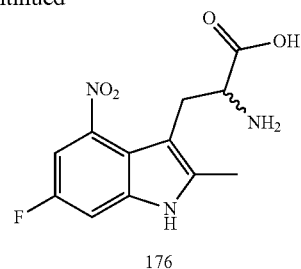

176

Example 176 can be prepared from 6-fluoro-2-methyl-1H-indole as shown above and in a similar manner as described in Examples 1-7.

Example 177: Preparation of 2-amino-3-(7-fluoro-2-methyl-4-nitro-1H-indol-3-yl)propanoic acid (177)

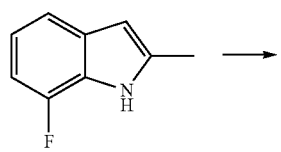

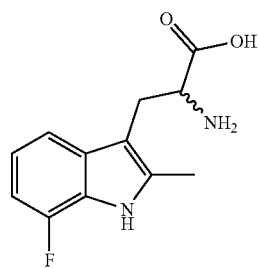

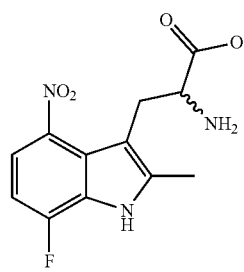

177

Example 177 can be prepared from 7-fluoro-2-methyl-indole as shown above and in a similar manner as described in Examples 1-7.

Example 178: Preparation of 2-amino-3-(4-fluoro-2-methyl-7-nitro-1H-indol-3-yl)propanoic acid (178)

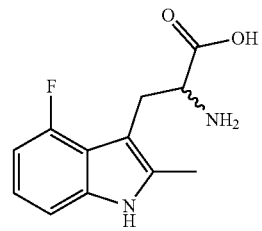

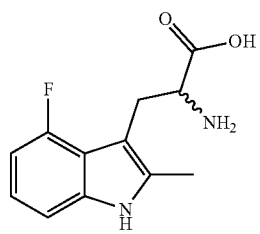

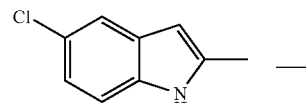

178

Example 178 can be prepared from 4-fluoro-2-methyl-indole as shown above and in a similar manner as described in Examples 1-7.

Example 179: Preparation of 2-amino-3-(5-chloro-2-methyl-4-nitro-1H-indol-3-yl)propanoic acid (179)

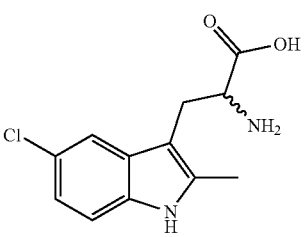

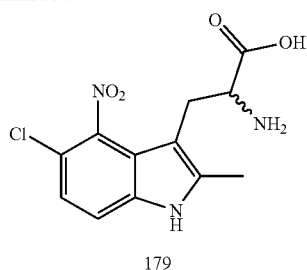

179

Example 179 can be prepared from 5-chloro-2-methyl-indole as shown above and in a similar manner as described in Examples 1-7.

Example 180: Preparation of 2-amino-3-(6-chloro-2-methyl-4-nitro-1H-indol-3-yl)propanoic acid (180)

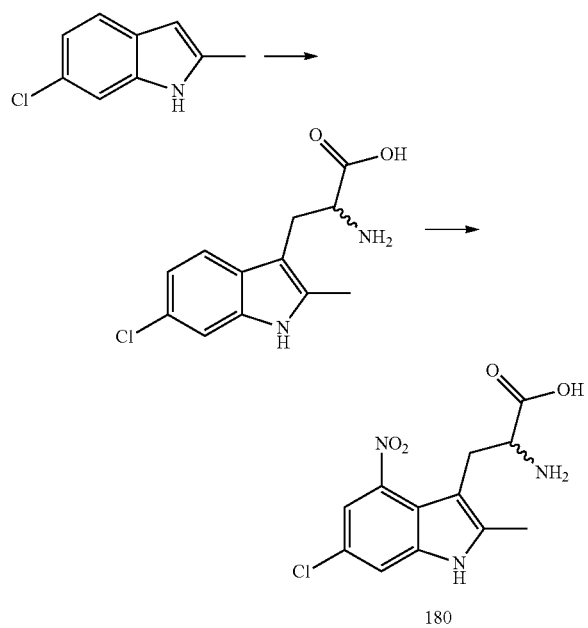

180

Example 180 can be prepared from 6-chloro-2-methyl-indole as shown above and in a similar manner as described in Examples 1-7.

Example 181: Preparation of 2-amino-3-(7-chloro-2-methyl-4-nitro-1H-indol-3-yl)propanoic acid (181)

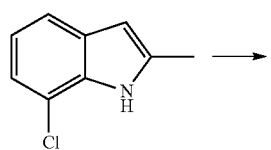

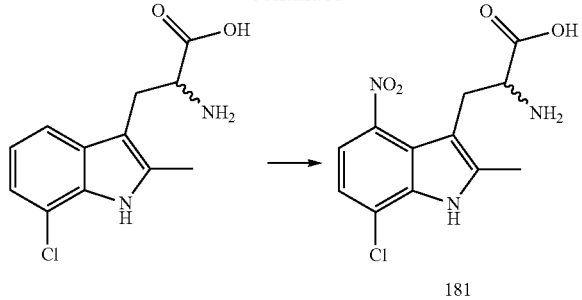

181

Example 181 can be prepared from 7-chloro-2-methyl-indole as shown above and in a similar manner as described in Examples 1-7.

Example 182: Preparation of 2-amino-3-(4-chloro-2-methyl-7-nitro-1H-indol-3-yl)propanoic acid (182)

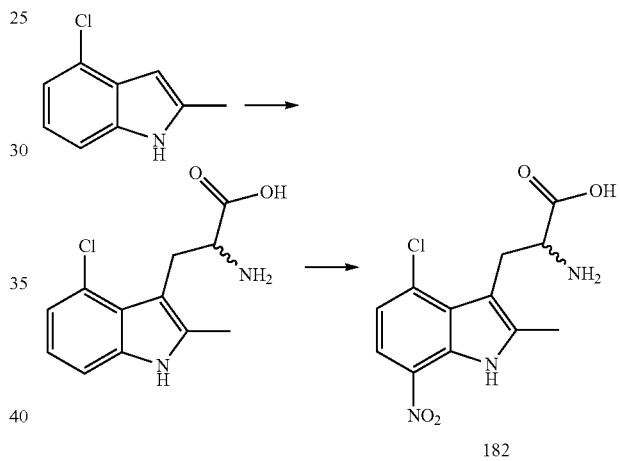

182

Example 182 can be prepared from 4-chloro-2-methyl-indole as shown above and in a similar manner as described in Examples 1-7.

Example 183: Preparation of 2-amino-3-(5-bromo-2-methyl-4-nitro-1H-indol-3-yl)propanoic acid (183)

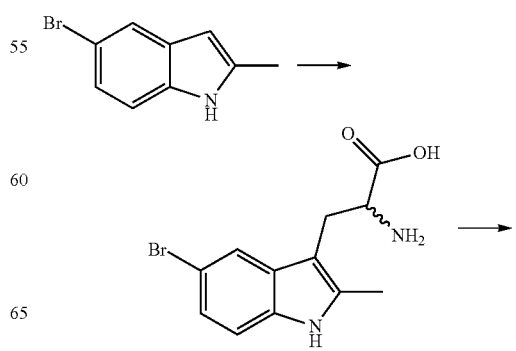

183
-continued

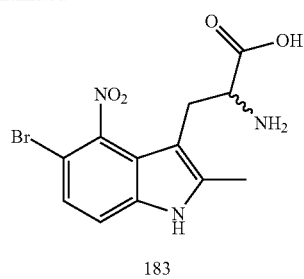

183

Example 183 can be prepared from 5-bromo-2-methyl-indole as shown above and in a similar manner as described in Examples 1-7.

Example 184: Preparation of 2-amino-3-(6-bromo-2-methyl-4-nitro-1H-indol-3-yl)propanoic acid (184)

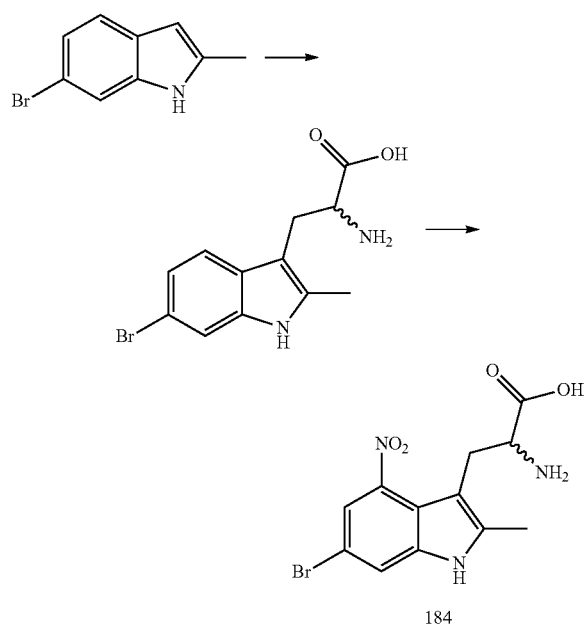

184

Example 184 can be prepared from 6-bromo-2-methyl-indole as shown above and in a similar manner as described in Examples 1-7.

Example 185: Preparation of 2-amino-3-(7-bromo-2-methyl-4-nitro-1H-indol-3-yl)propanoic acid (185)

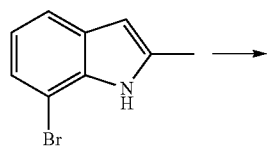

-continued

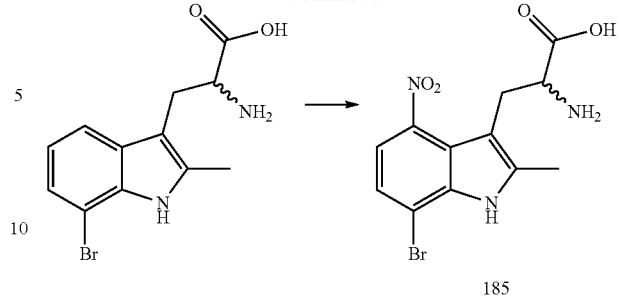

185

Example 185 can be prepared from 7-bromo-2-methyl-indole as shown above and in a similar manner as described in Examples 1-7.

Example 186: Preparation of 2-amino-3-(4-bromo-2-methyl-7-nitro-1H-indol-3-yl)propanoic acid (186)

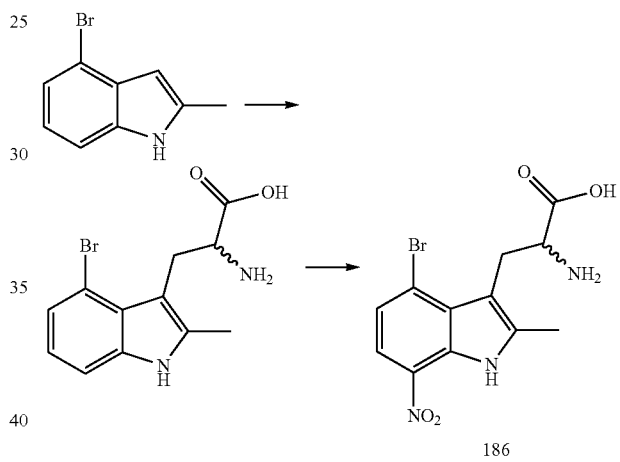

186

Example 186 can be prepared from 4-bromo-2-methyl-indole as shown above and in a similar manner as described in Examples 1-7.

Example 187: Preparation of 2-amino-3-(5-methoxy-2-methyl-4-nitro-1H-indol-3-yl)propanoic acid (187)

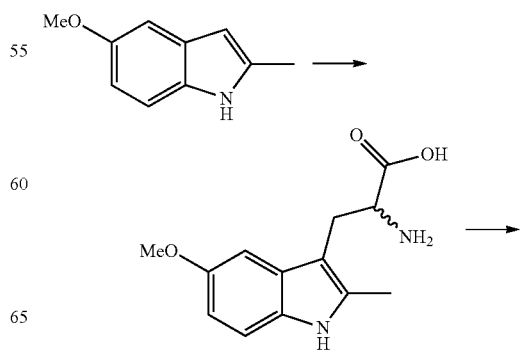

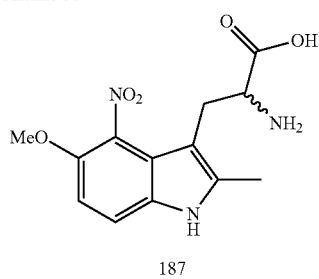

187

Example 187 can be prepared from 5-methoxy-2-methyl-indole as shown above and in a similar manner as described in Examples 1-7.

Example 188: Preparation of 2-amino-3-(6-methoxy-2-methyl-4-nitro-1H-indol-3-yl)propanoic acid (188)

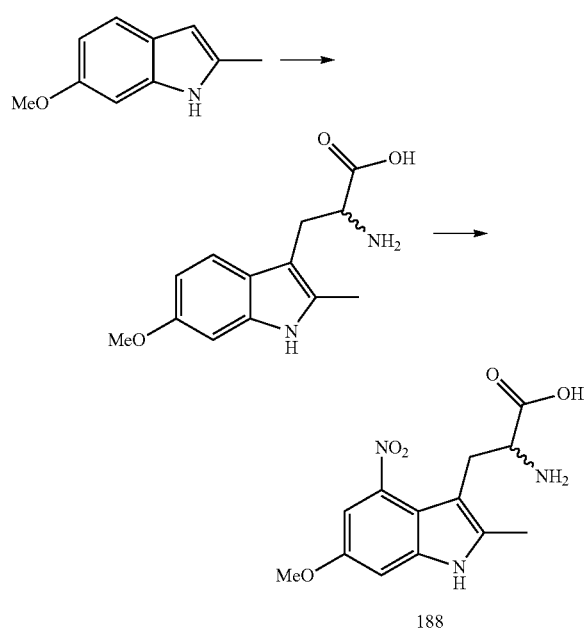

188

Example 188 can be prepared from 6-methoxy-2-methyl-indole as shown above and in a similar manner as described in Examples 1-7.

Example 189: Preparation of 2-amino-3-(7-methoxy-2-methyl-4-nitro-1H-indol-3-yl)propanoic acid (189)

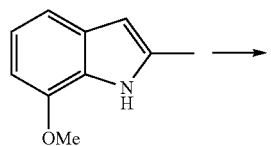

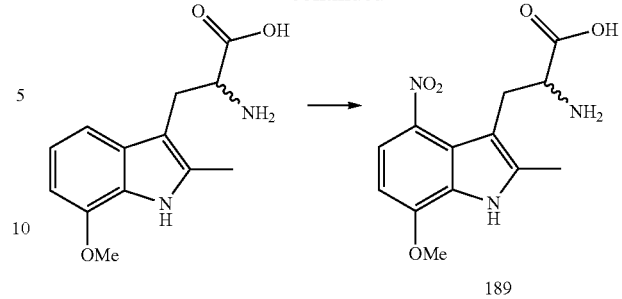

189

Example 189 can be prepared from 7-methoxy-2-methyl-indole as shown above and in a similar manner as described in Examples 1-7.

Example 190: Preparation of 2-amino-3-(4-methoxy-2-methyl-7-nitro-1H-indol-3-yl)propanoic acid (190)

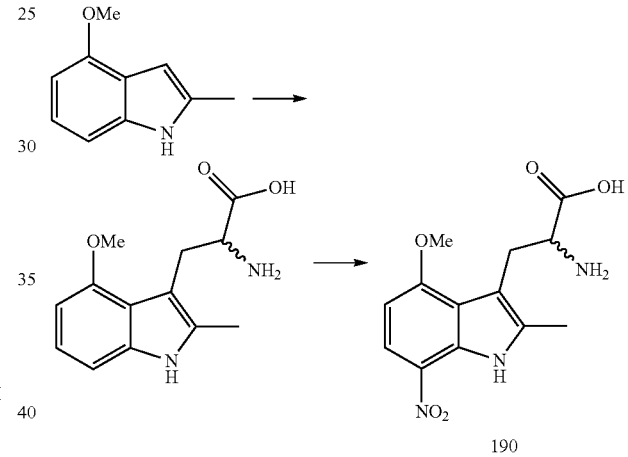

190

Example 190 can be prepared from 4-methoxy-2-methyl-indole as shown above and in a similar manner as described in Examples 1-7.

Example 191: Preparation of 2-amino-3-(5-amino-2-methyl-4-nitro-1H-indol-3-yl)propanoic acid (191)

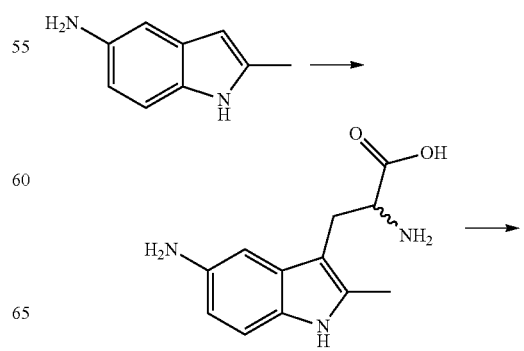

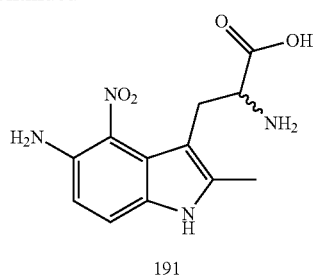

191

Example 191 can be prepared from 5-amino-2-methyl-indole as shown above and in a similar manner as described in Examples 1-7.

Example 192: Preparation of 2-amino-3-(6-amino-2-methyl-4-nitro-1H-indol-3-yl)propanoic acid (192)

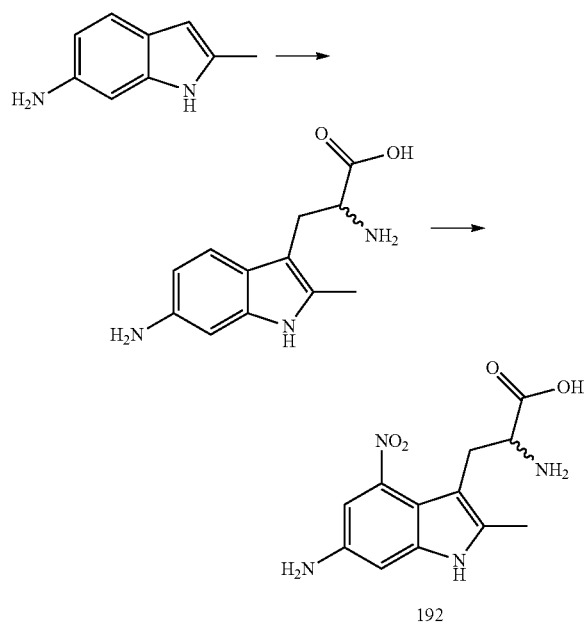

192

Example 192 can be prepared from 6-amino-2-methyl-indole as shown above and in a similar manner as described in Examples 1-7.

Example 193: Preparation of 2-amino-3-(7-amino-2-methyl-4-nitro-1H-indol-3-yl)propanoic acid (193)

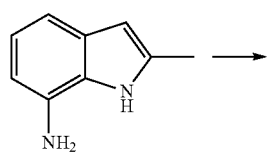

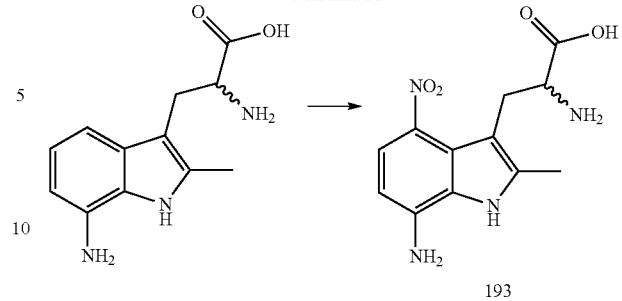

193

Example 193 can be prepared from 7-amino-2-methyl-indole as shown above and in a similar manner as described in Examples 1-7.

Example 194: Preparation of 2-amino-3-(4-amino-2-methyl-7-nitro-1H-indol-3-yl)propanoic acid (194)

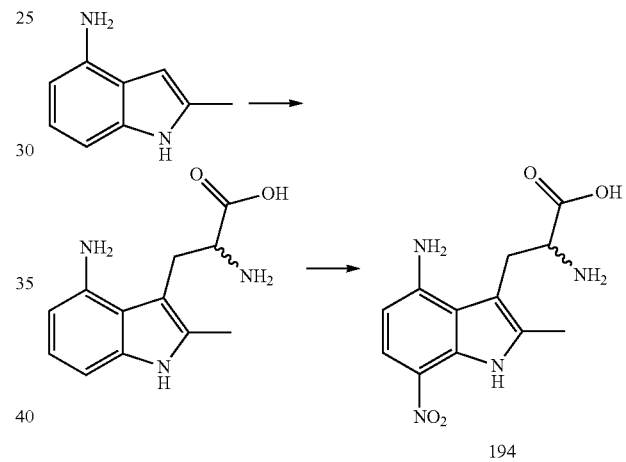

194

Example 194 can be prepared from 4-amino-2-methyl-indole as shown above and in a similar manner as described in Examples 1-7.

Example 195: Preparation of 2-amino-3-(5-hydroxy-2-methyl-4-nitro-1H-indol-3-yl)propanoic acid (195)

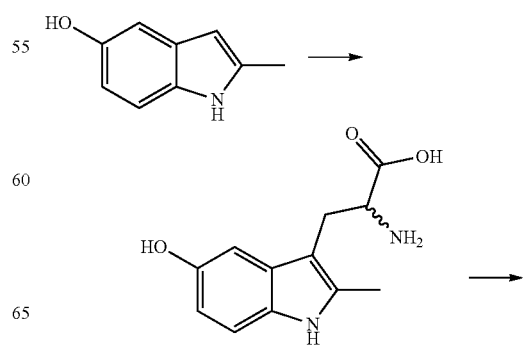

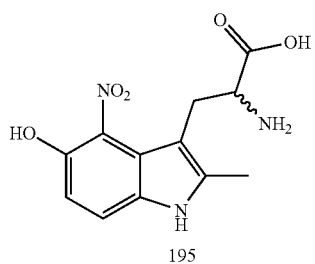
195

Example 195 can be prepared from 5-hydroxy-2-methyl-indole as shown above and in a similar manner as described in Examples 1-7.

Example 196: Preparation of 2-amino-3-(6-hydroxy-2-methyl-4-nitro-1H-indol-3-yl)propanoic acid (196)

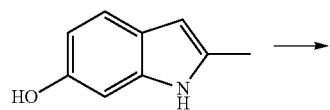

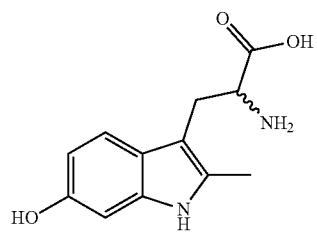

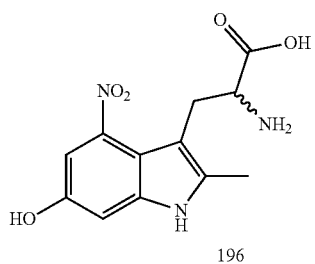
196

Example 196 can be prepared from 6-hydroxy-2-methyl-indole as shown above and in a similar manner as described in Examples 1-7.

Example 197: Preparation of 2-amino-3-(7-hydroxy-2-methyl-4-nitro-1H-indol-3-yl)propanoic acid (197)

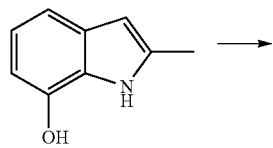

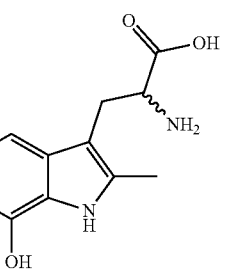

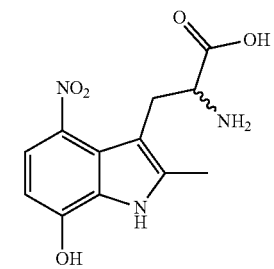
197

Example 197 can be prepared from 7-hydroxy-2-methyl-indole as shown above and in a similar manner as described in Examples 1-7.

Example 198: Preparation of 2-amino-3-(4-hydroxy-2-methyl-7-nitro-1H-indol-3-yl)propanoic acid (198)

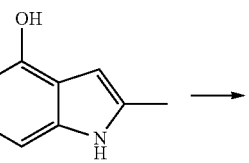

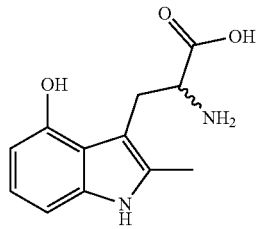

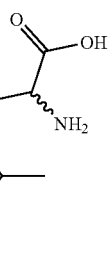
198

Example 198 can be prepared from 4-hydroxy-2-methyl-indole as shown above and in a similar manner as described in Examples 1-7.

Example 199: Preparation of 2-amino-3-(2-methyl-4-nitro-5-phenyl-1H-indol-3-yl)propanoic acid (199)

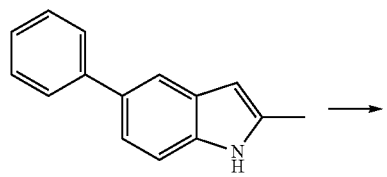

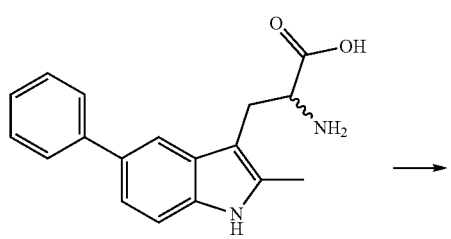

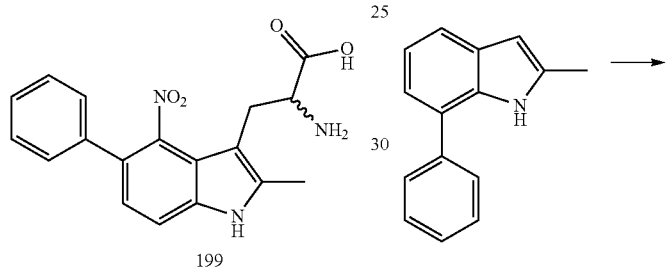

199

Example 199 can be prepared from 5-phenyl-2-methyl-indole as shown above and in a similar manner as described in Examples 1-7.

Example 200: Preparation of 2-amino-3-(2-methyl-4-nitro-6-phenyl-1H-indol-3-yl)propanoic acid (200)

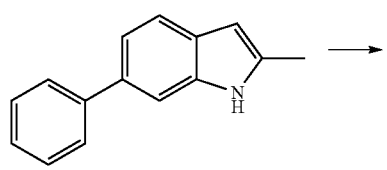

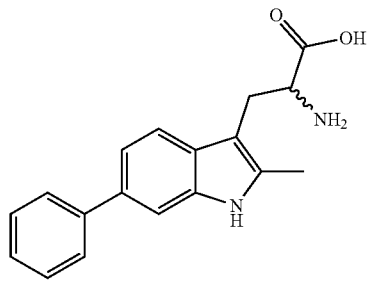

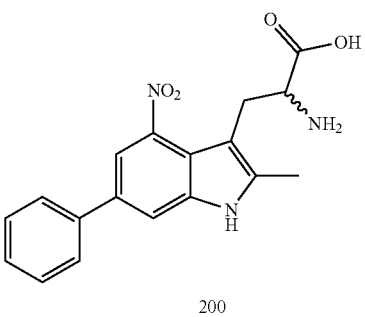

200

Example 200 can be prepared from 6-phenyl-2-methyl-indole as shown above and in a similar manner as described in Examples 1-7.

Example 201: Preparation of 2-amino-3-(2-methyl-4-nitro-7-phenyl-1H-indol-3-yl)propanoic acid (201)

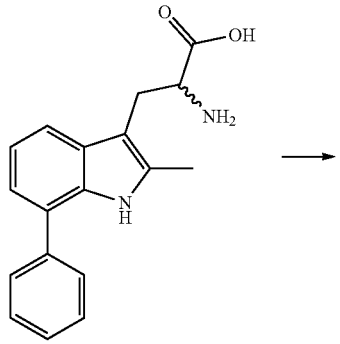

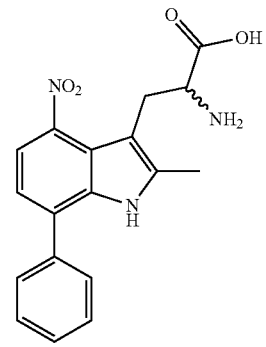

201

Example 201 can be prepared from 7-phenyl-2-methyl-indole as shown above and in a similar manner as described in Examples 1-7.

Example 202: Preparation of 2-amino-3-(2-methyl-7-nitro-4-phenyl-1H-indol-3-yl)propanoic acid (202)

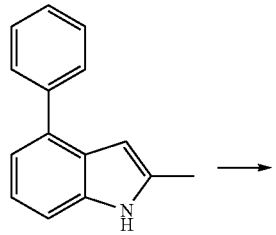

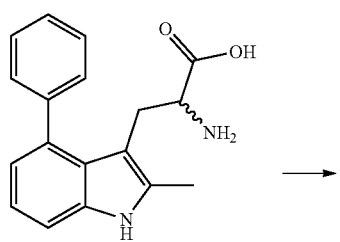

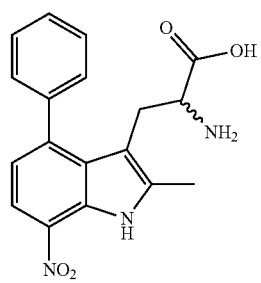

Example 202 can be prepared from 4-phenyl-2-methyl-indole as shown above and in a similar manner as described in Examples 1-7.

Example 203: Preparation of 2-amino-3-(5-cyclopropyl-2-methyl-4-nitro-1H-indol-3-yl)propanoic acid (203)

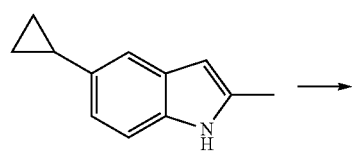

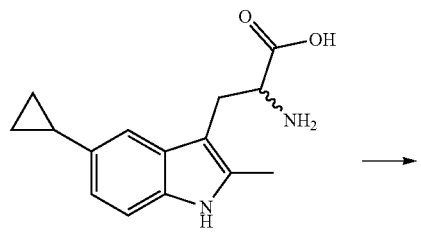

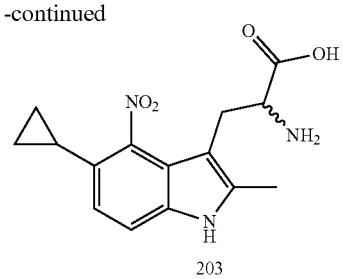

Example 203 can be prepared from 5-cyclopropyl-2-methyl-indole as shown above and in a similar manner as described in Examples 1-7.

Example 204: Preparation of 2-amino-3-(6-cyclopropyl-2-methyl-4-nitro-1H-indol-3-yl)propanoic acid (204)

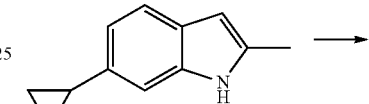

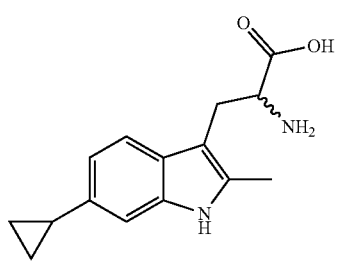

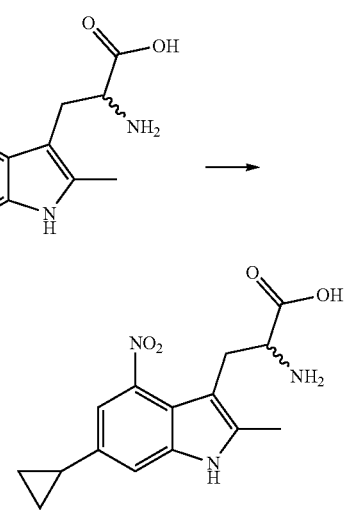

Example 204 can be prepared from 6-cyclopropyl-2-methyl-indole as shown above and in a similar manner as described in Examples 1-7.

Example 205: Preparation of 2-amino-3-(7-cyclopropyl-2-methyl-4-nitro-1H-indol-3-yl)propanoic acid (205)

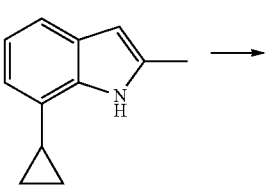

-continued

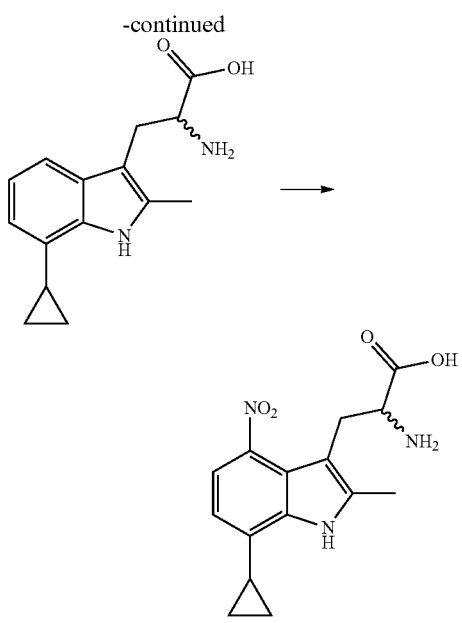

205

Example 205 can be prepared from 7-cyclopropyl-2-methyl-indole as shown above and in a similar manner as described in Examples 1-7.

Example 206: Preparation of 2-amino-3-(4-cyclopropyl-2-methyl-7-nitro-1H-indol-3-yl)propanoic acid (206)

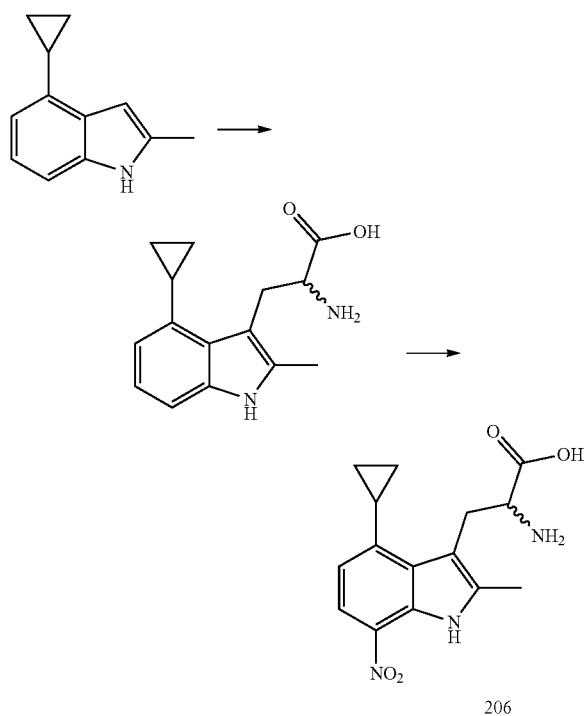

206

Example 206 can be prepared from 4-cyclopropyl-2-methyl-indole as shown above and in a similar manner as described in Examples 1-7.

Example 207: Preparation of 2-amino-3-(2-methyl-4-nitro-5-vinyl-1H-indol-3-yl)propanoic acid (207)

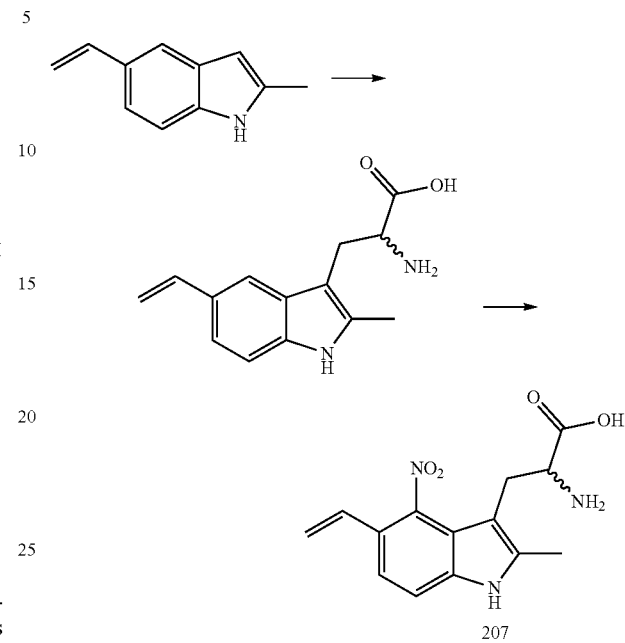

207

Example 207 can be prepared from 5-vinyl-2-methyl-indole as shown above and in a similar manner as described in Examples 1-7.

Example 208: Preparation of 2-amino-3-(2-methyl-4-nitro-6-vinyl-1H-indol-3-yl)propanoic acid (208)

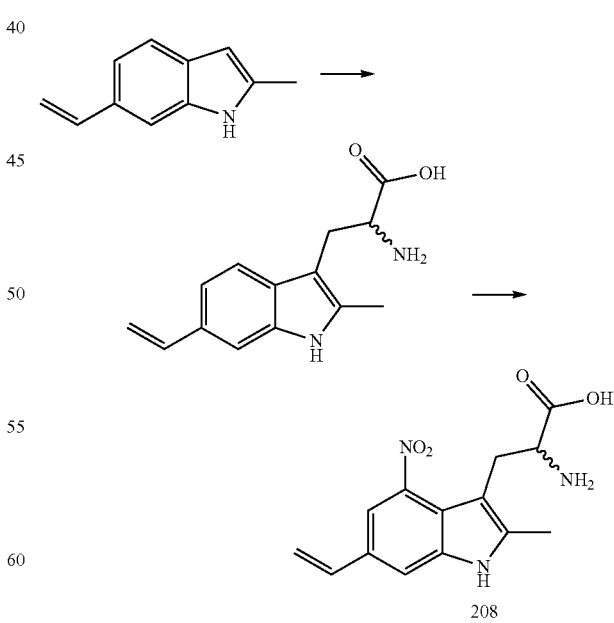

208

Example 208 can be prepared from 6-vinyl-2-methyl-indole as shown above and in a similar manner as described in Examples 1-7.

Example 209: Preparation of 2-amino-3-(2-methyl-4-nitro-7-vinyl-1H-indol-3-yl)propanoic acid (209)

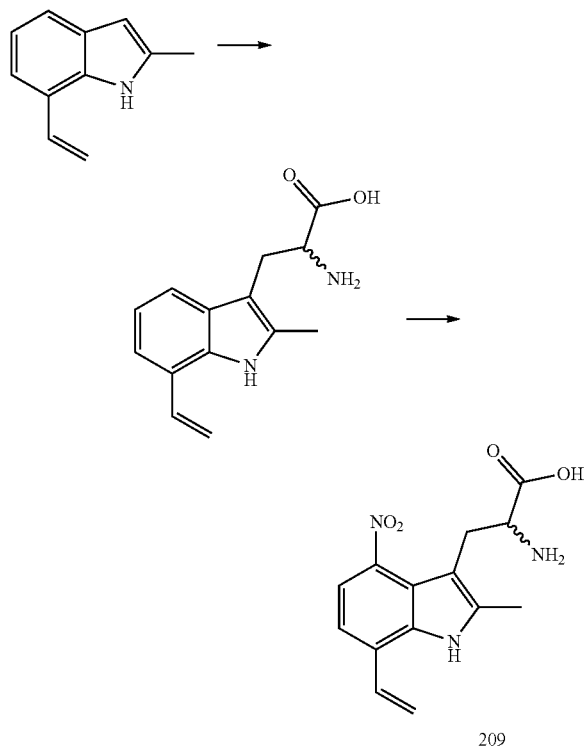

209

Example 209 can be prepared from 7-vinyl-2-methyl-indole as shown above and in a similar manner as described in Examples 1-7.

Example 210: Preparation of 2-amino-3-(2-methyl-7-nitro-4-vinyl-1H-indol-3-yl)propanoic acid (210)

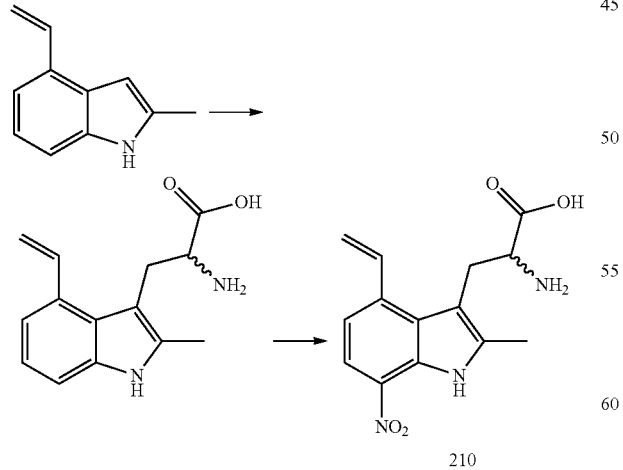

210

Example 210 can be prepared from 4-vinyl-2-methyl-indole as shown above and in a similar manner as described in Examples 1-7.

Example 211: Preparation of 2-amino-3-(5-ethynyl-2-methyl-4-nitro-1H-indol-3-yl)propanoic acid (211)

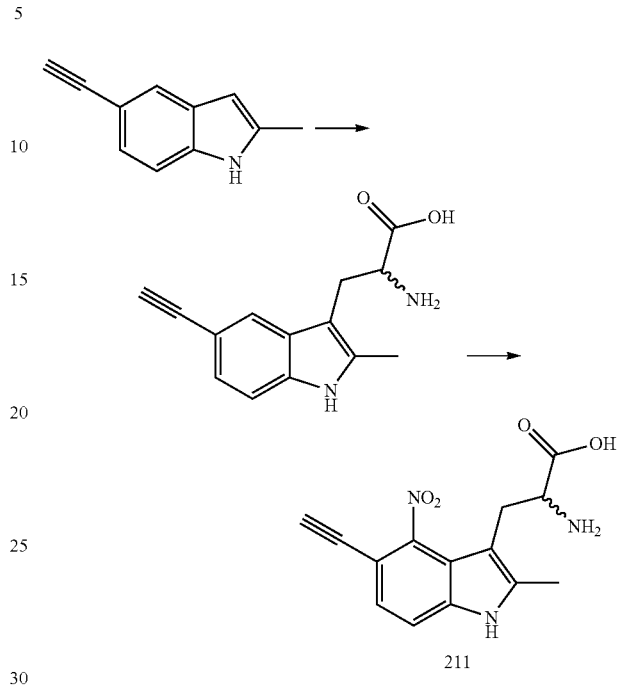

211

Example 211 can be prepared from 5-ethynyl-2-methyl-indole as shown above and in a similar manner as described in Examples 1-7.

Example 212: Preparation of 2-amino-3-(6-ethynyl-2-methyl-4-nitro-1H-indol-3-yl)propanoic acid (212)

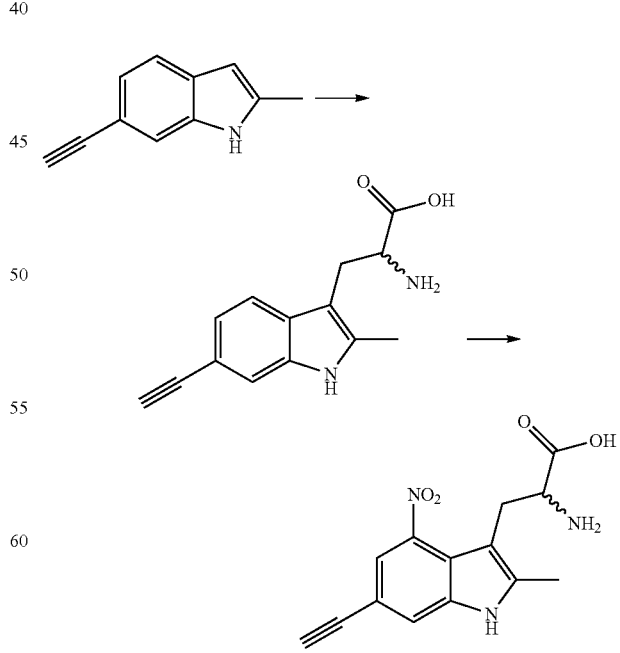

212

Example 212 can be prepared from 6-ethynyl-2-methyl-indole as shown above and in a similar manner as described in Examples 1-7.

Example 213: Preparation of 2-amino-3-(7-ethynyl-2-methyl-4-nitro-1H-indol-3-yl)propanoic acid (213)

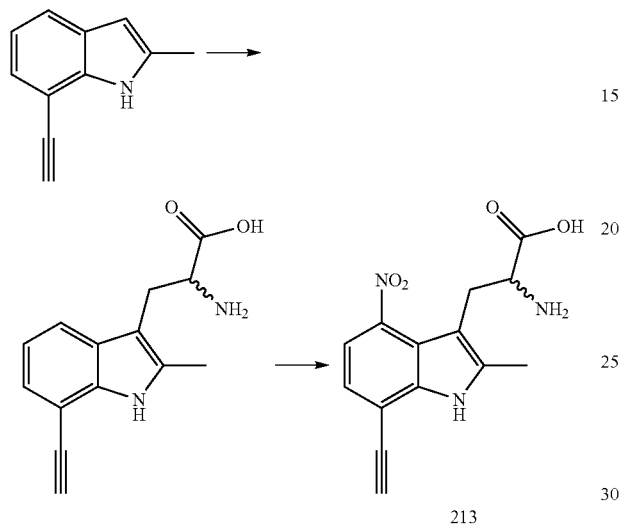

Example 213 can be prepared from 7-ethynyl-2-methyl-indole as shown above and in a similar manner as described in Examples 1-7.

Example 214: Preparation of 2-amino-3-(4-ethynyl-2-methyl-7-nitro-1H-indol-3-yl)propanoic acid (214)

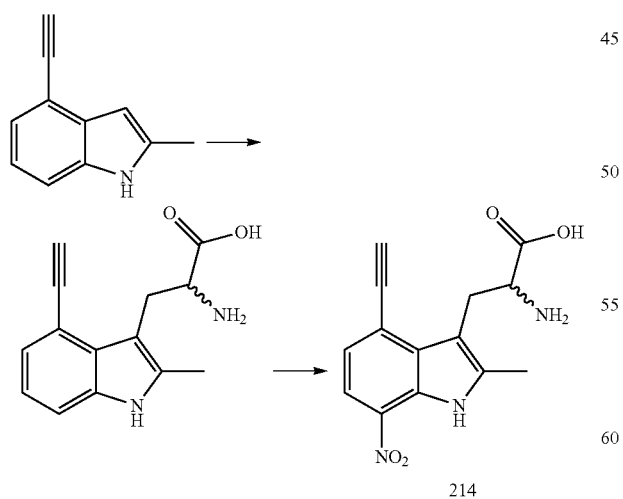

Example 214 can be prepared from 4-ethynyl-2-methyl-indole as shown above and in a similar manner as described in Examples 1-7.

Example 215: Preparation of 2-amino-3-(2-methyl-5-morpholino-4-nitro-1H-indol-3-yl)propanoic acid (215)

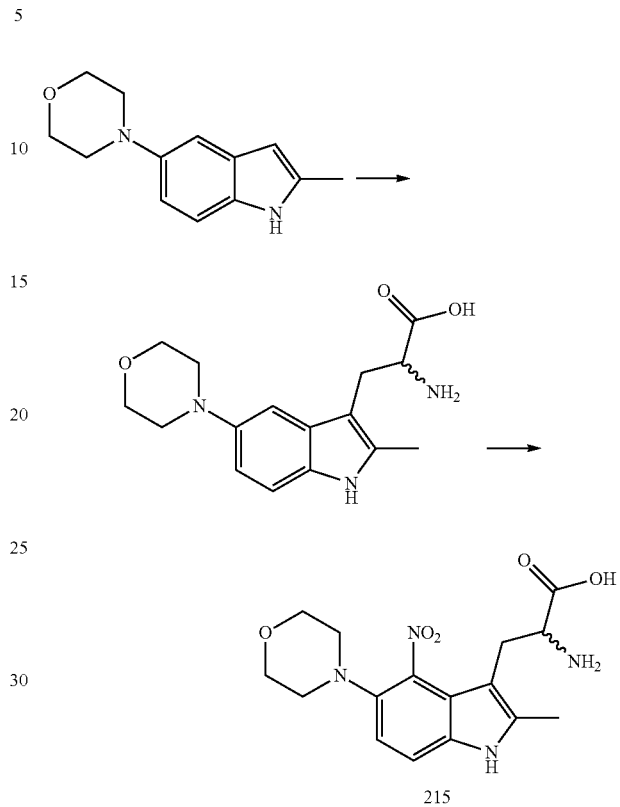

Example 215 can be prepared from 5-morpholino-2-methyl-indole as shown above and in a similar manner as described in Examples 1-7.

Example 216: Preparation of 2-amino-3-(2-methyl-6-morpholino-4-nitro-1H-indol-3-yl)propanoic acid (216)

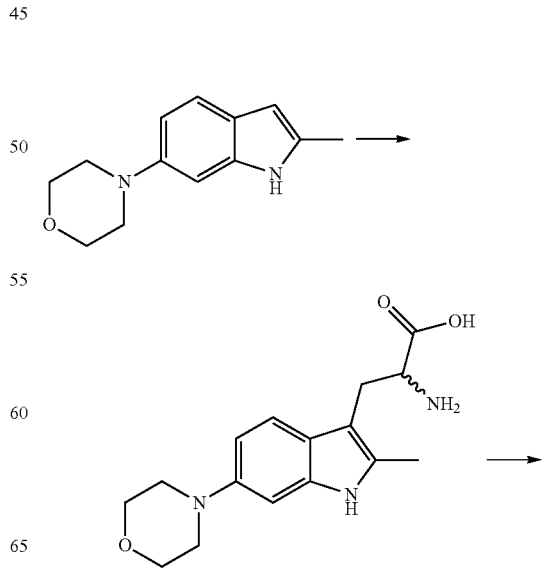

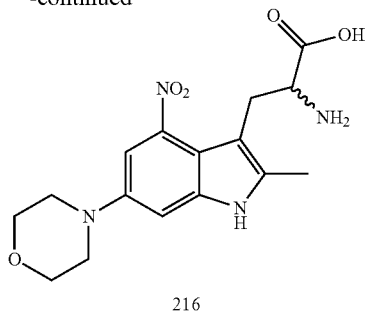

216

Example 216 can be prepared from 6-morpholino-2-methyl-indole as shown above and in a similar manner as described in Examples 1-7.

Example 217: Preparation of 2-amino-3-(2-methyl-7-morpholino-4-nitro-1H-indol-3-yl)propanoic acid (217)

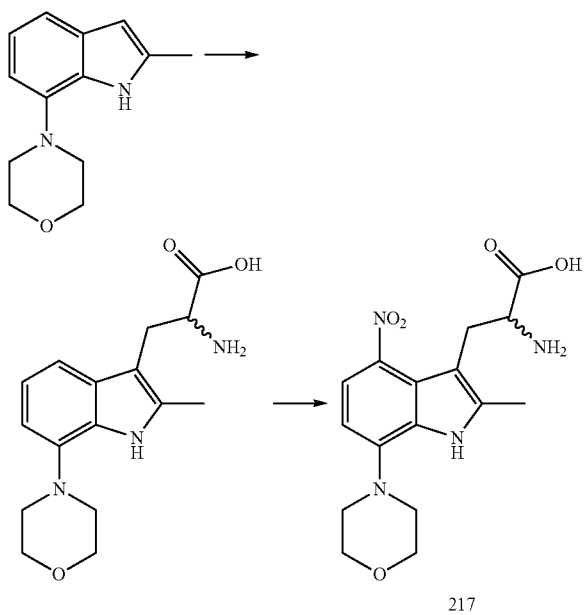

217

Example 217 can be prepared from 7-morpholino-2-methyl-indole as shown above and in a similar manner as described in Examples 1-7.

Example 218: Preparation of 2-amino-3-(2-methyl-4-morpholino-7-nitro-1H-indol-3-yl)propanoic acid (218)

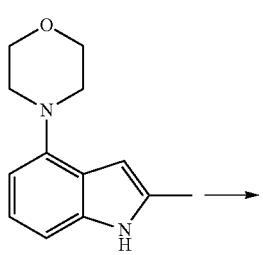

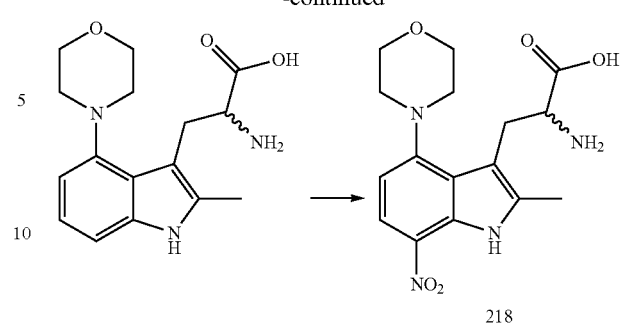

218

Example 218 can be prepared from 4-morpholino-2-methyl-indole as shown above and in a similar manner as described in Examples 1-7.

Example 219: Preparation of 2-amino-3-(2-methyl-5-(methylthio)-4-nitro-1H-indol-3-yl)propanoic acid (219)

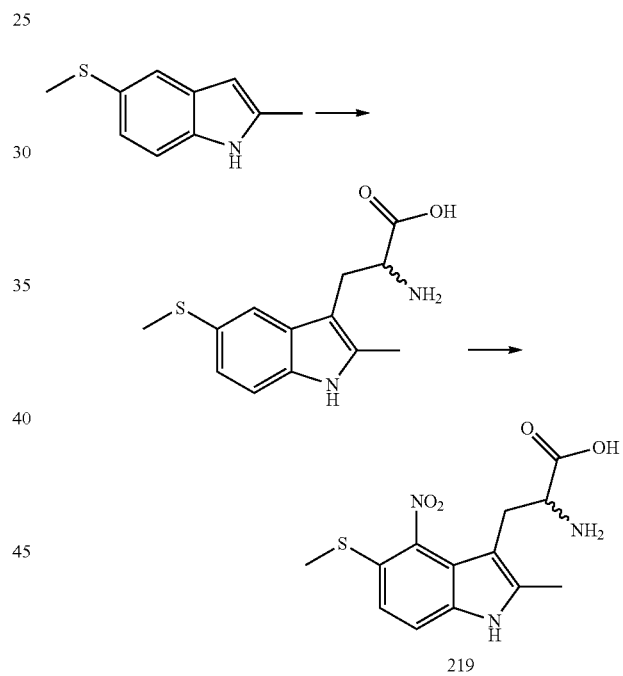

219

Example 219 can be prepared from 5-(methylthio)-2-methyl-indole as shown above and in a similar manner as described in Examples 1-7.

Example 220: Preparation of 2-amino-3-(2-methyl-6-(methylthio)-4-nitro-1H-indol-3-yl)propanoic acid (220)

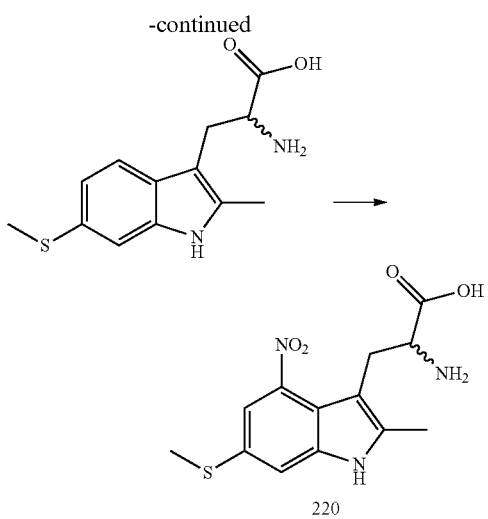

220

Example 220 can be prepared from 6-(methylthio)-2-methyl-indole as shown above and in a similar manner as described in Examples 1-7.

Example 221: Preparation of 2-amino-3-(2-methyl-7-(methylthio)-4-nitro-1H-indol-3-yl)propanoic acid (221)

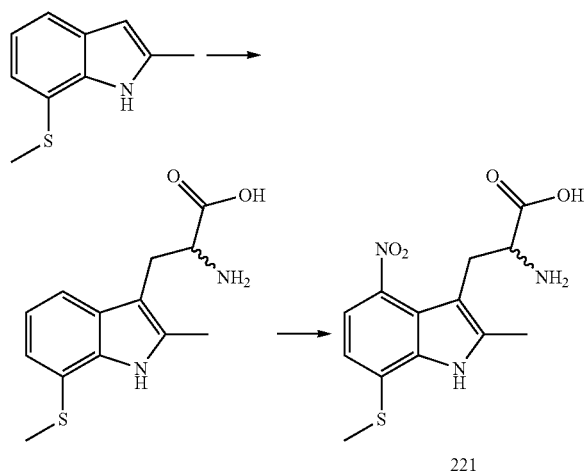

221

Example 221 can be prepared from 7-(methylthio)-2-methyl-indole as shown above and in a similar manner as described in Examples 1-7.

Example 222: Preparation of 2-amino-3-(2-methyl-4-(methylthio)-7-nitro-1H-indol-3-yl)propanoic acid (222)

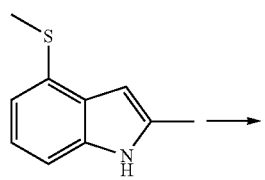

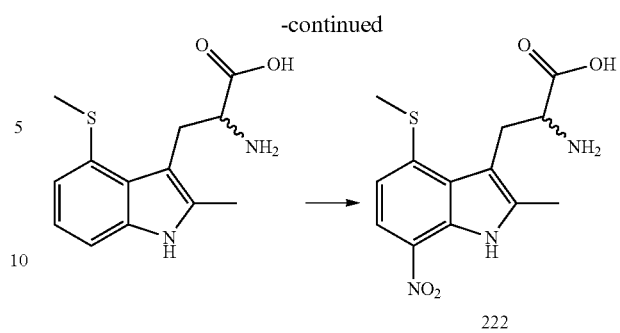

222

Example 222 can be prepared from 4-(methylthio)-2-methyl-indole as shown above and in a similar manner as described in Examples 1-7.

Example 223: Preparation of 2-amino-3-(2-methyl-4-nitro-5-(pyridin-4-yl)-1H-indol-3-yl)propanoic acid (223)

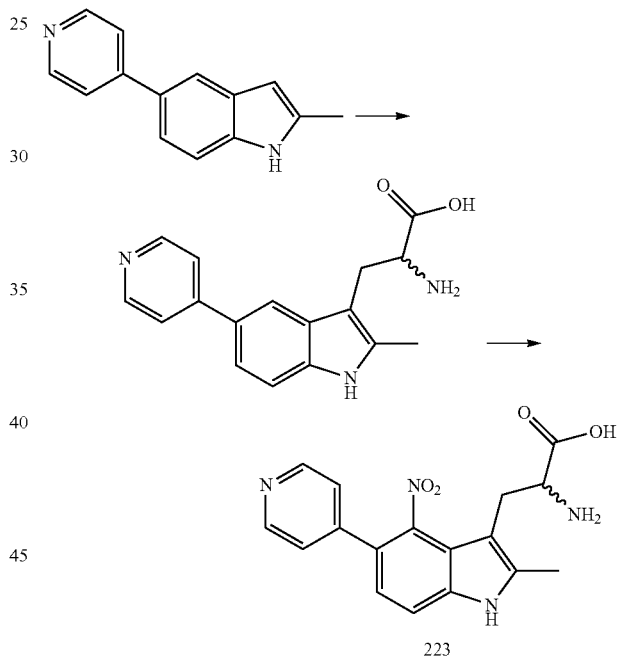

223

Example 223 can be prepared from 5-(pyridin-4-yl)-2-methyl-indole as shown above and in a similar manner as described in Examples 1-7.

Example 224: Preparation of 2-amino-3-(2-methyl-4-nitro-6-(pyridin-4-yl)-1H-indol-3-yl)propanoic acid (224)

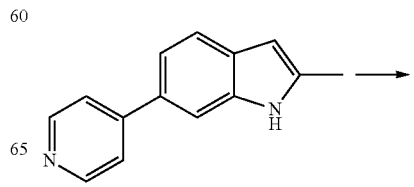

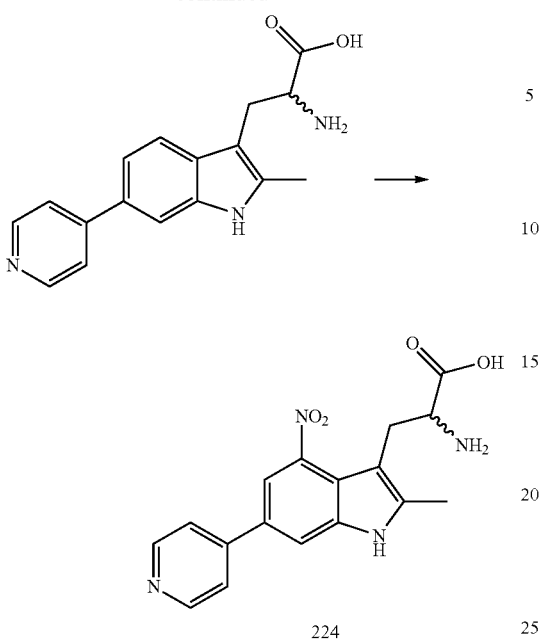

224

Example 224 can be prepared from 6-(pyridin-4-yl)-2-methyl-indole as shown above and in a similar manner as described in Examples 1-7.

Example 225: Preparation of 2-amino-3-(2-methyl-4-nitro-7-(pyridin-4-yl)-1H-indol-3-yl)propanoic acid (225)

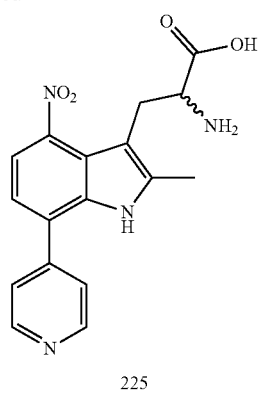

225

Example 225 can be prepared from 7-(pyridin-4-yl)-2-methyl-indole as shown above and in a similar manner as described in Examples 1-7.

Example 226: Preparation of 2-amino-3-(2-methyl-7-nitro-4-(pyridin-4-yl)-1H-indol-3-yl)propanoic acid (226)

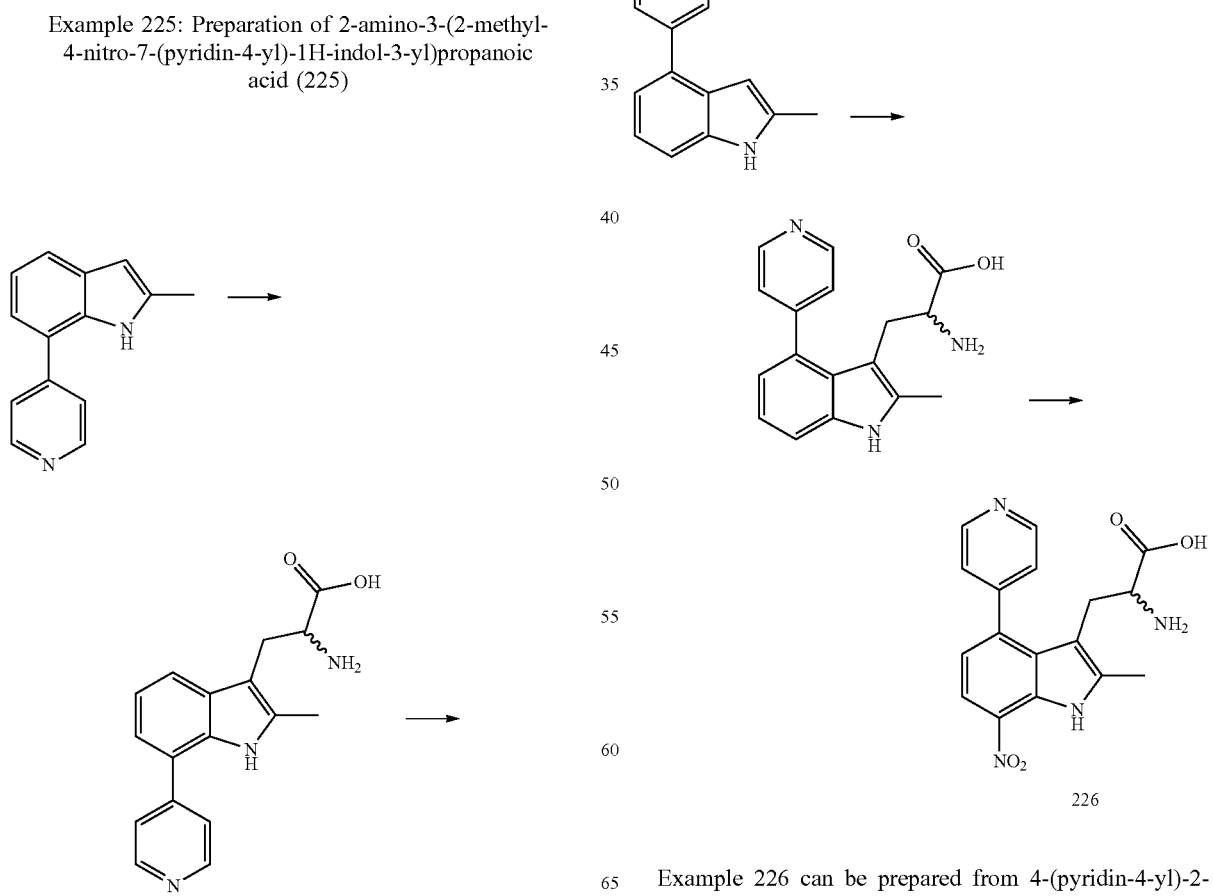

226

Example 226 can be prepared from 4-(pyridin-4-yl)-2-methyl-indole as shown above and in a similar manner as described in Examples 1-7.

Example 227: Preparation of 2-amino-3-(1,2,5-trimethyl-4-nitro-1H-indol-3-yl)propanoic acid (227)

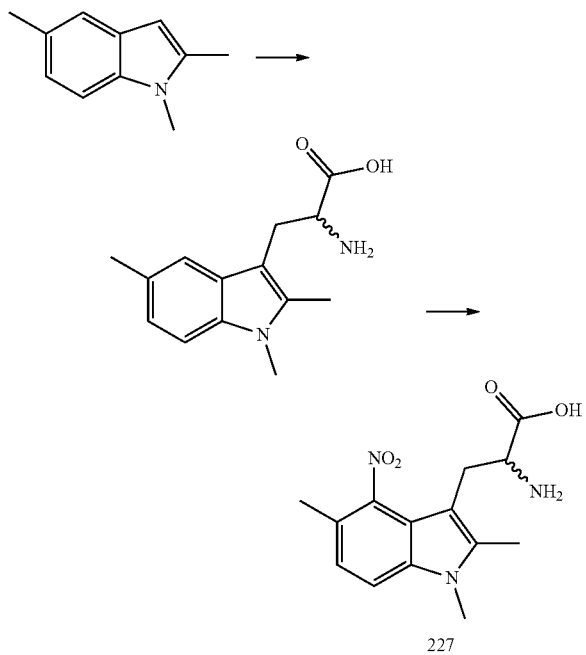

227

Example 227 can be prepared from 1,2,5-trimethyl-1H-indole as shown above and in a similar manner as described in Examples 1-7.

Example 228: Preparation of 2-amino-3-(1,2,6-trimethyl-4-nitro-1H-indol-3-yl)propanoic acid (228)

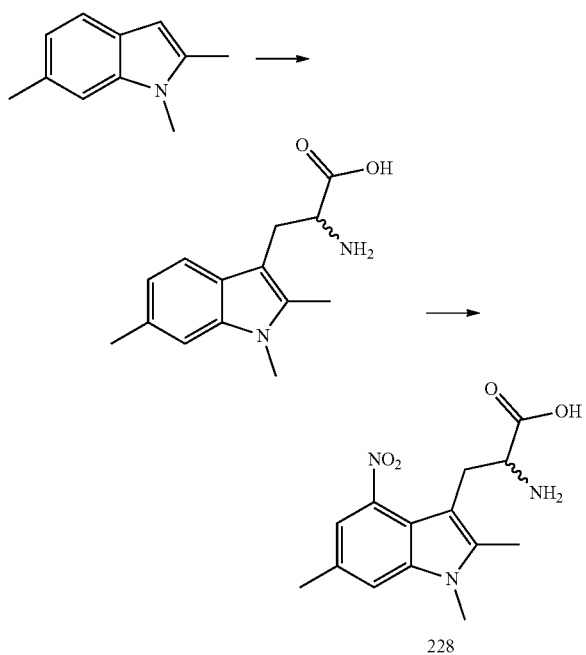

228

Example 228 can be prepared from 1,2,6-trimethyl-1H-indole as shown above and in a similar manner as described in Examples 1-7.

Example 229: Preparation of 2-amino-3-(1,2,7-trimethyl-4-nitro-1H-indol-3-yl)propanoic acid (229)

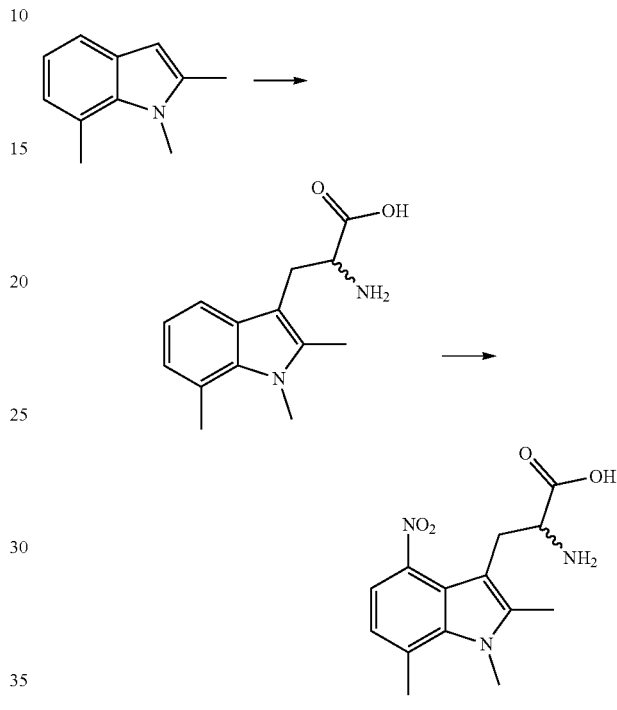

229

Example 229 can be prepared from 1,2,7-trimethyl-1H-indole as shown above and in a similar manner as described in Examples 1-7.

Example 230: Preparation of 2-amino-3-(1,2,4-trimethyl-7-nitro-1H-indol-3-yl)propanoic acid (230)

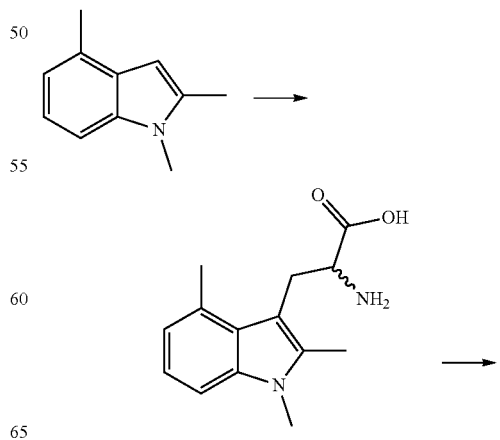

-continued

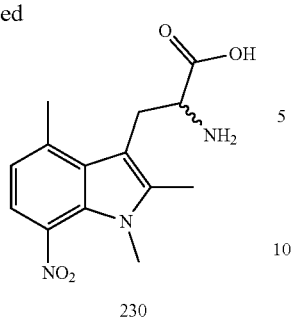

230

Example 230 can be prepared from 1,2,4-trimethyl-1H-indole as shown above and in a similar manner as described in Examples 1-7.

Example 231: Preparation of 2-amino-3-(6-fluoro-1,2-dimethyl-4-nitro-1H-indol-3-yl)propanoic acid (231)

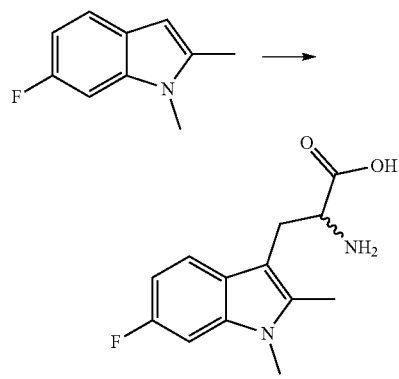

231

Example 231 can be prepared from 6-fluoro-1,2-dimethyl-1H-indole as shown above and in a similar manner as described in Examples 1-7.

Example 232: Preparation of 2-amino-3-(7-fluoro-1,2-dimethyl-4-nitro-1H-indol-3-yl)propanoic acid (232)

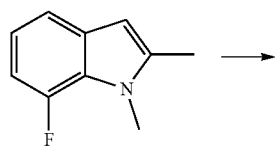

-continued

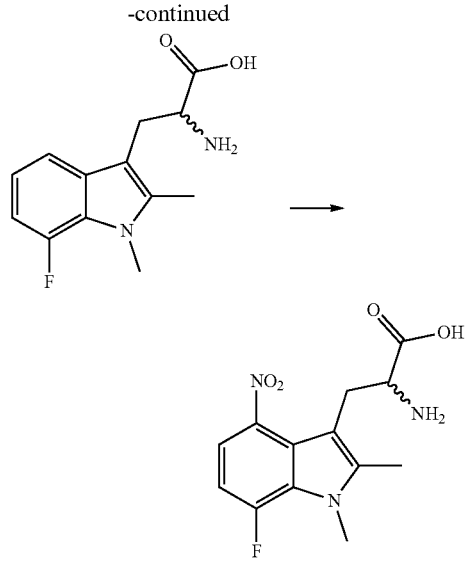

232

Example 232 can be prepared from 7-fluoro-1,2-dimethyl-indole as shown above and in a similar manner as described in Examples 1-7.

Example 233: Preparation of 2-amino-3-(4-fluoro-1,2-dimethyl-7-nitro-1H-indol-3-yl)propanoic acid (233)

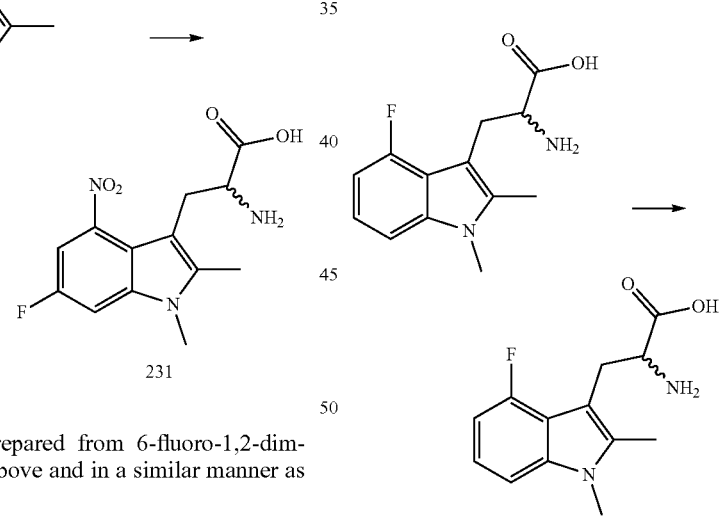

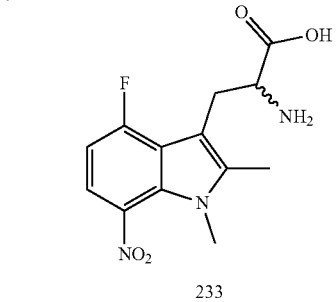

233

Example 233 can be prepared from 4-fluoro-1,2-dimethyl-indole as shown above and in a similar manner as described in Examples 1-7.

Example 234: Preparation of 2-amino-3-(5-chloro-1,2-dimethyl-4-nitro-1H-indol-3-yl)propanoic acid (234)

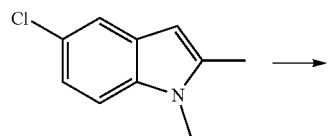

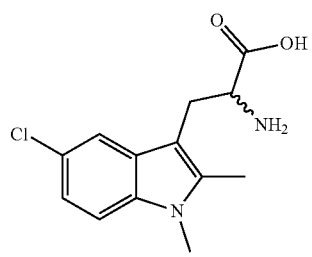

Example 234 can be prepared from 5-chloro-1,2-dimethyl-indole as shown above and in a similar manner as described in Examples 1-7.

Example 235: Preparation of 2-amino-3-(6-chloro-1,2-dimethyl-4-nitro-1H-indol-3-yl)propanoic acid (235)

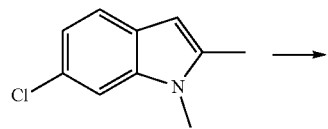

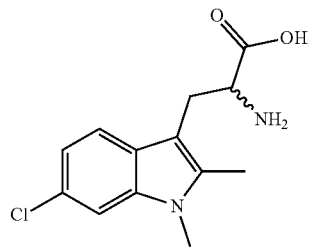

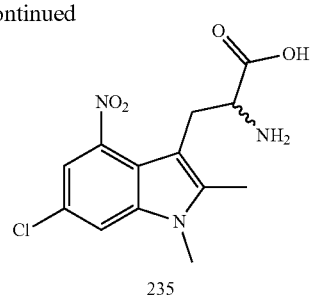

Example 235 can be prepared from 6-chloro-1,2-dimethyl-indole as shown above and in a similar manner as described in Examples 1-7.

Example 236: Preparation of 2-amino-3-(7-chloro-1,2-dimethyl-4-nitro-1H-indol-3-yl)propanoic acid (236)

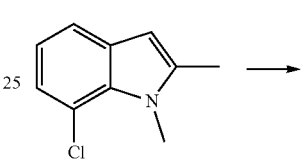

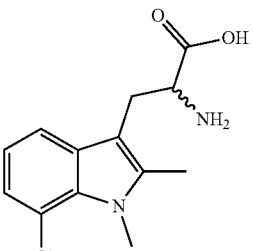

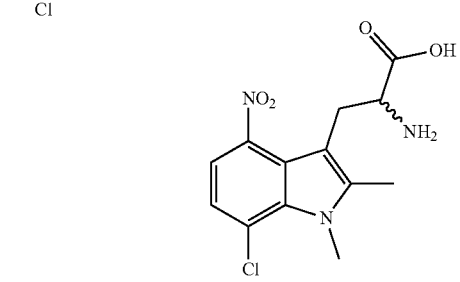

Example 236 can be prepared from 7-chloro-1,2-dimethyl-indole as shown above and in a similar manner as described in Examples 1-7.

Example 237: Preparation of 2-amino-3-(4-chloro-1,2-dimethyl-7-nitro-1H-indol-3-yl)propanoic acid (237)

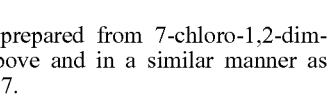

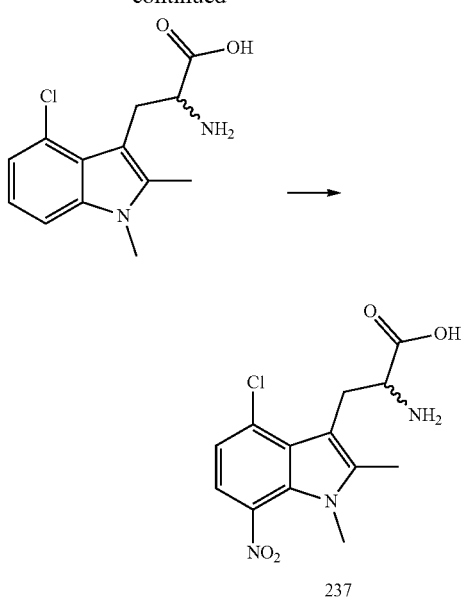

237

Example 237 can be prepared from 4-chloro-1,2-dimethyl-indole as shown above and in a similar manner as described in Examples 1-7.

Example 238: Preparation of 2-amino-3-(5-bromo-1,2-dimethyl-4-nitro-1H-indol-3-yl)propanoic acid (238)

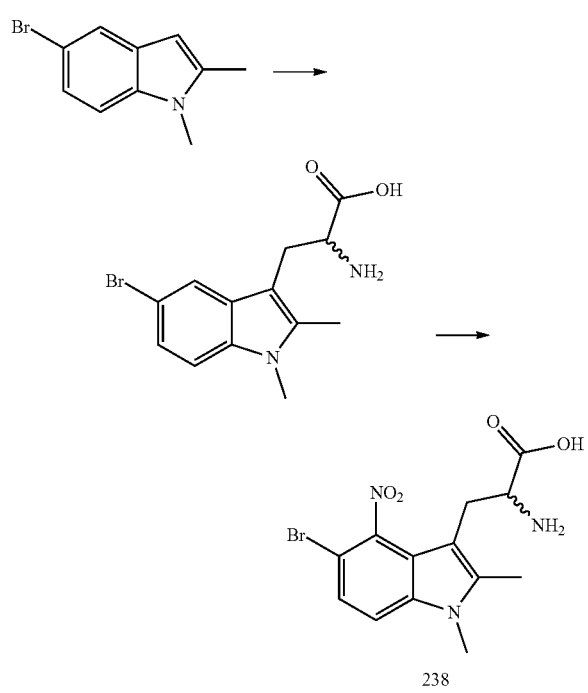

238

Example 238 can be prepared from 5-bromo-1,2-dimethyl-indole as shown above and in a similar manner as described in Examples 1-7.

Example 239: Preparation of 2-amino-3-(6-bromo-1,2-dimethyl-4-nitro-1H-indol-3-yl)propanoic acid (239)

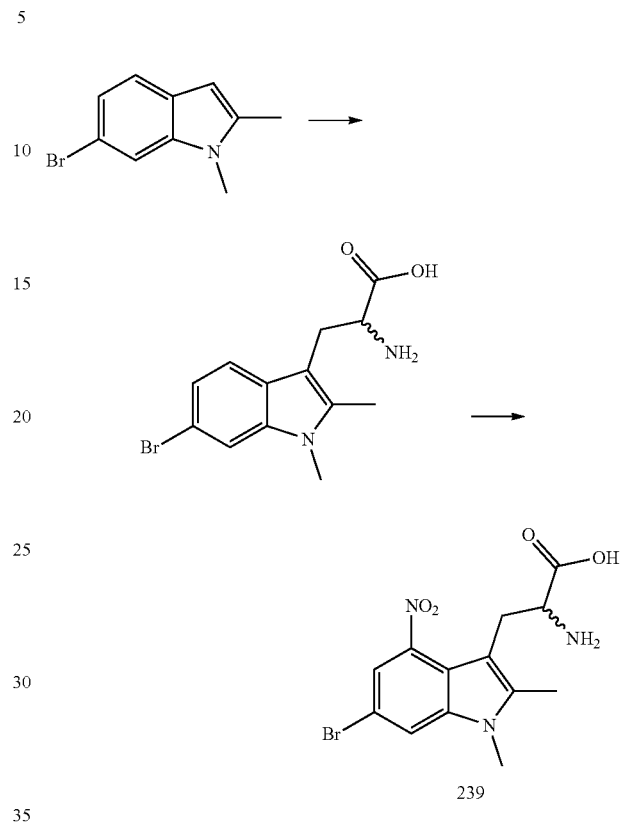

239

Example 239 can be prepared from 6-bromo-1,2-dimethyl-indole as shown above and in a similar manner as described in Examples 1-7.

Example 240: Preparation of 2-amino-3-(7-bromo-1,2-dimethyl-4-nitro-1H-indol-3-yl)propanoic acid (240)

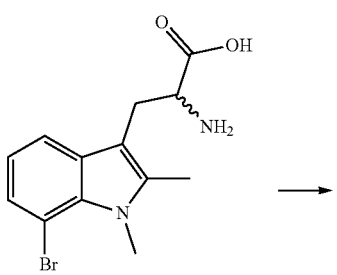

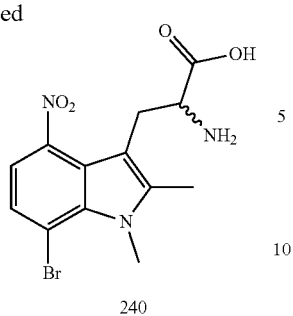

240

Example 240 can be prepared from 7-bromo-1,2-dimethyl-indole as shown above and in a similar manner as described in Examples 1-7.

Example 241: Preparation of 2-amino-3-(4-bromo-1,2-dimethyl-7-nitro-1H-indol-3-yl)propanoic acid (241)

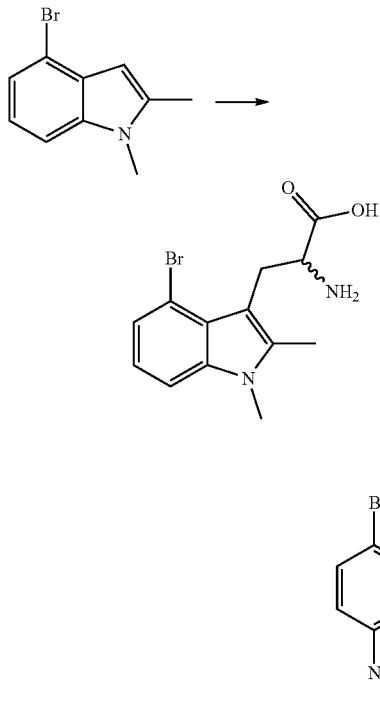

241

Example 241 can be prepared from 4-bromo-1,2-dimethyl-indole as shown above and in a similar manner as described in Examples 1-7.

Example 242: Preparation of 2-amino-3-(5-methoxy-1,2-dimethyl-4-nitro-1H-indol-3-yl)propanoic acid (242)

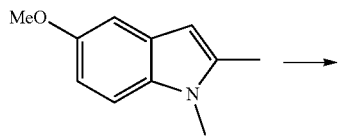

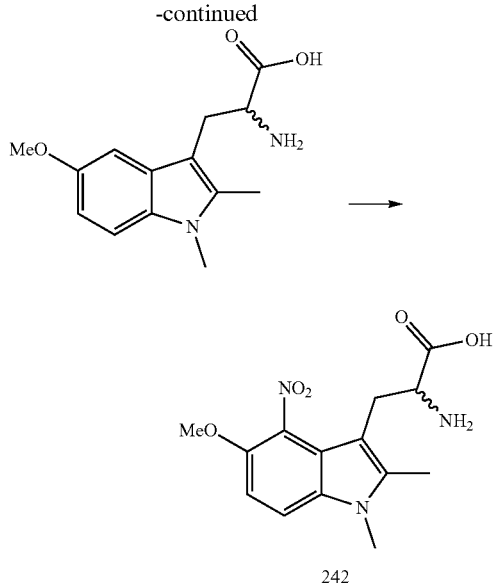

242

Example 242 can be prepared from 5-methoxy-1,2-dimethyl-indole as shown above and in a similar manner as described in Examples 1-7.

Example 243: Preparation of 2-amino-3-(6-methoxy-1,2-dimethyl-4-nitro-1H-indol-3-yl)propanoic acid (243)

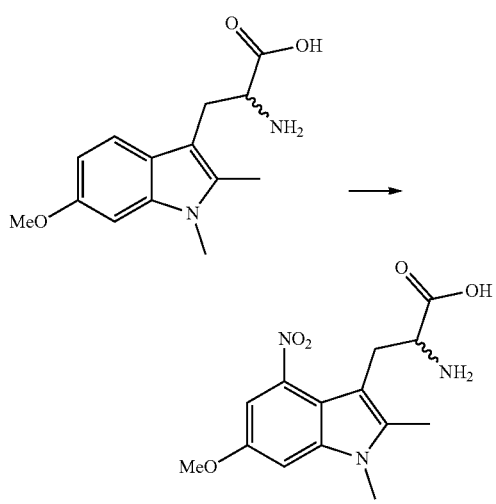

243

Example 243 can be prepared from 6-methoxy-1,2-dimethyl-indole as shown above and in a similar manner as described in Examples 1-7.

Example 244: Preparation of 2-amino-3-(7-methoxy-1,2-dimethyl-4-nitro-1H-indol-3-yl)propanoic acid (244)

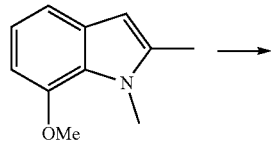

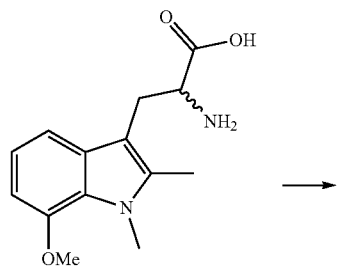

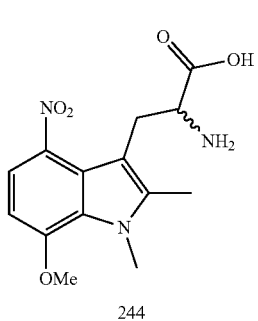

244

Example 244 can be prepared from 7-methoxy-1,2-dimethyl-indole as shown above and in a similar manner as described in Examples 1-7.

Example 245: Preparation of 2-amino-3-(4-methoxy-1,2-dimethyl-7-nitro-1H-indol-3-yl)propanoic acid (245)

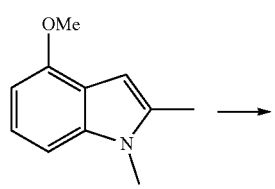

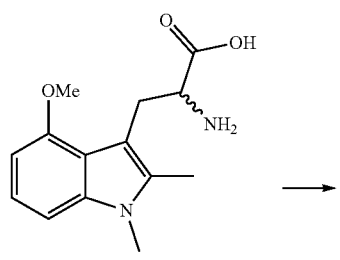

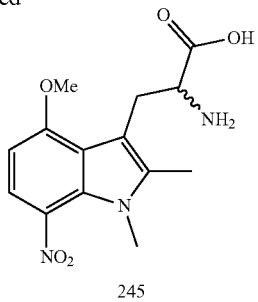

245

Example 245 can be prepared from 4-methoxy-1,2-dimethyl-indole as shown above and in a similar manner as described in Examples 1-7.

Example 246: Preparation of 2-amino-3-(5-amino-1,2-dimethyl-4-nitro-1H-indol-3-yl)propanoic acid (246)

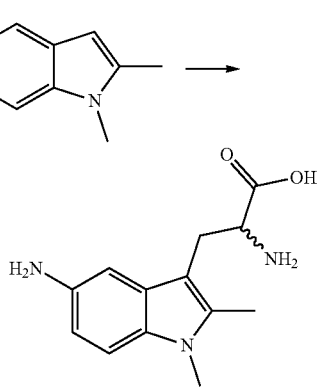

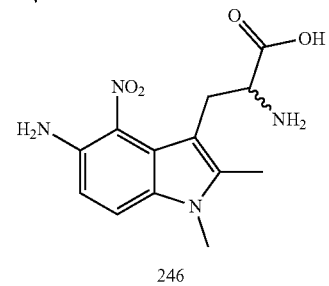

246

Example 246 can be prepared from 5-amino-1,2-dimethyl-indole as shown above and in a similar manner as described in Examples 1-7.

Example 247: Preparation of 2-amino-3-(6-amino-1,2-dimethyl-4-nitro-1H-indol-3-yl)propanoic acid (247)

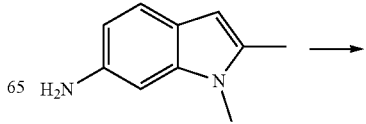

219
-continued

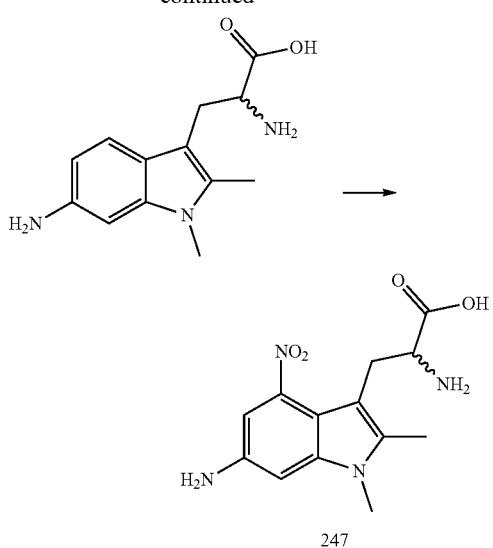

247

Example 247 can be prepared from 6-amino-1,2-dimethyl-indole as shown above and in a similar manner as described in Examples 1-7.

Example 248: Preparation of 2-amino-3-(7-amino-1,2-dimethyl-4-nitro-1H-indol-3-yl)propanoic acid (248)

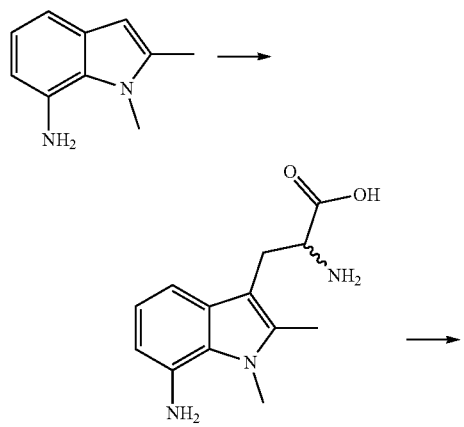

248

Example 248 can be prepared from 7-amino-1,2-dimethyl-indole as shown above and in a similar manner as described in Examples 1-7.

220

Example 249: Preparation of 2-amino-3-(4-amino-1,2-dimethyl-7-nitro-1H-indol-3-yl)propanoic acid (249)

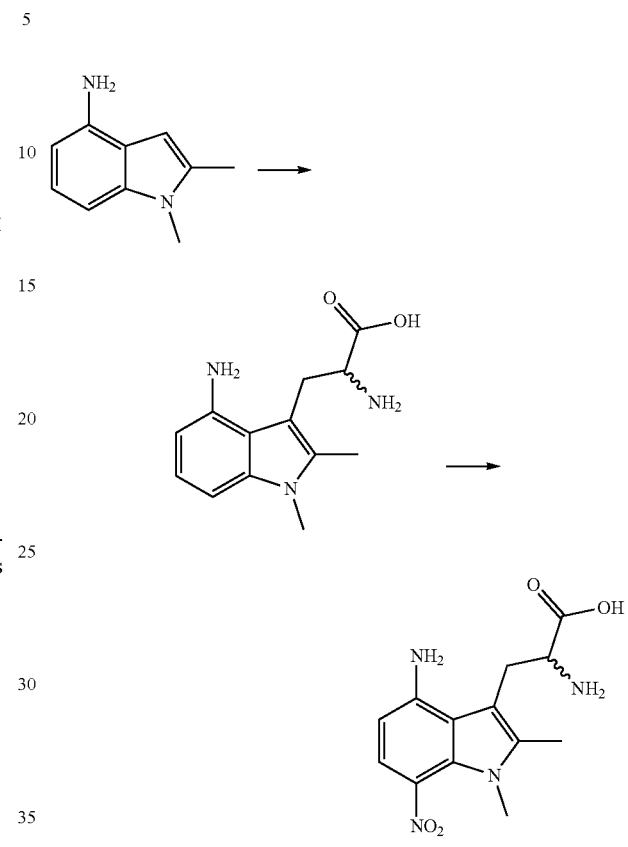

249

Example 249 can be prepared from 4-amino-1,2-dimethyl-indole as shown above and in a similar manner as described in Examples 1-7.

Example 250: Preparation of 2-amino-3-(5-hydroxy-1,2-dimethyl-4-nitro-1H-indol-3-yl)propanoic acid (250)

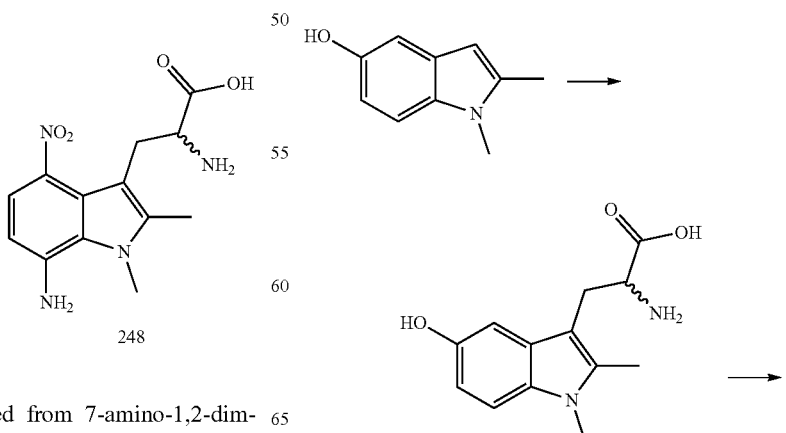

-continued

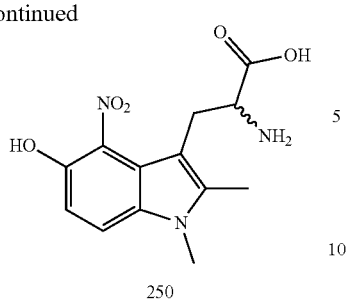
250

Example 250 can be prepared from 5-hydroxy-1,2-dimethyl-indole as shown above and in a similar manner as described in Examples 1-7.

Example 251: Preparation of 2-amino-3-(6-hydroxy-1,2-dimethyl-4-nitro-1H-indol-3-yl)propanoic acid (251)

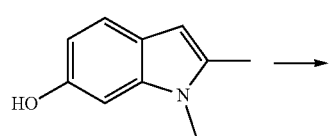

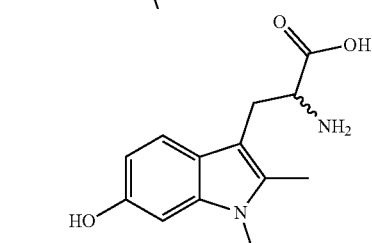

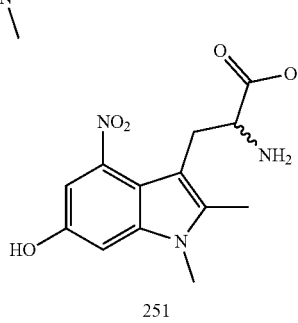
251

Example 251 can be prepared from 6-hydroxy-1,2-dimethyl-indole as shown above and in a similar manner as described in Examples 1-7.

Example 252: Preparation of 2-amino-3-(7-hydroxy-1,2-dimethyl-4-nitro-1H-indol-3-yl)propanoic acid (252)

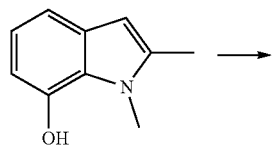

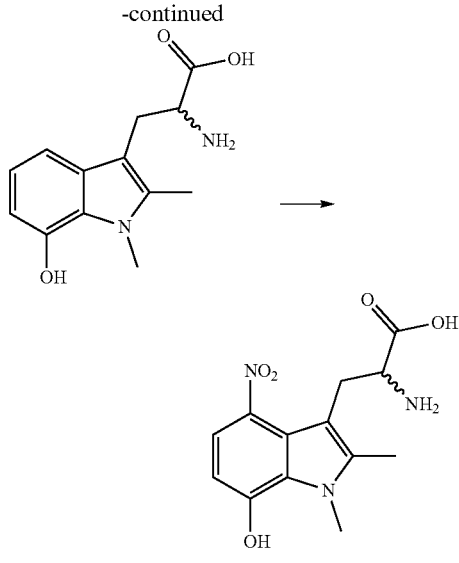
252

Example 252 can be prepared from 7-hydroxy-1,2-dimethyl-indole as shown above and in a similar manner as described in Examples 1-7.

Example 253: Preparation of 2-amino-3-(4-hydroxy-1,2-dimethyl-7-nitro-1H-indol-3-yl)propanoic acid (253)

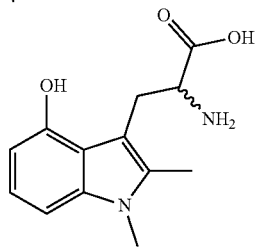

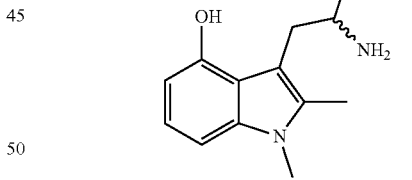

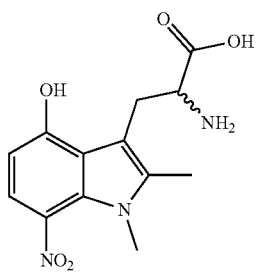
253

Example 253 can be prepared from 4-hydroxy-1,2-dimethyl-indole as shown above and in a similar manner as described in Examples 1-7.

Example 254: Preparation of 2-amino-3-(1,2-dimethyl-4-nitro-5-phenyl-1H-indol-3-yl)propanoic acid (254)

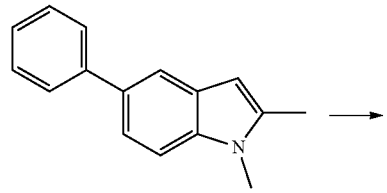

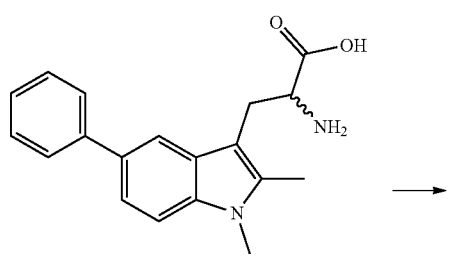

254

Example 254 can be prepared from 5-phenyl-1,2-dimethyl-indole as shown above and in a similar manner as described in Examples 1-7.

Example 255: Preparation of 2-amino-3-(1,2-dimethyl-4-nitro-6-phenyl-1H-indol-3-yl)propanoic acid (255)

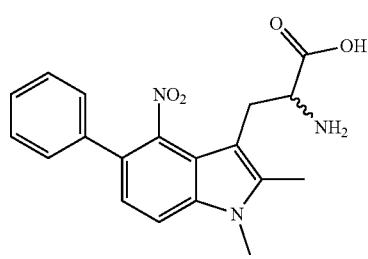

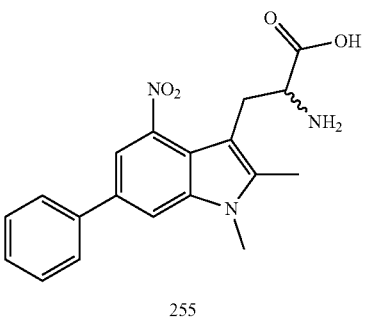

255

Example 255 can be prepared from 6-phenyl-1,2-dimethyl-indole as shown above and in a similar manner as described in Examples 1-7.

Example 256: Preparation of 2-amino-3-(1,2-dimethyl-4-nitro-7-phenyl-1H-indol-3-yl)propanoic acid (256)

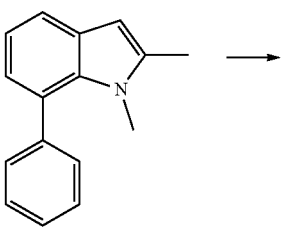

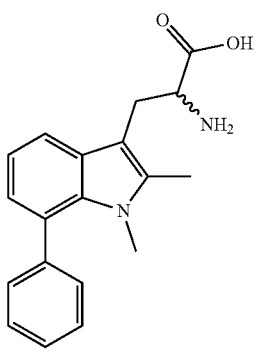

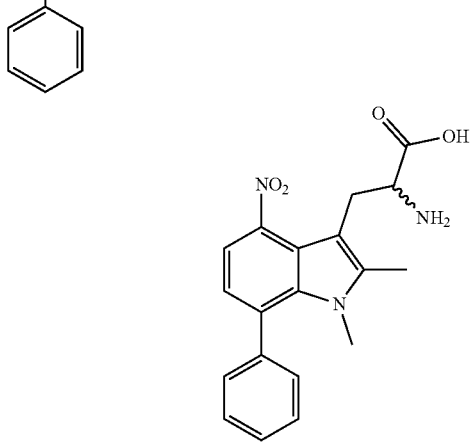

256

Example 256 can be prepared from 7-phenyl-1,2-dimethyl-indole as shown above and in a similar manner as described in Examples 1-7.

Example 257: Preparation of 2-amino-3-(1,2-dimethyl-7-nitro-4-phenyl-1H-indol-3-yl)propanoic acid (257)

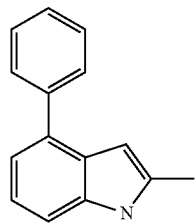

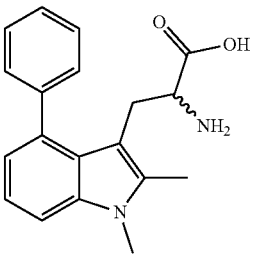

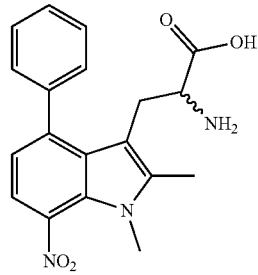

257

Example 257 can be prepared from 4-phenyl-1,2-dimethyl-indole as shown above and in a similar manner as described in Examples 1-7.

Example 258: Preparation of 2-amino-3-(5-cyclopropyl-1,2-dimethyl-4-nitro-1H-indol-3-yl)propanoic acid (258)

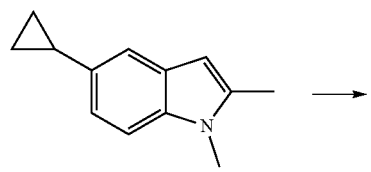

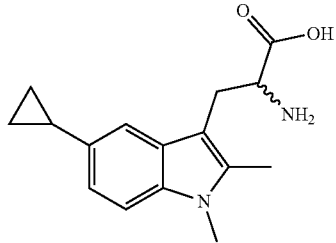

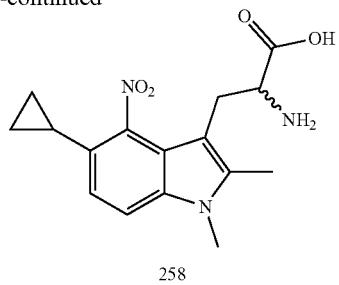

258

Example 258 can be prepared from 5-cyclopropyl-1,2-dimethyl-indole as shown above and in a similar manner as described in Examples 1-7.

Example 259: Preparation of 2-amino-3-(6-cyclopropyl-1,2-dimethyl-4-nitro-1H-indol-3-yl)propanoic acid (259)

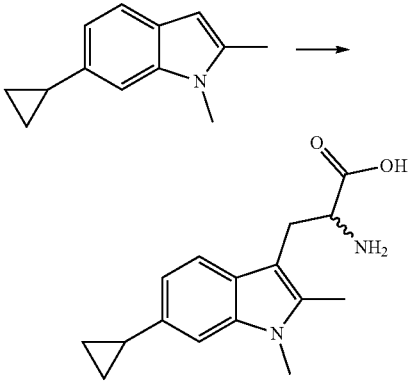

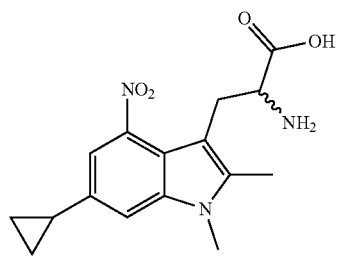

259

Example 259 can be prepared from 6-cyclopropyl-1,2-dimethyl-indole as shown above and in a similar manner as described in Examples 1-7.

Example 260: Preparation of 2-amino-3-(7-cyclopropyl-1,2-dimethyl-4-nitro-1H-indol-3-yl)propanoic acid (260)

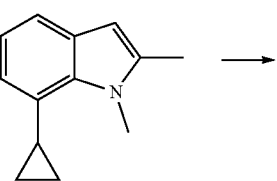

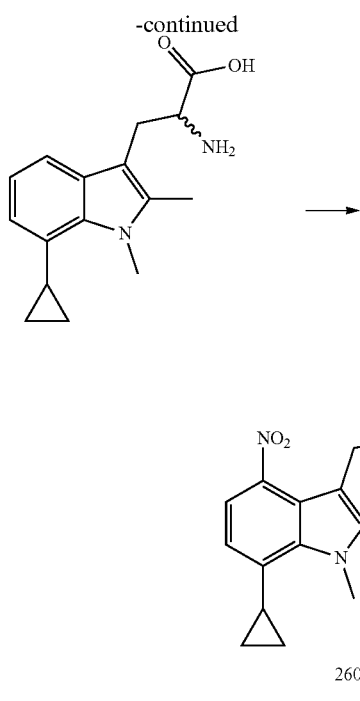

260

Example 260 can be prepared from 7-cyclopropyl-1,2-dimethyl-indole as shown above and in a similar manner as described in Examples 1-7.

Example 261: Preparation of 2-amino-3-(4-cyclopropyl-1,2-dimethyl-7-nitro-1H-indol-3-yl)propanoic acid (261)

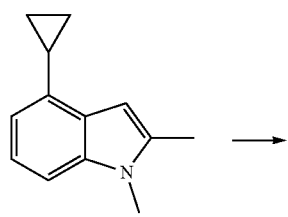

261

Example 261 can be prepared from 4-cyclopropyl-1,2-dimethyl-indole as shown above and in a similar manner as described in Examples 1-7.

Example 262: Preparation of 2-amino-3-(1,2-dimethyl-4-nitro-5-vinyl-1H-indol-3-yl)propanoic acid (262)

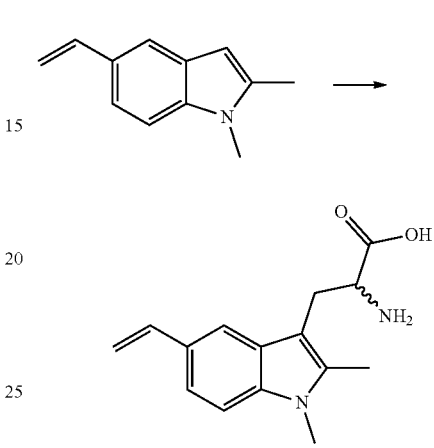

262

Example 262 can be prepared from 5-vinyl-1,2-dimethyl-indole as shown above and in a similar manner as described in Examples 1-7.

Example 263: Preparation of 2-amino-3-(1,2-dimethyl-4-nitro-6-vinyl-1H-indol-3-yl)propanoic acid (263)

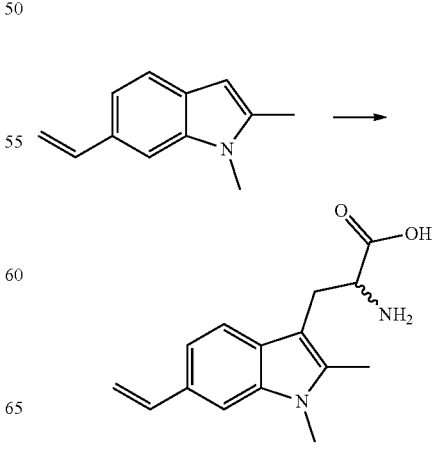

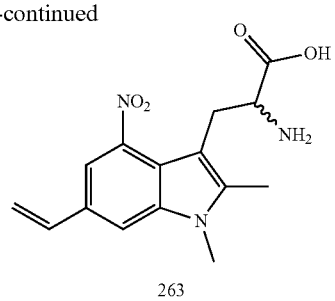

263

Example 263 can be prepared from 6-vinyl-1,2-dimethyl-indole as shown above and in a similar manner as described in Examples 1-7.

Example 264: Preparation of 2-amino-3-(1,2-dimethyl-4-nitro-7-vinyl-1H-indol-3-yl)propanoic acid (264)

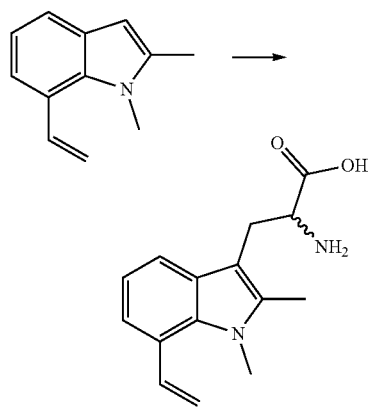

264

Example 264 can be prepared from 7-vinyl-1,2-dimethyl-indole as shown above and in a similar manner as described in Examples 1-7.

Example 265: Preparation of 2-amino-3-(1,2-dimethyl-7-nitro-4-vinyl-1H-indol-3-yl)propanoic acid (265)

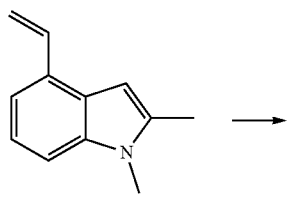

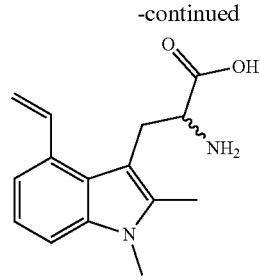

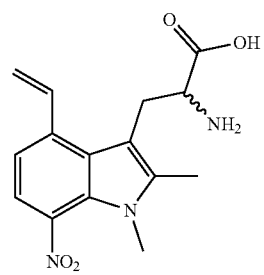

265

Example 265 can be prepared from 4-vinyl-1,2-dimethyl-indole as shown above and in a similar manner as described in Examples 1-7.

Example 266: Preparation of 2-amino-3-(5-ethynyl-1,2-dimethyl-4-nitro-1H-indol-3-yl)propanoic acid (266)

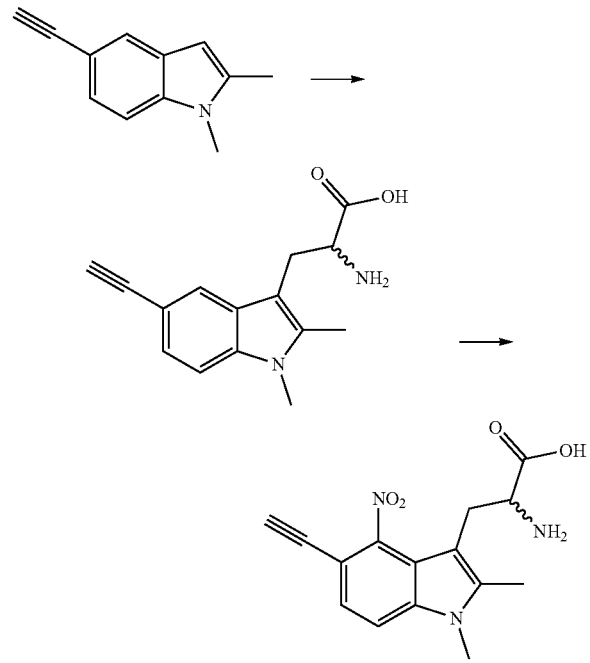

266

Example 266 can be prepared from 5-ethynyl-1,2-dimethyl-indole as shown above and in a similar manner as described in Examples 1-7.

Example 267: Preparation of 2-amino-3-(6-ethynyl-1,2-dimethyl-4-nitro-1H-indol-3-yl)propanoic acid (267)

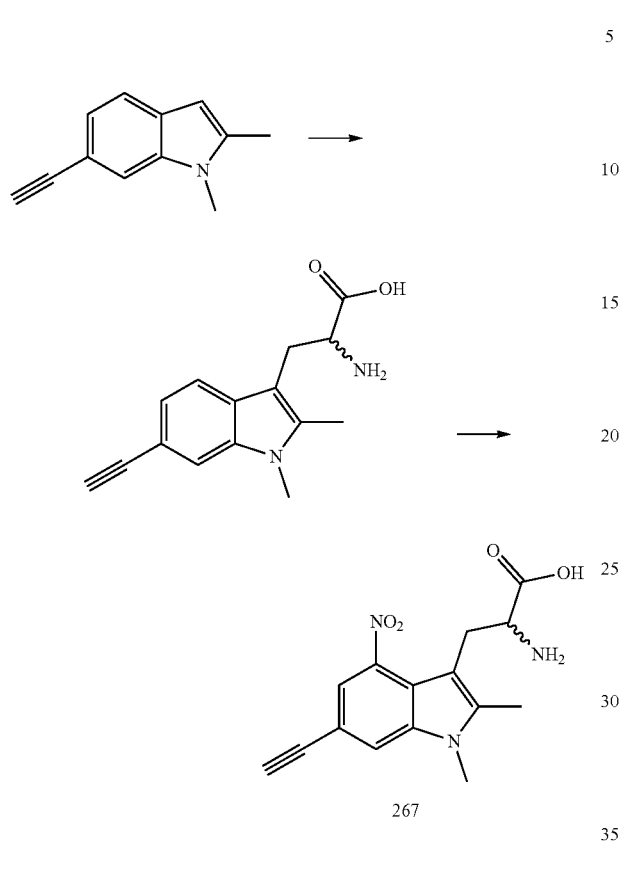

267

Example 267 can be prepared from 6-ethynyl-1,2-dimethyl-indole as shown above and in a similar manner as described in Examples 1-7.

Example 268: Preparation of 2-amino-3-(7-ethynyl-1,2-dimethyl-4-nitro-1H-indol-3-yl)propanoic acid (268)

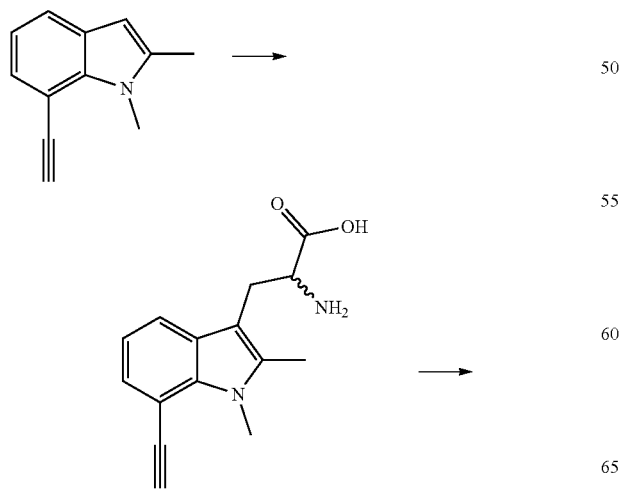

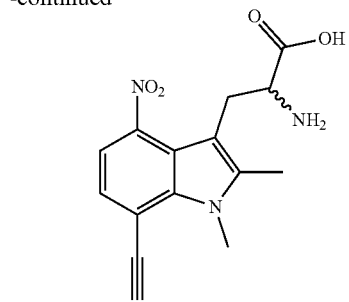

268

Example 268 can be prepared from 7-ethynyl-1,2-dimethyl-indole as shown above and in a similar manner as described in Examples 1-7.

Example 269: Preparation of 2-amino-3-(4-ethynyl-1,2-dimethyl-7-nitro-1H-indol-3-yl)propanoic acid (269)

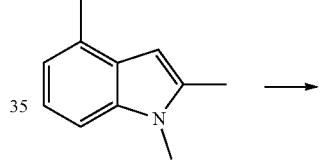

269

Example 269 can be prepared from 4-ethynyl-1,2-dimethyl-indole as shown above and in a similar manner as described in Examples 1-7.

Example 270: Preparation of 2-amino-3-(1,2-dimethyl-5-morpholino-4-nitro-1H-indol-3-yl)propanoic acid (270)

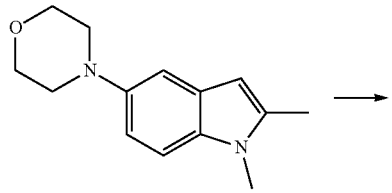

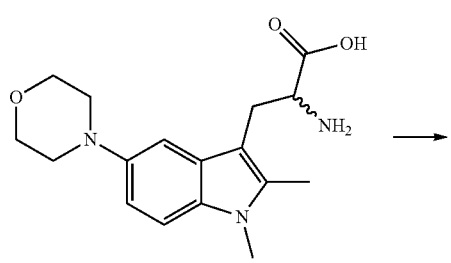

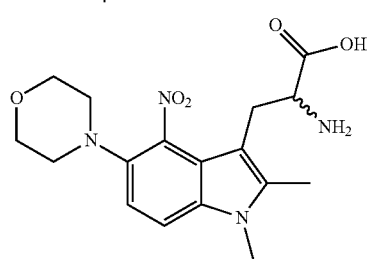

270

Example 270 can be prepared from 5-morpholino-1,2-dimethyl-indole as shown above and in a similar manner as described in Examples 1-7.

Example 271: Preparation of 2-amino-3-(1,2-dimethyl-6-morpholino-4-nitro-1H-indol-3-yl)propanoic acid (271)

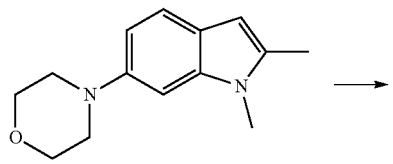

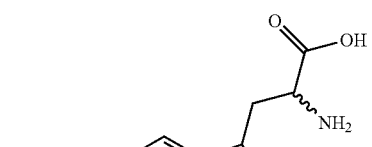

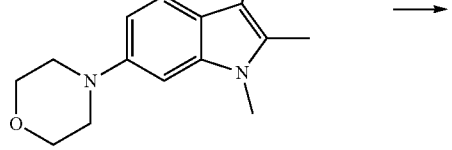

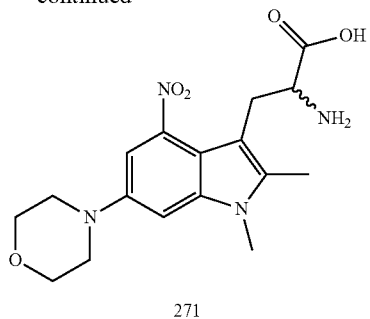

271

Example 271 can be prepared from 6-morpholino-1,2-dimethyl-indole as shown above and in a similar manner as described in Examples 1-7.

Example 272: Preparation of 2-amino-3-(1,2-dimethyl-7-morpholino-4-nitro-1H-indol-3-yl)propanoic acid (272)

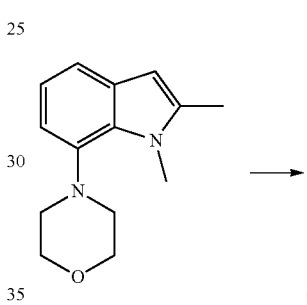

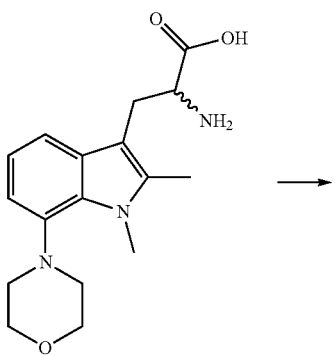

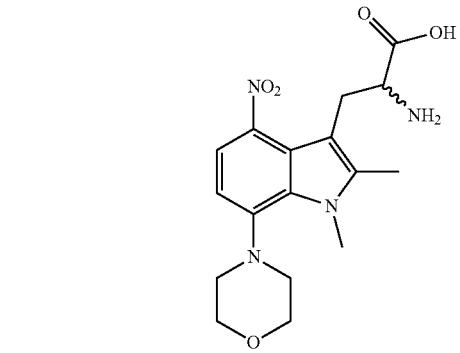

272

Example 272 can be prepared from 7-morpholino-1,2-dimethyl-indole as shown above and in a similar manner as described in Examples 1-7.

Example 273: Preparation of 2-amino-3-(1,2-dimethyl-4-morpholino-7-nitro-1H-indol-3-yl)propanoic acid (273)

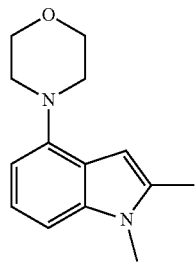
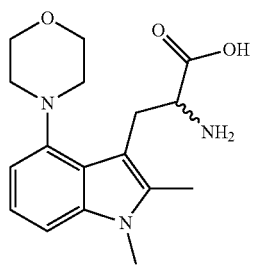
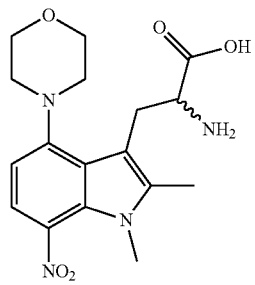

273

Example 273 can be prepared from 4-morpholino-1,2-dimethyl-indole as shown above and in a similar manner as described in Examples 1-7.

Example 274: Preparation of 2-amino-3-(1,2-dimethyl-5-(methylthio)-4-nitro-1H-indol-3-yl)propanoic acid (274)

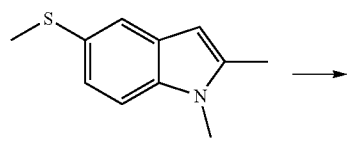
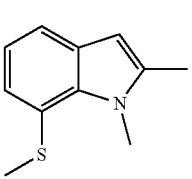

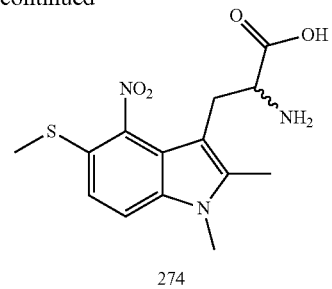

274

Example 274 can be prepared from 5-(methylthio)-1,2-dimethyl-indole as shown above and in a similar manner as described in Examples 1-7.

Example 275: Preparation of 2-amino-3-(1,2-dimethyl-6-(methylthio)-4-nitro-1H-indol-3-yl)propanoic acid (275)

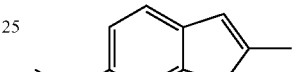
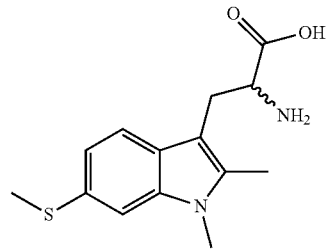
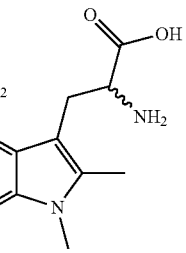

275

Example 275 can be prepared from 6-(methylthio)-1,2-dimethyl-indole as shown above and in a similar manner as described in Examples 1-7.

Example 276: Preparation of 2-amino-3-(1,2-dimethyl-7-(methylthio)-4-nitro-1H-indol-3-yl)propanoic acid (276)

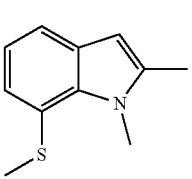

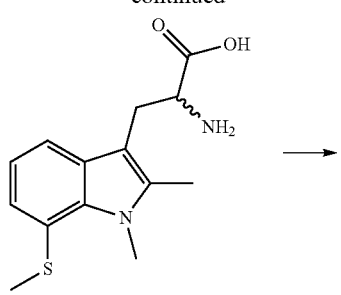

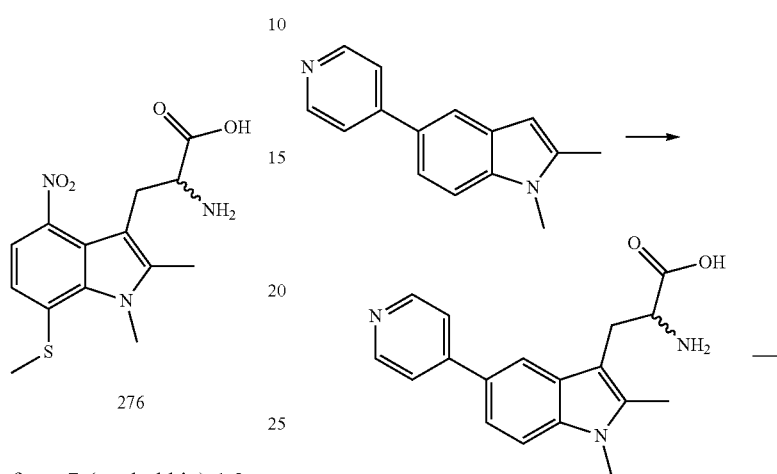

Example 277 can be prepared from 4-(methylthio)-1,2-dimethyl-indole as shown above and in a similar manner as described in Examples 1-7.

Example 278: Preparation of 2-amino-3-(1,2-dimethyl-4-nitro-5-(pyridin-4-yl)-1H-indol-3-yl)propanoic acid (278)

Example 276 can be prepared from 7-(methylthio)-1,2-dimethyl-indole as shown above and in a similar manner as described in Examples 1-7.

Example 277: Preparation of 2-amino-3-(1,2-dimethyl-4-(methylthio)-7-nitro-1H-indol-3-yl)propanoic acid (277)

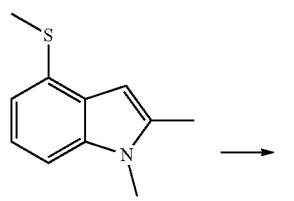

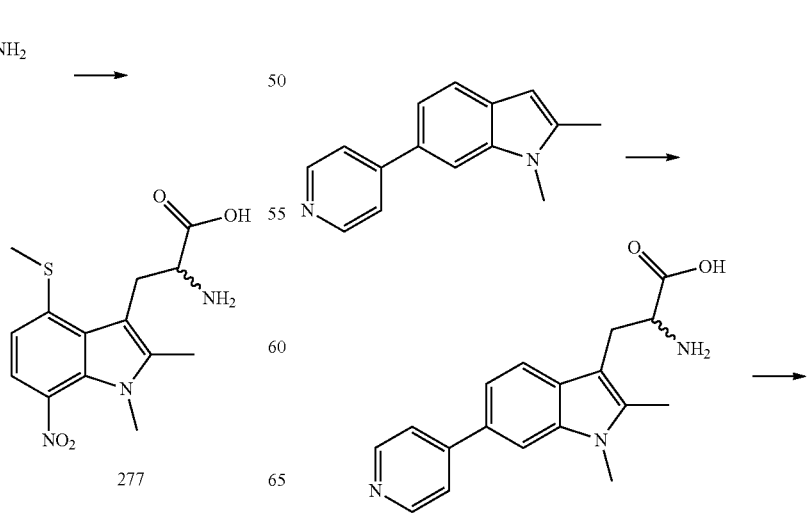

Example 278 can be prepared from 5-(pyridin-4-yl)-1,2-dimethyl-indole as shown above and in a similar manner as described in Examples 1-7.

Example 279: Preparation of 2-amino-3-(1,2-dimethyl-4-nitro-6-(pyridin-4-yl)-1H-indol-3-yl)propanoic acid (279)

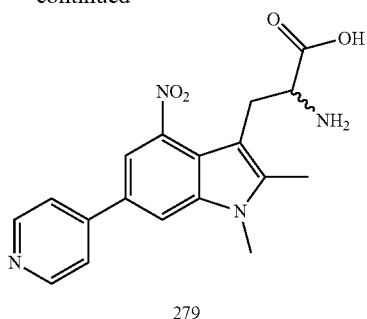

Example 279 can be prepared from 6-(pyridin-4-yl)-1,2-dimethyl-indole as shown above and in a similar manner as described in Examples 1-7.

Example 280: Preparation of 2-amino-3-(1,2-dimethyl-4-nitro-7-(pyridin-4-yl)-1H-indol-3-yl)propanoic acid (280)

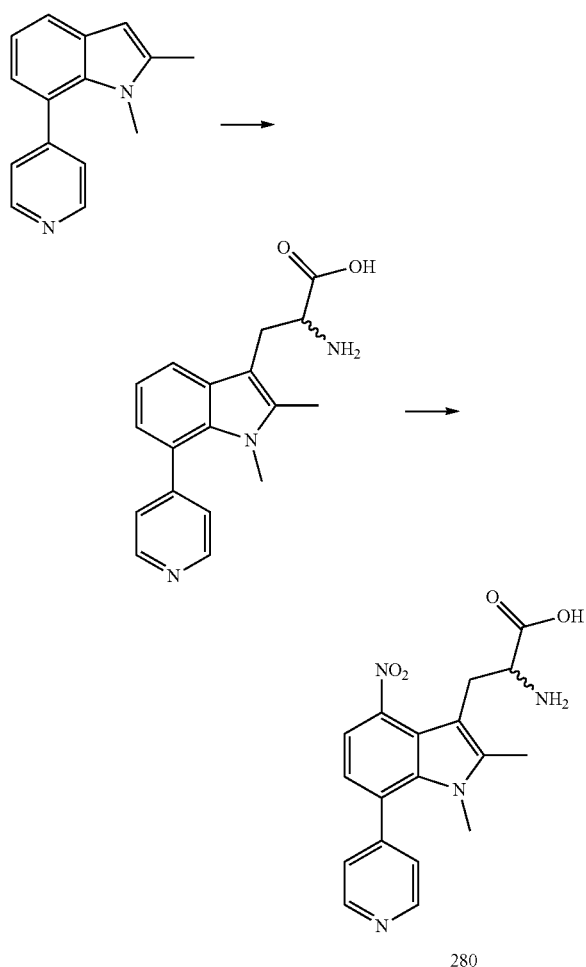

Example 280 can be prepared from 7-(pyridin-4-yl)-1,2-dimethyl-indole as shown above and in a similar manner as described in Examples 1-7.

Example 281: Preparation of 2-amino-3-(1,2-dimethyl-7-nitro-4-(pyridin-4-yl)-1H-indol-3-yl)propanoic acid (281)

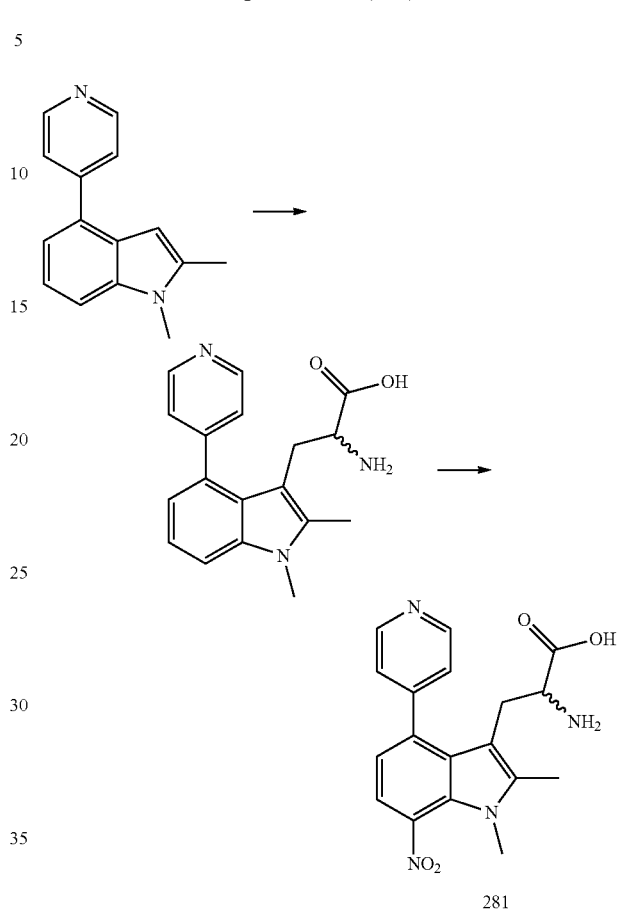

Example 281 can be prepared from 4-(pyridin-4-yl)-1,2-dimethyl-indole as shown above and in a similar manner as described in Examples 1-7.

REFERENCE

Aneja R, Vangapandu S N, Lopus M, Chandra R, Panda D, Joshi H C (2006). Development of a novel nitro-derivative of noscapine for the potential treatment of drug-resistant ovarian cancer and t-cell lymphoma. Mol Pharmacol 69: 1801-1809

Barry S M, Kers J A, Johnson E G, Song L, Aston P R, Patel B, Krasnoff S B, Crane B R, Gibson D M, Loria R, Challis G L (2012). Cytochrome p450-catalyzed l-tryptophan nitration in thaxtomin phytotoxin biosynthesis. Nat Chem Biol 8: 814-816

Bell S G, Chen X, Xu F, Rao Z, Wong L L (2003). Engineering substrate recognition in catalysis by cytochrome p450cam. Biochem Soc Trans 31: 558-562

Boddupalli S S, Pramanik B C, Slaughter C A, Estabrook R W, Peterson J A (1992). Fatty-acid monooxygenation by p450bm-3—product identification and proposed mechanisms for the sequential hydroxylation reactions. Arch Biochem Biophys 292: 20-28

Budde C L, Beyer A, Munir I Z, Dordick J S, Khmelnitsky Y L (2001). Enzymatic nitration of phenols. J Mol Catal B: Enzy 15: 55-64

Carlson J C, Li S, Gunatilleke S S, Anzai Y, Burr D A, Podust L M, Sherman D H (2011). Tirandamycin biosynthesis is mediated by co-dependent oxidative enzymes. Nat Chem 3: 628-633

Carter G T, Nietsche J A, Goodman J J, Torrey M J, Dunne T S, Siegel M M, Borders D B (1989). Direct biochemical nitration in the biosynthesis of dioxapyrrolomycin—a unique mechanism for the introduction of nitro-groups in microbial products. J Chem Soc-Chem Comm: 1271-1273

Casella L, Monzani E, Roncone R, Nicolis S, Sala A, De Riso A (2002). Formation of reactive nitrogen species at biologic heme centers: A potential mechanism of nitric oxide-dependent toxicity. Environ Health Perspect 110 Suppl 5: 709-711

Caswell J M, O'Neill M, Taylor S J C, Moody T S (2013). Engineering and application of p450 monooxygenases in pharmaceutical and metabolite synthesis. Curr Opin Chem Biol 17: 271-275

Das J P, Sinha P, Roy S (2002). A nitro-hunsdiecker reaction: From unsaturated carboxylic acids to nitrostyrenes and nitroarenes. Org Lett 4: 3055-3058

De Mot R, Parret A H A (2002). A novel class of self-sufficient cytochrome p450 monooxygenases in prokaryotes. Trends Microbiol 10: 502-508

Ding Y, Seufert W H, Beck Z Q, Sherman D H (2008). Analysis of the cryptophycin p450 epoxidase reveals substrate tolerance and cooperativity. J Am Chem Soc 130: 5492-5498

Dodani S C, Cahn J K, Heinisch T, Brinkmann-Chen S, McIntosh J A, Arnold F H (2014). Structural, functional, and spectroscopic characterization of the substrate scope of the novel nitrating cytochrome p450 txte. Chembiochem 15: 2259-2267

Dodhia V R, Fantuzzi A, Gilardi G (2006). Engineering human cytochrome p450 enzymes into catalytically self-sufficient chimeras using molecular lego. J Biol Inorg Chem 11: 903-916

Fors B P, Buchwald S L (2009). Pd-catalyzed conversion of aryl chlorides, triflates, and nonaflates to nitroaromatics. J Am Chem Soc 131(36):12898-12899

Gillam E M J, Hayes M A (2013). The evolution of cytochrome p450 enzymes as biocatalysts in drug discovery and development. Curr Topics Med Chem 13: 2254-2280

Hannemann F, Bichet A, Ewen K M, Bernhardt R (2007). Cytochrome p450 systems—biological variations of electron transport chains. Biochim Biophys Acta 1770: 330-344

Higuchi R, Krummel B, Saiki R K (1988). A general method of in vitro preparation and specific mutagenesis of DNA fragments: Study of protein and DNA interactions. Nucleic Acids Res 16: 7351-7367

Ilardi E A, Vitaku E, Njardarson J T (2014). Data-mining for sulfur and fluorine: An evaluation of pharmaceuticals to reveal opportunities for drug design and discovery. J Med Chem 57: 2832-2842

Ju K S, Parales R E (2010). Nitroaromatic compounds, from synthesis to biodegradation. Microbiol Mol Biol Rev 74: 250-272

Kersten R D, Dorrestein P C (2010). Metalloenzymes: Natural product nitrosation. Nat Chem Biol 6: 636-637

Kulkarni M, Chaudhari A (2007). Microbial remediation of nitro-aromatic compounds: An overview. J Environ Manage 85: 496-512

Lee J K, Simurdiak M, Zhao H M (2005). Reconstitution and characterization of aminopyrrolnitrin oxygenase, a rieske n-oxygenase that catalyzes unusual arylamine oxidation. J Biol Chem 280: 36719-36728

Li H Y, Poulos T L (1997). The structure of the cytochrome p450bm-3 haem domain complexed with the fatty acid substrate, palmitoleic acid. Nat Struct Biol 4: 140-146

Li S Y, Podust L M, Sherman D H (2007). Engineering and analysis of a self-sufficient biosynthetic cytochrome p450 pikc fused to the rhfred reductase domain. J Am Chem Soc Society 129: 12940-12941

Loida P J, Sligar S G (1993). Molecular recognition in cytochrome-p-450—mechanism for the control of uncoupling reactions. Biochemistry 32: 11530-11538

Loria R, Bignell D R, Moll S, Huguet-Tapia J C, Joshi M V, Johnson E G, Seipke R F, Gibson D M (2008). Thaxtomin biosynthesis: The path to plant pathogenicity in the genus streptomyces. Antonie Van Leeuwenhoek 94: 3-10

Martino P D, Fursy R, Bret L, Sundararaju B, Phillips R S (2003). Indole can act as an extracellular signal to regulate biofilm formation of *Escherichia coli* and other indole-producing bacteria. Can J Microbiol 49: 443-449

McIntosh J A, Farwell C C, Arnold F H (2014). Expanding p450 catalytic reaction space through evolution and engineering. Curr Opin Chem Biol 19: 126-134

Narhi L O, Fulco A J (1986). Characterization of a catalytically self-sufficient 119,000-dalton cytochrome p-450 monooxygenase induced by barbiturates in *Bacillus megaterium*. J Biol Chem 261: 7160-7169

Noble M A, Miles C S, Chapman S K, Lysek D A, Mackay A C, Reid G A, Hanzlik R P, Munro A W (1999). Roles of key active-site residues in flavocytochrome p450 bm3. Biochem J 339: 371-379

Nodate M, Kubota M, Misawa N (2006). Functional expression system for cytochrome p450 genes using the reductase domain of self-sufficient p450rhf from rhodococcus sp ncimb 9784. Appl Microbiol Biotechnol 71: 455-462

Olah G A, Lin H C, Olah J A, Narang S C (1978). Aromatic-substitution 0.42. Electrophilic and free-radical nitration of benzene and toluene with various nitrating agents. Proc Natl Acad Sci USA 75: 1045-1049

Omura T, Sato R (1964). The carbon monoxide-binding pigment of liver microsomes. Ii. Solubilization, purification, and properties. J Biol Chem 239: 2379-2385

Padda R S, Wang C, Hughes J B, Kutty R, Bennett G N (2003). Mutagenicity of nitroaromatic degradation compounds. Environ Toxicol Chem 22: 2293-2297

Parry R, Nishino S, Spain J (2011). Naturally-occurring nitro compounds. Nat Prod Rep 28: 152-167

Roberts G A, Celik A, Hunter D J B, Ost T W B, White J H, Chapman S K, Turner N J, Flitsch S L (2003). A self-sufficient cytochrome p450 with a primary structural organization that includes a flavin domain and a [2fe-2s] redox center. J Biol Chem 278: 48914-48920

Robin A, Roberts G A, Kisch J, Sabbadin F, Grogan G, Bruce N, Turner N J, Flitsch S L (2009). Engineering and improvement of the efficiency of a chimeric [p450cam-rhfred reductase domain] enzyme. Chem Comm: 2478-2480

Rozen S, Carmeli M (2003). From azides to nitro compounds in a few seconds using hof.Ch3cn. J Am Chem Soc 125: 8118-8119

Rudolf J D, Poulter C D (2013). Tyrosine o-prenyltransferase sird catalyzes s-, c-, and n-prenylations on tyrosine and tryptophan derivatives. Acs Chem Biol 8: 2707-2714

Sabbadin F, Hyde R, Robin A, Hilgarth E M, Delenne M, Flitsch S, Turner N, Grogan G, Bruce N C (2010). Licred:

A versatile drop-in vector for rapid generation of redox-self-sufficient cytochrome p450s. Chembiochem 11: 987-994

Sakihama Y, Tamaki R, Shimoji H, Ichiba T, Fukushi Y, Tahara S, Yamasaki H (2003). Enzymatic nitration of phytophenolics: Evidence for peroxynitrite-independent nitration of plant secondary metabolites. FEBS Lett 553: 377-380

Savile C K, Janey J M, Mundorff E C, Moore J C, Tam S, Jarvis W R, Colbeck J C, Krebber A, Fleitz F J, Brands J, Devine P N, Huisman G W, Hughes G J (2010). Biocatalytic asymmetric synthesis of chiral amines from ketones applied to sitagliptin manufacture. Science 329: 305-309

Sawayama A M, Chen M M, Kulanthaivel P, Kuo M S, Hemmerle H, Arnold F H (2009). A panel of cytochrome p450 bm3 variants to produce drug metabolites and diversify lead compounds. Chemistry 15: 11723-11729

Sevrioukova I F, Li H Y, Zhang H, Peterson J A, Poulos T L (1999). Structure of a cytochrome p450-redox partner electron-transfer complex. Proc Natl Acad Sci U S 96: 1863-1868

Sherman D H, Li S, Yermalitskaya L V, Kim Y, Smith J A, Waterman M R, Podust L M (2006). The structural basis for substrate anchoring, active site selectivity, and product formation by p450 pikc from Streptomyces venezuelae. J Biol Chem 281: 26289-26297

Sherman D H, Li S Y, Yermalitskaya L V, Kim Y C, Smith J A, Waterman M R, Podust L M (2006). The structural basis for substrate anchoring, active site selectivity, and product formation by p450 pike from Streptomyces venezuelae. J Biol Chem 281: 26289-26297

Suyama M, Ohara O (2003). Domcut: Prediction of interdomain linker regions in amino acid sequences. Bioinformatics 19: 673-674

Tani K, Lukin K, Eaton P E (1997). Nitration of organolithiums and grignards with dinitrogen tetroxide: Success at melting interfaces. J Am Chem Soc 119: 1476-1477

Truan G, Komandla M R, Falck J R, Peterson J A (1999). P450bm-3: Absolute configuration of the primary metabolites of palmitic acid. Arch Biochem Biophys 366: 192-198

Urlacher V B, Girhard M (2012). Cytochrome p450 monooxygenases: An update on perspectives for synthetic application. Trends Biotechnol 30: 26-36

Walsh C T (2014). Biological matching of chemical reactivity: Pairing indole nucleophilicity with electrophilic isoprenoids. Acs Chem Biol 9: 2718-2728

Whitehouse C J, Bell S G, Wong L L (2012). P450(bm3) (cyp102a1): Connecting the dots. Chem Soc Rev 41: 1218-1260

Winkler R, Hertweck C (2007). Biosynthesis of nitro compounds. Chembiochem 8: 973-977

Winkler R, Richter M E, Knupfer U, Merten D, Hertweck C (2006). Regio- and chemoselective enzymatic n-oxygenation in vivo, in vitro, and in flow. Angew Chem Int Ed Engl 45: 8016-8018

Winkler R, Zocher G, Richter I, Friedrich T, Schulz G E, Hertweck C (2007). A binuclear manganese cluster that catalyzes radical-mediated n-oxygenation. Angew Chem Int Ed Engl 46: 8605-8608

Xue Y, Wilson D, Zhao L, Liu H, Sherman D H (1998). Hydroxylation of macrolactones yc-17 and narbomycin is mediated by the pikc-encoded cytochrome p450 in Streptomyces venezuelae. Chem Biol 5: 661-667

Yan G, Yang M (2013). Recent advances in the synthesis of aromatic nitro compounds. Org Biomol Chem 11: 2554-2566

Yang Y, Wong S E, Lightstone F C (2014). Understanding a substrate's product regioselectivity in a family of enzymes: A case study of acetaminophen binding in cytochrome p450s. PLoS One 9: e87058

Yu X, Xie X, Li S M (2011). Substrate promiscuity of secondary metabolite enzymes: Prenylation of hydroxynaphthalenes by fungal indole prenyltransferases. Appl Microbiol Biotechnol 92: 737-748

Zhang L, Liu Z H, Li H Q, Fang G C, Barry B D, Belay T A, Bi X H, Liu Q (2011). Copper-mediated chelation-assisted ortho nitration of (hetero)arenes. Org Lett 13: 6536-6539

Zhou L, Stewart G, Rideau E, Westwood N J, Smith T K (2013). A class of 5-nitro-2-furancarboxylamides with potent trypanocidal activity against Trypanosoma brucei in vitro. J Med Chem 56: 796-806

The invention claimed is:

1. A cell comprising a fusion protein, wherein the fusion protein comprises:

(i) a cytochrome P450 enzyme which catalyzes transfer of a nitro functional group to provide a compound represented by Formula V:

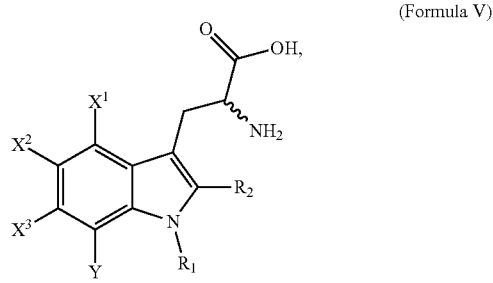

(Formula V)

wherein:

$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{41a}$, —$N(R^{41a})_2$, or —$SR^{41a}$, wherein $R^{41a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{41a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted, monocyclic, $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{41a}$, —$N(R^{41a})_2$, or —$SR^{41a}$, wherein $R^{41a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{41a}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and Y is $NO_2$;

or a pharmaceutically acceptable salt thereof;

(ii) an amino acid linker; and, (iii) a catalytic domain of a reductase enzyme;

wherein the linker joins (iii) to a terminus of (i).

2. The cell of claim 1, wherein the P450 enzyme occurs naturally in *Streptomyces*.

3. The cell of claim 1, wherein the P450 enzyme is a TxtE enzyme, wherein a TxtE enzyme is defined as:

(i) TxtE;

(ii) a portion of TxtE which catalyzes transfer of a nitro functional group to provide a compound represented by Formula V:

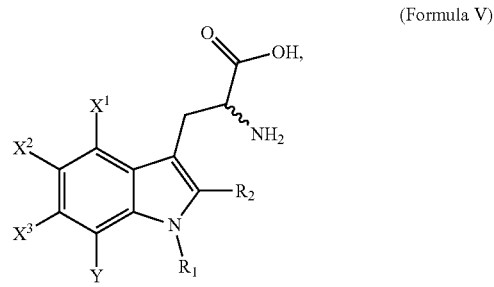

(Formula V)

wherein:

$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and Y is $NO_2$;

or a pharmaceutically acceptable salt thereof; or, (iii) an enzyme which is at least 95% homologous to the amino acid sequence of TxtE and which catalyzes transfer of a nitro functional group to provide a compound represented by Formula V:

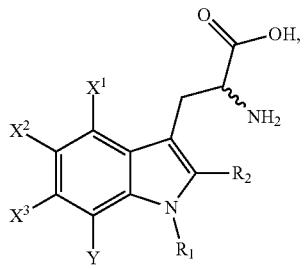

(Formula V)

wherein:

$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$, wherein $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and Y is $NO_2$;

or a pharmaceutically acceptable salt thereof.

4. The cell of claim 1, wherein the cytochrome P450 enzyme shares at least 90% amino acid sequence similarity with TxtE.

5. The cell of claim 1, wherein the cell is a prokaryotic cell.

6. The cell of claim 5, wherein the prokaryotic cell is a bacterial cell.

7. The cell of claim 6, wherein the bacterial cell is an *E. coli* cell.

8. The cell of claim 1, wherein the fusion protein is encoded by an expression construct.

9. The cell of claim 8, wherein the expression construct is a plasmid.

* * * * *